(12) United States Patent      (10) Patent No.:   US 12,655,407 B2

Smith et al.      (45) Date of Patent:   *Jun. 16, 2026

---

(54) ENGINEERED MEGANUCLEASES HAVING SPECIFICITY FOR A RECOGNITION SEQUENCE IN THE HEPATITIS B VIRUS GENOME

(71) Applicant: Precision BioSciences, Inc., Durham, NC (US)

(72) Inventors: James Jefferson Smith, Morrisville, NC (US); Emily B. Harrison, Durham, NC (US); Haley Grimason, Chapel Hill, NC (US); Janel Lape, Wake Forest, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/347,136

(22) Filed: Oct. 1, 2025

(65) Prior Publication Data

US 2026/0028603 A1     Jan. 29, 2026

Related U.S. Application Data

(63) Continuation of application No. 19/273,915, filed on Jul. 18, 2025, which is a continuation of application No. PCT/US2024/055215, filed on Nov. 8, 2024.

(60) Provisional application No. 63/703,603, filed on Oct. 4, 2024, provisional application No. 63/696,652, filed on Sep. 19, 2024, provisional application No. 63/597,251, filed on Nov. 8, 2023.

(51) Int. Cl.
    *C12N 9/22*       (2006.01)

(52) U.S. Cl.
    CPC ...................................... *C12N 9/22* (2013.01)

(58) Field of Classification Search
    CPC .......... C12N 9/22; C12N 15/86; C12N 15/52; C12N 2750/14143; C12N 5/067; A61P 31/20; A61P 31/12; A61P 1/16; C12Y 301/21001
    USPC ........................................................ 435/194
    See application file for complete search history.

(56) References Cited

FOREIGN PATENT DOCUMENTS

WO     WO 2021/113765 A1     6/2021

OTHER PUBLICATIONS

Accession BJL49723. Jul. 22, 2021 (Year: 2021).

*Primary Examiner* — Tekchand Saidha
*Assistant Examiner* — Mohammad Y Meah
(74) *Attorney, Agent, or Firm* — Womble Bond Dickinson (US) LLP

(57) ABSTRACT

The present disclosure encompasses engineered nucleases which recognize and cleave a recognition sequence within a Hepatitis B virus (HBV) genome. The engineered meganucleases described herein can exhibit improved characteristics, such as enhanced specificity and/or efficiency of indel formation, when compared to previously described HBV meganucleases. Further, the disclosure encompasses pharmaceutical compositions comprising engineered meganuclease proteins, nucleic acids encoding engineered meganucleases, and the use of such compositions for treating HBV infections or diseases associated with HBV infections.

9 Claims, 34 Drawing Sheets

Specification includes a Sequence Listing.

HBV 11-12              TGCCGATCCATACTGCGGAACT        SEQ ID NO:3

Recognition Sequence   ACGGCTAGGTATGACGCCTTGA        SEQ ID NO:4

HBV 11-12L.109000    MNTKYNKEFLLYLAGFVDSDGSINASISPRQSFKFKHGLKLRFEVGQKTQHRWFLDKLVD 60
HBV 1923(1/2)        MNTKYNKEFLLYLAGFVDSDGSINASISPRQSFKFKHGLKLRFEVGQKTQHRWFLDKLVD 60
HBV 1090QE           MNTKYNKEFLLYLAGFVDSDGSINASISPRQSFKFKHGLKLRFEVGQKTQHRWFLDKLVD 60
HBV Linker1          ************************************************************

HBV 11-12L.109000    EIGVGYVYDKGSVSVYSLSQIKPLHNFLTQLQPFLALKADQANLVLKIIEQLPSAKESPD 120
HBV 1923(1/2)        EIGVGYVYDKGSVSVYSLSQIKPLHNFLTQLQPFLALKADQANLVLKIIEQLPSAKESPD 120
HBV 1090QE           EIGVGYVYDKGSVSVYSLSQIKPLHNFLTQLQPFLKLKQKQANLVLKIIEQLPSAKESPD 120
HBV Linker1          ********************************  ***********************

HBV 11-12L.109000    KFLEVCTWVDQIAALNDSKTRKTTSETVRAVLDSLPGIQLNKESNHNAS------TQRPS- 174
HBV 1923(1/2)        KFLEVCTWVDQIAALNDSKTRKTTSETVRAVLDSLPGIQLNKESNHNAS------TQRPS- 174
HBV 1090QE           KFLEVCTWVDQIAALNDSKTRKTTSETVRAVLDSLPGSVGGLSPSQASSAASSASSSPGS 180
HBV Linker1          *********************************** *

HBV 11-12L.109000    ------RNMNNFPYSGYNKEFLLYLAGFVDGDGSIFASIRPRQHAKFKHDLELCFNVRQKT 229
HBV 1923(1/2)        ------RNMNNFPYSGYNKEFLLYLAGFVDGDGSIFASIRPRQHAKFKHDLELCFNVRQKT 229
HBV 1090QE           GTSEALRAGAGSGTGYNKEFLLYLAGFVDGDGSIFASIRPRQHAKFKHDLELCFNVRQKT 240
HBV Linker1          ********************************************

HBV 11-12L.109000    QRRWFLDYLVDTIGVGYVIDRGASTYKLSQIKPLHNFLTQLQPFLKLKQQANLVLKII 289
HBV 1923(1/2)        QRRWFLDYLVDTIGVGYVIDRGASTYKLSEIKPLHNFLTQLQPFLKLKQQANLVLKII 289
HBV 1090QE           QRRWFLDKLVDEIGVGYVIDRGASTYKLSQIKPLHNFLTQLQPFLKLKQQANLVLKII 300
HBV Linker1          ********************************* *******************

HBV 11-12L.109000    EQLPSAKESPDKFLEVCTWVDQIAALNDSKTRKTTSETVRAVLDSLSEKKKSSP 343 (SEQ ID NO: 5)
HBV 1923(1/2)        EQLPSAKESPDKFLEVCTWVDQIAALNDSKTRKTTSETVRAVLDSLSEKKKSSP 343 (SEQ ID NO: 6)
HBV 1090QE           EQLPSAKESPDKFLEVCTWVDQIAALNDSKTRKTTSETVRAVLDSLSEKKKSSP 354 (SEQ ID NO: 13)
HBV Linker1          *****************************************************

FIG. 3

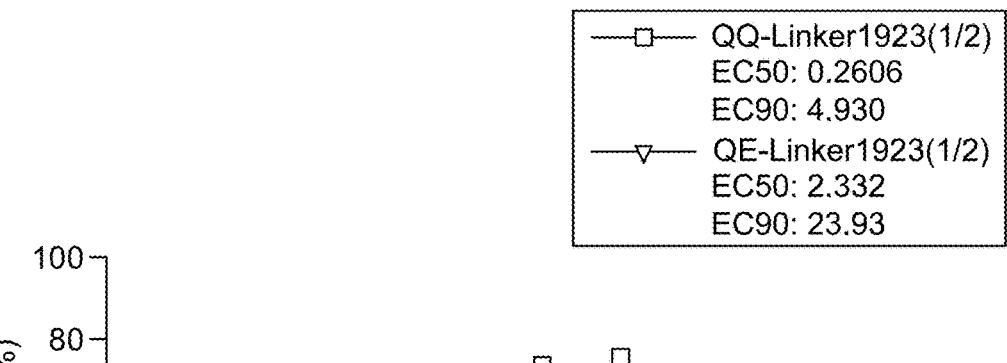
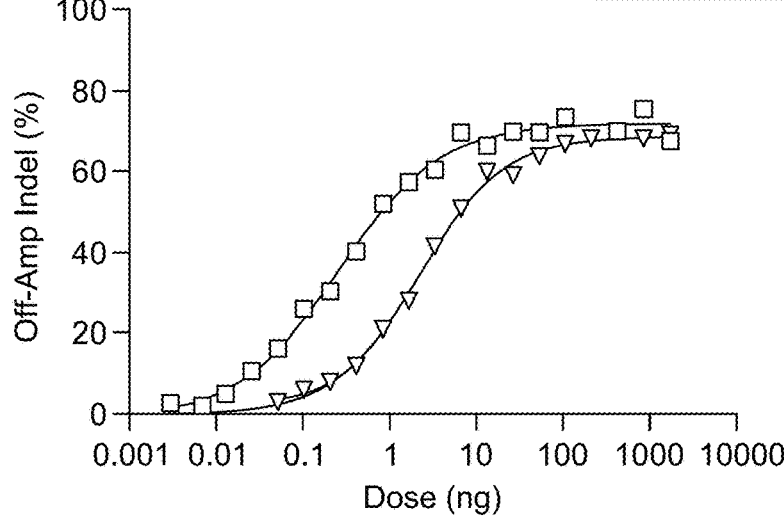
FIG. 8A
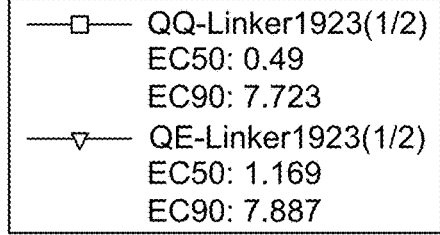
sAg CLIA Dose Curve (D2)
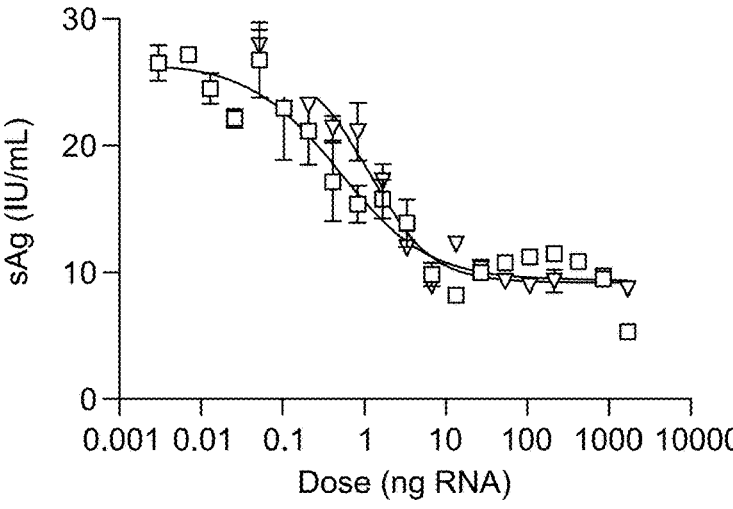
FIG. 8B

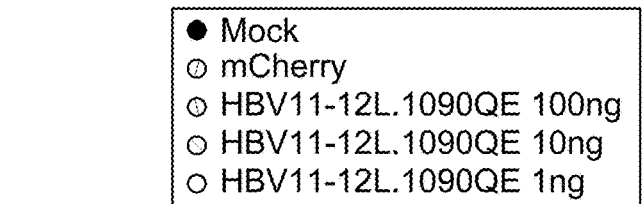
Huh-1 Dex Indels
FIG. 13A
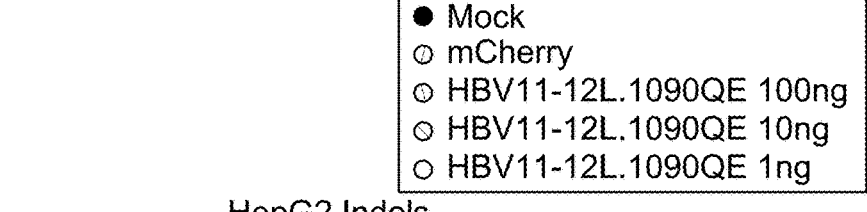
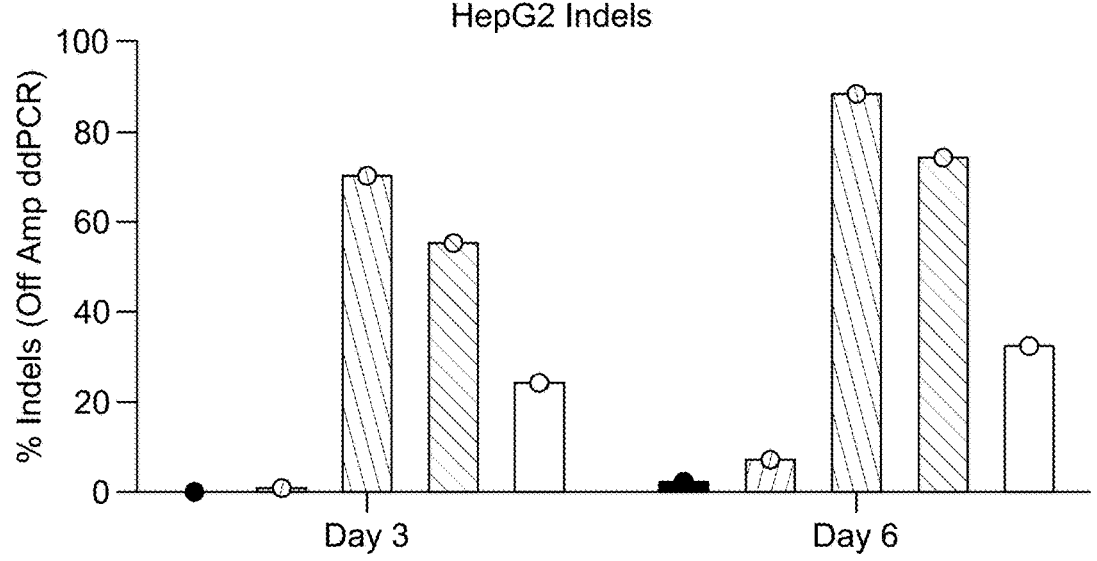
HepG2 Indels
FIG. 13B

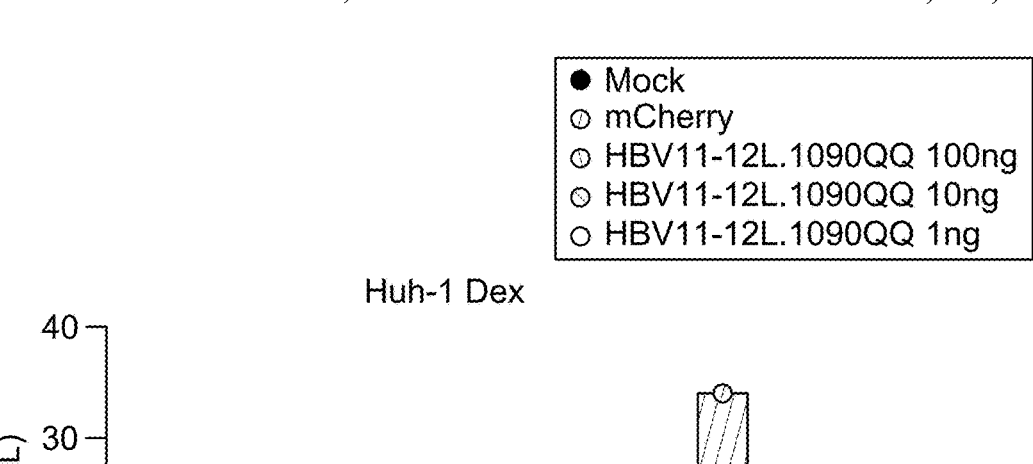
Huh-1 Dex
FIG. 14A
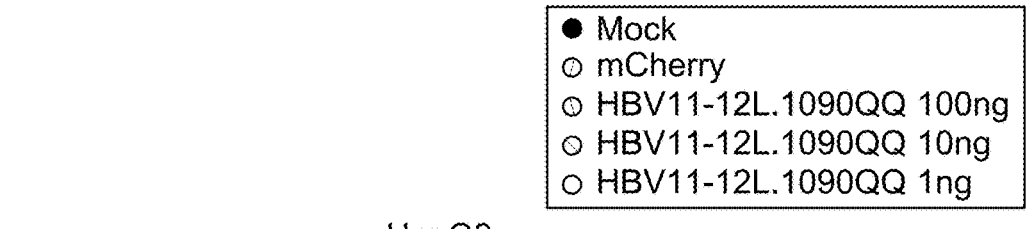
HepG2
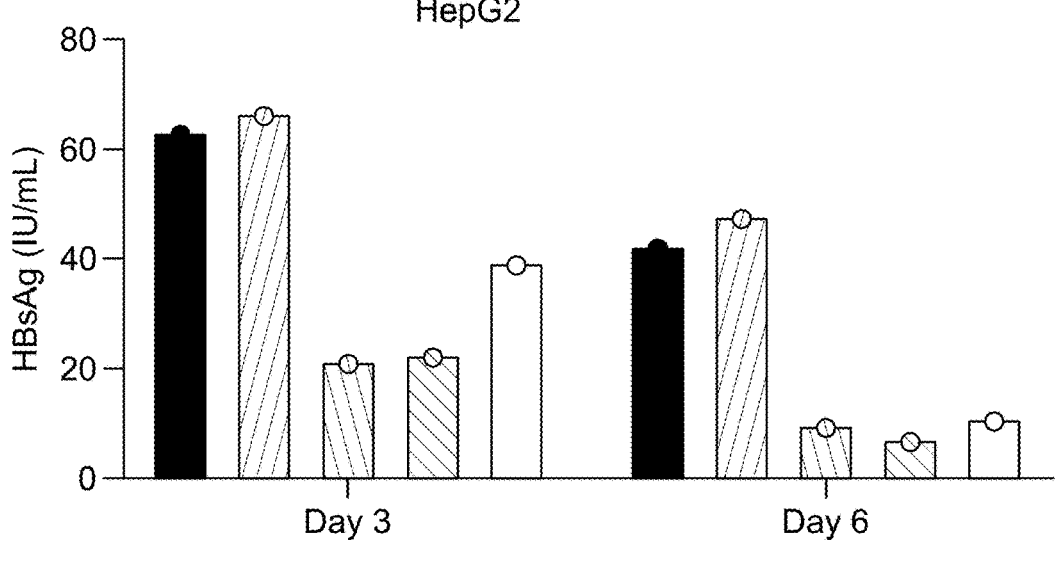
FIG. 14B

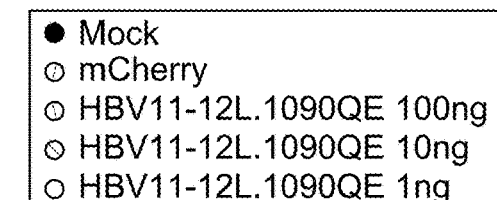
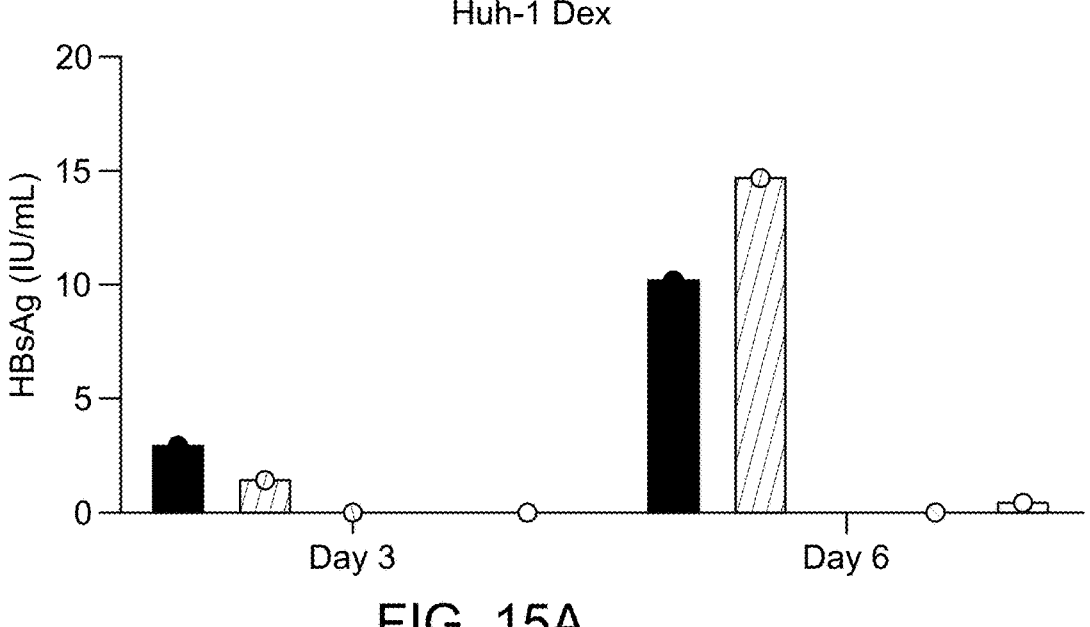
FIG. 15A
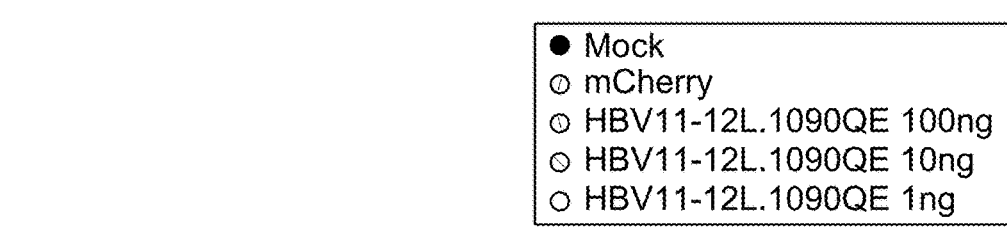
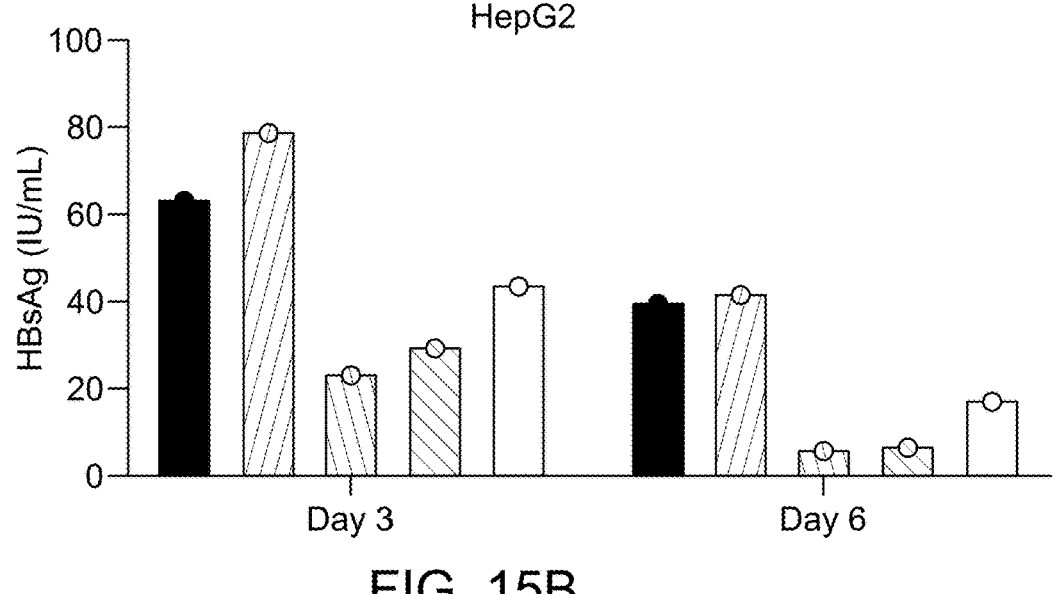
FIG. 15B

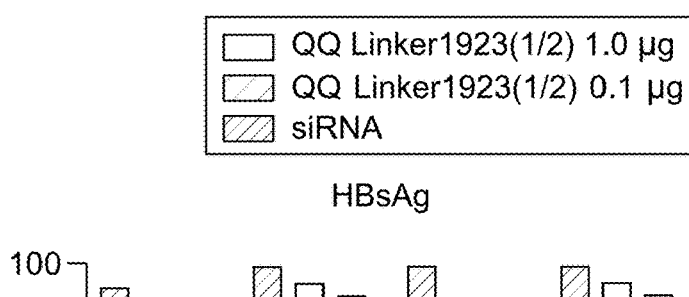
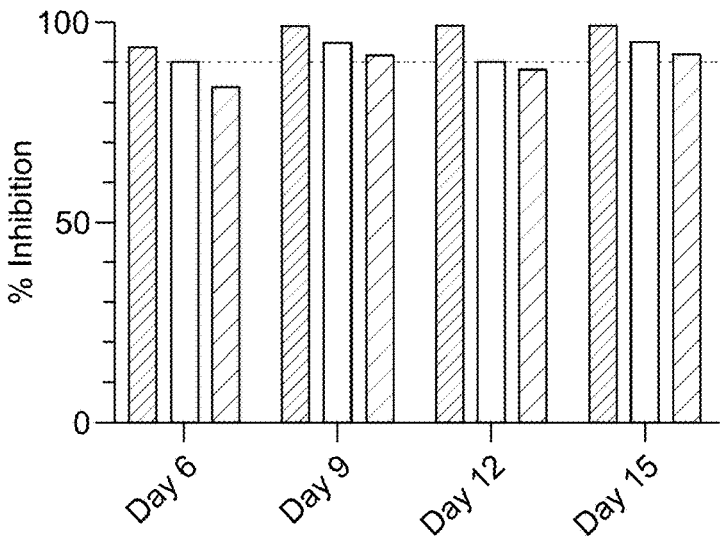
FIG. 16A
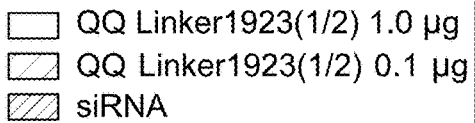
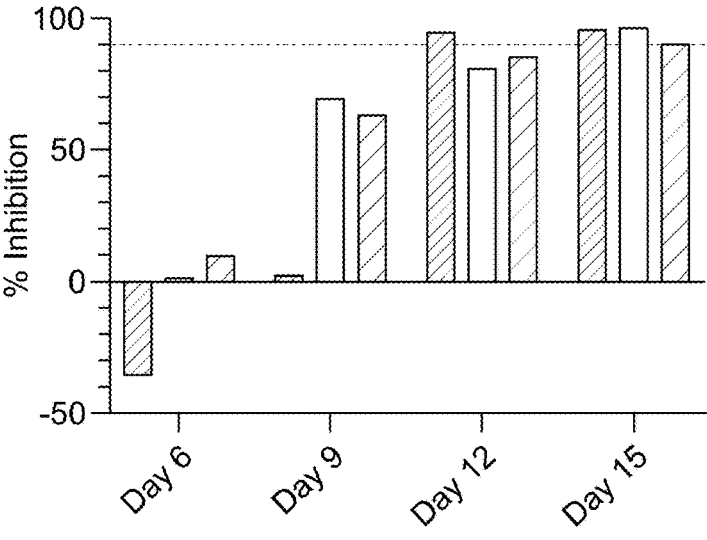
FIG. 16B

ENGINEERED MEGANUCLEASES HAVING SPECIFICITY FOR A RECOGNITION SEQUENCE IN THE HEPATITIS B VIRUS GENOME

CROSS-REFERENCE TO RELATED APPLICATIONS

This application is a continuation of U.S. Non-provisional application Ser. No. 19/273,915, filed Jul. 18, 2025, which is a continuation of International Application No. PCT/US2024/055215, filed Nov. 8, 2024, which claims priority to U.S. Provisional Application Nos. 63/597,251, filed Nov. 8, 2023, 63/696,652, filed Sep. 19, 2024, and 63/703,603, filed Oct. 4, 2024, each of which is incorporated by reference herein in its entirety.

FIELD OF THE INVENTION

The disclosure relates to the field of virology, molecular biology, and recombinant nucleic acid technology. In particular, the disclosure relates to optimized engineered meganucleases having specificity for a recognition sequence within the genome of genotypes A-G of the Hepatitis B virus. Such engineered meganucleases are useful in methods for treating Hepatitis B virus infections and diseases caused by Hepatitis B virus.

REFERENCE TO A SEQUENCE LISTING SUBMITTED ELECTRONICALLY AS AN XML FILE

The instant application contains a Sequence Listing which has been submitted in XML format via USPTO Patent Center and is hereby incorporated by reference in its entirety. Said XML copy, created on Oct. 2, 2024, is named "P89339_2030USP3.xml," and is 108,321 bytes in size.

BACKGROUND OF THE INVENTION

The Hepatitis B virus (HBV) is a major health problem worldwide and more than 350 million people are chronic carriers. HBV infection is a serious and common infectious disease of the liver. Chronic infection is associated with an increased risk to develop severe liver diseases, including liver cirrhosis and hepatocellular carcinoma (HCC), one of the most common forms of human cancer. The estimated risk of HCC in chronic HBV carriers is approximately 100 times greater than in uninfected individuals. About a third of the world population has been infected at one point in their lives, including 240 million to 350 million who have chronic infections. Over 750,000 people die of hepatitis B each year. About 300,000 of these are due to liver cancer. Currently available anti-HBV drugs have limitations. For example, interferon alpha administration is associated with severe adverse reactions. Nucleoside analogues are virostatic and require long-term administration.

The HBV genome exhibits genetic variability with an estimated rate of $1.4\text{-}3.2 \times 10^{-5}$ nucleotide substitutions per site per year. A large number of virus variants arise during replication as a result of nucleotide misincorporations in the absence of any proof reading capacity by the viral polymerase. This variability has resulted in well-recognized subtypes of the virus. HBV has been classified into well-defined genotypes on the basis of an inter-group divergence of 8% or more in the complete genomic sequence, each having a distinct geographical distribution. For example, Genotype A is widespread in sub-Saharan Africa, Northern Europe, and Western Africa; genotypes B and C are common in Asia; genotype C is primarily observed in Southeast Asia; genotype D is dominant in Africa, Europe, Mediterranean countries, and India; genotype G is reported in France, Germany, and the United States; and genotype H is commonly encountered in Central and South America. Genotype I has recently been reported in Vietnam and Laos. The newest HBV genotype, genotype J, has been identified in the Ryukyu Islands in Japan.

HBV is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The circular DNA genome of HBV is unusual because the DNA is not fully double-stranded. One end of the full length strand is linked to the viral DNA polymerase. The genome is approximately 3020-3320 nucleotides long (for the full-length strand) and 1700-2800 nucleotides long (for the short length-strand). The negative-sense (non-coding) is complementary to the viral mRNA.

There are four known genes encoded by the genome, referred to as C, X, P, and S. The core protein is coded for by gene C (HBcAg), and its start codon is preceded by an upstream in-frame AUG start codon from which the pre-core protein is produced. The HBeAg is produced by proteolytic processing of the pre-core protein. The DNA polymerase is encoded by gene P. Gene S codes for the surface antigen (HBsAg). The HBsAg gene is one long open reading frame but contains three in frame "start" (ATG) codons that divide the gene into three sections: pre-S1, pre-S2, and S. Because of the multiple start codons, polypeptides of three different sizes called Large (the order from surface to the inside: pre-S1/pre-S2/S), Middle (pre-S2/S), and Small (S) are produced. The function of the protein coded for by gene X is not fully understood but it is associated with the development of liver cancer. It stimulates genes that promote cell growth and inactivates growth regulating molecules.

The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined.

The HBV life cycle begins when the virus attaches to the host cell and is internalized. Recent studies have demonstrated that sodium-taurocholate co-transporting polypeptide (NTCP) is a functional receptor in HBV infection. The virion relaxed circular DNA (rcDNA) is delivered to the nucleus, where it is repaired to form a covalently closed-circular DNA (cccDNA). The episomal cccDNA serves as the template for the transcription of the pregenomic RNA (pgRNA) and the other viral mRNAs by the host RNA polymerase II. The transcripts are then exported to the cytoplasm, where translation of the viral proteins occurs. Reverse transcriptase (RT) binds to pgRNA and triggers assembly of the core proteins into immature, RNA-containing nucleocapsids. The immature nucleocapsids then undergo a process of maturation whereby pgRNA is reversed transcribed by RT to make the mature rcDNA. A unique feature of hepadnavirus reverse transcription is the RT primed initiation of minus-strand DNA synthesis, which leads to the covalent linkage of RT to the 5' end of the minus-strand DNA.

The mature, rcDNA-containing nucleocapsids are then enveloped by the viral surface proteins and secreted as virions (secretion pathway) or, alternatively, are recycled back to the nucleus to further amplify the pool of cccDNA (recycling pathway). Persistence of cccDNA in hepatocytes plays a key role in viral persistence, reactivation of viral replication after cessation of antiviral therapy, and resistance to therapy.

Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG motif (see Chevalier et al. (2001), Nucleic Acids Res. 29(18): 3757-3774). The LAGLIDADG homing endonucleases with a single copy of the LAGLIDADG motif form homodimers, whereas members with two copies of the LAGLIDADG motif are found as monomers. Methods for producing homing endonucleases are known in the art.

I-CreI (SEQ ID NO: 1) is a member of the LAGLIDADG family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J. Mol. Biol. 342: 31-41; Chames et al. (2005), Nucleic Acids Res. 33: e178; Seligman et al. (2002), Nucleic Acids Res. 30: 3870-9, Arnould et al. (2006), J. Mol. Biol. 355: 443-58). Methods for rationally-designing mono-LAGLIDADG homing endonucleases were described which are capable of comprehensively redesigning I-CreI and other homing endonucleases to target widely-divergent DNA sites, including sites in mammalian, yeast, plant, bacterial, and viral genomes (see, e.g., WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (see also Li et al. (2009), Nucleic Acids Res. 37:1650-62; Grizot et al. (2009), Nucleic Acids Res. 37:5405-19). Thus, a functional "single-chain" meganuclease can be expressed from a single transcript.

The use of engineered meganucleases for treatment of HBV infections has been suggested. For example, WO 2010/136841 suggests the use of engineered meganucleases for cleaving the genome of non-genomically integrating viruses. Such meganucleases include variants of I-CreI targeting 22 base pair meganuclease recognition sequences which differ from those described herein, and which are only present in a few HBV genotypes.

Applicants previously disclosed in PCT/US2017/56638, PCT/US2019/27203, and PCT/US2020/063479 a number of engineered meganucleases having specificity for recognition sequences present in the HBV genome, including the HBV 11-12 recognition sequence (SEQ ID NO: 3) which is advantageously present in the genome of at least HBV genotypes A-G.

The present disclosure improves upon the engineered meganucleases previously described in the art in a number of aspects. When generating an endonuclease for therapeutic administration to a patient, it is critical that on-target specificity is enhanced (i.e., increased) while reducing or eliminating off-target cutting within the target cell genome. Here, Applicants have developed additional engineered meganucleases which target the HBV 11-12 recognition sequence. The meganucleases of the present disclosure have novel and unique sequences which were generated through extensive experimentation. Additionally, the meganucleases described herein have a number of improved and unexpected properties when compared to the previously disclosed engineered meganucleases, including a significant reduction in off-target cutting in the host cell genome. In particular, the engineered meganucleases described herein demonstrate a significant enhancement (i.e., increase) in the formation of indels (i.e., insertions or deletions within the HBV genome at the cleavage site, indicative of on-target cutting) in cell lines comprising an integrated copy of the HBV genome. Thus, the meganucleases of the disclosure further advance the art in a number of ways that are necessary for development of a clinical product targeting HBV infection and HBV-related hepatocellular carcinoma.

SUMMARY OF THE INVENTION

In one aspect, the disclosure provides an engineered meganuclease that binds and cleaves a recognition sequence comprising or consisting of SEQ ID NO: 3 within a Hepatitis B virus (HBV) genome, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 204-259 of SEQ ID NO: 5 or SEQ ID NO: 6.

In some embodiments, the HVR1 region comprises an amino acid sequence having at least 97% sequence identity to residues 204-259 of SEQ ID NO: 5 or SEQ ID NO: 6.

In some embodiments, the HVR1 region comprises one or more residues corresponding to residues 204, 206, 208, 210, 212, 213, 218, 220, 222, 224, 226, 248, 250, 255, and 257 of SEQ ID NO: 5 or SEQ ID NO: 6.

In some embodiments, the HVR1 region comprises residues corresponding to residues 204, 206, 208, 210, 212, 213, 218, 220, 222, 224, 226, 248, 250, 255, and 257 of SEQ ID NO: 5 or SEQ ID NO: 6.

In some embodiments, the HVR1 region comprises a residue corresponding to residue 237 of SEQ ID NO: 5 or SEQ ID NO: 6.

In some embodiments, the HVR1 region comprises a residue corresponding to residue 241 of SEQ ID NO: 5 or SEQ ID NO: 6.

In some embodiments, the HVR1 region comprises a residue corresponding to residue 251 of SEQ ID NO: 5 or SEQ ID NO: 6.

In some embodiments, the HVR1 region comprises a residue corresponding to residue 252 of SEQ ID NO: 5 or SEQ ID NO: 6.

In some embodiments, the HVR1 region comprises a residue corresponding to residue 253 of SEQ ID NO: 5 or SEQ ID NO: 6.

In some embodiments, the HVR1 region comprises Y, R, K, or D at a residue corresponding to residue 246 of SEQ ID NO: 5 or SEQ ID NO: 6.

In some embodiments, the HVR1 region comprises residues 204-259 of SEQ ID NO: 5 or SEQ ID NO: 6.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 187-333 of SEQ ID NO: 5 or SEQ ID NO: 6.

In some embodiments, the first subunit comprises an amino acid sequence having at least 99% sequence identity to residues 187-333 of SEQ ID NO: 5 or SEQ ID NO: 6.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 185-343 of SEQ ID NO: 5 or SEQ ID NO: 6.

In some embodiments, the first subunit comprises an amino acid sequence having at least 99% sequence identity to residues 185-343 of SEQ ID NO: 5 or SEQ ID NO: 6.

In some embodiments, the first subunit comprises a residue corresponding to residue 260 of SEQ ID NO: 6.

In some embodiments, the first subunit comprises G, S, or A at a residue corresponding to residue 199 of SEQ ID NO: 5 or SEQ ID NO: 6.

In some embodiments, the first subunit comprises E, Q, or K at a residue corresponding to residue 260 of SEQ ID NO: 5 or SEQ ID NO: 6.

In some embodiments, the first subunit comprises residues 187-333 of any one of SEQ ID NO: 5 or SEQ ID NO: 6.

In some embodiments, the first subunit comprises residues 185-343 of any one of SEQ ID NO: 5 or SEQ ID NO: 6.

In some embodiments, the HVR2 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 24-79 of SEQ ID NO: 5 or SEQ ID NO: 6.

In some embodiments, the HVR2 region comprises one or more residues corresponding to residues 24, 26, 28, 30, 32, 33, 38, 40, 42, 44, 46, 68, 70, 75, and 77 of SEQ ID NO: 5 or SEQ ID NO: 6.

In some embodiments, the HVR2 region comprises residues corresponding to residues 24, 26, 28, 30, 32, 33, 38, 40, 42, 44, 46, 68, 70, 75, and 77 of SEQ ID NO: 5 or SEQ ID NO: 6.

In some embodiments, the HVR2 region comprises a residue corresponding to residue 51 of SEQ ID NO: 5 or SEQ ID NO: 6.

In some embodiments, the HVR2 region comprises Y, R, K, or D at a residue corresponding to residue 66 of SEQ ID NO: 5 or SEQ ID NO: 6.

In some embodiments, the HVR2 region comprises residues 24-79 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 5 or SEQ ID NO: 6.

In some embodiments, the second subunit comprises an amino acid sequence having at least 99% sequence identity to residues 7-153 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 5 or SEQ ID NO: 6.

In some embodiments, the second subunit comprises an amino acid sequence having at least 99% sequence identity to residues 6-153 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 5 or SEQ ID NO: 6.

In some embodiments, the second subunit comprises an amino acid sequence having at least 99% sequence identity to residues 5-153 of SEQ ID NO: 5 or SEQ ID NO: 6.

In some embodiments, the second subunit is an N-terminal subunit and comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 5 or SEQ ID NO: 6.

In some embodiments, the second subunit comprises an amino acid sequence having at least 99% sequence identity to residues 4-153 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 5 or SEQ ID NO: 6.

In some embodiments, the second subunit comprises an amino acid sequence having at least 99% sequence identity to residues 3-153 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 5 or SEQ ID NO: 6. In some embodiments, the second subunit comprises a residue other than M at a position corresponding to position 1 of SEQ ID NO: 5 or SEQ ID NO: 6.

In some embodiments, the second subunit comprises an amino acid sequence having at least 99% sequence identity to residues 2-153 of SEQ ID NO: 5 or SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 5 or SEQ ID NO: 6.

In some embodiments, the second subunit comprises an amino acid sequence having at least 99% sequence identity to residues 1-153 of SEQ ID NO: 5 or SEQ ID NO: 6.

In some embodiments, the second subunit comprises a residue corresponding to residue 19 of SEQ ID NO: 5 or SEQ ID NO: 6.

In some embodiments, the second subunit comprises a residue corresponding to residue 80 of SEQ ID NO: 5 or SEQ ID NO: 6.

In some embodiments, the second subunit comprises a residue corresponding to residue 96 of SEQ ID NO: 5 or SEQ ID NO: 6.

In some embodiments, the second subunit comprises a residue corresponding to residue 99 of SEQ ID NO: 5 or SEQ ID NO: 6.

In some embodiments, the second subunit comprises a residue corresponding to residue 100 of SEQ ID NO: 5 or SEQ ID NO: 6.

In some embodiments, the second subunit comprises G, S, or A at a residue corresponding to residue 19 of SEQ ID NO: 5 or SEQ ID NO: 6.

In some embodiments, the second subunit comprises E, Q, or K at a residue corresponding to residue 80 of SEQ ID NO: 5 or SEQ ID NO: 6.

In some embodiments, the second subunit comprises residues 7-153 of SEQ ID NO: 5 or SEQ ID NO: 6.

In some embodiments, the second subunit comprises residues 6-153 of SEQ ID NO: 5 or SEQ ID NO: 6.

In some embodiments, the second subunit comprises residues 5-153 of SEQ ID NO: 5 or SEQ ID NO: 6.

In some embodiments, the second subunit comprises residues 4-153 of SEQ ID NO: 5 or SEQ ID NO: 6.

In some embodiments, the second subunit comprises residues 3-153 of SEQ ID NO: 5 or SEQ ID NO: 6.

In some embodiments, the second subunit comprises residues 2-153 of SEQ ID NO: 5 or SEQ ID NO: 6. In some embodiments, the second subunit comprises a residue other than M at a position corresponding to position 1 of SEQ ID NO: 5 or SEQ ID NO: 6.

In some embodiments, the second subunit comprises residues 1-153 of SEQ ID NO: 5 or SEQ ID NO: 6.

In some embodiments, the engineered meganuclease is a single-chain meganuclease comprising a linker and wherein the linker covalently joins the first subunit and the second subunit.

In some embodiments, the linker comprises an amino acid sequence set forth in SEQ ID NO: 15 or SEQ ID NO: 16.

In some embodiments, the linker comprises an amino acid sequence set forth in SEQ ID NO: 15.

In some embodiments, the N-terminus of the linker is fused to the residue (i.e., a D residue) corresponding to residue 153 of SEQ ID NO: 5 or SEQ ID NO: 6, and the C-terminus of the linker is fused to the residue (i.e., a Y residue) corresponding to residue 185 of SEQ ID NO: 5 or SEQ ID NO: 6.

In some embodiments, the engineered meganuclease comprises a first subunit comprising an amino acid sequence having at least 99% sequence identity residues 187-333 of SEQ ID NO: 5 or SEQ ID NO: 6; a linker comprising an amino acid sequence set forth in SEQ ID NO: 15, wherein the linker covalently joins the first subunit and the second subunit; and a second subunit comprising an amino acid sequence having at least 99% sequence identity to residues 7-153 of SEQ ID NO: 5 or SEQ ID NO: 6.

In some embodiments, the engineered meganuclease comprises a first subunit comprising an amino acid sequence having at least 99% sequence identity residues 185-343 of SEQ ID NO: 5 or SEQ ID NO: 6; a linker comprising an amino acid sequence set forth in SEQ ID NO: 15, wherein the linker covalently joins the first subunit and the second subunit; and a second subunit comprising an amino acid sequence having at least 99% sequence identity to residues 1-153 of SEQ ID NO: 5 or SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-343 of SEQ ID NO: 5 or SEQ ID NO: 6.

In some embodiments, the engineered meganuclease comprises an amino acid sequence having at least 92% sequence identity to residues 4-343 of SEQ ID NO: 5 or SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-343 of SEQ ID NO: 5 or SEQ ID NO: 6.

In some embodiments, the engineered meganuclease comprises an amino acid sequence having at least 92% sequence identity to residues 3-343 of SEQ ID NO: 5 or SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-343 of SEQ ID NO: 5 or SEQ ID NO: 6. In some embodiments, the second subunit comprises a residue other than M at a position corresponding to position 1 of SEQ ID NO: 5 or SEQ ID NO: 6.

In some embodiments, the engineered meganuclease comprises an amino acid sequence having at least 92% sequence identity to residues 2-343 of SEQ ID NO: 5 or SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 5 or SEQ ID NO: 6.

In some embodiments, the engineered meganuclease comprises an amino acid sequence having at least 92% sequence identity to SEQ ID NO: 5 or SEQ ID NO: 6.

In some embodiments, the engineered meganuclease comprises an amino acid sequence of residues 4-343 of SEQ ID NO: 5 or SEQ ID NO: 6.

In some embodiments, the engineered meganuclease comprises an amino acid sequence of residues 3-343 of SEQ ID NO: 5 or SEQ ID NO: 6.

In some embodiments, the engineered meganuclease comprises an amino acid sequence of residues 2-343 of SEQ ID NO: 5 or SEQ ID NO: 6. In some embodiments, the second subunit comprises a residue other than M at a position corresponding to position 1 of SEQ ID NO: 5 or SEQ ID NO: 6.

In some embodiments, the engineered meganuclease comprises an amino acid sequence of SEQ ID NO: 5 or SEQ ID NO: 6. In some embodiments, the engineered meganuclease comprises an amino acid sequence of SEQ ID NO: 5. In some embodiments, the engineered meganuclease comprises an amino acid sequence of SEQ ID NO: 6.

In some embodiments, the engineered meganuclease is encoded by a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 11 or SEQ ID NO: 12.

In some embodiments, the engineered meganuclease is encoded by a nucleic acid sequence of SEQ ID NO: 11 or SEQ ID NO: 12.

In some embodiments, the engineered meganuclease comprises a nuclear localization signal.

In some embodiments, the nuclear localization signal is at the N-terminus of the engineered meganuclease.

In some embodiments, the nuclear localization signal is at the C-terminus of the engineered meganuclease.

In some embodiments, the engineered meganuclease comprises a first nuclear localization signal at the N-terminus and a second nuclear localization signal at the C-terminus.

In some embodiments, the nuclear localization signal comprises an amino acid sequence having at least 80% or at least 90% sequence identity to SEQ ID NO: 17. In some embodiments, the nuclear localization signal comprises SEQ ID NO: 17.

In some embodiments, the nuclear localization signal comprises an amino acid sequence having at least 85% sequence identity to SEQ ID NO: 65. In some embodiments, the nuclear localization sequence comprises SEQ ID NO: 65.

In some embodiments, the engineered meganuclease comprises an N-terminal nuclear localization sequence comprising an amino acid sequence having at least 80% or at least 90% sequence identity to SEQ ID NO: 17, and a C-terminal nuclear localization sequence comprising an amino acid sequence having at least 80% or at least 90% sequence identity to SEQ ID NO: 17.

In some embodiments, the engineered meganuclease comprises an N-terminal nuclear localization sequence comprising an amino acid sequence set forth in SEQ ID NO: 17 and a C-terminal nuclear localization sequence comprising an amino acid sequence set forth in SEQ ID NO: 17.

In some embodiments, the engineered meganuclease comprises an N-terminal nuclear localization sequence comprising an amino acid sequence having at least 80% or at least 90% sequence identity to SEQ ID NO: 17, and a C-terminal nuclear localization sequence comprising an amino acid sequence having at least 85% sequence identity to SEQ ID NO: 65.

In some embodiments, the engineered meganuclease comprises an N-terminal nuclear localization sequence comprising an amino acid sequence set forth in SEQ ID NO: 17 and a C-terminal nuclear localization sequence comprising an amino acid sequence set forth in SEQ ID NO: 65.

In some embodiments, the engineered meganuclease comprises an N-terminal nuclear localization sequence comprising an amino acid sequence having at least 85% sequence identity to SEQ ID NO: 65, and a C-terminal nuclear localization sequence comprising an amino acid sequence having at least 80% or at least 90% sequence identity to SEQ ID NO: 17.

In some embodiments, the engineered meganuclease comprises an N-terminal nuclear localization sequence comprising an amino acid sequence set forth in SEQ ID NO: 65 and a C-terminal nuclear localization sequence comprising an amino acid sequence set forth in SEQ ID NO: 17.

In some embodiments, the engineered meganuclease comprises an N-terminal nuclear localization sequence comprising an amino acid sequence having at least 85% sequence identity to SEQ ID NO: 65, and a C-terminal nuclear localization sequence comprising an amino acid sequence having at least 85% sequence identity to SEQ ID NO: 65.

In some embodiments, the engineered meganuclease comprises an N-terminal nuclear localization sequence comprising an amino acid sequence set forth in SEQ ID NO: 65 and a C-terminal nuclear localization sequence comprising an amino acid sequence set forth in SEQ ID NO: 65.

In another aspect, the disclosure provides an engineered meganuclease described herein for use as a medicament.

In another aspect, the disclosure provides a polynucleotide comprising a nucleic acid sequence encoding an engineered meganuclease described herein.

In some embodiments, the polynucleotide comprises a 5' ALB untranslated region (UTR) comprising a nucleic acid sequence having at least 95% sequence identity to SEQ ID NO: 18 or SEQ ID NO: 82. In some embodiments, the polynucleotide comprises a 5' ALB untranslated region (UTR) comprising a nucleic acid sequence set forth in SEQ ID NO: 18 or SEQ ID NO: 82.

In some embodiments, the polynucleotide comprises a 3' SNRPB UTR comprising a nucleic acid sequence having at least 95% sequence identity to SEQ ID NO: 19 or SEQ ID NO: 83. In some embodiments, the polynucleotide comprises a 3' SNRPB UTR comprising a nucleic acid sequence set forth in SEQ ID NO: 19 or SEQ ID NO: 83.

In some embodiments, the polynucleotide comprises a termination sequence. In some embodiments, the polynucleotide comprises a polyA termination sequence. In some embodiments, the polyA termination sequence comprises a nucleic acid sequence having at least 95% sequence identity to SEQ ID NO: 20. In some embodiments, the polyA termination sequence comprises a nucleic acid sequence set forth in SEQ ID NO: 20.

In some embodiments, the polynucleotide comprises a Kozak sequence. In some embodiments, the polynucleotide comprises a Kozak sequence comprising a nucleic acid sequence set forth in SEQ ID NO: 21 or SEQ ID NO: 84.

In some embodiments, the nucleic acid sequence encoding the engineered meganuclease is thymidine or uridine depleted.

In some embodiments, the nucleic acid sequence encoding the engineered meganuclease is codon-optimized for liver expression.

In some embodiments, the polynucleotide is an mRNA.

In some embodiments, the mRNA comprises: (a) a 5' ALB UTR comprising a nucleic acid sequence set forth in SEQ ID NO: 82; (b) the nucleic acid sequence encoding the engineered meganuclease, wherein the nucleic acid sequence is uridine depleted and codon-optimized for liver expression; (c) a 3' SNRPB UTR comprising a nucleic acid sequence set forth in SEQ ID NO: 83; and (d) a polyA termination sequence.

In some embodiments, the mRNA comprises: (a) a 5' ALB UTR comprising a nucleic acid sequence set forth in SEQ ID NO: 82; (b) a Kozak sequence comprising a nucleic acid sequence set forth in SEQ ID NO: 84; (c) the nucleic acid sequence encoding the engineered meganuclease, wherein the nucleic acid sequence is uridine depleted and codon-optimized for liver expression; (d) a 3' SNRPB UTR comprising a nucleic acid sequence set forth in SEQ ID NO: 83; and (e) a polyA termination sequence.

In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 74. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 75. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 76. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 77. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 78. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 79. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 80. In some embodiments, the mRNA comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 81.

In some embodiments, the mRNA comprises a nucleic acid sequence set forth in SEQ ID NO: 74. In some embodiments, the mRNA comprises a nucleic acid sequence set forth in SEQ ID NO: 75. In some embodiments, the mRNA comprises a nucleic acid sequence set forth in SEQ ID NO: 76. In some embodiments, the mRNA comprises a nucleic acid sequence set forth in SEQ ID NO: 77. In some embodiments, the mRNA comprises a nucleic acid sequence set forth in SEQ ID NO: 78. In some embodiments, the mRNA comprises a nucleic acid sequence set forth in SEQ ID NO: 79. In some embodiments, the mRNA comprises a nucleic acid sequence set forth in SEQ ID NO: 80. In some embodiments, the mRNA comprises a nucleic acid sequence set forth in SEQ ID NO: 81.

In another aspect, the disclosure provides a polynucleotide comprising a nucleic acid sequence encoding an engineered meganuclease described herein for use as a medicament.

In another aspect, the disclosure provides a recombinant DNA construct comprising a polynucleotide described herein (i.e., comprising a nucleic acid sequence encoding an engineered meganuclease described herein).

In some embodiments, the recombinant DNA construct is a plasmid DNA.

In some embodiments, the polynucleotide comprises: (a) a 5' ALB untranslated region (UTR) comprising a nucleic acid sequence set forth in SEQ ID NO: 18; (b) the nucleic acid sequence encoding the engineered meganuclease; (c) a 3' SNRPB UTR comprising a nucleic acid sequence set forth in SEQ ID NO: 19; and (d) a polyA termination sequence. Preferably, the nucleic acid sequence is thymidine depleted and codon-optimized for liver expression.

In some embodiments, the polynucleotide comprises: (a) a 5' ALB UTR comprising a nucleic acid sequence set forth in SEQ ID NO: 18; (b) a Kozak sequence comprising a nucleic acid sequence set forth in SEQ ID NO: 21; (c) the nucleic acid sequence encoding the engineered meganuclease; (d) a 3' SNRPB UTR comprising a nucleic acid sequence set forth in SEQ ID NO: 19; and (e) a polyA termination sequence. Preferably, the nucleic acid sequence is thymidine depleted and codon-optimized for liver expression.

In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 66. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 67. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 68. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 69. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 70. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 71. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 72. In some embodiments, the polynucleotide comprises a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence set forth in SEQ ID NO: 73.

In some embodiments, the polynucleotide comprises a nucleic acid sequence set forth in SEQ ID NO: 66. In some embodiments, the polynucleotide comprises a nucleic acid sequence set forth in SEQ ID NO: 67. In some embodiments, the polynucleotide comprises a nucleic acid sequence set forth in SEQ ID NO: 68. In some embodiments, the polynucleotide comprises a nucleic acid sequence set forth in SEQ ID NO: 69. In some embodiments, the polynucleotide comprises a nucleic acid sequence set forth in SEQ ID NO: 70. In some embodiments, the polynucleotide comprises a nucleic acid sequence set forth in SEQ ID NO: 71. In some embodiments, the polynucleotide comprises a nucleic acid sequence set forth in SEQ ID NO: 72. In some embodiments, the polynucleotide comprises a nucleic acid sequence set forth in SEQ ID NO: 73. In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV.

In some embodiments, the polynucleotide comprises a promoter operably linked to the nucleic acid sequence encoding the engineered meganuclease. In some embodiments, the promoter is a liver-specific promoter.

In another aspect, the disclosure provides a recombinant DNA construct comprising a polynucleotide described herein (i.e., comprising a nucleic acid sequence encoding an engineered meganuclease described herein) for use as a medicament.

In another aspect, the disclosure provides a recombinant virus comprising a polynucleotide described herein (i.e., comprising a nucleic acid sequence encoding an engineered meganuclease described herein).

In some embodiments, the recombinant virus is a recombinant adenovirus, a recombinant lentivirus, a recombinant retrovirus, or a recombinant AAV. In some embodiments, the recombinant virus is a recombinant AAV.

In some embodiments, the polynucleotide comprises a promoter operably linked to the nucleic acid sequence encoding the engineered meganuclease. In some embodiments, the promoter is a liver-specific promoter.

In another aspect, the disclosure provides a recombinant virus comprising a polynucleotide described herein (i.e., comprising a nucleic acid sequence encoding an engineered meganuclease described herein) for use as a medicament.

In another aspect, the disclosure provides a lipid nanoparticle composition comprising lipid nanoparticles comprising a polynucleotide described herein (i.e., comprising a nucleic acid sequence encoding an engineered meganuclease described herein).

In another aspect, the disclosure provides a lipid nanoparticle composition described herein for use as a medicament.

In another aspect, the disclosure provides a pharmaceutical composition comprising a pharmaceutically acceptable carrier and an engineered meganuclease described herein.

In another aspect, the disclosure provides a pharmaceutical composition comprising a pharmaceutically acceptable carrier and a polynucleotide described herein (i.e., comprising a nucleic acid sequence encoding an engineered meganuclease described herein).

In another aspect, the disclosure provides a pharmaceutical composition comprising a pharmaceutically acceptable carrier and a recombinant DNA construct described herein (i.e., comprising a polynucleotide described herein).

In another aspect, the disclosure provides a pharmaceutical composition comprising a pharmaceutically acceptable carrier and a recombinant virus described herein (i.e., comprising a polynucleotide described herein).

In another aspect, the disclosure provides a pharmaceutical composition comprising a pharmaceutically acceptable carrier and a lipid nanoparticle composition described herein.

In another aspect, the disclosure provides a pharmaceutical composition described herein for use as a medicament.

In another aspect, the disclosure provides a host cell comprising a polynucleotide described herein (i.e., comprising a nucleic acid sequence encoding an engineered meganuclease described herein).

In another aspect, the disclosure provides a method for inactivating a polymerase (pol) gene of an HBV genome or an HBV genome fragment, the method comprising introducing into a eukaryotic cell comprising the HBV genome or HBV genome fragment: (a) a polynucleotide comprising a nucleic acid sequence encoding an engineered meganuclease described herein, wherein the engineered meganuclease is expressed in the eukaryotic cell; or (b) an engineered meganuclease described herein; wherein the engineered meganuclease produces a cleavage site at a recognition sequence comprising or consisting of SEQ ID NO: 3 within the pol gene, wherein the pol gene is inactivated by introduction of an insertion or deletion (indel) at the cleavage site, or wherein the pol gene is inactivated by elimination of the HBV genome or the HBV genome fragment.

In some embodiments, the HBV genome or the HBV genome fragment is comprised by covalently closed circular DNA (cccDNA). In some embodiments, the cccDNA is eliminated following generation of the cleavage site. In some embodiments, the pol gene is inactivated in the cccDNA by introduction of the indel at the cleavage site. In some embodiments, the indel is introduced by non-homologous end joining (NHEJ). In some embodiments, the inactivated pol gene does not encode an active and/or full-length HBV polymerase protein.

In some embodiments, the HBV genome or the HBV genome fragment is comprised in the genome of the eukaryotic cell. In some embodiments, the genome is the nuclear genome. In some embodiments, the genome is the mitochondrial genome. In some embodiments, the indel is introduced by NHEJ. In some embodiments, the inactivated pol gene does not encode an active and/or full-length HBV polymerase protein.

In some embodiments, the method inactivates an HBV S antigen (HBsAg) gene in the HBV genome or the HBV genome fragment.

In some embodiments, the eukaryotic cell is a human cell. In some embodiments, the human cell is a liver cell. In some embodiments, the liver cell is a hepatocyte.

In some embodiments, the polynucleotide is a polynucleotide described herein (i.e., comprising a nucleic acid sequence encoding an engineered meganuclease described herein).

In some embodiments, the polynucleotide is introduced into the eukaryotic cell by an mRNA or a recombinant virus.

In some embodiments, the mRNA is an mRNA described herein. In some embodiments, the mRNA is introduced into the eukaryotic cell by contacting the eukaryotic cell with a lipid nanoparticle comprising the mRNA.

In some embodiments, the recombinant virus is a recombinant virus described herein. In some embodiments, the recombinant virus is a recombinant AAV. In some embodiments, the recombinant AAV has a serotype of AAV8.

In another aspect, the disclosure provides a method for inactivating a pol gene of an HBV genome or an HBV genome fragment in a target cell in a subject, the method comprising delivering to the target cell comprising the HBV genome or HBV genome fragment: (a) a polynucleotide comprising a nucleic acid sequence encoding an engineered meganuclease described herein, wherein the engineered meganuclease is expressed in the target cell; or (b) an engineered meganuclease described herein; wherein the engineered meganuclease produces a cleavage site at a recognition sequence comprising or consisting of SEQ ID NO: 3 within the pol gene, wherein the pol gene is inactivated by introduction of an indel at the cleavage site, or wherein the pol gene is inactivated by elimination of the HBV genome or the HBV genome fragment.

In some embodiments, the HBV genome or the HBV genome fragment is comprised by cccDNA. In some embodiments, the cccDNA is eliminated following generation of the cleavage site. In some embodiments, the pol gene is inactivated in the cccDNA by introduction of the indel at the cleavage site. In some embodiments, the indel is introduced by NHEJ. In some embodiments, the inactivated pol gene does not encode an active and/or full-length HBV polymerase protein.

In some embodiments, the HBV genome or the HBV genome fragment is comprised in the genome of the target cell. In some embodiments, the genome is the nuclear genome. In some embodiments, the genome is the mitochondrial genome. In some embodiments, the indel is introduced by NHEJ. In some embodiments, the inactivated pol gene does not encode an active and/or full-length HBV polymerase protein.

In some embodiments, the method inactivates an HBsAg gene in the HBV genome or the HBV genome fragment. In some embodiments, the serum concentration of HBsAg is reduced in the subject.

In some embodiments, the target cell is a liver cell. In some embodiments, the liver cell is a hepatocyte.

In some embodiments, the polynucleotide is a polynucleotide described herein (i.e., comprising a nucleic acid sequence encoding an engineered meganuclease described herein).

In some embodiments, the polynucleotide is an mRNA or is comprised in the genome of a recombinant virus.

In some embodiments, the mRNA is an mRNA described herein. In some embodiments, the mRNA is delivered to the target cell using a lipid nanoparticle comprising the mRNA. In some embodiments, the polynucleotide is delivered to the target cell using a recombinant virus described herein comprising the polynucleotide in its genome. In some embodiments, the recombinant virus is a recombinant virus described herein. In some embodiments, the recombinant virus is a recombinant AAV. In some embodiments, the recombinant AAV has a serotype of AAV8.

In another aspect, the disclosure provides a method for treating an HBV infection or a disease associated with hepatitis B virus infection, the method comprising delivering to a target cell in the subject: (a) a therapeutically effective amount of a polynucleotide comprising a nucleic acid sequence encoding an engineered meganuclease described herein, wherein the engineered meganuclease is expressed in the target cell; or (b) a therapeutically effective amount of an engineered meganuclease described herein; wherein the target cell comprises an HBV genome or HBV genome fragment comprising a pol gene, wherein the engineered meganuclease produces a cleavage site at a recognition sequence comprising or consisting of SEQ ID NO: 3 within the pol gene, wherein the pol gene is inactivated by introduction of an indel at the cleavage site, or wherein the pol gene is inactivated by elimination of the HBV genome or the HBV genome fragment.

In some embodiments, the disease is chronic hepatitis B. In some embodiments, the disease is hepatocellular carcinoma. In some embodiments, the disease is cirrhosis.

In some embodiments, the HBV genome or the HBV genome fragment is comprised by cccDNA. In some embodiments, the cccDNA is eliminated following generation of the cleavage site. In some embodiments, the pol gene is inactivated in the cccDNA by introduction of the indel at the cleavage site. In some embodiments, the indel is introduced by NHEJ. In some embodiments, the inactivated pol gene does not encode an active and/or full-length HBV polymerase protein.

In some embodiments, the HBV genome or the HBV genome fragment is comprised in the genome of the target cell. In some embodiments, the genome is the nuclear genome. In some embodiments, the genome is the mitochondrial genome. In some embodiments, the indel is introduced by NHEJ. In some embodiments, the inactivated pol gene does not encode an active and/or full-length HBV polymerase protein. In some embodiments, the method inactivates an HBsAg gene in the HBV genome or the HBV genome fragment.

In some embodiments, the serum concentration of HBsAg is reduced in the subject.

In some embodiments, the target cell is a liver cell. In some embodiments, the liver cell is a hepatocyte.

In some embodiments, the polynucleotide is a polynucleotide described herein (i.e., comprising a nucleic acid sequence encoding an engineered meganuclease described herein). In some embodiments, the polynucleotide is an mRNA or is comprised in the genome of a recombinant virus. In some embodiments, the mRNA is an mRNA described herein. In some embodiments, the mRNA is delivered to the target cell using a lipid nanoparticle comprising the mRNA. In some embodiments, the polynucleotide is delivered to the target cell using a recombinant virus described herein comprising the polynucleotide in its genome. In some embodiments, the recombinant virus is a recombinant virus described herein. In some embodiments, the recombinant virus is a recombinant AAV. In some embodiments, the recombinant AAV has a serotype of AAV8.

In some embodiments, the subject is also administered one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, Bruton's tyrosine kinase (BTK) inhibitors, KDM inhibitors, HBV replication inhibitors, arginase inhibitors, gene therapy and cell therapy, gene editors, cellular therapy, and TCR-T cell therapy.

In some embodiments, the subject is also administered one, two, three, four or more additional therapeutic agents selected from 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 gene stimulator, toll-like receptor (TLR) modulators, and viral ribonucleotide reductase inhibitor.

In some embodiments, the subject is also administered an antiviral or an immune modulator. In some embodiments, the subject is also administered one or more pharmaceuticals selected from tenofovir disoproxil, tenofovir alafenamide, entecavir, bulevirtide, telbivudine, adefovir dipivoxil, lamivudine, pegylated interferon, and interferon alpha.

BRIEF DESCRIPTION OF THE FIGURES

FIG. 3. Alignment of the HBV 11-12L.1090QQ Linker1923(1/2), HBV 11-12L.1090QE Linker1923(1/2), and HBV 11-12L.1090QQ Linker1 engineered meganucleases.

FIG. 7A, FIG. 7C, and FIG. 7E provides the percentage of indels in HepG2-sAg cells transfected with 1 ng, 10 ng, or 100 ng of RNA of each of the indicated meganucleases, respectively. FIG. 7B, FIG. 7D, and FIG. 7F provides the percentage HBsAg inhibition in HepG2-sAg Cells transfected with 1 ng, 10 ng, or 100 ng of RNA of each of the indicated meganucleases, respectively.

FIG. 8A and FIG. 8B. Provide dose response curve graphs for the percentage of indels (FIG. 8A) or HBsAg inhibition (FIG. 8B) in HepG2-sAg Cells transfected with either the HBV11-12L.1090 QQ-Linker1923(1/2) meganuclease (labelled as QQ-Linker1923(1/2)) or the HBV11-12L.1090 QE-Linker1923(1/2) meganuclease (labelled as QE-Linker1923(1/2)). The EC50 and EC90 values based on these curves for each meganuclease for either indels or HBsAg is also provided.

FIG. 10A provides the MTA results from HepG2-sAg cells transfected with the HBV11-12L.1090QQ Linker1 meganuclease. FIG. 10B provides the MTA results from HepG2-sAg cells transfected with the HBV11-12L.1090QQ Linker1923(1/2) meganuclease. FIG. 10C provides the MTA results from HepG2-sAg cells transfected with the HBV11-12L.1090QE Linker1923(1/2) meganuclease. FIG. 10D provides the combined results of the MTA assays for each of the meganucleases showing the % editing of the on-target site compared to the top-off-target site. In each figure, the grey bar highlights the percentage of editing at the on-target site and black bars indicate the off target sites at a limit of detection (LOD) >0.2%.

FIG. 11A shows the on target and off target results for the indicated meganucleases transfected in HepG2sAg cells at a limited dose curve of 1 ng, 10 ng, and 100 ng. FIG. 11B shows the on target and off target results for the indicated meganucleases transfected in HepG2sAg cells at either the EC50 or EC90 dosage utilizing either the Off amp MTA assay or On amp MTA assay. FIG. 11C shows the on target and off target results for the indicated meganucleases transfected in naïve PHH cells, which do not harbor the HBV 11-12 target site at a limited dose curve of 5 ng, 50 ng, or 500 ng six days following transfection.

FIG. 13A and FIG. 13B. Provides a bar graph that shows the percentage indels by ddPCR at day 3 and day 6 from Huh-1 Dex cells (FIG. 13A) or HepG2 cells (FIG. 13B) transfected at either a 100 ng, 10 ng, or 1 ng dosage of the HBV11-12L.1090QE Linker 1923(1/2) meganuclease (labelled as HBV11-12L.1090 QE). A mock and mCherry control is also shown.

FIG. 14A and FIG. 14B. Provides a bar graph that shows the level in IU/mL of HBsAg at day 3 and day 6 in Huh-1 Dex cells (FIG. 14A) or HepG2 cells (FIG. 14B) transfected at either a 100 ng, 10 ng, or 1 ng dosage of the HBV11-12L.1090QQ Linker 1923(1/2) meganuclease (labelled as HBV11-12L.1090 QQ). A mock and mCherry control is also shown.

FIG. 15A and FIG. 15B. Provides a bar graph that shows the level in IU/mL of HBsAg at day 3 and day 6 in Huh-1 Dex cells (FIG. 15A) or HepG2 cells (FIG. 15B) transfected at either a 100 ng, 10 ng, or 1 ng and 10 ng dosage of the HBV11-12L.1090QE Linker 1923(1/2) meganuclease (labelled as HBV11-12L.1090 QE). A mock and mCherry control is also shown.

FIG. 16A-FIG. 16F. Provides bar graphs showing the percentage of HBsAg inhibition (FIG. 16A), HBV DNA inhibition (FIG. 16B), HBV RNA inhibition (FIG. 16C), HBeAg inhibition (FIG. 16D), cccDNA inhibition (FIG. 16E), and percentage of cell viability (FIG. 16F) in PHH cells infected with 800 GE/cell HBV serotype B and transfected on days 3 and 6 post-infection with 1.0 µg or 0.1 µg of mRNA encoding the HBV 11-12L.1090QQ Linker1923 (1/2) engineered meganuclease (labelled as either QQ Linker1923(1/2) 1.0 µg or QQ Linker1923(1/2) 0.1 µg). Measurements were taken at days 6, 9, 12, and 15 post-infection for HBsAg, HBV DNA, HBV RNA, and HBeAg. Measurements were taken at days 9, 12, and 15 post-infection for cccDNA and cell viability levels.

FIG. 18A) or HBV 11-12L.1090QE Linker1923(1/2) (labelled as QE; FIG. 18B) engineered meganuclease. In FIG. 18A and FIG. 18B, each lane marked as TA1 or TA2 refers to lanes corresponding to cells transfected with either the QQ or QE meganucleases at the indicated dose with and without LAM at the indicated doses. An additional medium only control, LAM 6 nM control, and an HBV-targeting siRNA control is provided in lanes 11-13, respectively. HBV fragment DNA is provided in lanes 1 and 14 in both FIG. 18A and FIG. 18B. FIG. 18A has an additional cccDNA positive loading control in lane 15.

BRIEF DESCRIPTION OF THE SEQUENCES

Figure 1:
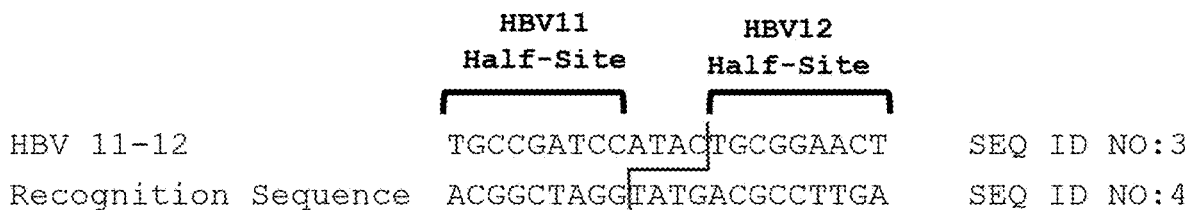
FIG. 1. HBV 11-12 recognition sequence in the HBV gene. The HBV 11-12 recognition sequence, targeted by engineered meganucleases of the present disclosure, comprises two recognition half-sites. Each recognition half-site comprises 9 base pairs, separated by a 4 base pair central sequence. The HBV 11-12 recognition sequence (SEQ ID NO: 3) comprises two recognition half-sites referred to as HBV11 and HBV12.
Figure 2:
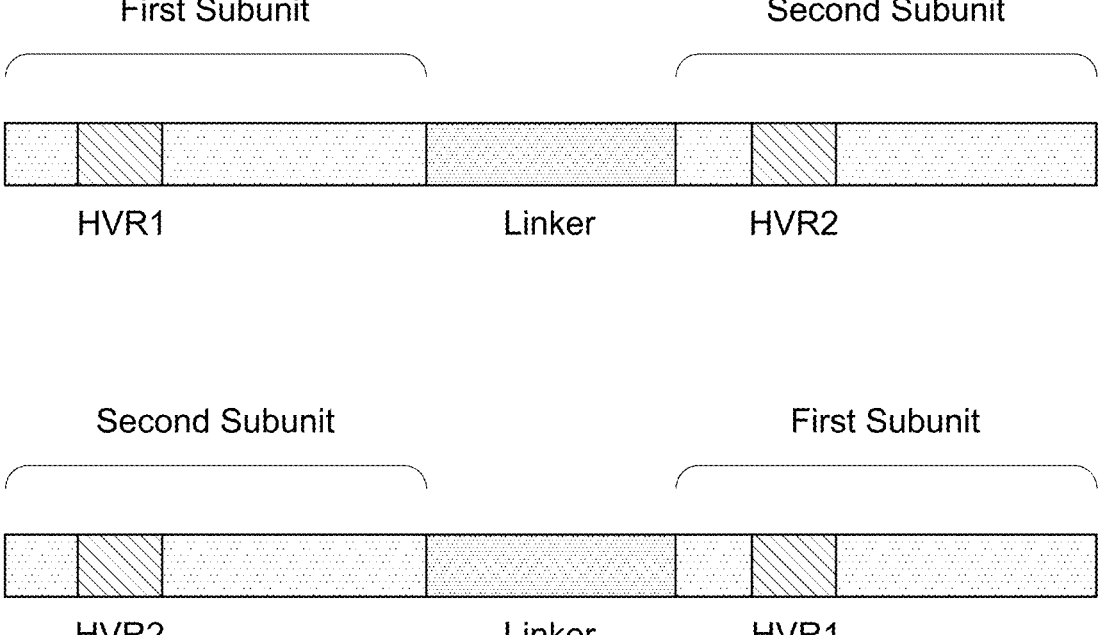
FIG. 2. The engineered meganucleases of the present disclosure comprise two subunits, wherein the first subunit comprising the HVR1 region binds to a first recognition half-site (e.g., HBV11) and the second subunit comprising the HVR2 region binds to a second recognition half-site (e.g., HBV12). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.
Figure 4A:
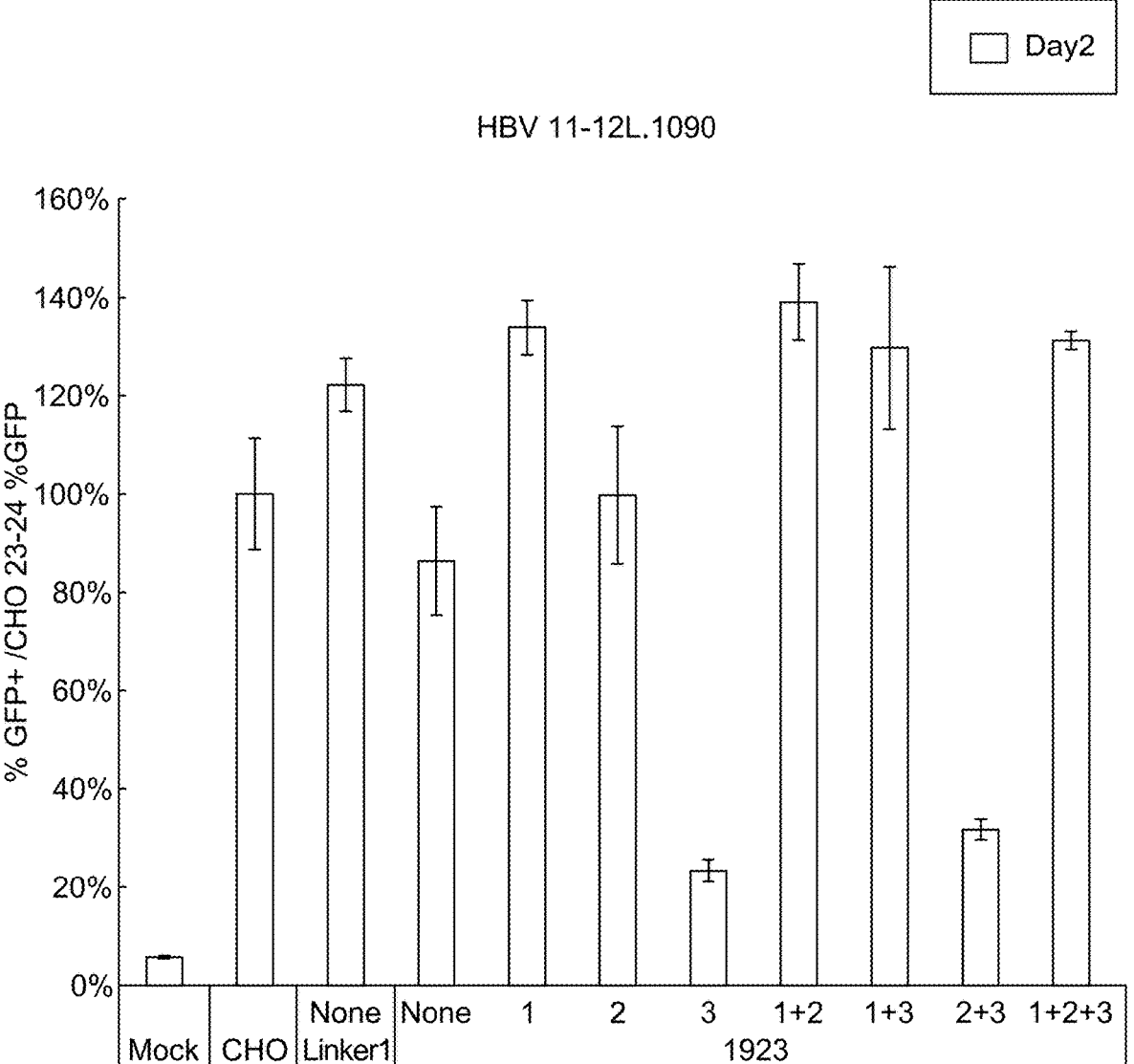
FIG. 4A-FIG. 4E. Results from a CHO reporter cell assay evaluating the activity of a parental HBV 11-12L.1090 engineered meganuclease and variants of HBV 11-12L.1090 comprising Linker1923 (FIG. 4A), Linker1766 (FIG. 4B), Linker1771 (FIG. 4C), Linker1808 (FIG. 4D), and Linker1814 (FIG. 4E), with and without various combinations of amino acid modifications in the N-terminal and C-terminal subunits, relative to mock and CHO 23-24 controls.
Figure 4B:
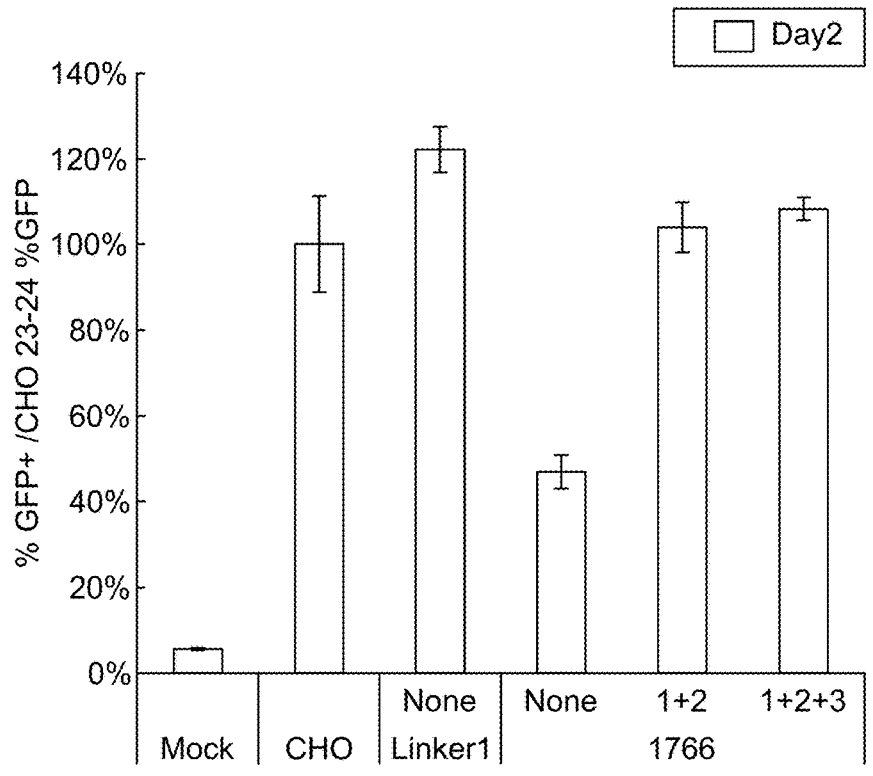
Figure 4C:
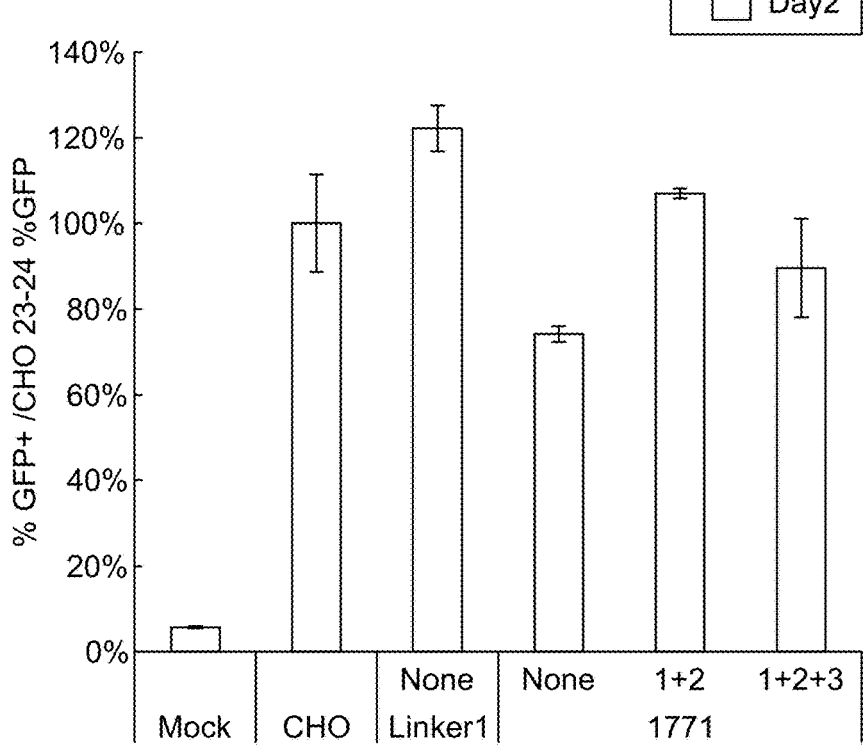
Figure 4D:
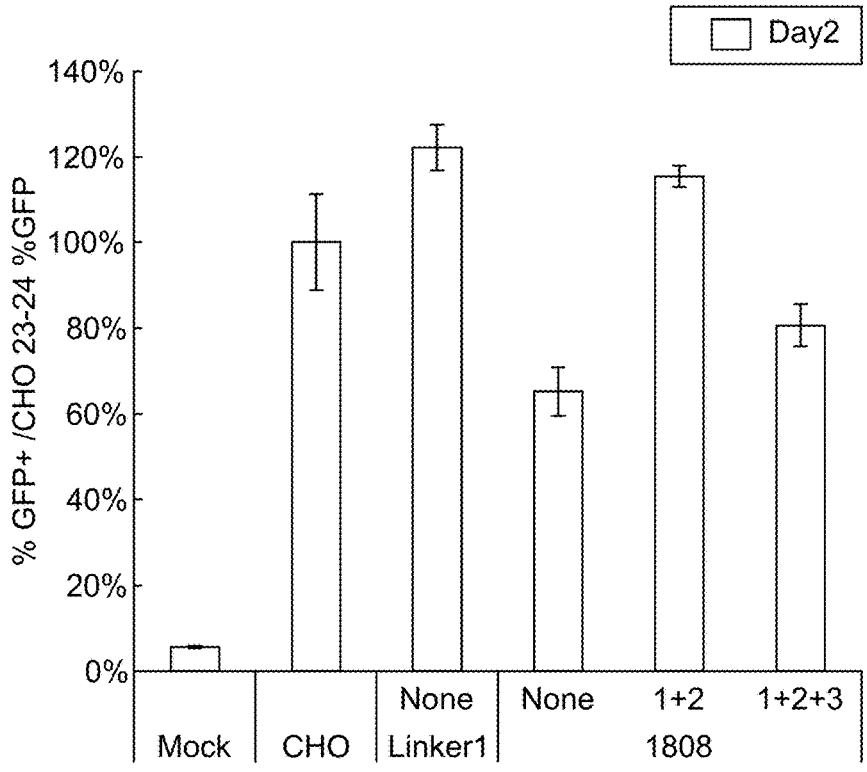
Figure 4E:
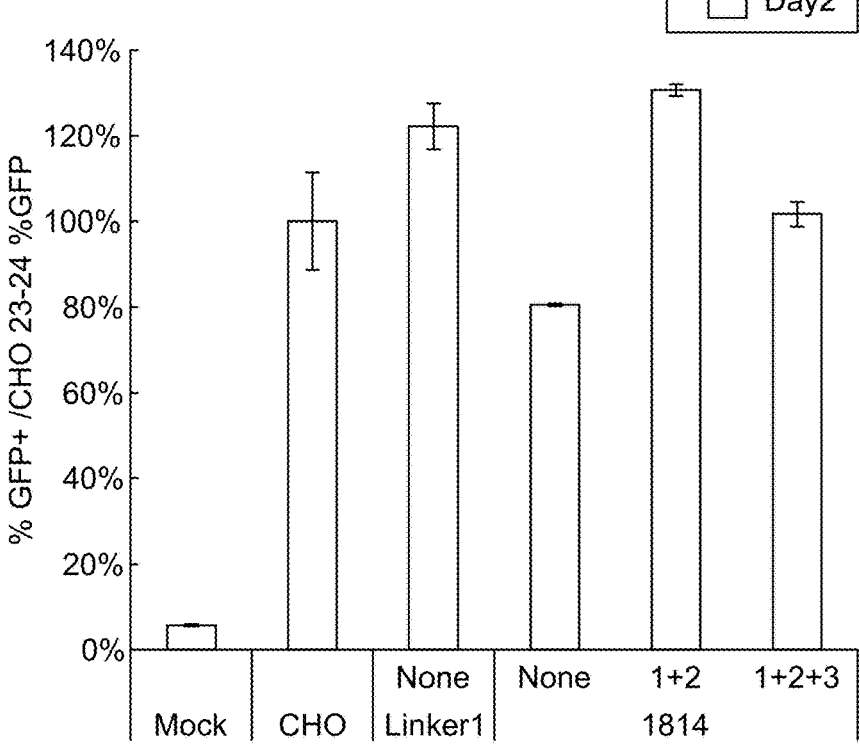

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the nucleic acid sequence of the sense strand of the HBV 11-12 recognition sequence.

SEQ ID NO: 4 sets forth the nucleic acid sequence of the antisense strand of the HBV 11-12 recognition sequence.

SEQ ID NO: 5 sets forth the amino acid sequence of the HBV 11-12L.1090QQ Linker1923(1/2) meganuclease.

SEQ ID NO: 6 sets forth the amino acid sequence of the HBV 11-12L.1090QE Linker1923(1/2) meganuclease.

SEQ ID NO: 7 sets forth the amino acid sequence of the HBV11 subunit of the HBV 11-12L.1090QQ Linker1923(1/2) meganuclease.

SEQ ID NO: 8 sets forth the amino acid sequence of the HBV11 subunit of the HBV 11-12L.1090QE Linker1923(1/2) meganuclease.

SEQ ID NO: 9 sets forth the amino acid sequence of the HBV12 subunit of the HBV 11-12L.1090QQ Linker1923(1/2) meganuclease.

SEQ ID NO: 10 sets forth the amino acid sequence of the HBV12 subunit of the HBV 11-12L.1090QE Linker1923(1/2) meganuclease.

SEQ ID NO: 11 sets forth the nucleic acid sequence of the HBV 11-12L.1090QQ Linker1923(1/2) meganuclease.

SEQ ID NO: 12 sets forth the nucleic acid sequence of the HBV 11-12L.1090QE Linker1923(1/2) meganuclease.

SEQ ID NO: 13 sets forth the amino acid sequence of the HBV 11-12L.1090QQ Linker1 meganuclease.

SEQ ID NO: 14 sets forth the amino acid sequence of the HBV 11-12L.1090QE Linker1 meganuclease.

SEQ ID NO: 15 sets forth the amino acid sequence of the Linker1923.

SEQ ID NO: 16 sets forth the amino acid sequence of the Linker1.

SEQ ID NO: 17 sets forth the amino acid sequence of an SV40 nuclear localization signal (NLS).

SEQ ID NO: 18 sets forth a nucleic acid sequence of the 5' ALB untranslated sequence region (UTR).

SEQ ID NO: 19 sets forth a nucleic acid sequence of the 3' SNRPB UTR.

SEQ ID NO: 20 sets forth a nucleic acid sequence of a polyA termination sequence.

SEQ ID NO: 21 sets forth a nucleic acid sequence of a Kozak sequence.

SEQ ID NO: 22 sets forth the nucleic acid sequence of a probe sequence.

SEQ ID NO: 23 sets forth the nucleic acid sequence of a forward primer sequence.

SEQ ID NO: 24 sets forth the nucleic acid sequence of a reverse primer sequence.

SEQ ID NO: 25 sets forth the nucleic acid sequence of a probe sequence.

SEQ ID NO: 26 sets forth the nucleic acid sequence of a forward primer sequence.

SEQ ID NO: 27 sets forth the nucleic acid sequence of a reverse primer sequence.

SEQ ID NO: 28 sets forth the nucleic acid sequence of a reverse primer sequence.

SEQ ID NO: 29 sets forth the nucleic acid sequence of a probe sequence.

SEQ ID NO: 30 sets forth the nucleic acid sequence of a forward primer sequence.

SEQ ID NO: 31 sets forth the nucleic acid sequence of a reverse primer sequence.

SEQ ID NO: 32 sets forth the nucleic acid sequence of a probe sequence.

SEQ ID NO: 33 sets forth the nucleic acid sequence of a forward primer sequence.

SEQ ID NO: 34 sets forth the nucleic acid sequence of a reverse primer sequence.

SEQ ID NO: 35 sets forth the nucleic acid sequence of a probe sequence.

SEQ ID NO: 36 sets forth the nucleic acid sequence of a forward primer sequence.

SEQ ID NO: 37 sets forth the nucleic acid sequence of a reverse primer sequence.

SEQ ID NO: 38 sets forth the nucleic acid sequence of a forward primer sequence.

SEQ ID NO: 39 sets forth the nucleic acid sequence of a reverse primer sequence.

SEQ ID NO: 40 sets forth the nucleic acid sequence of a forward primer sequence.

SEQ ID NO: 41 sets forth the nucleic acid sequence of a reverse primer sequence.

SEQ ID NO: 42 sets forth the amino acid sequence of Linker1766.

SEQ ID NO: 43 sets forth the amino acid sequence of Linker1771.

SEQ ID NO: 44 sets forth the amino acid sequence of Linker1808.

SEQ ID NO: 45 sets forth the amino acid sequence of Linker1814.

SEQ ID NO: 46 sets forth the amino acid sequence of an HBV 11-12L.1090 engineered meganuclease comprising Linker1923 and no subunit modifications.

SEQ ID NO: 47 sets forth the amino acid sequence of an HBV 11-12L.1090 engineered meganuclease comprising Linker1923 and Group 1 (K96A/K57Y, E61T) subunit modifications.

SEQ ID NO: 48 sets forth the amino acid sequence of an HBV 11-12L.1090 engineered meganuclease comprising Linker1923 and Group 2 (Q99A, K100D/none) subunit modifications.

SEQ ID NO: 49 sets forth the amino acid sequence of an HBV 11-12L.1090 engineered meganuclease comprising Linker1923 and Group 3 (H37Y/W53F) subunit modifications.

SEQ ID NO: 50 sets forth the amino acid sequence of an HBV 11-12L.1090 engineered meganuclease comprising Linker1923 and Group 1 (K96A/K57Y, E61T) and Group 3 (H37Y/W53F) subunit modifications.

SEQ ID NO: 51 sets forth the amino acid sequence of an HBV 11-12L.1090 engineered meganuclease comprising Linker1923 and Group 2 (Q99A, K100D/none) and Group 3 (H37Y/W53F) subunit modifications.

SEQ ID NO: 52 sets forth the amino acid sequence of an HBV 11-12L.1090 engineered meganuclease comprising Linker1923 and Group 1 (K96A/K57Y, E61T), Group 2 (Q99A, K100D/none), and Group 3 (H37Y/W53F) subunit modifications.

SEQ ID NO: 53 sets forth the amino acid sequence of an HBV 11-12L.1090 engineered meganuclease comprising Linker1766 and no subunit modifications.

SEQ ID NO: 54 sets forth the amino acid sequence of an HBV 11-12L.1090 engineered meganuclease comprising Linker1766 and Group 1 (K96A/K57Y, E61T) and Group 2 (Q99A, K100D/none) subunit modifications.

SEQ ID NO: 55 sets forth the amino acid sequence of an HBV 11-12L.1090 engineered meganuclease comprising Linker1766 and Group 1 (K96A/K57Y, E61T), Group 2 (Q99A, K100D/none), and Group 3 (H37Y/W53F) subunit modifications.

SEQ ID NO: 56 sets forth the amino acid sequence of an HBV 11-12L.1090 engineered meganuclease comprising Linker1771 and no subunit modifications.

SEQ ID NO: 57 sets forth the amino acid sequence of an HBV 11-12L.1090 engineered meganuclease comprising Linker1771 and Group 1 (K96A/K57Y, E61T) and Group 2 (Q99A, K100D/none) subunit modifications.

SEQ ID NO: 58 sets forth the amino acid sequence of an HBV 11-12L.1090 engineered meganuclease comprising Linker1771 and Group 1 (K96A/K57Y, E61T), Group 2 (Q99A, K100D/none), and Group 3 (H37Y/W53F) subunit modifications.

SEQ ID NO: 59 sets forth the amino acid sequence of an HBV 11-12L.1090 engineered meganuclease comprising Linker1808 and no subunit modifications.

SEQ ID NO: 60 sets forth the amino acid sequence of an HBV 11-12L.1090 engineered meganuclease comprising Linker1808 and Group 1 (K96A/K57Y, E61T) and Group 2 (Q99A, K100D/none) subunit modifications.

SEQ ID NO: 61 sets forth the amino acid sequence of an HBV 11-12L.1090 engineered meganuclease comprising Linker1808 and Group 1 (K96A/K57Y, E61T), Group 2 (Q99A, K100D/none), and Group 3 (H37Y/W53F) subunit modifications.

SEQ ID NO: 62 sets forth the amino acid sequence of an HBV 11-12L.1090 engineered meganuclease comprising Linker1814 and no subunit modifications.

SEQ ID NO: 63 sets forth the amino acid sequence of an HBV 11-12L.1090 engineered meganuclease comprising Linker1814 and Group 1 (K96A/K57Y, E61T) and Group 2 (Q99A, K100D/none) subunit modifications.

SEQ ID NO: 64 sets forth the amino acid sequence of an HBV 11-12L.1090 engineered meganuclease comprising Linker1814 and Group 1 (K96A/K57Y, E61T), Group 2 (Q99A, K100D/none), and Group 3 (H37Y/W53F) subunit modifications.

SEQ ID NO: 65 sets forth the amino acid sequence of an SV40 nuclear localization signal (NLS).

SEQ ID NO: 66 sets forth a nucleic acid sequence encoding an mRNA construct encoding the HBV 11-12L.1090QQ Linker1923(1/2) meganuclease.

SEQ ID NO: 67 sets forth a nucleic acid sequence encoding an mRNA construct encoding the HBV 11-12L.1090QQ Linker1923(1/2) meganuclease.

SEQ ID NO: 68 sets forth a nucleic acid sequence encoding an mRNA construct encoding the HBV 11-12L.1090QQ Linker1923(1/2) meganuclease.

SEQ ID NO: 69 sets forth a nucleic acid sequence encoding an mRNA construct encoding the HBV 11-12L.1090QQ Linker1923(1/2) meganuclease.

SEQ ID NO: 70 sets forth a nucleic acid sequence encoding an mRNA construct encoding the HBV 11-12L.1090QE Linker1923(1/2) meganuclease.

SEQ ID NO: 71 sets forth a nucleic acid sequence encoding an mRNA construct encoding the HBV 11-12L.1090QE Linker1923(1/2) meganuclease.

SEQ ID NO: 72 sets forth a nucleic acid sequence encoding an mRNA construct encoding the HBV 11-12L.1090QE Linker1923(1/2) meganuclease.

SEQ ID NO: 73 sets forth a nucleic acid sequence encoding an mRNA construct encoding the HBV 11-12L.1090QE Linker1923(1/2) meganuclease.

SEQ ID NO: 74 sets forth a nucleic acid sequence of an mRNA construct encoding the HBV 11-12L.1090QQ Linker1923(1/2) meganuclease.

SEQ ID NO: 75 sets forth a nucleic acid sequence of an mRNA construct encoding the HBV 11-12L.1090QQ Linker1923(1/2) meganuclease.

SEQ ID NO: 76 sets forth a nucleic acid sequence of an mRNA construct encoding the HBV 11-12L.1090QQ Linker1923(1/2) meganuclease.

SEQ ID NO: 77 sets forth a nucleic acid sequence of an mRNA construct encoding the HBV 11-12L.1090QQ Linker1923(1/2) meganuclease.

SEQ ID NO: 78 sets forth a nucleic acid sequence of an mRNA construct encoding the HBV 11-12L.1090QE Linker1923(1/2) meganuclease.

SEQ ID NO: 79 sets forth a nucleic acid sequence of an mRNA construct encoding the HBV 11-12L.1090QE Linker1923(1/2) meganuclease.

SEQ ID NO: 80 sets forth a nucleic acid sequence of an mRNA construct encoding the HBV 11-12L.1090QE Linker1923(1/2) meganuclease.

SEQ ID NO: 81 sets forth a nucleic acid sequence of an mRNA construct encoding the HBV 11-12L.1090QE Linker1923(1/2) meganuclease.

SEQ ID NO: 82 sets forth a nucleic acid sequence of the 5' ALB untranslated sequence region (UTR).

SEQ ID NO: 83 sets forth a nucleic acid sequence of the 3' SNRPB UTR.

SEQ ID NO: 84 sets forth a nucleic acid sequence of a Kozak sequence.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the disclosure to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant disclosure.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a propensity to form a specific three-dimensional structure under physiological conditions, such as turns and/or coils. In some embodiments, the linker is 31 amino acids in length. In some embodiments, a linker may have at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 15.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic." As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 base-pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the terms "target site" or "target sequence" refers to a region of the chromosomal DNA of a cell comprising a recognition sequence for a nuclease.

As used herein, the terms "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" refers to the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art, such as unbiased identification of DSBs enabled by sequencing (GUIDE-seq), oligonucleotide (oligo) capture assay, whole genome sequencing, and long-range next generation sequencing of the recognition sequence. In some embodiments, specificity is measured using GUIDE-seq. As used herein, "specificity" is synonymous with a low incidence of cleavage of sequences different from the target sequences (non-target sequences), i.e., off-target cutting. A low incidence of off-target cutting may comprise an incidence of cleavage of non-target sequences of less than 25%, less than 20%, less than 18%, less than 15%, less than 12.5%, less than 10%, less than 9%, less than 8%, less than 7%, less than 6%, less than 5%, less than 4%, less than 3%, less than 2.5%, less than 2%, less than 1.5%, less than 1%, less than 0.75%, less than 0.5%, or less than 0.25%.

As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

In some embodiments, the presently disclosed engineered meganucleases have improved (i.e., increased) specificity for the target recognition sequence that comprises SEQ ID NO: 3 (i.e., HBV 11-12) as compared to the HBV 11-12L.1090QQ Linker1 meganuclease (the amino acid sequence of which is set forth as SEQ ID NO: 13). Thus, in certain embodiments, the presently disclosed engineered meganucleases exhibit reduced off-target cleavage as compared to the HBV 11-12L.1090QQ Linker1 meganuclease. Off-target cleavage by a meganuclease can be measured using any method known in the art, including for example, oligo capture analysis as described here, a T7 endonuclease (T7E) assay as described herein, digital PCR as described herein, targeted sequencing of particular off-target sites, exome sequencing, whole genome sequencing, direct in situ breaks labeling enrichment on streptavidin and next-generation sequencing (BLESS), genome-wide, GUIDE-seq, and linear amplification-mediated high-throughput genome-wide translocation sequencing (LAM-HTGTS) (see, e.g., Zischewski et al. (2017), Biotechnology Advances 35(1): 95-104, which is incorporated by reference in its entirety).

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein, "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddPCR. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, 75%, 76%, 77%, 78%, 79%, or 80% at the recognition sequence.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered meganucleases can be used to effectively knock-out a gene in a population of cells.

As used herein, the term "homology arms" or "sequences homologous to sequences flanking a meganuclease cleavage site" refer to sequences flanking the 5' and 3' ends of a nucleic acid molecule which promote insertion of the nucleic acid molecule into a cleavage site generated by a meganuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (the website at ncbi.nlm.nih.gov), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7 (1-2): 203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty= −2; match reward=1; and mismatch penalty=−3.

As used herein, the term "corresponding to" with respect to modifications of two proteins or amino acid sequences, is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program) and aligned for maximum sequence identity across the entire subunit or protein. Thus, the modification of residue "X" to amino acid "A" in the first protein will correspond to the modification of residue "Y" to amino acid "A" in the second protein if residues X and Y correspond to each other in a sequence alignment, and despite the fact that X and Y may be at different positions relative to the N-terminus or C-terminus.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 204-259 of SEQ ID NO: 5 or 6. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity.

In some embodiments, variable residues within a hypervariable region correspond to one or more of positions 24, 26, 28, 30, 32, 33, 38, 40, 42, 44, 46, 68, 70, 75, and 77 of SEQ ID NO: 5 or 6. In some embodiments, variable residues within a hypervariable region correspond to position 51 of SEQ ID NO: 5 or 6. In some embodiments, variable residues within a hypervariable region correspond to one or more of positions 24, 26, 28, 30, 32, 33, 38, 40, 42, 44, 46, 51, 68, 70, 75, and 77 of SEQ ID NO: 5 or 6.

In some embodiments, variable residues within a hypervariable region correspond to one or more of positions 204, 206, 208, 210, 212, 213, 218, 220, 222, 224, 226, 248, 250, 255, and 257 of SEQ ID NO: 5 or 6. In some embodiments, variable residues within a hypervariable region further correspond to one or more of positions 237, 241, 251, 252, and 253 of SEQ ID NO: 5 or 6. In other embodiments, variable residues within a hypervariable region correspond to one or more of positions 204, 206, 208, 210, 212, 213, 218, 220, 222, 224, 226, 237, 241, 248, 250, 251, 252, 253, 255, and 257 of SEQ ID NO: 5 or 6.

The terms "recombinant DNA construct," "recombinant construct," "expression cassette," "cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences described herein. In some embodiments, a "vector" also refers to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, the term "operably linked" is intended to mean a functional linkage between two or more elements. For example, an operable linkage between a nucleic acid sequence encoding a nuclease as described herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, "uridine depletion" refers to the removal or replacement of uridine residues from an RNA molecule (e.g., mRNA) or thymidine residues from a DNA molecule that encodes for an RNA molecule. The uridines can be replaced with any other residue, such as adenosine or pseudouridine, within any region of the RNA molecule, but in some embodiments, the uridines are removed and replaced within the non-coding region of an RNA molecule. In some embodiments, at least 10%, 15%, 20%, 25%, 30%, 35%, 40%, 45%, or 50% of the uridines in an RNA molecule are removed or replaced.

As used herein, "codon-optimized" refers to a coding sequence that has been modified to improve gene expression and increase the translational efficiency by accommodating the codon bias of the host organism or tissue, wherein the limitations associated with species-specific and tissue-specific differences in codon usage and transfer RNA (tRNA) abundance are lessened. The coding sequence can be codon-optimized for expression in mammalian cells and/or specific tissues. As it has been shown that the codon usage bias of genes specifically expressed in the human liver differ from the codon usage bias of the human genome coding DNA sequences (Dittmar et al. (2006) *PLoS Genet.* 2:e221), in some embodiments, sequences encoding an engineered meganuclease described herein are optimized for expression in liver.

As used herein, "inactivating" in reference to a gene refers to either the introduction of a mutation into the gene such that the resultant inactivated gene does not encode an active and/or full-length protein or the gene is eliminated (i.e., degraded). An HBV genome or fragment thereof can be eliminated, thus inactivating any HBV genes present in the HBV genome or fragment thereof, through the cleavage of the genome or genome fragment that results in the subsequent degradation of the genome or fragment thereof.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. A control subject may comprise, for example: a wild-type subject, i.e., a subject not having an HBV infection, which is not exposed to conditions or stimuli or further genetic modifications (e.g., administration of an engineered meganuclease described herein). Alternatively, a control subject may comprise, for example: a subject having an HBV infection, which is not exposed to conditions or stimuli or further genetic modifications (e.g., administration of an engineered meganuclease described herein) that can alter the HBV infection status of the subject.

As used herein, the terms "treatment" or "treating a subject" refers to the administration of an engineered meganuclease of the disclosure, or a nucleic acid encoding an engineered meganuclease of the disclosure to a subject infected with HBV for the purpose of slowing or stopping the rate of HBV proliferation of the virus by cleaving the genome of at least one HBV particle. Such treatment reduces or prevents transfection and replication of HBV in the subject, and provides either partial or complete relief of one or more symptoms of HBV infection or a disease associated with HBV infection in the subject. Means to assess alleviation of symptoms of HBV infection or a disease associated with HBV infection may include measurement of liver functions by determining levels of the enzyme alanine aminotransferase (ALT) or by measuring sero conversion, namely disappearance and/or reduction of the circulating HBeAg and/or HBsAg levels. Further, alleviation or reduction of symptoms of HBV infection or a disease associated with HBV infection can be determined by examining liver biopsies and measuring the level of tissue fibrosis by methods well known in the art. The number of circulating viral particles can be determined for example by measuring HBV DNA levels using PCR or by detecting HBsAg levels in the blood. The terms "treatment" or "treating a subject" can further refer to the administration of a cell (e.g., hepatocyte cell) comprising a nucleic acid encoding an engineered meganuclease, wherein the cell is delivered to a target tissue (e.g., liver) and produces the engineered meganuclease in an amount sufficient to treat an HBV infection or a disease associated with an HBV infection in the subject, thereby resulting in either partial or complete relief of one or more symptoms of the HBV infection or the disease associated with the HBV infection. In some aspects, an engineered meganuclease of the disclosure or a nucleic acid encoding the same is administered during treatment in the form of a pharmaceutical composition of the disclosure.

The term "a disease associated with Hepatitis B virus infection" refers to any condition related to or resulting from infection with a Hepatitis B virus, such as chronic liver diseases/disorders, inflammations, fibrotic conditions, and proliferative disorders, such as liver cancers. Chronic persistent HBV infection can cause fatigue, liver damage, cirrhosis of the liver, and hepatocellular carcinoma, a primary liver cancer.

The terms "proliferating" and "proliferation" as used herein refer to HBV viruses or HBV covalently closed circular DNA (cccDNA) actively dividing and/or infecting human cells. Thus, reduction in proliferation refers to any decrease in the proliferation of HBV including reduction of at least 1%, 2%, 3%, 4%, 5%, 10%, 15%, 20%, 25%, 30%, 40%, 50%, 60%, 70%, 80%, 90%, 91%, 92%, 93%, 94%, 95%, 96%, 97%, 98%, 99%, or 100% when compared to an appropriate control not having been administered the engineered meganuclease, or nucleic acid encoding the engineered meganuclease, described herein. Throughout this application, the term "proliferative disorder" refers to any disease/disorder marked by unwanted or aberrant proliferation of cells or tissue. As used herein, the term "proliferative disorder" also refers to conditions in which the unregulated and/or abnormal growth of cells can lead to the development of an unwanted condition or disease, which can be cancerous or non-cancerous.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition, and responsiveness of the subject to be treated. In specific embodiments, an effective amount of the engineered meganuclease or pharmaceutical compositions described herein reduces the level or proliferation of HBV or reduces at least one symptom of a disease associated with HBV infection in a subject with an HBV infection.

The term "gc/kg" or "gene copies/kilogram" refers to the number of copies of a nucleic acid encoding an engineered meganuclease described herein per weight in kilograms of a subject that is administered the nucleic acid encoding the engineered meganuclease.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Invention

The present disclosure is based, in part, on the discovery of HBV 11-12 meganucleases which have improved properties when compared to previously described HBV 11-12 meganucleases, such as improved (i.e., increased) specificity resulting in reduced off-target cutting, and enhanced (i.e., increased) efficiency of cleavage and indel formation at the HBV 11-12 recognition sequence, particularly in cells comprising an integrated copy of the HBV genome.

The presently disclosed HBV 11-12 meganucleases recognize the HBV 11-12 recognition sequence (SEQ ID NO: 3) in the polymerase (P) gene of the Hepatitis B virus genome that encodes the viral DNA polymerase. The HBV 11-12 recognition sequence is conserved across at least HBV genotypes A-G, which advantageously allows for the presently disclosed engineered meganucleases to target HBV infections around the globe.

The presently disclosed HBV 11-12 meganucleases are referred to as HBV 11-12L.1090QQ Linker1923(1/2), which is set forth as SEQ ID NO: 5, and HBV 11-12L.1090QE Linker1923(1/2), which is set forth as SEQ ID NO: 6. The nomenclature "QQ" refers to the presence of an amino acid residue Q at position 80 and position 260 of SEQ ID NO: 5 and at position 80 and position 271 of SEQ ID NO: 13. The nomenclature "QE" refers to the presence of an amino acid residue Q at position 80 of SEQ ID NO: 6 and SEQ ID NO: 14 and the presence of an amino acid residue E at position 260 of SEQ ID NO: 6 and position 271 of SEQ ID NO: 14. The sequence of Linker1923 that joins the first and second subunits of these engineered meganucleases is set forth as SEQ ID NO: 15 and is shorter in length (i.e., 31 amino acid residues) than the Linker1 sequence set forth as SEQ ID NO: 16 (i.e., 42 amino acid residues) present in the previously identified HBV 11-12L.1090QQ Linker1 engineered meganuclease. The term "(1/2)" refers to the presence of amino acid modifications in the first and second subunits of an engineered meganuclease when the subunits are joined by the Linker1923 sequence. In the HBV11-12L.1090 meganucleases described herein that comprise the Linker1923 sequence, the N-terminal subunit includes an A at position 96, an A at position 99, and a D at position 100, and the C-terminal subunit includes a Y at a position corresponding to position 57 of SEQ ID NO: 1 (i.e., position 237 of SEQ ID NO: 5 or 6) and a T at a position corresponding to position 61 of SEQ ID NO: 1 (i.e., position 241 of SEQ ID NO: 5 or 6). While not being held to any particular theory or mechanism of action, it is believed that the Linker1923 interacts with these modified "(1/2)" residues within the I-CreI scaffold, leading to stabilization of the engineered meganuclease.

Cleavage at the HBV 11-12 recognition sequence can allow for non-homologous end joining (NHEJ) at the cleavage site and can disrupt expression of one or more viral proteins (e.g., viral DNA polymerase) due to NHEJ at the cleavage site that results in insertions, deletions, or frameshift mutations. Alternatively, cleavage of the HBV genome at the HBV 11-12 recognition sequence may promote degradation of the HBV genome and/or HBV cccDNA. Disruption of the expression of the viral protein(s) can reduce or eliminate the infection and/or proliferation of HBV.

Additionally, cleavage at the HBV 11-12 recognition sequence can further allow for homologous recombination of exogenous nucleic acid sequences directly into the HBV genome to disrupt the expression of one or more viral proteins. For example, a "suicide gene" can be introduced into an HBV genome via homologous recombination.

Thus, the present disclosure encompasses engineered meganucleases which recognize and cleave the HBV 11-12 recognition sequence within an HBV genome. The present disclosure also encompasses methods of using such engineered meganucleases in a pharmaceutical composition and in methods for inactivating a polymerase gene of an HBV genome or an HBV genome fragment in a eukaryotic cell and methods for treating an HBV infection or a disease associated with HBV infection. Further, the disclosure encompasses pharmaceutical compositions comprising engineered meganuclease proteins, or nucleic acids encoding engineered meganucleases, and the use of such compositions for the treatment of HBV infection and diseases associated with HBV infection (e.g., hepatocellular carcinoma (HCC)).

2.2 Meganucleases that Recognize and Cleave the HBV 11-12 Recognition Sequence within the Hepatitis B Viral Genome Recognition Sequences It is known in the art that it is possible to use a site-specific nuclease to make a DNA break in the genome of a virus, and that such a DNA break can result in permanent modification of the genome via mutagenic NHEJ repair or via homologous recombination with a transgenic DNA sequence such that the HBV virion can no longer divide/replicate or infect human cells.

Engineered meganucleases of the disclosure have been designed to bind and cleave an HBV 11-12 recognition sequence (SEQ ID NO: 3). The HBV 11-12 recognition sequence is positioned within the polymerase gene ORF multiple HBV genotypes, including at least genotypes A, B, C, D, E, F, and G.

Exemplary Engineered Meganucleases

It is known in the art that it is possible to use a site-specific nuclease to make a DNA break in the genome of a virus, and that such a DNA break can result in permanent modification of the genome via NHEJ such that the HBV virion can no longer divide/replicate or infect human cells. Generating a DNA break in a viral genome can also lead to degradation of the viral genome, rendering it unable to divide, replicate, or be infective.

Thus, in some embodiments, the present disclosure provides engineered nucleases, particularly engineered meganucleases. In particular embodiments, the meganucleases are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some embodiments, the presently disclosed engineered meganucleases exhibit at least one optimized characteristic in comparison to the previously described meganuclease HBV 11-12L.1090QQ Linker1. Such optimized characteristics include improved (i.e. increased) specificity resulting in reduced off-target cutting, and enhanced (i.e. increased) efficiency of cleavage and indel (i.e., insertion or deletion) formation at the HBV 11-12 recognition sequence, particularly in cells comprising an integrated copy of the HBV genome. Thus, in particular embodiments, the presently disclosed engineered meganucleases, when delivered to a population of HBV-infected target cells, is able to generate a greater percentage of virions or cells with a cleavage and/or an indel in the HBV genome (either incorporated or unincorporated). In some of these embodiments, the population of HBV or target cells comprises at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% of HBV or target cells comprising a cleavage and/or an indel in the HBV genome (either incorporated or unincorporated). Cleavage and/or indel formation by a meganuclease can be measured using any method known in the art, including T7E assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety).

In some embodiments, the target cell is a liver cell. In some embodiments, the liver cell is a hepatocyte. In some embodiments, the target cell is a primary human hepatocyte (PHH). In some embodiments, the target cell is a non-human, mammalian hepatocyte.

Engineered meganucleases described herein comprise a first subunit, comprising a first hypervariable (HVR1) region, and a second subunit, comprising a second hypervariable (HVR2) region. Further, the first subunit binds to a first recognition half-site in the recognition sequence (i.e., the HBV11 half-site), and the second subunit binds to a second recognition half-site in the recognition sequence (i.e., the HBV12 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary engineered meganucleases that recognize and cleave the HBV 11-12 recognition sequence are provided in SEQ ID NOs: 5 and 6 and are further described below.

HBV 11-12L.109000 Linker1923(1/2) (SEQ ID NO: 5)

In some embodiments, the HVR1 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 204-259 of SEQ ID NO: 5.

In some embodiments, the HVR1 region comprises an amino acid sequence having at least 97% sequence identity to residues 204-259 of SEQ ID NO: 5.

In some embodiments, the HVR1 region comprises one or more residues corresponding to residues 204, 206, 208, 210, 212, 213, 218, 220, 222, 224, 226, 248, 250, 255, and 257 of SEQ ID NO: 5.

In some embodiments, the HVR1 region comprises residues corresponding to residues 204, 206, 208, 210, 212, 213, 218, 220, 222, 224, 226, 248, 250, 255, and 257 of SEQ ID NO: 5.

In some embodiments, the HVR1 region comprises a residue corresponding to residue 237 of SEQ ID NO: 5.

In some embodiments, the HVR1 region comprises a residue corresponding to residue 241 of SEQ ID NO: 5.

In some embodiments, the HVR1 region comprises a residue corresponding to residue 251 of SEQ ID NO: 5.

In some embodiments, the HVR1 region comprises a residue corresponding to residue 252 of SEQ ID NO: 5.

In some embodiments, the HVR1 region comprises a residue corresponding to residue 253 of SEQ ID NO: 5.

In some embodiments, the HVR1 region comprises Y, R, K, or D at a residue corresponding to residue 246 of SEQ ID NO: 5.

In some embodiments, the HVR1 region comprises residues 204-259 of SEQ ID NO: 5.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 187-333 of SEQ ID NO: 5.

In some embodiments, the first subunit comprises an amino acid sequence having at least 99% sequence identity to residues 187-333 of SEQ ID NO: 5.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 185-343 of SEQ ID NO: 5.

In some embodiments, the first subunit comprises an amino acid sequence having at least 99% sequence identity to residues 185-343 of SEQ ID NO: 5.

In some embodiments, the first subunit comprises G, S, or A at a residue corresponding to residue 199 of SEQ ID NO: 5.

In some embodiments, the first subunit comprises E, Q, or K at a residue corresponding to residue 260 of SEQ ID NO: 5.

In some embodiments, the first subunit comprises residues 187-333 of SEQ ID NO: 5.

In some embodiments, the first subunit comprises residues 185-343 of SEQ ID NO: 5.

In some embodiments, the HVR2 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 24-79 of SEQ ID NO: 5.

In some embodiments, the HVR2 region comprises one or more residues corresponding to residues 24, 26, 28, 30, 32, 33, 38, 40, 42, 44, 46, 68, 70, 75, and 77 of SEQ ID NO: 5.

In some embodiments, the HVR2 region comprises residues corresponding to residues 24, 26, 28, 30, 32, 33, 38, 40, 42, 44, 46, 68, 70, 75, and 77 of SEQ ID NO: 5.

In some embodiments, the HVR2 region comprises a residue corresponding to residue 51 of SEQ ID NO: 5.

In some embodiments, the HVR2 region comprises Y, R, K, or D at a residue corresponding to residue 66 of SEQ ID NO: 5.

In some embodiments, the HVR2 region comprises residues 24-79 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 5.

In some embodiments, the second subunit comprises an amino acid sequence having at least 99% sequence identity to residues 7-153 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 5.

In some embodiments, the second subunit comprises an amino acid sequence having at least 99% sequence identity to residues 6-153 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 5.

In some embodiments, the second subunit comprises an amino acid sequence having at least 99% sequence identity to residues 5-153 of SEQ ID NO: 5.

In some embodiments, the second subunit is an N-terminal subunit and comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 5.

In some embodiments, the second subunit comprises an amino acid sequence having at least 99% sequence identity to residues 4-153 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 5.

In some embodiments, the second subunit comprises an amino acid sequence having at least 99% sequence identity to residues 3-153 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 5. In some embodiments, the second subunit comprises a residue other than M at a position corresponding to position 1 of SEQ ID NO: 5.

In some embodiments, the second subunit comprises an amino acid sequence having at least 99% sequence identity to residues 2-153 of SEQ ID NO: 5.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 5.

In some embodiments, the second subunit comprises an amino acid sequence having at least 99% sequence identity to residues 1-153 of SEQ ID NO: 5.

In some embodiments, the second subunit comprises a residue corresponding to residue 19 of SEQ ID NO: 5.

In some embodiments, the second subunit comprises a residue corresponding to residue 80 of SEQ ID NO: 5.

In some embodiments, the second subunit comprises a residue corresponding to residue 96 of SEQ ID NO: 5.

In some embodiments, the second subunit comprises a residue corresponding to residue 99 of SEQ ID NO: 5.

In some embodiments, the second subunit comprises a residue corresponding to residue 100 of SEQ ID NO: 5.

In some embodiments, the second subunit comprises G, S, or A at a residue corresponding to residue 19 of SEQ ID NO: 5.

In some embodiments, the second subunit comprises E, Q, or K at a residue corresponding to residue 80 of SEQ ID NO: 5.

In some embodiments, the second subunit comprises residues 7-153 of SEQ ID NO: 5.

In some embodiments, the second subunit comprises residues 6-153 of SEQ ID NO: 5.

In some embodiments, the second subunit comprises residues 5-153 of SEQ ID NO: 5.

In some embodiments, the second subunit comprises residues 4-153 of SEQ ID NO: 5.

In some embodiments, the second subunit comprises residues 3-153 of SEQ ID NO: 5.

In some embodiments, the second subunit comprises residues 2-153 of SEQ ID NO: 5. In some embodiments, the second subunit comprises a residue other than M at a position corresponding to position 1 of SEQ ID NO: 5.

In some embodiments, the second subunit comprises residues 1-153 of SEQ ID NO: 5.

In some embodiments, the engineered meganuclease is a single-chain meganuclease comprising a linker and wherein the linker covalently joins the first subunit and the second subunit.

In some embodiments, the linker comprises an amino acid sequence set forth in SEQ ID NO: 15 or SEQ ID NO: 16.

In some embodiments, the linker comprises an amino acid sequence set forth in SEQ ID NO: 15.

In some embodiments, the N-terminus of the linker is fused to the residue (i.e., a D residue) corresponding to residue 153 of SEQ ID NO: 5, and the C-terminus of the linker is fused to the residue (i.e., a Y residue) corresponding to residue 185 of SEQ ID NO: 5.

In some embodiments, the engineered meganuclease comprises a first subunit comprising an amino acid sequence having at least 99% sequence identity residues 187-333 of SEQ ID NO: 5; a linker comprising an amino acid sequence set forth in SEQ ID NO: 15, wherein the linker covalently joins the first subunit and the second subunit; and a second subunit comprising an amino acid sequence having at least 99% sequence identity to residues 7-153 of SEQ ID NO: 5.

In some embodiments, the engineered meganuclease comprises a first subunit comprising an amino acid sequence having at least 99% sequence identity residues 185-343 of SEQ ID NO: 5; a linker comprising an amino acid sequence set forth in SEQ ID NO: 15, wherein the linker covalently joins the first subunit and the second subunit; and a second subunit comprising an amino acid sequence having at least 99% sequence identity to residues 1-153 of SEQ ID NO: 5.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-343 of SEQ ID NO: 5.

In some embodiments, the engineered meganuclease comprises an amino acid sequence having at least 92% sequence identity to residues 4-343 of SEQ ID NO: 5.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-343 of SEQ ID NO: 5.

In some embodiments, the engineered meganuclease comprises an amino acid sequence having at least 92% sequence identity to residues 3-343 of SEQ ID NO: 5.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-343 of SEQ ID NO: 5. In some embodiments, the second subunit comprises a residue other than M at a position corresponding to position 1 of SEQ ID NO: 5.

In some embodiments, the engineered meganuclease comprises an amino acid sequence having at least 92% sequence identity to residues 2-343 of SEQ ID NO: 5.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 5. In some embodiments, the engineered meganuclease comprises an amino acid sequence having at least 92% sequence identity to SEQ ID NO: 5.

In some embodiments, the engineered meganuclease comprises an amino acid sequence of residues 4-343 of SEQ ID NO: 5.

In some embodiments, the engineered meganuclease comprises an amino acid sequence of residues 3-343 of SEQ ID NO: 5.

In some embodiments, the engineered meganuclease comprises an amino acid sequence of residues 2-343 of SEQ ID NO: 5. In some embodiments, the second subunit comprises a residue other than M at a position corresponding to position 1 of SEQ ID NO: 5.

In some embodiments, the engineered meganuclease comprises an amino acid sequence of SEQ ID NO: 5.

In some embodiments, the engineered meganuclease is encoded by a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 11.

In some embodiments, the engineered meganuclease is encoded by a nucleic acid sequence of SEQ ID NO: 11.

In some embodiments, the engineered meganuclease comprises a nuclear localization signal.

In some embodiments, the nuclear localization signal is at the N-terminus of the engineered meganuclease.

In some embodiments, the nuclear localization signal is at the C-terminus of the engineered meganuclease.

In some embodiments, the engineered meganuclease comprises a first nuclear localization signal at the N-terminus and a second nuclear localization signal at the C-terminus.

In some embodiments, the nuclear localization signal comprises an amino acid sequence having at least 80% or at least 90% sequence identity to SEQ ID NO: 17. In some embodiments, the nuclear localization signal comprises SEQ ID NO: 17.

HBV 11-12L.10900E Linker1923(1/2) (SEO ID NO: 6)

In some embodiments, the HVR1 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 204-259 of SEQ ID NO: 6.

In some embodiments, the HVR1 region comprises an amino acid sequence having at least 97% sequence identity to residues 204-259 of SEQ ID NO: 6.

In some embodiments, the HVR1 region comprises one or more residues corresponding to residues 204, 206, 208, 210, 212, 213, 218, 220, 222, 224, 226, 248, 250, 255, and 257 of SEQ ID NO: 6.

In some embodiments, the HVR1 region comprises residues corresponding to residues 204, 206, 208, 210, 212, 213, 218, 220, 222, 224, 226, 248, 250, 255, and 257 of SEQ ID NO: 6.

In some embodiments, the HVR1 region comprises a residue corresponding to residue 237 of SEQ ID NO: 6.

In some embodiments, the HVR1 region comprises a residue corresponding to residue 241 of SEQ ID NO: 6.

In some embodiments, the HVR1 region comprises a residue corresponding to residue 251 of SEQ ID NO: 6.

In some embodiments, the HVR1 region comprises a residue corresponding to residue 252 of SEQ ID NO: 6.

In some embodiments, the HVR1 region comprises a residue corresponding to residue 253 of SEQ ID NO: 6.

In some embodiments, the HVR1 region comprises Y, R, K, or D at a residue corresponding to residue 246 of SEQ ID NO: 6.

In some embodiments, the HVR1 region comprises residues 204-259 of SEQ ID NO: 6.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 187-333 of SEQ ID NO: 6.

In some embodiments, the first subunit comprises an amino acid sequence having at least 99% sequence identity to residues 187-333 of SEQ ID NO: 6.

In some embodiments, the first subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 185-343 of SEQ ID NO: 6.

In some embodiments, the first subunit comprises an amino acid sequence having at least 99% sequence identity to residues 185-343 of SEQ ID NO: 6.

In some embodiments, the first subunit comprises a residue corresponding to residue 260 of SEQ ID NO: 6.

In some embodiments, the first subunit comprises G, S, or A at a residue corresponding to residue 199 of SEQ ID NO: 6.

In some embodiments, the first subunit comprises E, Q, or K at a residue corresponding to residue 260 of SEQ ID NO: 6.

In some embodiments, the first subunit comprises residues 187-333 of any one of SEQ ID NO: 6.

In some embodiments, the first subunit comprises residues 185-343 of any one of SEQ ID NO: 6.

In some embodiments, the HVR2 region comprises an amino acid sequence having at least 80%, at least 85%, at least 86%, at least 87%, at least 88%, at least 90%, at least 91%, at least 92%, at least 93%, at least 94%, at least 95%, at least 96%, at least 97%, at least 98%, at least 99%, or more, sequence identity to residues 24-79 of SEQ ID NO: 6.

In some embodiments, the HVR2 region comprises one or more residues corresponding to residues 24, 26, 28, 30, 32, 33, 38, 40, 42, 44, 46, 68, 70, 75, and 77 of SEQ ID NO: 6.

In some embodiments, the HVR2 region comprises residues corresponding to residues 24, 26, 28, 30, 32, 33, 38, 40, 42, 44, 46, 68, 70, 75, and 77 of SEQ ID NO: 6.

In some embodiments, the HVR2 region comprises a residue corresponding to residue 51 of SEQ ID NO: 6.

In some embodiments, the HVR2 region comprises Y, R, K, or D at a residue corresponding to residue 66 of SEQ ID NO: 6.

In some embodiments, the HVR2 region comprises residues 24-79 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 6.

In some embodiments, the second subunit comprises an amino acid sequence having at least 99% sequence identity to residues 7-153 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 6.

In some embodiments, the second subunit comprises an amino acid sequence having at least 99% sequence identity to residues 6-153 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 6.

In some embodiments, the second subunit comprises an amino acid sequence having at least 99% sequence identity to residues 5-153 of SEQ ID NO: 6.

In some embodiments, the second subunit is an N-terminal subunit and comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 6.

In some embodiments, the second subunit comprises an amino acid sequence having at least 99% sequence identity to residues 4-153 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 6.

In some embodiments, the second subunit comprises an amino acid sequence having at least 99% sequence identity to residues 3-153 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 6. In some embodiments, the second subunit comprises a residue other than M at a position corresponding to position 1 of SEQ ID NO: 6.

In some embodiments, the second subunit comprises an amino acid sequence having at least 99% sequence identity to residues 2-153 of SEQ ID NO: 6.

In some embodiments, the second subunit comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 6.

In some embodiments, the second subunit comprises an amino acid sequence having at least 99% sequence identity to residues 1-153 of SEQ ID NO: 6.

In some embodiments, the second subunit comprises a residue corresponding to residue 19 of SEQ ID NO: 6.

In some embodiments, the second subunit comprises a residue corresponding to residue 80 of SEQ ID NO: 6.

In some embodiments, the second subunit comprises a residue corresponding to residue 96 of SEQ ID NO: 6.

In some embodiments, the second subunit comprises a residue corresponding to residue 99 of SEQ ID NO: 6.

In some embodiments, the second subunit comprises a residue corresponding to residue 100 of SEQ ID NO: 6.

In some embodiments, the second subunit comprises G, S, or A at a residue corresponding to residue 19 of SEQ ID NO: 6.

In some embodiments, the second subunit comprises E, Q, or K at a residue corresponding to residue 80 of SEQ ID NO: 6.

In some embodiments, the second subunit comprises residues 7-153 of SEQ ID NO: 6.

In some embodiments, the second subunit comprises residues 6-153 of SEQ ID NO: 6.

In some embodiments, the second subunit comprises residues 5-153 of SEQ ID NO: 6.

In some embodiments, the second subunit comprises residues 4-153 of SEQ ID NO: 6.

In some embodiments, the second subunit comprises residues 3-153 of SEQ ID NO: 6.

In some embodiments, the second subunit comprises residues 2-153 of SEQ ID NO: 6. In some embodiments, the second subunit comprises a residue other than M at a position corresponding to position 1 of SEQ ID NO: 5 or SEQ ID NO: 6.

In some embodiments, the second subunit comprises residues 1-153 of SEQ ID NO: 6.

In some embodiments, the engineered meganuclease is a single-chain meganuclease comprising a linker and wherein the linker covalently joins the first subunit and the second subunit.

In some embodiments, the linker comprises an amino acid sequence set forth in SEQ ID NO: 15 or SEQ ID NO: 16.

In some embodiments, the linker comprises an amino acid sequence set forth in SEQ ID NO: 15.

In some embodiments, the N-terminus of the linker is fused to the residue (i.e., a D residue) corresponding to residue 153 of SEQ ID NO: 6, and the C-terminus of the linker is fused to the residue (i.e., a Y residue) corresponding to residue 185 of SEQ ID NO: 6.

In some embodiments, the engineered meganuclease comprises a first subunit comprising an amino acid sequence having at least 99% sequence identity residues 187-333 of SEQ ID NO: 6; a linker comprising an amino acid sequence set forth in SEQ ID NO: 15, wherein the linker covalently joins the first subunit and the second subunit; and a second subunit comprising an amino acid sequence having at least 99% sequence identity to residues 7-153 of SEQ ID NO: 6.

In some embodiments, the engineered meganuclease comprises a first subunit comprising an amino acid sequence having at least 99% sequence identity residues 185-343 of SEQ ID NO: 6; a linker comprising an amino acid sequence set forth in SEQ ID NO: 15, wherein the linker covalently joins the first subunit and the second subunit; and a second subunit comprising an amino acid sequence having at least 99% sequence identity to residues 1-153 of SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-343 of SEQ ID NO: 6.

In some embodiments, the engineered meganuclease comprises an amino acid sequence having at least 92% sequence identity to residues 4-343 of SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-343 of SEQ ID NO: 6.

In some embodiments, the engineered meganuclease comprises an amino acid sequence having at least 92% sequence identity to residues 3-343 of SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-343 of SEQ ID NO: 6. In some embodiments, the second subunit comprises a residue other than M at a position corresponding to position 1 of SEQ ID NO: 6.

In some embodiments, the engineered meganuclease comprises an amino acid sequence having at least 92% sequence identity to residues 2-343 of SEQ ID NO: 6.

In some embodiments, the engineered meganuclease comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 6.

In some embodiments, the engineered meganuclease comprises an amino acid sequence having at least 92% sequence identity to SEQ ID NO: 6.

In some embodiments, the engineered meganuclease comprises an amino acid sequence of residues 4-343 of SEQ ID NO: 6.

In some embodiments, the engineered meganuclease comprises an amino acid sequence of residues 3-343 of SEQ ID NO: 6.

In some embodiments, the engineered meganuclease comprises an amino acid sequence of residues 2-343 of SEQ ID NO: 6. In some embodiments, the second subunit comprises a residue other than M at a position corresponding to position 1 of SEQ ID NO: 6.

In some embodiments, the engineered meganuclease comprises an amino acid sequence of SEQ ID NO: 6.

In some embodiments, the engineered meganuclease is encoded by a nucleic acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 12.

In some embodiments, the engineered meganuclease is encoded by a nucleic acid sequence of SEQ ID NO: 12.

In some embodiments, the engineered meganuclease comprises a nuclear localization signal.

In some embodiments, the nuclear localization signal is at the N-terminus of the engineered meganuclease.

In some embodiments, the nuclear localization signal is at the C-terminus of the engineered meganuclease.

In some embodiments, the engineered meganuclease comprises a first nuclear localization signal at the N-terminus and a second nuclear localization signal at the C-terminus.

In some embodiments, the nuclear localization signal comprises an amino acid sequence having at least 80% or at least 90% sequence identity to SEQ ID NO: 17. In some embodiments, the nuclear localization signal comprises SEQ ID NO: 17.

In certain embodiments of the engineered meganucleases described herein, the first subunit (i.e., comprising HVR1) can be positioned as the C-terminal subunit, and the second subunit (i.e., comprising HVR2) can be positioned as the N-terminal subunit. In some embodiments of such a configuration, such as those exemplified in SEQ ID NO: 5 and SEQ ID NO: 6, the first subunit (i.e., the C-terminal subunit) can lack residues at its N-terminus that correspond to residues 1-4 of wild-type I-CreI because the binding site of the polypeptide linker is at the Y residue corresponding to position 5 of wild-type I-CreI. The first subunit can further comprise residues at its C-terminus that correspond to residues 154-163 of wild-type I-CreI. Also, in some embodiments of such a configuration, the second subunit (i.e., the N-terminal subunit) can lack residues at its C-terminus that correspond to residues 154-163 of wild-type I-CreI because the binding site of the polypeptide linker is at the D residue corresponding to position 153 of wild-type I-CreI. The second subunit can further comprise one or more residues at its N-terminus that correspond to one or more of residues 1-6 of wild-type I-CreI (e.g., residues 1-6, 2-6, 3-6, 4-6, or 5-6).

In other embodiments of the engineered meganucleases described herein, the first subunit (i.e., comprising HVR1) can be positioned as the N-terminal subunit, and the second subunit (i.e., comprising HVR2) can be positioned as the C-terminal subunit. In some embodiments of such a configuration, the first subunit (i.e., the N-terminal subunit) can lack residues at its C-terminus that correspond to residues 154-163 of wild-type I-CreI because the binding site of the polypeptide linker is at the D residue corresponding to position 153 of wild-type I-CreI. The first subunit can further comprise one or more residues at its N-terminus that correspond to one or more of residues 1-6 of wild-type I-CreI (e.g., residues 1-6, 2-6, 3-6, 4-6, or 5-6). Also, in some embodiments of such a configuration, the second subunit (i.e., the C-terminal subunit) can lack residues at its N-terminus that correspond to residues 1-4 of wild-type I-CreI because the binding site of the polypeptide linker is at the Y residue corresponding to position 5 of wild-type I-CreI. The second subunit can further comprise residues at its C-terminus that correspond to residues 154-163 of wild-type I-CreI.

In some embodiments, the disclosed engineered meganucleases comprise (i) an inactivating amino acid in the N-terminal subunit that reduces or abolishes cleavage activity; (ii) an inactivating amino acid in the C-terminal subunit that reduces or abolishes cleavage activity; or (iii) an inactivating amino acid in the N-terminal subunit that reduces or abolishes cleavage activity and an inactivating amino acid in the C-terminal subunit that reduces or abolishes cleavage activity.

As used here, an inactivating amino acid that "reduces" cleavage activity of an engineered meganuclease inactivates only the subunit comprising that amino acid, while not affecting the ability of the other subunit to cleave its DNA strand. For example, in cases where only one subunit comprises an inactivating amino acid that reduces cleavage activity, the other subunit remains active and the engineered meganuclease becomes a nickase that remains capable of cleaving one strand of the double-stranded DNA. In other cases where both subunits comprise an inactivating amino acid that reduces cleavage activity, neither subunit is active, the engineered meganuclease does not comprise any cleavage activity, and it cannot generate a single-strand or double-strand break in the DNA.

By comparison, an inactivating amino acid that "abolishes" cleavage activity of an engineered meganuclease can be present in only one subunit but will inactivate both subunits of the engineered meganuclease, such that it does not comprise any cleavage activity and cannot generate a single-strand or double-strand break in the DNA.

In some embodiments, the inactivating amino acid is an A at a position corresponding to position 20 or position 200 of SEQ ID NO: 5 or SEQ ID NO: 6. In some embodiments, the inactivating amino acid is an E at a position corresponding to position 47 or position 227 of SEQ ID NO: 5 or SEQ ID NO: 6.

In some embodiments, the N-terminal subunit comprises an E at a position corresponding to position 47 of SEQ ID NO: 5 or SEQ ID NO: 6, and the C-terminal subunit comprises an E at a position corresponding to position 227 of SEQ ID NO: 5 or SEQ ID NO: 6, wherein the engineered meganuclease does not comprise cleavage activity (i.e., activity is abolished).

In some embodiments, the N-terminal subunit comprises an A at a position corresponding to position 20 of SEQ ID NO: 5 or SEQ ID NO: 6, and/or the C-terminal subunit comprises an A at a position corresponding to position 200 of SEQ ID NO: 5 or SEQ ID NO: 6, wherein the engineered meganuclease does not comprise cleavage activity (i.e., activity is abolished).

In some embodiments, the N-terminal subunit comprises an E at a position corresponding to position 47 of SEQ ID NO: 5 or SEQ ID NO: 6 and the C-terminal subunit does not comprise an inactivating amino acid, wherein the engineered meganuclease is a nickase that is only capable of cleaving the antisense strand of a dsDNA target site.

In some embodiments, the C-terminal subunit comprises an E at a position corresponding to position 227 of SEQ ID NO: 5 or SEQ ID NO: 6 and the N-terminal subunit does not comprise an inactivating amino acid, wherein the engineered meganuclease is a nickase that is only capable of cleaving the sense strand of a dsDNA target site.

In those embodiments wherein the engineered meganuclease does not comprise cleavage activity (i.e., activity is abolished) due to one or more inactivating amino acid modifications, such engineered meganucleases are capable of binding to a double-stranded DNA comprising the recognition sequence of SEQ ID NO: 3 (i.e., HBV 11-12) without cleaving the double-stranded DNA. In those embodiments wherein the engineered meganuclease comprises an inactivating amino acid modification such that only one subunit has cleavage activity, and the engineered meganuclease is a nickase, such engineered meganucleases are capable of binding to a double-stranded DNA comprising the recognition sequence of SEQ ID NO: 3 (i.e., HBV 11-12) and cleaving either the sense or antisense strand of the DNA.

2.3 Methods for Delivering and Expressing Optimized Engineered Meganucleases Described herein are methods for inactivating a polymerase (pol) gene of an HBV genome or an HBV genome fragment comprising introducing into a eukaryotic cell comprising the HBV genome or fragment thereof an engineered meganuclease described herein or a nucleic acid encoding the engineered meganuclease, wherein the engineered meganuclease produces a cleavage site at a recognition sequence comprising or consisting of SEQ ID NO: 3 (i.e., HBV 11-12) and the pol gene is inactivated by introduction of an indel at the cleavage site or by elimination of the HBV genome or fragment thereof. Likewise, methods are provided for reducing the symptoms of an HBV infection and/or a disease associated with HBV infection, reducing the amount of HBV, reducing the rate of proliferation of HBV, and/or treating an HBV infection and/or a disease associated with HBV infection in a subject comprising administering a pharmaceutical composition comprising a pharmaceutically acceptable carrier and an engineered meganuclease described herein, or a nucleic acid encoding the engineered meganuclease, or a cell expressing the engineered meganuclease. In the methods described herein, an engineered meganuclease of the disclosure can be delivered to and/or expressed from DNA/RNA in target cells that can provide the engineered meganuclease to the HBV genome.

Introduction of Engineered Meganucleases into Cells

Engineered meganuclease proteins described herein, or polynucleotides encoding the same, can be delivered into cells to cleave genomic DNA or an HBV genome fragment by a variety of different mechanisms known in the art, including those further detailed herein below.

Engineered meganucleases described herein can be delivered into a cell in the form of protein or, preferably, as a polynucleotide comprising a nucleic acid sequence encoding the engineered meganuclease. Such polynucleotides can be, for example, DNA (e.g., circular or linearized plasmid DNA, PCR products, or viral genomes) or RNA (e.g., mRNA).

For embodiments in which the engineered meganuclease coding sequence is delivered in DNA form, it should be operably linked to a promoter to facilitate transcription of the meganuclease gene. Mammalian promoters suitable for use include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290(5804): 304-10) as well as inducible promoters such as the tetracycline-inducible promoter (Dingermann et al. (1992), *Mol Cell Biol.* 12(9):4038-45). An engineered meganuclease of the disclosure can also be operably linked to a synthetic promoter. Synthetic promoters can include, without limitation, the JeT promoter (WO 2002/012514). In specific embodiments, a nucleic acid sequence encoding an engineered meganuclease as described herein can be operably linked to a liver-specific promoter. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In some embodiments, wherein a single polynucleotide comprises two separate nucleic acid sequences each encoding an engineered meganuclease such as those described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymczak and Vignali (2005) *Expert Opin Biol Ther.* 5:627-38). Such 2A peptide sequences can include, for example, a T2A, P2A, E2A, or F2A sequence.

In specific embodiments, a polynucleotide comprising a nucleic acid sequence encoding at least one engineered meganuclease described herein is delivered on a recombinant DNA construct or expression cassette. For example, the recombinant DNA construct can comprise an expression cassette (i.e., "cassette") comprising a promoter and a nucleic acid sequence encoding an engineered meganuclease described herein.

In other embodiments, the recombinant DNA construct comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which binds and cleaves a second recognition sequence which is present in a Hepatitis B virus genome but differs from SEQ ID NO: 3.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In another particular embodiment, a polynucleotide comprising a nucleic acid sequence encoding an engineered meganuclease described herein is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, a polynucleotide comprising a nucleic acid sequence encoding an engineered meganuclease described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, mRNA encoding an engineered meganuclease is delivered to a cell because this reduces the likelihood that the gene encoding the engineered meganuclease will integrate into the genome of the cell.

Such mRNA can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression of the encoded engineered meganuclease and/or stability of the mRNA itself. Non-limiting examples of such elements include a 5' albumin (ALB) untranslated region (UTR) having the sequence set forth as SEQ ID NO: 82 (e.g., encoded by SEQ ID NO: 18), a Kozak sequence having the sequence set forth as SEQ ID NO: 84 (e.g., encoded by SEQ ID NO: 21), a 3' small nuclear ribonucleoprotein B (SNRPB) UTR having the sequence set forth as SEQ ID NO: 83 (e.g., encoded by SEQ ID NO: 19), and a polyA termination sequence such as the sequence set forth as SEQ ID NO: 20. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036. As uridine-rich RNA sequences can trigger the innate immune response, the mRNA can be uridine depleted. The polynucleotide comprising a nucleic acid sequence encoding an engineered meganuclease described herein can be codon-optimized for expression in mammalian cells and more specifically, for expression in particular tissues, such as liver.

In particular embodiments, an mRNA encoding an engineered meganuclease described herein can be a polycistronic mRNA encoding two or more meganucleases, such as those described herein, which are simultaneously expressed in a cell. In some embodiments, a polycistronic mRNA can encode at least a first and a second engineered meganuclease, wherein the first engineered meganuclease is an engineered meganuclease described herein, and wherein the second engineered meganuclease binds and cleaves a second recognition sequence in the HBV genome that differs from SEQ ID NO: 3, such that the HBV genome is cleaved at multiple sites. In some embodiments, a polycistronic mRNA can encode an engineered meganuclease described herein and at least one additional protein which induces a therapeutically beneficial effect in the cell. A polycistronic mRNA can comprise any element known in the art to allow for the translation of two or more genes from the same mRNA molecule including, but not limited to, an IRES element, a T2A element, a P2A element, an E2A element, and an F2A element.

In some embodiments, the methods comprise delivering an engineered meganuclease described herein (or a nucleic acid encoding the same) and a nucleic acid comprising a polynucleotide sequence encoding a suicide gene and sequences homologous to sequences flanking the meganuclease cleavage site, wherein the engineered meganuclease binds and cleaves a recognition sequence comprising or consisting of SEQ ID NO: 3 within the Hepatitis B virus genome, thus cleaving the HBV genome, wherein the suicide gene is inserted into the cleaved HBV genome by homologous recombination.

A suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). In some embodiments, the suicide gene is directly lethal to the HBV or a target cell (e.g., HCC cell). In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

Purified meganuclease proteins can be delivered into cells to cleave genomic DNA by a variety of different mechanisms known in the art, including those further detailed herein below.

The target tissue(s) for delivery of engineered meganucleases of the disclosure include, without limitation, cells of the liver, such as a hepatocyte cell or preferably a primary hepatocyte, more preferably a human hepatocyte or a human primary hepatocyte, a HepG2.2.15 or a HepG2-hNTCP cell. As discussed, meganucleases disclosed herein can be delivered as purified protein or as RNA or DNA encoding the meganuclease. In one embodiment, meganuclease proteins, or mRNA, or DNA vectors encoding meganucleases, are supplied to target cells (e.g., cells in the liver) via injection directly to the target tissue. Alternatively, meganuclease protein, mRNA, DNA, or cells expressing meganucleases can be delivered systemically via the circulatory system.

In some embodiments, the meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, meganuclease proteins, or DNA/mRNA encoding meganucleases, are coupled covalently or non-covalently to an antibody that recognizes a specific cell-surface receptor expressed on target cells such that the meganuclease protein/DNA/mRNA binds to and is internalized by the target cells. Alternatively, meganuclease protein/DNA/mRNA can be coupled covalently or non-covalently to the natural ligand (or a portion of the natural ligand) for such a cell-surface receptor. (McCall, et al. (2014) Tissue Barriers. 2(4): e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid (referred to as a lipid nanoparticle), polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., LIPOFECTAMINE, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding engineered meganucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, polynucleotides comprising a nucleic acid sequence encoding an engineered meganuclease described herein are introduced into a cell using a recombinant virus (i.e., a recombinant viral vector). Such recombinant viruses are known in the art and include recombinant retroviruses, recombinant lentiviruses, recombinant adenoviruses, and recombinant adeno-associated viruses (AAVs) (reviewed in Vannucci, et al. (2013 New Microbiol. 36:1-22). Recombinant AAVs can have any serotype that allows for transduction of the virus into a target cell type and expression of the meganuclease gene in the target cell. For example, in some embodiments, recombinant AAVs have a serotype (i.e. capsid) of AAV1, AAV2, AAV5 AAV6, AAV7, AAV8, AAV9, and AAV12. In some embodiments, the viral vectors are injected directly into target tissues (e.g., liver tissue). In alternative embodiments, the viral vectors are delivered systemically via the circulatory system. It is known in the art that different AAVs tend to localize to different tissues (Wang et al., Expert Opin Drug Deliv 11(3). 2014). In liver target tissues, effective transduction of hepatocytes has been shown, for example, with AAV serotypes 2, 8, and 9 (Sands (2011) Methods Mol. Biol. 807:141-157). In some embodiments, the AAV serotype is AAV2. In some embodiments, the AAV serotype is AAV8. In some embodiments, the AAV serotype is AAV9. AAVs can also be self-complementary such that they do not require second-strand DNA synthesis in the host cell (McCarty, et al. (2001) Gene Ther. 8:1248-54). Polynucleotides delivered by recombinant AAVs can include left (5') and right (3') inverted terminal repeats as part of the viral genome. In some embodiments, the recombinant viruses are injected directly into target tissues. In alternative embodiments, the recombinant viruses are delivered systemically via the circulatory system.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If a polynucleotide comprising a nucleic acid sequence encoding an engineered meganuclease described herein is delivered to a cell by a recombinant virus (e.g. an AAV), the nucleic acid sequence encoding the engineered meganuclease can be operably linked to a promoter. In some embodiments, this can be a viral promoter such as endogenous promoters from the recombinant virus (e.g. the LTR of a lentivirus) or the well-known cytomegalovirus- or SV40 virus-early promoters. In particular embodiments, the nucleic acid sequence encoding the engineered meganuclease is operably linked to a promoter that drives gene expression preferentially in the target cells (e.g., liver cells). Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In particular embodiments, the viral vector comprises a cassette comprising a promoter and a nucleic acid sequence encoding an engineered meganuclease described herein. The viral vector could also comprise two or more cassettes, wherein at least a first cassette comprises a promoter and a nucleic acid sequence encoding an engineered meganuclease described herein, and wherein at least a second cassette comprises a promoter and a nucleic acid sequence encoding an engineered meganuclease that has specificity for a different HBV recognition sequence other than the HBV 11-12 recognition sequence. In some embodiments, the viral vector comprises one cassette comprising a promoter and a polycistronic nucleic acid sequence, wherein the promoter drives expression of the polycistronic nucleic acid sequence to generate a polycistronic mRNA, such as polycistronic mRNA encoding an engineered meganuclease, described herein in a target cell.

In some embodiments, engineered meganucleases described herein, or polynucleotides (e.g., mRNA) comprising a nucleic acid sequence encoding an engineered meganuclease described herein, are encapsulated in lipid nanoparticles and introduced into a cell.

Some lipid nanoparticles contemplated for use comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'- dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-7-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), or a PEG-distearyloxypropyl (C18), or mixtures thereof.

Additional PEG-lipid conjugates suitable for use include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N',N', N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethyl-amronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+ N,N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition which specifically enhances delivery and uptake in the liver, and specifically within hepatocytes.

Methods and compositions are provided for delivering a meganuclease described herein to the liver of a subject infected with HBV. In one embodiment, native hepatocytes which have been removed from the mammal can be transduced with a vector which encodes the engineered meganuclease. Alternatively, native hepatocytes of the HBV-infected subject can be transduced ex vivo with an adenoviral vector (i.e., an AAV vector) which encodes the engineered meganuclease and/or a molecule that stimulates liver regeneration, such as a hepatotoxin. Preferably the hepatotoxin is uPA, and has been modified to inhibit its secretion from the hepatocyte once expressed by the viral vector. In another embodiment, the vector encodes tPA, which can stimulate hepatocyte regeneration de novo. The transduced hepatocytes which have been removed from the mammal can then be returned to the mammal, where conditions are provided which are conducive to expression of the engineered meganuclease. Typically, the transduced hepatocytes can be returned to the patient by infusion through the spleen or portal vasculature, and administration may be single or multiple over a period of 1 to 5 or more days.

Administration

In an in vivo aspect of the methods described herein, a retroviral, pseudotype or adenoviral associated virus (i.e., an AAV) is constructed which encodes the engineered meganuclease and is administered to the subject. Administration of a vector encoding the engineered meganuclease can occur with administration of an adenoviral vector that encodes a secretion-impaired hepatotoxin, or encodes tPA, which stimulates hepatocyte regeneration without acting as a hepatotoxin.

In various embodiments of the methods and compositions described herein, such as the engineered meganucleases described herein, polynucleotides encoding the same, recombinant viruses comprising such polynucleotides, or lipid nanoparticles comprising such polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the engineered meganuclease proteins, polynucleotides encoding the same, recombinant viruses comprising such polynucleotides, or lipid nanoparticles comprising such polynucleotides, are supplied to target cells (e.g., liver cells) via injection directly to the target tissue (e.g., liver tissue). Other suitable routes of administration can be readily determined by the treating physician as necessary.

In some embodiments, a therapeutically effective amount of an engineered meganuclease described herein, or a polynucleotide encoding the same, is administered to a subject in need thereof for the treatment of HBV infection or a disease associated with HBV infection. Such administration may be carried out until sAg is no longer detectable in the serum or plasma of the subject. In some embodiments, after one or more administrations of the one or more engineered meganucleases, polynucleotides encoding such engineered meganucleases, lipid nanoparticles or recombinant viruses comprising one or more polynucleotides encoding such engineered meganucleases, as described herein, optionally with one or more additional therapeutic agents, described herein, the subject does not exhibit symptoms of the disease associated with HBV infection in the absence of antiviral treatment. In some embodiments, after one or more administrations of the one or more engineered meganucleases, polynucleotides encoding such engineered meganucleases, or vectors comprising one or more polynucleotides encoding such engineered meganucleases, as described herein, optionally with one or more additional therapeutic agents, described herein, sAg is no longer detectable in the serum or plasma of the subject, in the absence of antiviral treatment.

In some embodiments, a subject is administered a pharmaceutical composition comprising a polynucleotide comprising a nucleic acid sequence encoding an engineered meganuclease described herein, wherein the encoding nucleic acid sequence is administered at a dose of about $1{\times}10^{10}$ gc/kg to about $1{\times}10^{14}$ gc/kg (e.g., about $1{\times}10^{10}$ gc/kg, about $1{\times}10^{11}$ gc/kg, about $1{\times}10^{12}$ gc/kg, about $1{\times}10^{13}$ gc/kg, or about $1{\times}10^{14}$ gc/kg). In some embodiments, a subject is administered a pharmaceutical composition comprising a polynucleotide comprising a nucleic acid sequence encoding an engineered meganuclease described herein, wherein the encoding nucleic acid sequence is administered at a dose of about $1{\times}10^{10}$ gc/kg, about $1{\times}10^{11}$ gc/kg, about $1{\times}10^{12}$ gc/kg, about $1{\times}10^{13}$ gc/kg, or about $1{\times}10^{14}$ gc/kg. In some embodiments, a subject is administered a pharmaceutical composition comprising a polynucleotide comprising a nucleic acid sequence encoding an engineered meganuclease described herein, wherein the encoding nucleic acid sequence is administered at a dose of about $1{\times}10^{10}$ gc/kg to about $1{\times}10^{11}$ gc/kg, about $1{\times}10^{11}$ gc/kg to about $1{\times}10^{12}$ gc/kg, about $1{\times}10^{12}$ gc/kg to about $1{\times}10^{13}$ gc/kg, or about $1{\times}10^{13}$ gc/kg to about $1{\times}10^{14}$ gc/kg. It should be understood that these doses can relate to the administration of a single polynucleotide comprising a single nucleic acid sequence encoding a single engineered meganuclease described herein or, alternatively, can relate to a single polynucleotide comprising a first nucleic acid sequence encoding a first engineered meganuclease described herein and a second nucleic acid sequence encoding a second engineered meganuclease described herein or one that binds and in some embodiments, cleaves, a recognition sequence within the HBV genome other than HBV 11-12, wherein each of the two encoding nucleic acid sequences is administered at the indicated dose.

In some embodiments, a subject is administered a lipid nanoparticle formulation comprising an mRNA comprising a nucleic acid sequence encoding an engineered meganuclease described herein. In some such embodiments, the dose of the mRNA is about 0.1 mg/kg to about 3 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

As appropriate, the dosage or dosing frequency of the engineered meganuclease, or the polynucleotide encoding the same, may be adjusted over the course of the treatment, based on the judgment of the administering physician. Appropriate doses will depend, among other factors, on the specifics of any AAV chosen (e.g., serotype, etc.), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

2.4 Pharmaceutical Compositions

In some embodiments, the disclosure provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein. In some such examples, the polynucleotide in the pharmaceutical composition can be comprised by a lipid nanoparticle or can be comprised by a recombinant virus (e.g., a recombinant AAV). Pharmaceutical compositions of the disclosure can be useful for treating a subject having HBV, reducing the level or proliferation of HBV, reducing at least one symptom of a disease associated with HBV infection, or treating a disease associated with HBV infection.

Pharmaceutical compositions can be designed or selected according to the genotype of the target HBV strain. As described in detail herein, meganucleases described herein have been engineered to recognize and cleave a recognition sequence in specific genotypes of HBV. The presently disclosed HBV 11-12 meganucleases (e.g., SEQ ID NOs: 5 and 6), recognize and cleave the HBV 11-12 recognition sequence that is at least found in the genome of HBV genotypes A, B, C, D, E, F, and G. In some embodiments, the pharmaceutical compositions described herein can be administered to a subject having any genotype of HBV comprising a recognition sequence set forth in SEQ ID NO: 3.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the disclosure, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions disclosed herein can further comprise one or more additional agents or biological molecules useful in the treatment of a disease in the subject. Likewise, the additional agent(s) and/or biological molecule(s) can be co-administered as a separate composition.

Given that the presently disclosed engineered meganucleases can have improved (i.e., increased) specificity resulting in reduced off-target cutting, and enhanced (i.e., increased) efficiency of cleavage and indel formation, particularly in cells comprising an integrated copy of the HBV genome, as compared to the HBV 11-12L.1090QQ Linker1 meganuclease, in some embodiments, the presently disclosed pharmaceutical compositions comprising optimized engineered meganucleases, nucleic acid sequences encoding the same, or cells expressing the same, also have improved (i.e., increased) efficacy in treating HBV infection, reducing the level or proliferation of HBV, reducing at least one symptom of a disease associated with HBV infection, or treating a disease associated with HBV infection in a subject, when compared to the administration of pharmaceutical compositions comprising the HBV 11-12L.1090QQ Linker1 meganuclease.

In particular embodiments, pharmaceutical compositions disclosed herein can include combinations of the engineered meganucleases described herein (or nucleic acids encoding engineered meganucleases or cells expressing engineered meganucleases). In other embodiments, pharmaceutical compositions can include at least two engineered meganucleases (or nucleic acids encoding engineered meganucleases or cells expressing engineered meganucleases), wherein at least a first engineered meganuclease is one described herein that binds and cleaves the HBV 11-12 recognition sequence, and wherein at least a second engineered meganuclease binds and cleaves a second recognition sequence in the HBV genome other than the HBV 11-12 recognition sequence, such that a single pharmaceutical composition is broadly useful for the treatment of a wide array of HBV genotypes and/or genotype isolates in a subject. Likewise, in other embodiments, pharmaceutical compositions can include polycistronic mRNAs (or recombinant DNA constructs or viral vectors having cassettes which, when expressed, produce polycistronic mRNAs) that encode multiple engineered meganucleases described herein. In other embodiments, pharmaceutical compositions can include polycistronic mRNAs (or recombinant DNA constructs or viral vectors having cassettes which, when expressed, produce polycistronic mRNAs) that encode at least two engineered meganucleases, wherein at least a first engineered meganuclease is one described herein that binds and cleaves the HBV 11-12 recognition sequence, and wherein at least a second engineered meganuclease binds and cleaves a second recognition sequence in the HBV genome other than the HBV 11-12 recognition sequence. Such pharmaceutical compositions are also broadly useful for the treatment of a wide array of HBV genotypes and/or genotype isolates in a subject. In either case, such pharmaceutical compositions can be useful as a single treatment when the specific HBV genotype or isolate is known or unknown in the subject.

For example, pharmaceutical compositions comprising multiple different engineered meganucleases (including at least one of the engineered meganucleases described herein) or comprising nucleic molecules encoding multiple different engineered meganucleases (including at least one of the engineered meganucleases described herein) that target recognition sequences within the HBV genome, can be administered to a patient infected with multiple genotypes of HBV, or infected with unknown genotypes of HBV. Accordingly, providing pharmaceutical compositions with multiple different engineered meganucleases or comprising nucleic molecules encoding multiple different engineered meganucleases affords a flexible option for treatment and control of HBV infection where resources do not allow for accurate genotyping of HBV and where fast and broad treatment solutions are desired.

The pharmaceutical compositions described herein can include a therapeutically effective amount of any engineered meganuclease described herein, or any polynucleotide described herein encoding any engineered meganuclease described herein. For example, in some embodiments, the pharmaceutical composition can include polynucleotides described herein at any of the doses (e.g., gc/kg of an encoding nucleic acid sequence or mg/kg of mRNA) described herein.

In some embodiments, pharmaceutical compositions can further comprise one or more additional agents useful in the treatment of an HBV infection or a disease associated with HBV infection in the subject.

The present disclosure also provides engineered meganucleases described herein (or nucleic acids encoding the same or cells expressing the engineered meganucleases) for use as a medicament. The present disclosure further provides the use of an engineered meganuclease described herein (or a nucleic acid encoding the same or cells expressing an engineered meganuclease) in the manufacture of a medicament for treating an HBV infection, for reducing the level or proliferation of HBV, reducing the symptoms associated with a disease associated with HBV infection, or treating a disease associated with HBV infection.

2.5 Engineered Meganuclease Variants

Embodiments of the disclosure encompass the engineered meganucleases described herein, and variants thereof. Further embodiments of the disclosure encompass polynucleotides comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave the HBV 11-12 recognition sequence (SEQ ID NO: 3) within the genome of a Hepatitis B virus, and in some embodiments, exhibit at least one improved property over previously described engineered HBV meganucleases (e.g., the HBV 11-12L.1090QQ Linker1 meganuclease), such as improved (i.e., increased) specificity and enhanced (i.e., increased) efficiency of cleavage and indel formation. Such variants may result, for example, from human manipulation. Biologically active variants of a native polypeptide of the embodiments (e.g., SEQ ID NOs: 5 and 6), or biologically active variants of the recognition half-site binding subunits described herein, will have at least about 40%, about 45%, about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, or about 99%, sequence identity to the amino acid sequence of the native polypeptide, native subunit, native HVR1 region, and/or native HVR2 region, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases described herein can comprise variants of the HVR1 and HVR2 regions described herein. Parental HVR regions can comprise, for example, residues 24-79 or residues 204-259 of the exemplified engineered meganucleases. Thus, variant HVRs can comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more, sequence identity to an amino acid sequence corresponding to residues 24-79 or residues 204-259 of the engineered meganucleases exemplified herein, such that the variant HVR regions maintain the biological activity of the engineered meganuclease (i.e., binding to and cleaving the recognition sequence). Further, in some embodiments of the disclosure, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases described herein comprise an HVR1 that has at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more sequence identity to an amino acid sequence corresponding to residues 204-259 of SEQ ID NO: 5 or 6.

In certain embodiments, engineered meganucleases described herein comprise an HVR2 region that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to an amino acid sequence corresponding to residues 24-79 of SEQ ID NO: 5 or 6.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 1 provides potential substitutions that can be made in an engineered meganuclease monomer or subunit to enhance specificity based on the base present at each half-site position (−1 through −9) of a recognition half-site.

TABLE 1

| | | | | | Favored Sense-Strand Base | | | | | | |
|---|---|---|---|---|---|---|---|---|---|---|---|
| Posn. | A | C | G | T | A/T | A/C | A/G | C/T | G/T | A/G/ T | A/C/ G/T |
| −1 | Y75 | R70* | K70 | Q70* | | | | | T46* | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |

TABLE 1-continued

| | | | | | Favored Sense-Strand Base | | | | | | |
| Posn. | A | C | G | T | A/T | A/C | A/G | C/T | G/T | A/G/T | A/C/G/T |
|---|---|---|---|---|---|---|---|---|---|---|---|
| | A46* | R46* | | H75* | | | | | | | |
| | | | | H139 | | | | | | | |
| | | | | Q46* | | | | | | | |
| | | | | H46* | | | | | | | |
| -2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| -3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| -4 | A26* | E77 | R77 | | | | | S77 | | | S26* |
| | Q77 | K26* | E26* | | | | | Q26* | | | |
| -5 | | E42 | R42 | | | K28* | C28* | | | | M66 |
| | | | | | | | Q42 | | | | K66 |
| -6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| -7 | N30* | E38 | K38 | I38 | | | C38 | | | | H38 |
| | Q38 | K30* | R38 | L38 | | | | | | | N38 |
| | | R30* | E30* | | | | | | | | Q30* |
| -8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| -9 | | E32 | R32 | L32 | | | | D32 | | | S32 |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, 5, or A at a residue corresponding to position 19 of I-CreI or position 199 of SEQ ID NO: 5 or 6 (WO 2009/001159), a Y, R, K, or D at a residue corresponding to position 66 of I-CreI or position 246 of SEQ ID NO: 5 or 6, and/or an E, Q, or K at a residue corresponding to position 80 of I-CreI or position 260 of SEQ ID NO: 5 or 6 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide its intended activity. For example, variants of an engineered meganuclease would be screened for their ability to preferentially bind and cleave the HBV 11-12 recognition sequence within the genome of a Hepatitis B virus.

2.6 Combination Therapy for HBV

In certain embodiments, a method for treating an HBV infection or a disease associated with HBV infection in a human having or at risk of having the infection is provided, comprising administering to the human a therapeutically effective amount of an engineered meganuclease described herein, or a nucleic acid encoding the same, in combination with a therapeutically effective amount of one or more (e.g., agents are combined or co-administered with one, two, three, four, one or two, one to three, or one to four) additional therapeutic agents. In one embodiment, a method for treating an HBV infection or a disease associated with an HBV infection in a human having or at risk of having the infection is provided, comprises administering to the human a therapeutically effective amount of an engineered meganuclease described herein, or a nucleic acid encoding the same, in combination with a therapeutically effective amount of one or more (e.g., one, two, three, four, one or two, one to three, or one to four) additional therapeutic agents.

In certain embodiments, the present disclosure provides a method for treating an HBV infection or a disease associated with HBV infection, comprising administering to a patient in need thereof a therapeutically effective amount of an engineered meganuclease described herein, or a nucleic acid encoding the same, in combination with a therapeutically effective amount of one or more (e.g., one, two, three, four, one or two, one to three, or one to four) additional therapeutic agents which are suitable for treating an HBV infection or a disease associated with HBV infection.

In certain embodiments, an engineered meganuclease described herein, or a nucleic acid encoding the same, is combined with one, two, three, four, or more additional therapeutic agents. In certain embodiments, an engineered meganuclease described herein, or a nucleic acid encoding the same, is combined with two additional therapeutic agents. In other embodiments, an engineered meganuclease described herein, or a nucleic acid encoding the same, is combined with three additional therapeutic agents. In further embodiments, an engineered meganuclease described herein, or a nucleic acid encoding the same, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when an engineered meganuclease described herein, or a nucleic acid encoding the same, is combined with one or more additional therapeutic agents as described above, the components of the composition are administered as a simultaneous or sequential regimen. When administered sequentially, the combination may be administered in two or more administrations.

Co-administration of an engineered meganuclease described herein, or a nucleic acid encoding the same, with one or more additional therapeutic agents generally refers to simultaneous or sequential administration of an engineered meganuclease described herein, or a nucleic acid encoding the same, and one or more additional therapeutic agents, such that therapeutically effective amounts of each agent are present in the body of the patient.

Co-administration includes administration of unit dosages of the compounds described herein before or after administration of unit dosages of one or more additional therapeutic agents. The engineered meganuclease described herein, or a nucleic acid encoding the same, may be administered within seconds, minutes, or hours of the administration of one or more additional therapeutic agents. For example, in some embodiments, a unit dose of an engineered meganuclease described herein, or a nucleic acid encoding the same, is administered first, followed within seconds or minutes by administration of a unit dose of one or more additional therapeutic agents. Alternatively, in other embodiments, a unit dose of one or more additional therapeutic agents is administered first, followed by administration of a unit dose of an engineered meganuclease described herein, or a nucleic acid encoding the same, within seconds or minutes. In some embodiments, a unit dose of an engineered meganuclease described herein, or a nucleic acid encoding the same, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an engineered meganuclease described herein, or a nucleic acid encoding the same.

In certain embodiments, an engineered meganuclease described herein, or a nucleic acid encoding the same, is combined with one or more additional therapeutic agents in a unitary dosage form for simultaneous administration to a patient.

HBV Combination Therapy

The engineered meganucleases described herein, or nucleic acids encoding the same, may be combined or co-administered with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, Bruton's tyrosine kinase (BTK) inhibitors, KDM inhibitors, HBV replication inhibitors, arginase inhibitors, gene therapy and cell therapy, gene editors, cellular therapy, TCR-T cell therapy, and other HBV drugs.

In certain embodiments, the engineered meganucleases described herein, or nucleic acids encoding the same, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors targeting HBV (e.g., CRISPR-Cas (e.g., Cas9, Cas12, Cascade, Cas13), zinc finger nucleases, homing endonucleases (e.g., engineered I-CreI variant meganucleases), synthetic nucleases, TALENs, cell therapies (e.g., T-cells, NK cells, macrophages having a chimeric antigen receptor (CAR)), and TCR-T (an engineered T cell receptor) or any combination thereof.

In some embodiments, an engineered meganuclease described herein is combined with one or more additional engineered nucleases, which bind and cleave a second recognition sequence other than the HBV 11-12 recognition sequence in the HBV genome. For example, one, two, three or more additional engineered nucleases (e.g., one, two, three or more engineered meganucleases) that bind and cleave a recognition sequence other than HBV 11-12 may be combined with the engineered meganucleases disclosed herein (e.g., SEQ ID NO: 5 or 6). The one or more additional engineered nucleases may bind and cleave a recognition sequence found in any location within the HBV genome including one or more HBV gene coding sequences or non-coding sequences. For example, the one or more additional engineered nucleases may bind and cleave a recognition sequence within a HBV genomic sequence including but not limited to, gene S, which encodes the major hepatitis B surface antigen (HBsAg) protein; sequences upstream from gene S, which encode the pre-S domain; gene C, which encodes the hepatitis B core antigen (HBcAg); the P region, which encodes the viral reverse transcriptase; gene X, which encodes the HBx viral protein; and within a pre-core region, which encodes the HBeAg gene. In some embodiments, the one or more additional engineered nucleases bind and cleave a recognition sequence described in PCT/US2017/056638. In some embodiments, the one or more additional nucleases are engineered I-CreI derived meganucleases, such as those described in PCT/US2017/056638 or a variant of the engineered meganucleases described therein, wherein the one or more additional engineered meganucleases bind and cleave a recognition sequence other than HBV 11-12 (SEQ ID NO: 3).

In certain embodiments, an engineered meganuclease described herein, or a nucleic acid encoding the same, are optionally combined or co-administered with one, two, three, four, or more additional therapeutic agents, e.g., 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 gene stimulator, toll-like receptor (TLR) modulators, viral ribonucleotide reductase inhibitor, and combinations thereof.

HBV Inhibiting Antiviral Drugs

In various embodiments, an engineered meganuclease described herein, or a nucleic acid encoding the same, are combined or co-administered with one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir disoproxil fumarate and emtricitabine (TRUVADA®), tenofovir alafenamide (TAF or VEMLIDY®) and ledipasvir and sofosbuvir (HARVONI®). In certain embodiments, the engineered meganuclease, or nucleic acid encoding the same are combined with long acting forms of anti-HBV drugs. Illustrative long acting forms of anti-HBV drugs that can be combined include entecavir (subcutaneous depot), long acting tenofovir (TFD and TAF) implants (devices) or subcutaneous depot. An example of long acting entecavir is described in Henry, et al., Eur J Pharm Sci. 2019 Aug. 1; 136:104958.

Other HBV Drugs

Examples of other drugs for the treatment of an HBV infection or diseases associated with HBV infection include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007, sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/ antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+ Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), MVA-BN, and Lm HBV. HBV arenavirus vaccines are described, e.g., in WO2017076988 and WO2017198726.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidoyl hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, RO-6871765, AIC-649, and IR-103.

Toll-Like Receptor (TLR) Agonists

In various embodiments, an engineered meganuclease described herein, or a nucleic acid encoding the same, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13. Examples of TLR3 modulators include rintatolimod, poly-ICLC, RIBOXXON®, Apoxxim, RIBOXXIM®, IPH-33, MCT-465, MCT-475 and ND-1.1.

Example TLR7 agonists that can be co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

An TLR7/TLR8 agonist that can be co-administered is NKTR-262, telratolimod and BDB-001.

Example TLR8 agonists that can be co-administered include without limitation E-6887, IMO-4200, IMO-8400, IMO-9200, MCT-465, MEDI-9197, motolimod, resiquimod, selgantolimod (GS-9688), VTX-1463, VTX-763, 3M-051, 3M-052, ZG-170607, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Example TLR9 agonists that can be co-administered include without limitation AST-008, cobitolimod, CMP-001, IMO-2055, IMO-2125, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), and WO2015023958 (University of Kansas).

In certain embodiments, an engineered meganuclease described herein, or a nucleic acid encoding the same, is co-administered with a TLR7, TLR8 or TLR9 agonist.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-nl (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTE-FEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031, REP-006, and REP-9AC'.

Examples of HBsAg secretion inhibitors include BM601, GST-HG-131, and AB-452.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-HBV-LRx, IONIS-GSK6-LRx, GSK-3389404, and RG-6004.

Short Interfering RNAs (siRNA) and ddRNAi.

Examples of siRNA include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, ALG-010133, ALG-ASO, LUNAR-HBV and DCR-HBVS (DCR-S219.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

Nonnucleoside Reverse Transcriptase Inhibitors

Examples of nonnucleoside reverse transcriptase inhibitors (NNRTIs) include the compounds disclosed in WO2018118826 (Merck), WO2018080903 (Merck), WO2018119013 (Merck), WO2017100108 (Idenix), WO2017027434 (Merck), WO2017007701 (Merck), and WO2008005555 (Gilead).

HBV Replication Inhibitors

Examples of hepatitis B virus replication inhibitors include GP-31502, isothiafludine, IQP-HBV, RM-5038, and Xingantie.

Covalently Closed Circular DNA (cccDNA) Inhibitors

Examples of cccDNA inhibitors include BSBI-25, ccc-R08, and CHR-101.

Farnesoid X Receptor Agonist

Examples of farnesoid x receptor agonists include, e.g., EYP-001, GS-9674, EDP-305, MET-409, Tropifexor, AKN-083, RDX-023, BWD-100, LMB-763, INV-3, NTX-023-1, EP-024297 and GS-8670.

Anti-HBV Antibodies

In various embodiments, an engineered meganuclease described herein, or a nucleic acid encoding the same, is combined or co-administered with one or more antibodies that specifically binds to an HBV antigen, including an HBV peptide presented in a major histocompatibility molecule (MHC) molecule (pMHC). Examples of HBV antibodies targeting the surface antigens of the hepatitis B virus that can be combined or co-administered include lenvervimab (GC-1102), XTL-17, XTL-19, KN-003, IV Hepabulin SN, and fully human monoclonal antibody therapy (hepatitis B virus infection, Humabs BioMed). Antibodies targeting HBV X protein (HBx) that can be combined or co-administered are described, e.g., in Kornyeyev, et al., *J Virol.* 2019 Jul. 30; 93(16).pii: e00248-19.

Examples of HBV antibodies, including monoclonal antibodies and polyclonal antibodies, that can be combined or co-administered include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal HBV antibodies that can be combined or co-administered include HBC-34.

Antibodies against HBV viral peptide/major histocompatibility complex (MHC) class I (pMHC) complexes that can be combined or co-administered are described, e.g., in Sastry, et al., J Virol. 2011 March; 85(5):1935-42 and in WO2011062562.

CCR2 Chemokine Antagonists

Examples of CCR2 chemokine antagonists include propagermanium.

Thymosin Agonists

Examples of thymosin agonists include Thymalfasin and recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Interleukin Agonists

In certain embodiments, an engineered meganuclease described herein, or a nucleic acid encoding the same, is combined with an interleukin agonist, such as IL-2, IL-7, IL-15, IL-10, IL-12 agonists. Examples of IL-2 agonists include proleukin (aldesleukin, IL-2); pegylated IL-2 (eg NKTR-214), modified variants of IL-2 (eg THOR-707), bempegaldesleukin, AIC-284, ALKS-4230, CUI-101, and Neo-2/15. Examples of IL-15 agonists include ALT-803, NKTR-255, hetIL-15, interleukin-15/Fc fusion protein, AM-0015, NIZ-985, SO-C101, IL-15 Synthorin (pegylated Il-15), P-22339, and a IL-15-PD-1 fusion protein N-809. Examples of IL-7 include CYT-107.

Nucleoprotein Modulators

Nucleoprotein modulators may be either HBV core or capsid protein inhibitors. Examples of nucleoprotein modulators include GS-4882, AB-423, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, ABI-H2158, CB-HBV-001, and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Innate Immune Activators

In some embodiments, an engineered meganuclease described herein, or a nucleic acid encoding the same, is combined or co-administered with one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992.

STING Agonists, RIG-I and NOD2 Modulators

In some embodiments, an engineered meganuclease described herein, or a nucleic acid encoding the same, is combined or co-administered with a stimulator of interferon response cGAMP interactor 1 (STING or STING1; NCBI Gene ID: 340061) agonist. In some embodiments, the STING/STING1 agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. Examples of STING agonists that can be combined or co-administered include the compounds disclosed in WO 2018065360 (Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

In some embodiments, an engineered meganuclease described herein, or a nucleic acid sequence encoding the same, is combined or co-administered with a DExD/H-box helicase 58 (DDX58; a.k.a., retinoic acid-inducible gene 1 (RIG-I), RIG1, RIGI, RLR-1, SGMRT2; NCBI Gene ID: 23586). Illustrative RIG-I agonists that can be combined or co-administered include inarigivir soproxil (SB-9200, GS-9992), SB-40, SB-44, ORI-7246, ORI-9350, ORI-7537, ORI-9020, ORI-9198, ORI-7170, and RGT-100.

In some embodiments, an engineered meganuclease described herein, or a nucleic acid sequence encoding the same, is combined or co-administered with a nucleotide binding oligomerization domain containing 2 (NOD2; NCBI Gene ID: 64127) agonist, such as inarigivir soproxil (SB-9200, GS-9992), and IR-103.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Immune Checkpoint Modulators

In various embodiments, an engineered meganuclease described herein, or a nucleic acid sequence encoding the same, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., *J Exp Clin Cancer Res.* (2018) 37:110). In various embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors include without limitation CD27 (NCBI Gene ID: 939); CD70 (NCBI Gene ID: 970); CD40 (NCBI Gene ID: 958); CD40LG (NCBI Gene ID: 959); CD47 (NCBI Gene ID: 961); CD48 (SLAMF2; NCBI Gene ID: 962); transmembrane and immunoglobulin domain containing 2 (TMIGD2, CD28H; NCBI Gene ID: 126259); CD84 (LY9B, SLAMF5; NCBI Gene ID: 8832); CD96 (NCBI Gene ID: 10225); CD160 (NCBI Gene ID: 11126); MS4A1 (CD20; NCBI Gene ID: 931); CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278;

NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943); TNFSF8 (CD30L; NCBI Gene ID: 944); TNFRSF10A (CD261, DR4, TRAILR1; NCBI Gene ID: 8797); TNFRSF9 (CD137; NCBI Gene ID: 3604); TNFSF9 (CD137L; NCBI Gene ID: 8744); TNFRSF10B (CD262, DR5, TRAILR2; NCBI Gene ID: 8795); TNFRSF10 (TRAIL; NCBI Gene ID: 8743); TNFRSF14 (HVEM, CD270; NCBI Gene ID: 8764); TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608); TNFSF13B (BAFF; NCBI Gene ID: 10673); TNFRSF18 (GITR; NCBI Gene ID: 8784); TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941); CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID:

3811) (e.g., Lirilumab (IPH2102/BMS-986015), IPH-4102); and killer cell lectin like receptor D1 (KLRD1; NCBI Gene ID: 3824).

In various embodiments, an engineered meganuclease described herein, or a nucleic acid sequence encoding the same, is combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, an engineered meganuclease described herein, or a nucleic acid sequence encoding the same, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4); and Poliovirus receptor (PVR) cell adhesion molecule (PVR, CD155). See, e.g., Xu, et al., *J Exp Clin Cancer Res*. (2018) 37:110.

In various embodiments, an engineered meganuclease described herein, or a nucleic acid sequence encoding the same, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, an engineered meganuclease described herein, or a nucleic acid sequence encoding the same, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); and SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO2016126646 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In various embodiments, an engineered meganuclease described herein, or a nucleic acid sequence encoding the same, is combined with anti-TIGIT antibodies, such as BMS-986207, RG-6058, and AGEN-1307.

TNF Receptor Superfamily (TNFRSF) Member Agonists or Activators

In various embodiments, an engineered meganuclease described herein, or a nucleic acid sequence encoding the same, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, IBI-101 and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-Pyrrole-2,3-Dioxygenase (IDO1) Inhibitors

In various embodiments, an engineered meganuclease described herein, or a nucleic acid sequence encoding the same, is combined with an inhibitor of indoleamine 2,3-dioxygenase 1 (IDO1; NCBI Gene ID: 3620). Examples of IDO1 inhibitors include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

LAG-3 and TIM-3 Inhibitors

In certain embodiments, an engineered meganuclease described herein, or a nucleic acid sequence encoding the same, is combined with an anti-TIM-3 antibody, such as TSR-022, LY-3321367, MBG-453, INCAGN-2390.

In certain embodiments, an engineered meganuclease described herein, or a nucleic acid sequence encoding the same, is combined with an anti LAG-3 (Lymphocyte-activation) antibody, such as relatlimab (ONO-4482), LAG-525, MK-4280, REGN-3767, INCAGN2385.

Inhibitor of Apoptosis Proteins Family Proteins (IAPs)

Examples of IAP inhibitors include APG-1387.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors include the compounds disclosed in U.S. Pat. No. 9,186,337B2 (Oryzon Genomics), GSK-2879552, RG-6016, and ORY-2001.

Arginase Inhibitors

Examples of Arginase inhibitors include CB-1158, C-201, and resminostat.

Bi- and Tri-Specific Natural Killer (NK)-Cell Engagers

In various embodiments, an engineered meganuclease described herein, or a nucleic acid sequence encoding the same, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (4-1BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., *Methods Mol Biol.* (2016) 1441:333-346; Fang, et al., *Semin Immunol.* (2017) 31:37-54.

Gene Therapy and Cell Therapy

In certain embodiments, an engineered meganuclease described herein, or a nucleic acid sequence encoding the same, is combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and/or genetic approaches to modify cellular activity to further alter endogenous immune responsiveness against the infection.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain described herein. In certain embodiments, the antigen-binding domain is other than a domain described herein. In certain embodiments, the antigen is HBsAg (i.e., HbsAg-CART). The immune effector cell is a T-cell or an NK cell. In certain embodiments, the T-cell is a CD4+ T-cell, a CD8+ T-cell, a NK cell, or a combination thereof. Cells can be autologous or allogeneic. An example of a CART directed to HBV is described in Cytotherapy. 2018 May; 20(5):697-705 doi: 10.1016/j.jcyt.2018.02.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, K. et al. *J Clin Invest.* 2019; 129(7):2932-2945.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, an engineered meganuclease described herein, or a nucleic acid encoding the same, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an engineered meganuclease described herein, or a nucleic acid encoding the same, is combined with at least a second additional therapeutic agent selected from the group consisting of: HBV DNA polymerase inhibitors, immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an engineered meganuclease described herein, or a nucleic acid encoding the same, is combined with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an engineered meganuclease described herein, or a nucleic acid encoding the same, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics). US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In one embodiment, kits comprising an engineered meganuclease described herein, or a nucleic acid encoding the same, in combination with one or more (e.g., one, two, three, four, one or two, or one to three, or one to four) additional therapeutic agents are provided.

EXAMPLES

The embodiments of the disclosure are further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Evaluation of Novel Polypeptide Linkers and Subunit Substitution Combinations in HBV 11-12 Meganucleases 1. Methods This study was designed to evaluate variants of the HBV 11-12L.1090 meganuclease (SEQ ID NO: 13), which binds and cleaves the HBV 11-12 recognition sequence (SEQ ID NO: 3) and comprises two modified I-CreI subunits linked together by a polypeptide linker, referred to as Linker1 (SEQ ID NO: 16). Variants included in this study comprised a novel linker selected from Linker1923 (SEQ ID NO: 15), Linker1766 (SEQ ID NO: 42), Linker1771 (SEQ ID NO: 43), Linker1808 (SEQ ID NO: 44), and Linker1814 (SEQ ID NO: 45). Each of these novel linkers was developed for potential use with I-CreI-derived single-chain meganucleases such as HBV 11-12L.1090. Similar to Linker1 in the parental HBV 11-12L.1090 meganuclease, the N-terminus of each novel linker was attached to N-terminal subunit at the D residue corresponding to position 153 of wild-type I-CreI, and the C-terminus of each novel linker was attached to C-terminal subunit at the Y residue corresponding to position 5 of wild-type I-CreI. Some variants comprising these novel linkers also comprised different combinations of amino acid modifications in the N-terminal and C-terminal subunits that were incorporated, in principle, to work in concert with the novel linker structures. These amino acid modifications were sorted into groups as shown in Table 2 below:

TABLE 2

| | Subunit Modification Groupings | |
|---|---|---|
| Mutation Group | Mutations within Subunit 1 (N-terminal) | Mutations within Subunit 2 (C-terminal) |
| 1 | K96A | K57Y, E61T |
| 2 | Q99A, K100D | |
| 3 | H37Y | W53F |
| 1 + 2 | K96A, Q99A, K100D | K57Y, E61T |
| 1 + 3 | H37Y, K96A | W53F, K57Y, E61T |
| 2 + 3 | H37Y, Q99A, K100D | W53F |
| 1 + 2 + 3 | H37Y, K96A, Q99A, K100D | W53F, K57Y, E61T |

The HBV 11-12L.1090 meganuclease variants prepared for this experiment are shown in Table 3 below:

TABLE 3

| Scaffold Nuclease | Linker | Subunit Modifications | SEQ ID NO: |
|---|---|---|---|
| HBV 11-12L.1090 | Linker1 | None | 13 |
| HBV 11-12L.1090 | Linker1923 | None | 46 |
| HBV 11-12L.1090 | Linker1923 | Group 1 | 47 |
| HBV 11-12L.1090 | Linker1923 | Group 2 | 48 |
| HBV 11-12L.1090 | Linker1923 | Group 3 | 49 |
| HBV 11-12L.1090 | Linker1923 | Group 1 + 2 | 5 |
| HBV 11-12L.1090 | Linker1923 | Group 1 + 3 | 50 |
| HBV 11-12L.1090 | Linker1923 | Group 2 + 3 | 51 |
| HBV 11-12L.1090 | Linker1923 | Group 1 + 2 + 3 | 52 |
| HBV 11-12L.1090 | Linker1766 | None | 53 |
| HBV 11-12L.1090 | Linker1766 | Group 1 + 2 | 54 |
| HBV 11-12L.1090 | Linker1766 | Group 1 + 2 + 3 | 55 |
| HBV 11-12L.1090 | Linker1771 | None | 56 |
| HBV 11-12L.1090 | Linker1771 | Group 1 + 2 | 57 |
| HBV 11-12L.1090 | Linker1771 | Group 1 + 2 + 3 | 58 |
| HBV 11-12L.1090 | Linker1808 | None | 59 |
| HBV 11-12L.1090 | Linker1808 | Group 1 + 2 | 60 |
| HBV 11-12L.1090 | Linker1808 | Group 1 + 2 + 3 | 61 |
| HBV 11-12L.1090 | Linker1814 | None | 62 |

TABLE 3-continued

| Scaffold Nuclease | Linker | Subunit Modifications | SEQ ID NO: |
|---|---|---|---|
| HBV 11-12L.1090 | Linker1814 | Group 1 + 2 | 63 |
| HBV 11-12L.1090 | Linker1814 | Group 1 + 2 + 3 | 64 |

The HBV 11-12L.1090 meganuclease and each meganuclease variant was evaluated for activity using a previously described CHO cell reporter assay (see, WO 2012/167192, which is incorporated by reference in its entirety). To perform the assays, CHO cell reporter lines were produced, which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene. In CHO reporter cell lines developed for this study, one recognition sequence inserted into the GFP gene was the human HBV 11-12 recognition sequence. The second recognition sequence inserted into the GFP gene was a CHO-23/24 recognition sequence, which is recognized and cleaved by a control meganuclease called "CHO-23/24."

CHO reporter cells were transfected with mRNA encoding individual clones isolated from the selections of the two libraries of meganucleases containing the two linker libraries. In 1 well out of 96, CHO reporter cells were also transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. The transfected CHO cells were evaluated by flow cytometry at 2 days post transfection to determine the percentage of GFP-positive cells compared to an untransfected negative control. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines ("normalized activity index").

2. Results

The activity results of each meganuclease variant, with the various linkers and combinations of subunit modifications, are shown in FIGS. 4A-4E. Each HBV 11-12L.1090 variant was evaluated at a low mRNA concentration (2.5 ng) due to the high level of activity of the parent meganuclease. It was observed that incorporating the different linkers alone had varying degrees of effect on activity of the meganuclease, and that various combinations of subunit modifications also resulted in differing levels of meganuclease activity.

For variants of HBV 11-12L.1090, it was observed that replacing the parental Linker1 with any of the five novel linkers, in the absence of any subunit modifications, resulted in a significant decrease in meganuclease activity (FIGS. 4A-4E). When incorporating Linker1923 (FIG. 4A), it was observed that the addition of the Group 1 subunit modifications enhanced activity to a level above that of the parental nuclease having Linker1. The addition of the Group 2 subunit modifications also enhanced activity to a lesser degree, while the addition of the Group 3 subunit modifications substantially suppressed activity. Incorporating the Group 1 and 2 subunit modifications (1+2) together produced the highest level of meganuclease activity, whereas with the Group 1 and 3 (1+3) and Group 1, 2, and 3 combinations (1+2+3) produced a slightly lower level of activity. By comparison, the addition of the Group 2 and 3 combination (2+3) exhibited suppressed activity, suggesting that in the absence of the Group 1 modifications, the Group 3 modifications act to suppress activity.

For the remaining novel linkers used with HBV 11-12L.1090, the only variants tested were novel linker with no modifications, a combination of the Group 1 and 2 modifications (1+2), and a combination of the Group 1, 2, and 3 modifications (1+2+3). Similar to Linker1923, all remaining linkers also exhibited reduced meganuclease activity relative to the parental linker when no subunit modifications are incorporated (FIGS. 4B-4E). Also similar to Linker1923, addition of the Group 1 and 2 modifications combination (1+2) improved activity to levels near (slightly higher or lower, or comparable to) the parent meganuclease activity. The combination of Group 1, 2, and 3 modifications produced variable changes in activity depending on the linker, with little change observed with Linker1766, and reductions of various degrees for Linker1771, Linker1808, and Linker1814.

3. Conclusions

It was observed in these studies that the activity of the HBV 11-12L.1090 meganuclease could be modulated by the use of novel linkers and various combinations of amino acid modifications within the N-terminal and C-terminal subunits. It was observed that incorporating Linker1923 with a combination of the Group 1 and Group 2 (1+2) subunit modifications produced the highest overall activity. Additionally, the combined Group 1 and 2 (1+2) modifications increased activity versus no modifications for nearly all of the linker combinations tested. Generally, incorporation of the Group 3 modifications suppressed activity, either alone or in combination with other group modifications. Based on its activity, the HBV 11-12L.1090 variant comprising Linker1923 and the Group 1+2 modifications was selected for further evaluation.

Example 2

Generation of Indels at the HBV 11-12 Recognition Sequence by HBV 11-12 Meganucleases Having Optimized Linker Sequences in HepG2-sAg Cells after Electroporation with HBV 11-12 mRNA 1. Methods HBV11-12 meganucleases are linked dimers. Linker1923 (SEQ ID NO: 15) was engineered to improve upon previously described HBV meganucleases, which contained the previous linker (Linker1) (SEQ ID NO: 16). In addition, amino acids within the nuclease backbone were modified to electrostatically interact with the new linker. The N-terminal subunit was modified to include an A at position 96, an A at position 99, and a D at position 100. The C-terminal subunit was modified to include an Y at a position corresponding to position 57 of SEQ ID NO: 1 (i.e., position 237 of SEQ ID NO: 5 or 6), and a T at a position corresponding to position 61 of SEQ ID NO: 1 (i.e., position 241 of SEQ ID NO: 5 or 6). Engineered meganucleases that include these modifications are denoted with "(1/2)" (i.e., having modifications in the first and second subunits). The original pRNA vector used as template for in vitro mRNA transcription (pRNA6) contained a HBA2 5' UTR, a WPRE 3' UTR and a single 5' SV40 nuclear localization signal (NLS; SEQ ID NO: 17).

The pRNA6 vector was modified to use untranslated regions (UTRs) optimized for liver expression (ALB 5' UTR, sequence set forth in SEQ ID NO: 18; and SNRPB 3' UTR, sequence set forth in SEQ ID NO: 19), an additional SV40 NLS (SEQ ID NO: 65) on the 3' end to facilitate nuclear import, and a stronger Kozak sequence (SEQ ID NO: 21). These modifications generated the pRNA8 vector. In conjunction with the pRNA8 vector, the meganuclease amino acid codon usage was modified to achieve maximum uridine depletion (MAX) to reduce immune responses and increase expression. The meganucleases assessed in this study are HBV11-12L.1090 pRNA8 MAX Linker1923(1/2) (SEQ ID NO: 5) and a previously generated meganuclease, HBV11-12L.1090 pRNA6 Linker1 (SEQ ID NO: 13) described in PCT International Patent Application Publication No. WO 2021/113765. This study was conducted to evaluate the efficacy of the described modifications within HBV11-12 meganucleases for causing insertions and/or deletions (indels) at their intended recognition sequence (i.e., the HBV 11-12 recognition sequence). Indel formation was detected in these experiments by digital PCR analysis.

To evaluate editing efficiency of the above mentioned HBV11-12 meganucleases to cleave an integrated hepatitis B sequence, we utilized an engineered HepG2 cell line (HepG2-sAg) containing a single integration of a partial HBV sequence. 1e6 HepG2-sAg cells were electroporated using the Lonza Amaxa 4D system with 100 ng, 10 ng or 1 ng of mRNA encoding the HBV11-12L.1090 pRNA6 Linker1 and HBV11-12L.1090 pRNA8 MAX Linker1923 (1/2) meganucleases. 100 ng of mCherry mRNA was included as a transfection control. Cells were collected at three- and six-days post transfection for genomic DNA extraction and evaluated for transfection efficiency using a Beckman Coulter CytoFlex S cytometer. Transfection efficiency exceeded 90%. Genomic DNA was prepared using the Macherey Nagel NucleoSpin Blood QuickPure kit.

Digital droplet PCR was utilized to determine the frequency of target indels at the HBV 11-12 binding site using primers F1 and R1 and probe P1 to generate an amplicon surrounding the binding site, as well as primers F2 and R2 and probe P2 to generate a reference amplicon. Amplifications were multiplexed in a 20 μL reaction containing 1×ddPCR Supermix for Probes (no dUTP, BioRad), 250 nM of each probe, 900 nM of each primer, 5 U of HindIII-HF, and ~50 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72° C. (2° C./s ramp) for 1.5 minutes, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive droplets for the binding site probe by the number of positive droplets for the reference probe. The sequences for the primers and probes used in this study are provided in the table below.

TABLE 4

Primer and probe sequences for Example 2

| Primer Identifier | SEQ ID NO: |
| --- | --- |
| P1: [5'-TGCCGATCCATACTGCGGAACT-3'] | 22 |
| F1: [5'-GGTCTGTGCCAAGTGTTTG-3'] | 23 |

TABLE 4-continued

Primer and probe sequences for Example 2

| Primer Identifier | SEQ ID NO: |
| --- | --- |
| R1: [5'-GCTGCGAGCAAAACAAG-3'] | 24 |
| P2: [5'-CCCGCCTGTAACACG-3'] | 25 |
| F2: [5'-CATCAGGATTCCTAGGACC-3'] | 26 |
| R2: [5'-AGTCCACCACGAGTCTA-3'] | 27 |

2. Results

Figure 5A:
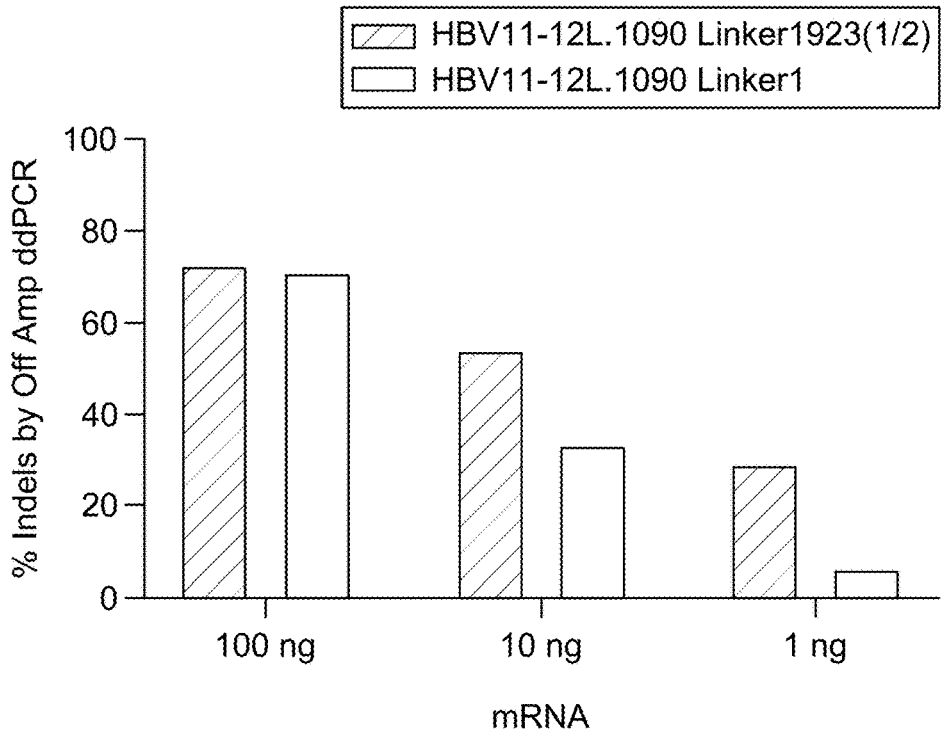
FIG. 5A-FIG. 5B. Provides a bar graph that shows indel formation by HBV 11-12L.1090QQ Linker1923(1/2) and HBV 11-12L.1090QQ Linker1 engineered meganucleases in HepG2-sAg cells at 2 days (FIG. 5A) and at 6 days (FIG. 5B).
Figure 5B:
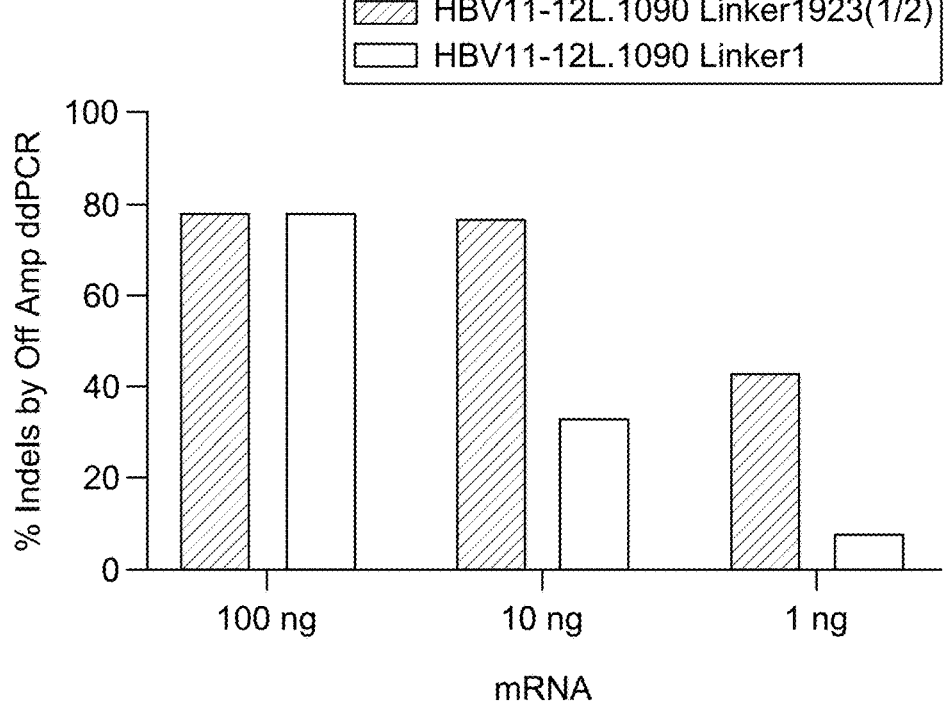

HBV11-12L.1090 pRNA6 Linker1 and HBV11-12L.1090 pRNA8 MAX Linker1923(1/2) were evaluated for on-target activity in HepG2-sAg cells. In combination, Linker1923(1/2) and pRNA8 vector with MAX codon usage greatly improve efficacy in HepG2-sAg cells at 2 days post transfection (FIG. 5A). By day 6, HBV 11-12L.1090 pRNA8 MAX Linker1923(1/2) achieved saturation at the 10 ng dose with 78% on-target editing compared to 33% editing with the previous construct (FIG. 5B). HBV11-12L.1090 MAX Linker1923(1/2) shows equivalent or increased on-target editing in all doses across both timepoints.

3. Conclusions

This data demonstrates that Linker1923 and associated modifications in the meganuclease backbone, in combination with the pRNA8 vector and maximal uridine depletion, give rise to higher editing rates of integrated hepatitis B sequence compared to the previously described engineered meganuclease HBV11-12L.1090 Linker1 using pRNA6.

Example 3

Generation of Indels at the HBV 11-12 Recognition Sequence by HBV 11-12 Meganucleases Having Optimized Linker Sequences in HepG2-sAg Cells after Electroporation with HBV 11-12 mRNA 1. Methods Studies were conducted to evaluate the efficacy of the structural modifications to the HBV 11-12L.1090 engineered meganuclease described in Examples 1 and 2 for generating indels at their intended recognition sequence (i.e., the HBV 11-12 recognition sequence). This study includes the same meganucleases as Example 2, HBV11-12L.1090 pRNA6 Linker1 and HBV11-12L.1090 pRNA8 MAX Linker1923(1/2) with the addition of a meganuclease using the pRNA8 vector with MAX codon usage with Linker1, HBV11-12L.1090 pRNA8 MAX Linker1 to specifically evaluate the editing efficiency of Linker1923 (and the accompanying subunit modifications) compared to Linker 1.

To evaluate editing efficiency of an HBV11-12 meganucleases to an integrated hepatitis B sequence, we electroporated 1e6 HepG2-sAg cells using the Lonza Amaxa 4D system with 100 ng or 10 ng of mRNA encoding the HBV11-12 L.1090 pRNA6 Linker1, HBV11-12 L.1090 MAX Linker1, or HBV11-12 L.1090 MAX Linker1923(1/2) engineered meganuclease or an mCherry control. Cells were collected at two- and six-days post transfection for genomic DNA extraction and evaluated for transfection efficiency using a Beckman Coulter CytoFlex S cytometer. Transfection efficiency exceeded 90%. Genomic DNA was prepared using the MagMax DNA Multi-Sample Ultra 2.0 kit with the KingFisher Apex. Digital droplet PCR was performed according to Example 2.

2. Results

Figure 6:
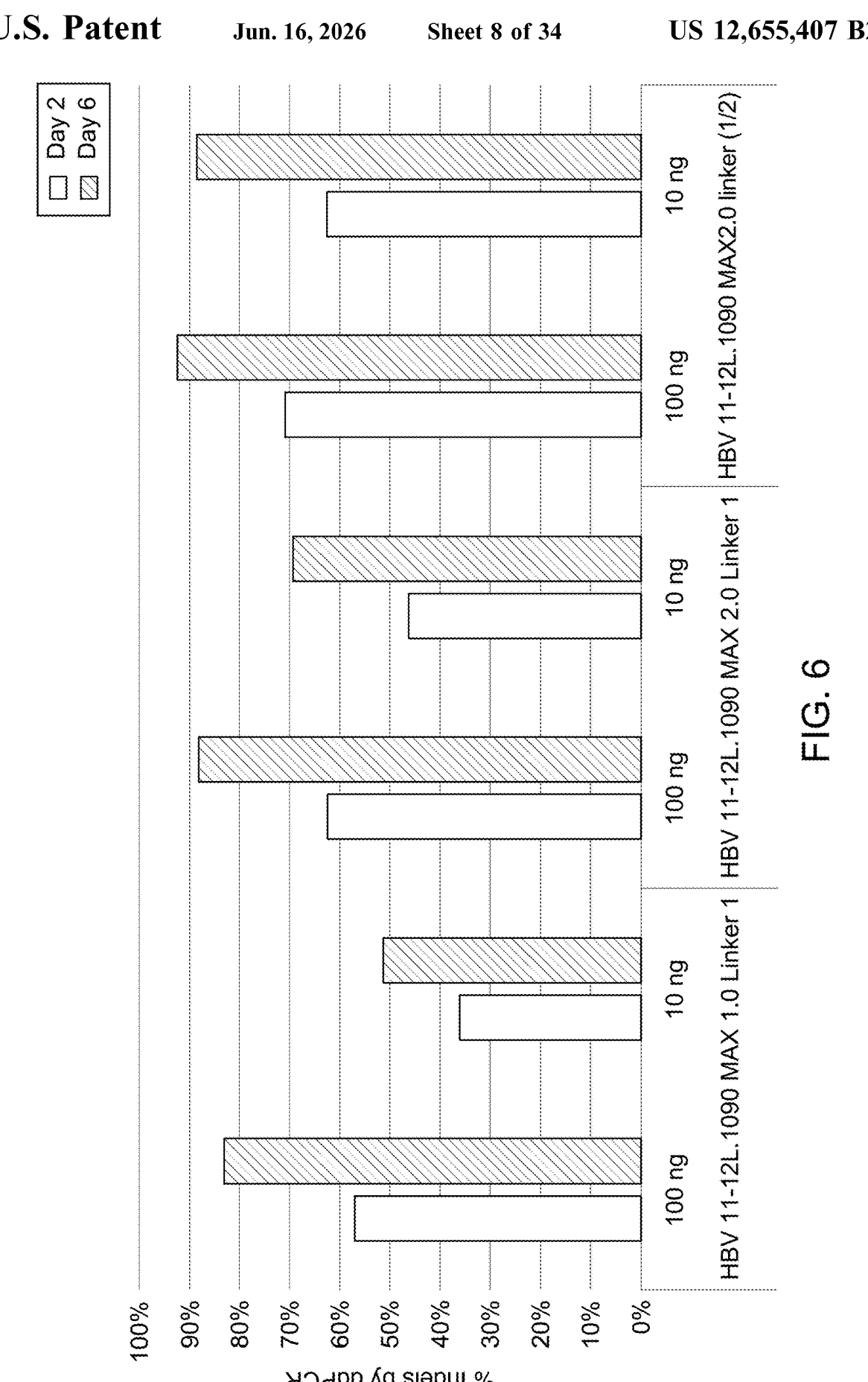
FIG. 6. Provides a bar graph that shows the percentage indels by ddPCR at day 2 and day 6 at a 100 ng and 10 ng dosage of the HBV11-12L.1090 meganuclease having either Linker 1 or Linker 1923. Meganucleases that have the Max 1.0 denotation utilized the pRNA6 vector and do not include uridine depletion in the RNA coding sequence and those that contain Max 2.0 utilized a pRNA8 vector that did include uridine depletion.

The HBV11-12L.1090 pRNA6 Linker1, HBV11-12L.1090 pRNA8 MAX Linker1, HBV11-12L.1090 pRNA8 MAX Linker 1923(1/2) meganucleases were evaluated for on-target activity in HepG2-sAg cells. The pRNA8 vector with MAX codon usage in combination with Linker1 or Linker1923 improved efficacy in HepG2-sAg cells. By day 6 at the 10 ng dose, HBV 11-12L.1090 MAX Linker1923(1/2) (denoted as "HBV 11-12L.1090 MAX2.0/ linker (1/2)") achieved 88% on-target editing compared to 51% editing by HBV11-12L.1090 pRNA6 Linker1 (denoted as "HBV 11-12L.1090 MAX1.0 Linker 1") and 69% editing by HBV 11-12L.1090 MAX that comprised Linker1 and no subunit modifications (denoted as "HBV 11-12L.1090 MAX 2.0 Linker 1") (FIG. 6).

3. Conclusions

These data demonstrate that pRNA8 vector modifications with MAX codon usage in conjunction with Linker1923 increase editing rates of an integrated hepatitis B sequence by the HBV11-12L.1090 meganuclease compared to the previously described engineered meganuclease, HBV11-12L.1090 pRNA6 Linker1, and that Linker1923 and associated changes to the meganuclease backbone further increases editing.

Example 4

Generation of Indels at the HBV 11-12 Recognition Sequence and HBV Surface Antigen Inhibition by HBV 11-12 Meganucleases Having Optimized Linker Sequences and Additional Structural Modifications in HepG2-sAg Cells 1. Methods An amino acid substitution from glutamine (Q) to glutamic acid (E) in the C-terminal subunit at a position corresponding to position 80 of I-Cre was made to determine if specificity of the HBV11-12L.1090 meganuclease could be improved. Variants generated from this substitution will subsequently be referred to as having a "QQ" to denote the presence of a Q in each subunit at a position corresponding to position 80 of I-CreI, or having a "QE" to denote the modification in the C-terminal subunit to an E at a position corresponding to position 80 of I-CreI (i.e., at position 260 of SEQ ID NO: 5 or 6). This study investigated how this substitution may affect the indel formation and HBV surface antigen (HBsAg) inhibition of the HBV11-12L.1090 meganuclease comprising either Linker1 or Linker1923 and the (1/2) modifications. Thus, variants evaluated in this study are referred to as HBV11-12L.1090QQ Linker1 (SEQ ID NO: 13), HBV11-12L.1090QQ Linker1923(1/2) (SEQ ID NO: 5), HBV11-12L.1090QE Linker1 (SEQ ID NO: 14), and HBV11-12L.1090QE Linker1923(1/2) (SEQ ID NO: 6). All meganucleases in this study used the pRNA8 vector with MAX codon usage. HBsAg is one of the main viral components of the envelope for infectious HBV that can be derived from cccDNA or integrations of HBV DNA in the genome. Sustained reduction of HBsAg is an important clinical endpoint for treatment of HBV disease. The engineered HepG2-sAg cells have a single integration of a partial HBV genome that contains the HBsAg ORF, which results in expression and secretion of HBsAg.

HepG2-sAg cells were electroporated according to Example 2 with 100 ng, 10 ng or 1 ng of mRNA encoding the four meganuclease variants, HBV11-12L.1090QQ Linker1, HBV11-12L.1090QQ Linker1923(1/2), HBV11-12L.1090QE Linker1, and HBV11-12L.1090QE Linker1923(1/2) or an mCherry control. Cells and supernatant were collected on day 2, 6 and 9 post-electroporation. Transfection efficiency was evaluated at 98%. Genomic DNA was isolated from cells using the MagMax DNA Multi-Sample Ultra 2.0 kit with the KingFisher Apex. This experiment was done in duplicate for increased strength in the study.

To assess percent indel formation, digital droplet PCR was performed in a similar approach to Example 2 with variations in the primers, probes and cycling conditions used. Cycling conditions were as follows: 1 cycle of 95° C. (0.2° C./s ramp) for 10 minutes, 45 cycles of 94° C. (0.2° C./s ramp) for 10 seconds, 61.1° C. (0.2° C./s ramp) for 30 seconds, 72° C. (0.2° C./s ramp) for 2 minutes, 1 cycle of 98° C. for 10 minutes, 4° C. hold. The sequences for the primers and probes used in this study are provided in the table below.

TABLE 5

Primer and probe sequences for Example 4

| Primer Identifier | | SEQ ID NO: |
|---|---|---|
| P1: | [5'-TGCCGATCCATACTGCGGAACT-3'] | 22 |
| F1: | [5'-GGTCTGTGCCAAGTGTTTG-3'] | 23 |
| R1: | [5'-GTATATTTCCGCGAGAGGAC-3'] | 28 |
| P2: | [5'-CTTGGCCCCCAATACCACATCATC-3'] | 29 |
| F2: | [5'-GGATGGAAATTGCACCTGTATTC-3'] | 30 |
| R2: | [5'-GGGTTTAAATGTATACCCAGAGAC-3'] | 31 |

To assess reduction of secreted HBsAg in cell supernatants, an HBsAg-specific chemiluminescence immunoassay (CLIA) from AutoBio was used according to the manufacturer's instructions. Luminescence was read using a SpectraMax i3× microplate reader. The amount of HBsAg (IU/ mL) was calculated based on a real-time calibration curve.

2. Results

Figures 7A, 7B:
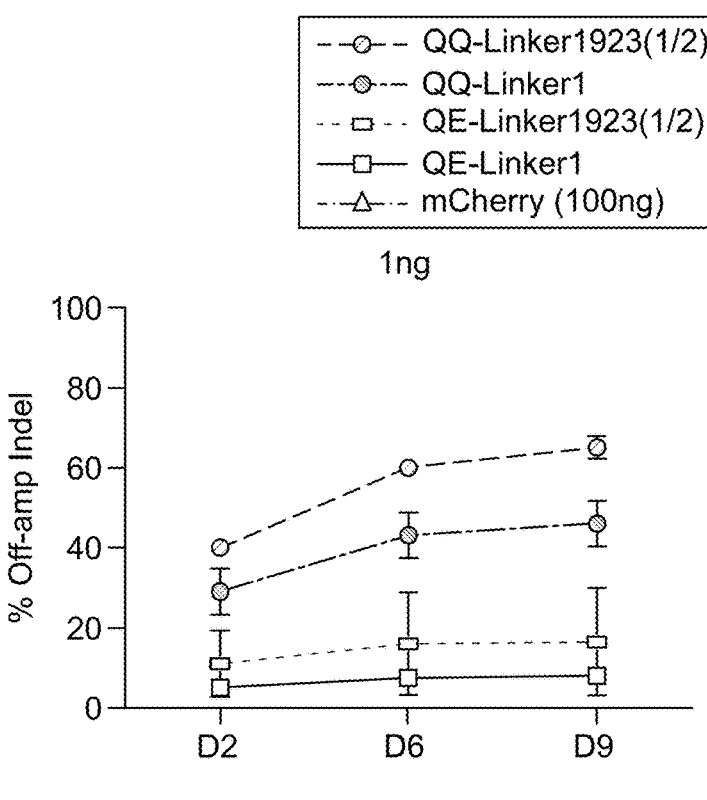
FIG. 7A-FIG. 7F. Provides line graphs showing the percentage of indels and HBsAg inhibition for the indicated meganucleases at D2, D6, and D9 post transfection at either a 1 ng, 10 ng, or 100 ng dosage. In each figure, four different meganucleases were tested. The first meganuclease was an HBV 11-12L.1090 meganuclease with the linker 1923 labeled as QQ-Linker1923(1/2). The second tested meganuclease was an HBV11-12L.1090 meganuclease with Linker1 labeled as QQ-Linker 1. The third tested meganuclease was the HBV11-12L.1090 meganuclease with a glutamine (Q) to glutamic acid (E) mutation at a position corresponding to position 80 of I-CreI in the C-terminal subunit with Linker1923 denoted as QE-Linker 1923(1/2). The fourth tested meganuclease was the HBV11-12L.1090 meganuclease with the same QE mutation but with Linker1 denoted as QE-Linker 1. An mCherry control is also shown at a 100 ng transfection dosage.
Figure 7C:
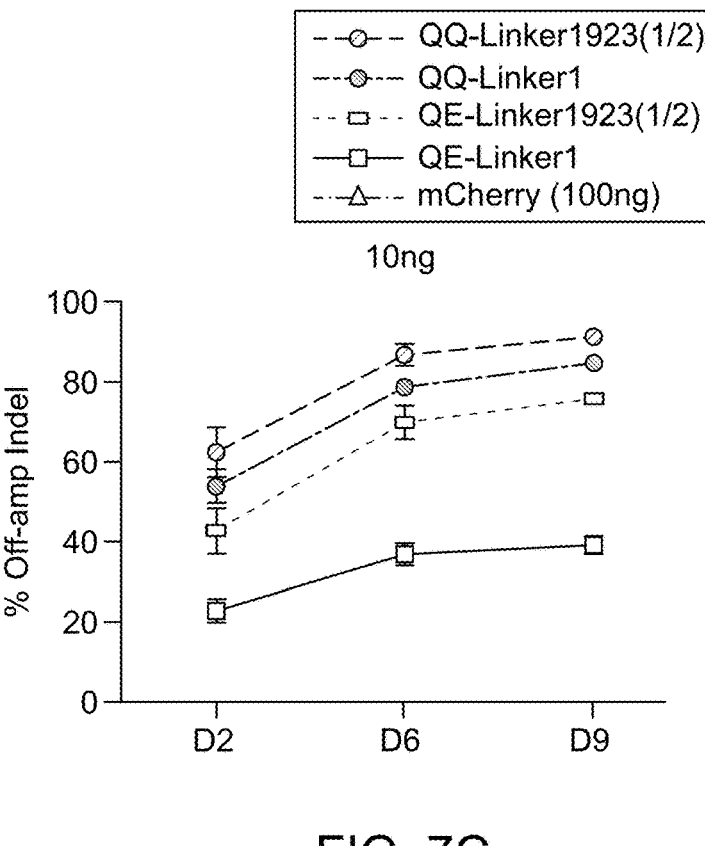
Figure 7D:
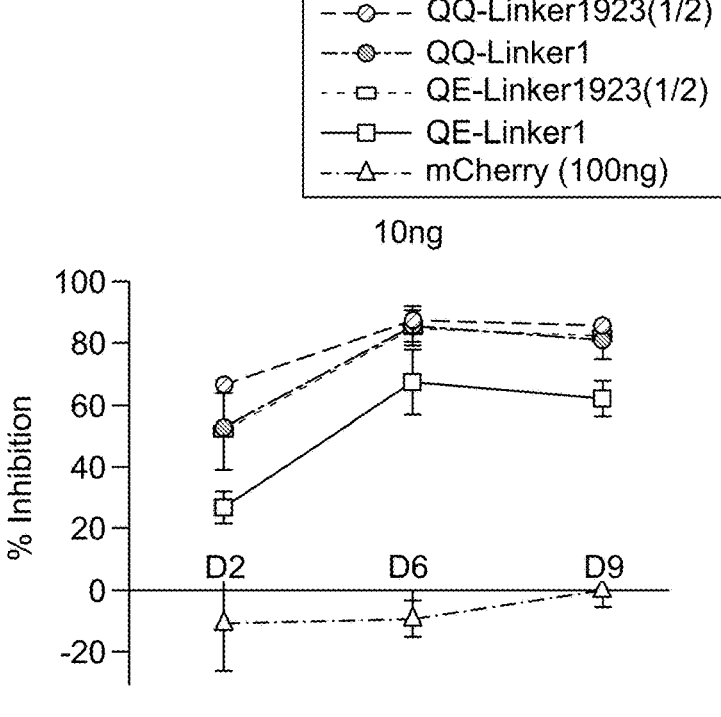
Figure 7E:
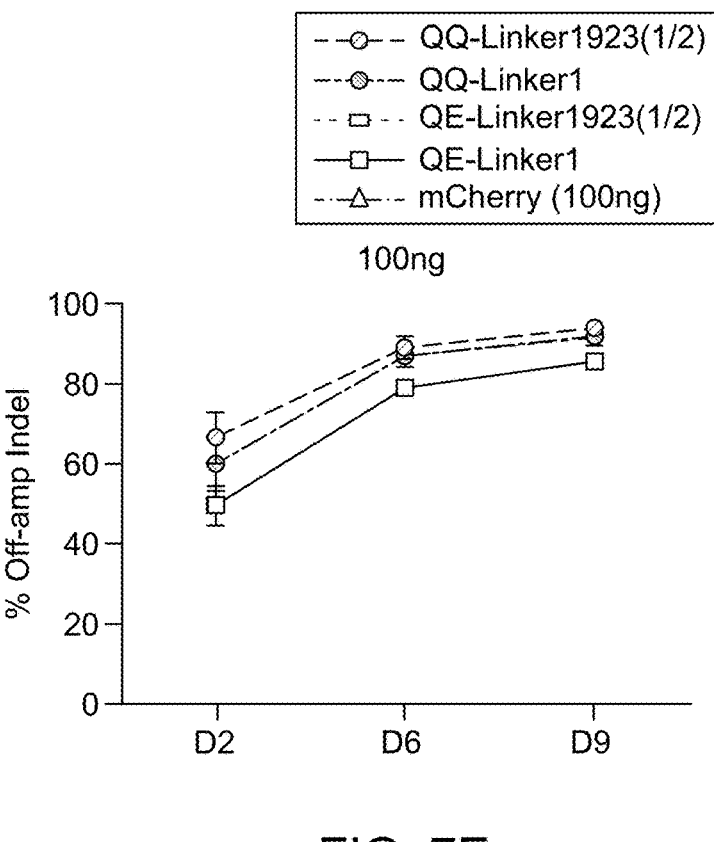
Figure 7F:
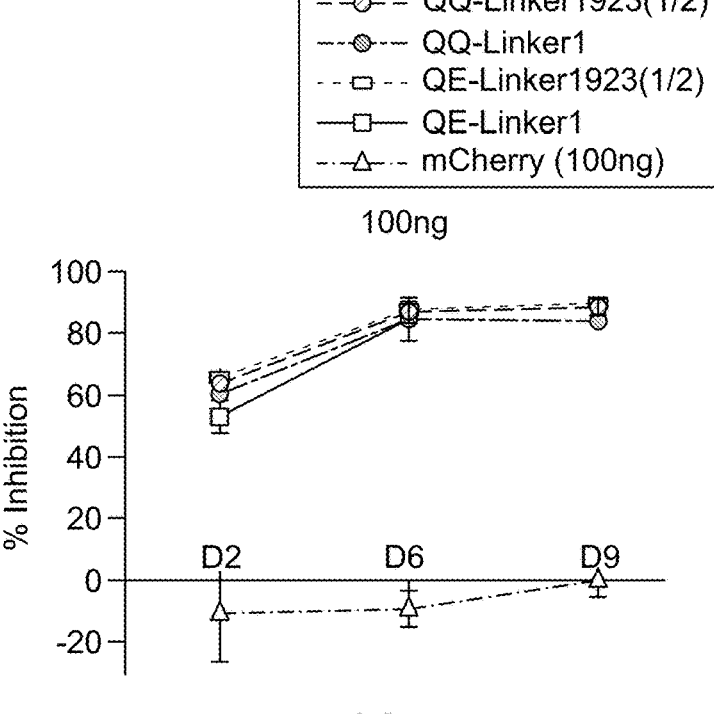

The QQ and QE variants were evaluated for indel formation and HBsAg reduction with Linker1 or Linker1923 and the (1/2) subunit modifications at three different dosages shown in FIG. 7A-FIG. 7F. Average indels at day 9 post-transfection increased from 46% with Linker1 to 65% with Linker1923(1/2) at the 1 ng dose with the QQ variant (FIG. 7A). Using the same conditions, an increase from 8% to 16.5% average indels was observed for the QE variant (FIG. 7A). A similar trend was observed at the higher 10 ng and 100 ng dosages as shown in FIG. 7C and FIG. 7E. Consistent with the indel results, the meganucleases with the linker 1923 (1/2) demonstrated higher levels of HBsAg inhibition in both the QQ and QE variants as shown in FIG. 7B at the 1 ng dose. Maximal HBsAg reduction of 90% was achieved by day 9 post-transfection using 10 ng of mRNA for both QQ and QE variants using Linker1923(1/2) (FIG. 7D). At a saturating dosage, all of the meganucleases performed similarly in reducing HBsAg as shown in FIG. 7F.

3. Conclusions

Use of Linker1923 with the (1/2) subunit modifications improved editing and HBsAg inhibition across all doses and timepoints for both variants. The QE variant is less potent than the QQ variant at creating indels at mid-low doses; however, at high doses a comparable potency is achieved, especially in variants containing Linker1923(1/2). HBsAg inhibition is equivalent in both variants with Linker1923(1/2) in mid-high doses.

Example 5

Generation of Indels at the HBV 11-12 Recognition Sequence and HBV sAG Inhibition by HBV 11-12 Meganucleases in HepG2-sAg Cells

1. Methods

The $EC_{50}$ and $EC_{90}$ are measures used to quantify the 50% of maximal effective concentration and 90% of maximal effective concentration of a particular drug or, as described herein, a meganuclease. The purpose of this study was to determine $EC_{50}$ and $EC_{90}$ of the HBV11-12L.1090QQ Linker1923(1/2) and HBV11-12L.1090QE Linker1923(1/2) meganucleases. Both meganucleases assessed in this study use pRNA8 and MAX codon usage. HepG2-sAg cells were electroporated according to Example 2 with a 1:2 serial dilution 20-point or 16-point dose curve of mRNA encoding HBV11-12L.1090QQ Linker1923(1/2) or HBV11-12L.1090QE Linker1923(1/2), respectively. Cells and supernatant were collected on day 2 post-transfection. Transfection efficiency was evaluated at 97%. Genomic DNA was isolated using the Macherey Nagel NucleoSpin Blood QuickPure kit. Percent indel formation was evaluated according to digital droplet PCR protocol used in Example 4. HBsAg levels were quantified according to the protocol described in Example 4. HBsAg CLIA samples were run in duplicate on the same plate. $EC_{50}$ and $EC_{90}$ concentrations were calculated from these dose-response curves using GraphPad Prism's Find ECAnything model with F constrained to 50 and 90, respectively.

2. Results

The QQ and QE variants with Linker1923 with the (1/2) subunit modifications were assessed for on-target editing at the HBV 11-12 recognition site and resulting HbsAg reduction in cell medium. Percent indel formation increased in a dose-dependent manner for both variants. Both variants achieved maximal percent indel formation of 70%, however the QE variant required a higher dose mRNA to achieve the same results (100-200 ng compared to 10 ng) (FIG. 8A). For the percentage of indel formation, the QQ variant was calculated to have an $EC_{50}$ of 0.26 ng and $EC_{90}$ of 4.93 ng of mRNA and the QE variant was calculated to have an $EC_{50}$ of 2.3 ng and $EC_{90}$ of 23.93 ng of mRNA. HbsAg levels decreased in a dose-dependent manner at low mRNA doses and then plateaued at 10 ng of mRNA for both variants tested (FIG. 8B). For the percentage of HbsAg inhibition, the QQ variant was calculated to have an $EC_{50}$ of 0.49 ng and $EC_{90}$ of 7.723 ng of mRNA and the QE variant was calculated to have an $EC_{50}$ of 1.17 ng and $EC_{90}$ of 7.89 ng of mRNA.

3. Conclusions

Equivalent maximal HBsAg reduction is achieved with both QQ and QE variants using Linker1923 with the (1/2) subunit modifications at the same dose. Both variants reach comparable peak on-target editing in HepG2-sAg cells at high doses of mRNA. The QE variant is less potent than the QQ variant; with the $EC_{50}$ and $EC_{90}$ of indel formation for the QE variant being about 10 times and 5 times higher, respectively, than the QQ variant.

Example 6

Off-Targeting Analysis of HBV 11-12 Meganucleases in Hep3B Cells

1. Methods

In these studies, an oligo capture assay was used to identify off-target cutting induced by the HBV11-12L.1090QQ MAX Linker1923(1/2) and HBV11-12L.1090QE MAX Linker1923(1/2) meganucleases. Off-target cutting was assessed in Hep3B cells, an HCC cell line with multiple hepatitis B integrations.

Similar to GUIDE-seq, the oligo capture assay identifies potential off-target sites produced by the HBV 11-12 meganucleases by capturing an oligonucleotide at break sites within the cell's genomic DNA. GUIDE-seq was developed for CRISPR-Cas9 generated DNA breaks and there are a few key modifications to the chemistry and analysis in order to apply this technique to the present nucleases. Unlike CRISPR-Cas9, the engineered meganucleases disclosed herein generate a four base pair 3' overhang. To accommodate for this difference, the oligonucleotides used in oligo capture have randomized four base pair overhangs that could be compatible with the overhangs generated with the HBV 11-12 meganuclease. A higher frequency of insertion is observed due to the greater efficiency of ligating sticky ends rather than blunt ends. Cells were transfected with 2000 ng of mRNA encoding the nuclease and 250 ng of the double stranded DNA oligonucleotides. After two days, the genomic DNA from these cells was isolated and sonicated to shear the DNA to smaller sizes. An oligonucleotide adapter was ligated to the sheared DNA and PCR was used to amplify any DNA pieces that contain an adapter at one end and the captured oligonucleotide at the other end. The amplified DNA was purified and sequencing libraries were prepared using standard commercial kits.

Sequencing libraries were run on an Illumina MiSeq using V2 2×150 kits. The data was filtered and analyzed for valid sites that captured an oligonucleotide and a potential off-target site is predicted. Here again, the protocol needed to be adjusted from the PAM search used for CRISPR-cas9 to the HBV 11-12 meganuclease search. The software developed checks each sequence to make sure there is an adapter and captured oligo flanking the sequence to verify that it is a valid read. The software also checks for PCR duplicates and removes reads that are identical to help reduce PCR bias. The sequence reads are aligned to a reference genome and grouped sequences within thousand base pair windows are scanned for a potential HBV 11-12 meganuclease site.

Each HBV 11-12 meganuclease is a linked dimer. Each monomer recognizes a nine base pair half site with a four base pair spacer in the center between the two half sites. The software looks for the closest sequence match for each half site with no allowed gaps. The middle four base pairs are not considered in the off-target selection because the HBV 11-12 meganucleases can generally tolerate a higher amount of degeneracy at these positions in the target site. The software outputs a list of potential off-target sites with the number of base mismatches in the combined half sites but not counting the middle four base pair mismatches. The software does not eliminate any off-targets based on an arbitrary mismatch filter, unlike CRISPR-Cas9 which eliminates any off-target identified with more than six base pairs mismatched. Instead, background noise generated from random capture of the oligo at fragile spots or hot spots within the genome can be reduced in two ways. First, an untreated mock sample is also run though oligo capture and windows of integration sites without the nuclease present can be subtracted from the nuclease containing samples. Running the assay in triplicate and eliminating any sites that do not repeat in at least two of the three repeats is a way to empirically remove random integration noise.

Figure 9:
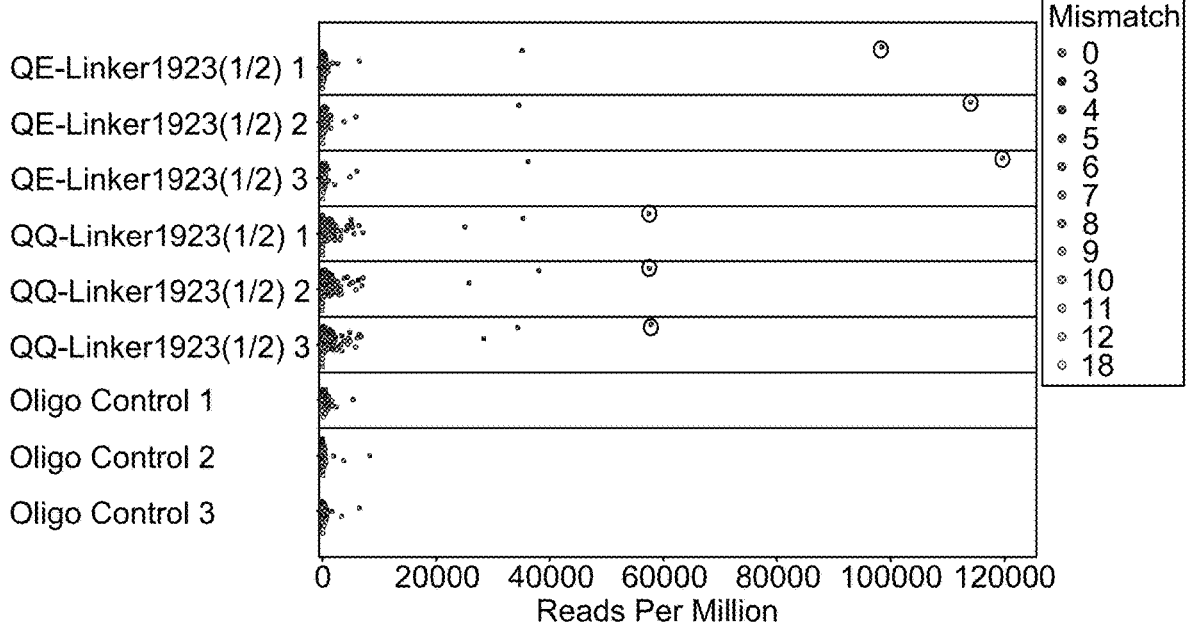
FIG. 9. Provides a graph depicting results from an oligo capture assay to identify off target cutting induced by the HBV11-12L.1090 QE-Linker1923(1/2) meganuclease (labelled as QE-Linker1923(1/2)), the HBV11-12L.1090 QQ-Linker1923(1/2) meganuclease (labelled as QQ-Linker1923(1/2)), or an oligo control. The experiment was done in triplicate and the circled dots indicate the on-target site.

Although read count does not directly correlate with cutting frequency at a particular site, it can generally highlight off-targets that are potentially more concerning or more valid because they occur more often. One way to graphically visualize the oligo capture data as a measure of number of potentially valid off-target sites is shown in FIG. 9. Each off-target generated by a particular nuclease is plotted based on the number of unique sequence reads aligned at that site. The number of base pair mismatches between the putative off-target site and the intended site are indicated by color scale with darker colors indicating sites that are more similar to the intended target site (circled dots). For a meganuclease with high-specificity, the intended site should have the highest read count. Better meganucleases remove both the higher count sites (to the right of the graph) and the sites with high similarity (darker colored points).

2. Results

In FIG. 9, HBV11-12L.1090QQ MAX Linker1923(1/2) and HBV11-12L.1090QE MAX Linker1923(1/2) were compared in the Hep3B cell line in triplicate. While the number of reads aligned at the intended site cannot be compared between samples as a measure of total activity at the intended site, the distance between the points indicating the intended site (circled dots) and the points indicating off-target sites can be compared. The far larger distance between the intended site and the off-target sites for HBV11-12L.1090QE MAX Linker1923(1/2) than that of HBV11-12L.1090QQ MAX Linker1923(1/2) indicates a large increase in the specificity of the enzyme and a large decrease in cleavage of off-target sites both in number of sites and percentage cleaved. In all cases, the intended target site was the most frequently recovered. HBV11-12L.1090QE MAX Linker1923(1/2) exhibited one potential off-target site above background compared to two sites with HBV11-12L.1090QQ MAX Linker1923(1/2).

3. Conclusions

Although the HBV11-12L.1090QE MAX Linker1923(1/2) meganuclease exhibited a higher $EC_{50}$ and $EC_{90}$ of indel formation (as described in Example 5) than HBV11-12L.1090QQ MAX Linker1923(1/2), these studies demonstrate that the substitution of Q to E at position 260 in the C-terminal subunit (corresponding to position 80 of I-CreI) conferred a higher specificity for the HBV11-12 recognition site compared to HBV11-12L.1090QQ MAX Linker1923(1/2). Thus, the balance of on-target activity and specificity observed with the HBV11-12L.1090QE MAX Linker1923(1/2) meganuclease makes it well-suited for further evaluation.

Example 7

HBV 11-12 Engineered Meganuclease Specificity Data

1. Methods

To further evaluate off-target editing, mRNA encoding the HBV11-12L.1090QQ Linker1, HBV11-12L.1090QQ Linker1923(1/2) or HBV11-12L.1090QE Linker1923(1/2) meganuclease was delivered to HepG2-sAg cells via electroporation and naïve cryopreserved primary human hepatocytes (PHHs) via Lipofectamine MessengerMax transfection (ThermoFisher). mRNA doses tested for off-targeting in HepG2-sAg cells were a limited dose curve of 100 ng, 10 ng, and 1 ng as well as the $EC_{50}$ and $EC_{90}$ for the variants with Linker1923 with the (1/2) subunit modifications. mRNA doses tested in PHHs were 500 ng, 50 ng, and 5 ng. HepG2-sAg cells were collected at two days and six days post-transfection and PHHs were collected six days post-transfection. Transfection efficiency was evaluated in HepG2-sAg cells using a Beckman Coulter CytoFlex S cytometer. Transfection efficiency exceeded 90%. Genomic DNA from both cell types was prepared using the Macherey Nagel NucleoSpin Blood QuickPure kit.

A multiplex targeted amplicon (MTA) sequencing panel was conducted on collected HepG2-sAg cells and PHH cells to evaluate and confirm whether off-target editing occurred at genomic sites identified in an oligo capture assay performed in triplicate on the mRNA-electroporated HepG2-sAg cells (as described in Example 6) and at genomic sites identified through an in-silico search that identified 4 or fewer basepair mismatches. MTA sequencing allows for highly sensitive quantification of off-target editing activity relative to mock-transfected cells. The MTA assay amplifies multiple target sequences in a single reaction using Integrated DNA Technologies' (IDT) rhAmpSeq custom amplicon panels.

2. Results

Figure 10A:
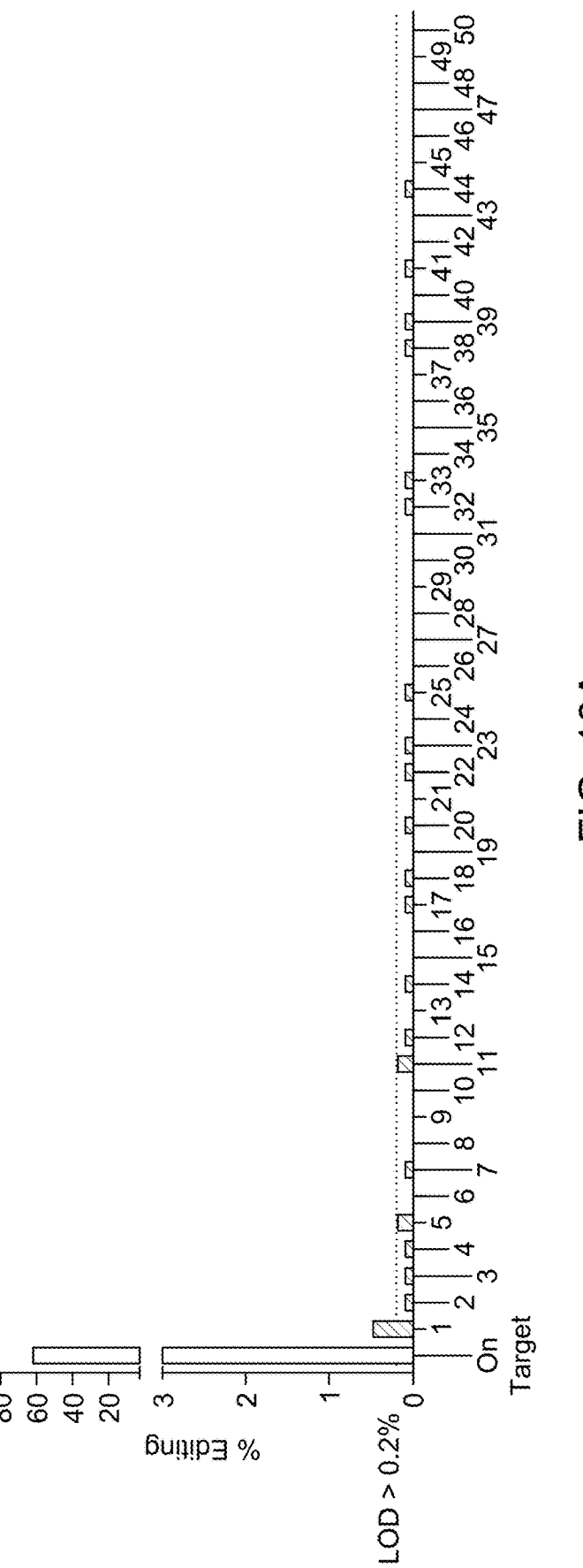
FIG. 10A-FIG. 10D. Provides bar graphs showing the results of an MTA assay run from HepG2-sAg cells transfected with the indicated meganucleases.
Figure 10B:
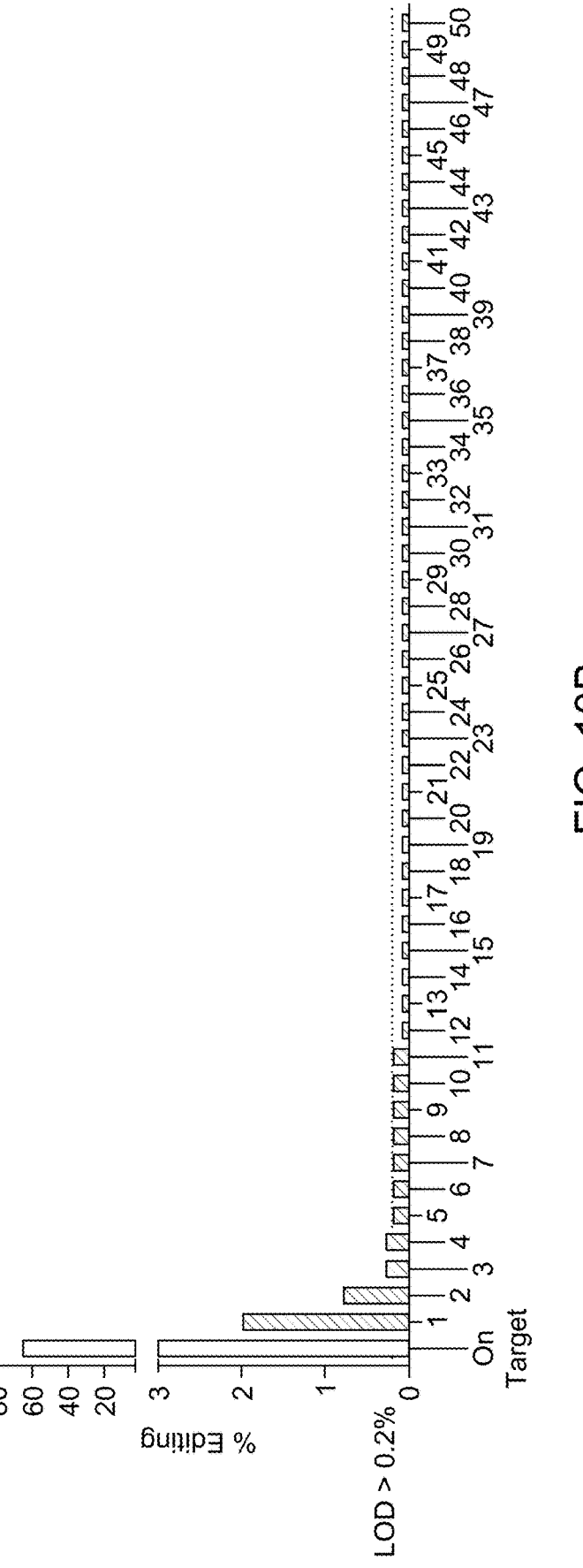
Figure 10C:
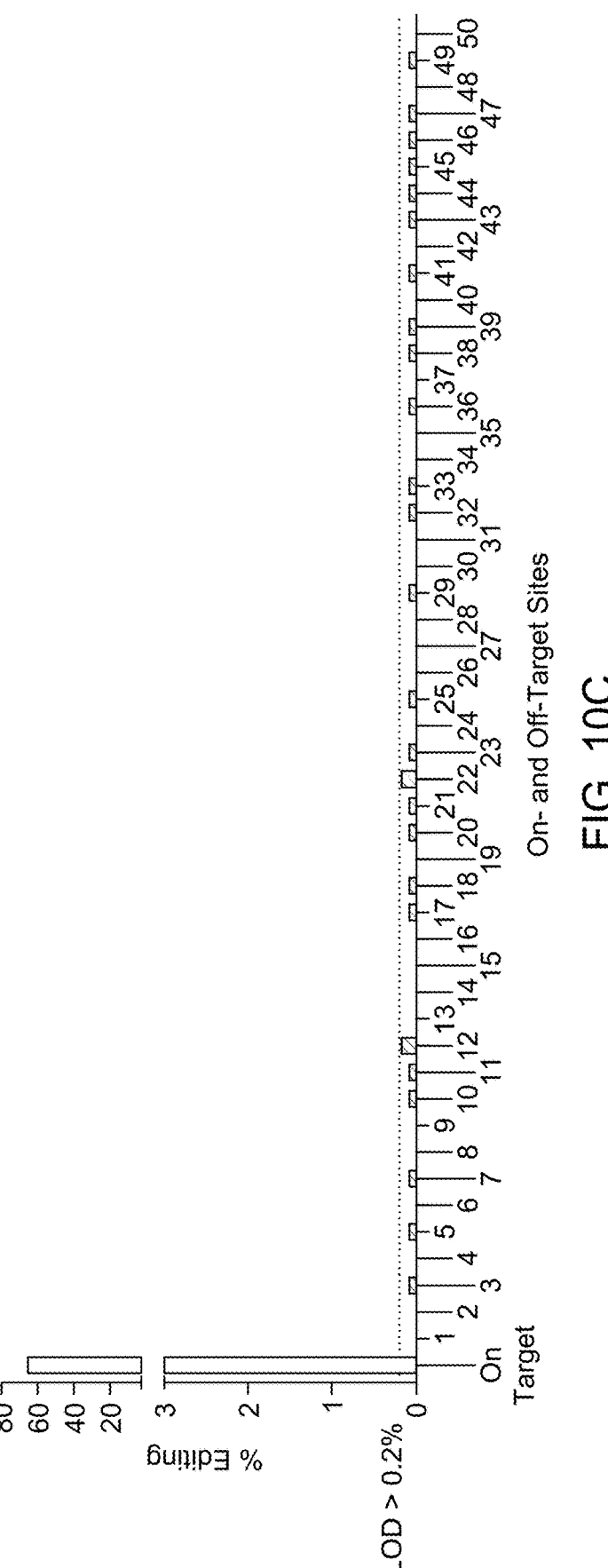
Figure 10D:
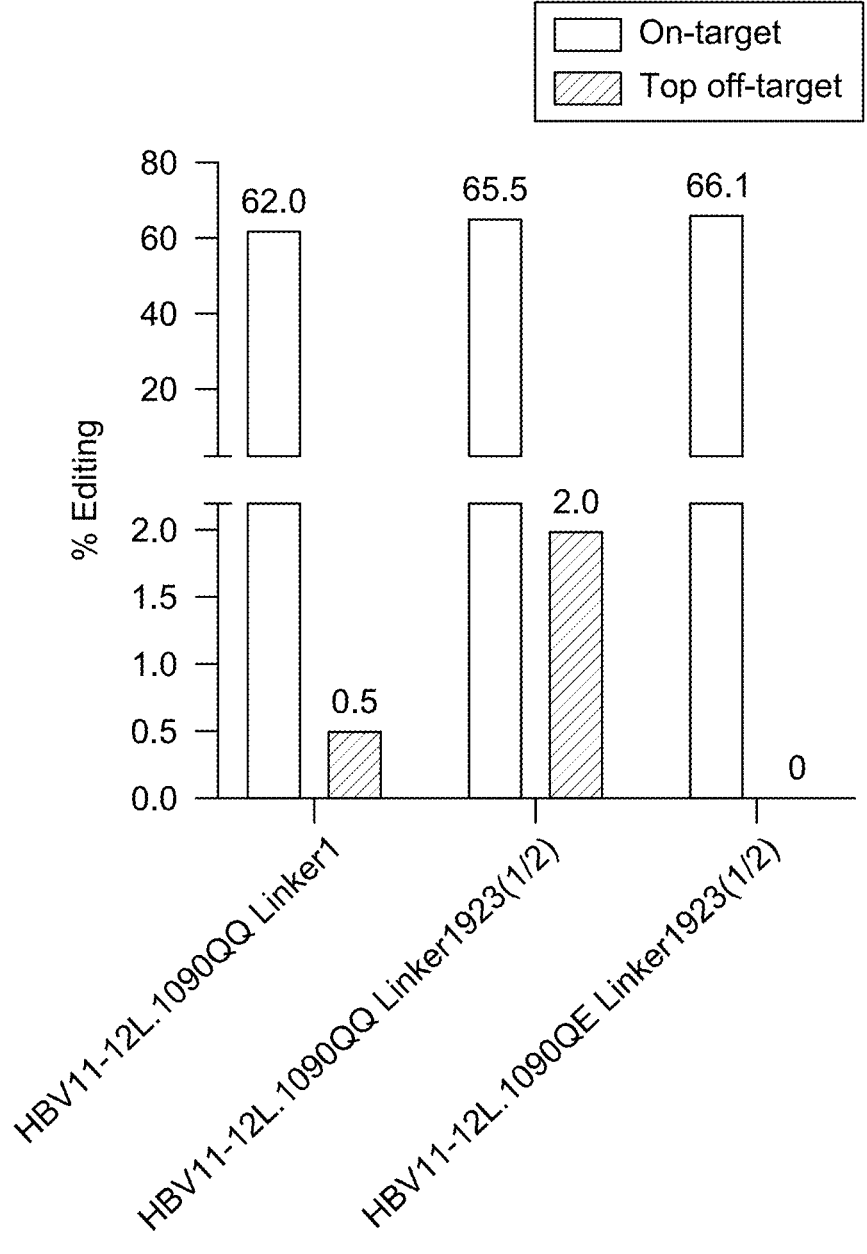

The QQ variant with Linker1, the QQ variant with Linker1923 with the (1/2) subunit modifications (i.e., QQLinker1923(1/2)), and the QE Linker1923(1/2) variant were each evaluated in HepG2-sAg cells and naïve PHHs for off-target editing using the above-described MTA panel. All variants achieved around 60% on-target editing in HepG2-sAg cells at 100 ng dose of mRNA (FIG. 10A-10C). The QE variant shown in FIG. 10C displays a large decrease in off-target sites compared to the QQ Linker1 variant shown in FIG. 10A and QQ Linker1923(1/2) in FIG. 10B. No off-target sites appeared above the limit of detection (0.2%) in HepG2-sAg cells treated with QE Linker1923(1/2) (FIG. 10C) whereas the QQ variants showed up to 10 times more off-target editing (0.2-2%) (FIGS. 10A and 10B). At 100 ng dose of mRNA, the top off-target site across all nucleases (Chr. 17; Pos. 17242769) showed no editing in the QE Linker1923(1/2) variant and 0.5% and 2% editing in the QQ Linker1 and QQ Linker1923(1/2) variants, respectively (FIG. 10D).

Figure 11A:
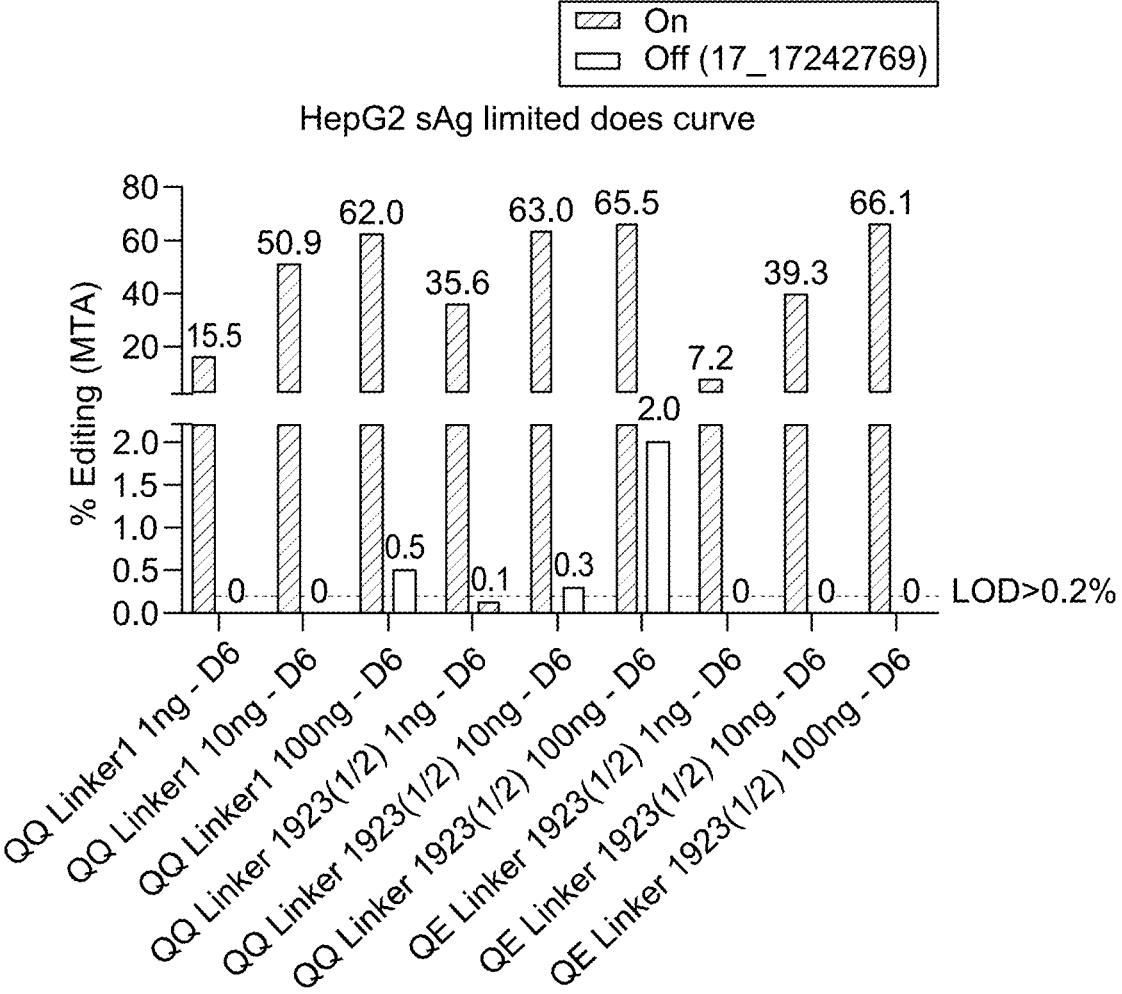
FIG. 11A-FIG. 11C. Provides bar graphs showing the results of an MTA assay run from HepG2sAg or naïve PHH cells transfected with the HBV 11-12L.1090QQ Linker1 (labelled as QQ Linker1), the HBV11-12L.1090QQ Linker1923(1/2) (labelled as QQ Linker 1923(1/2), or the HBV11-12L.1090QE Linker1923(1/2) (labelled as QE Linker 1923(1/2)) meganuclease and the percentage of editing at either the on target site (black bars) or off target sites (gray bars).
Figure 11B:
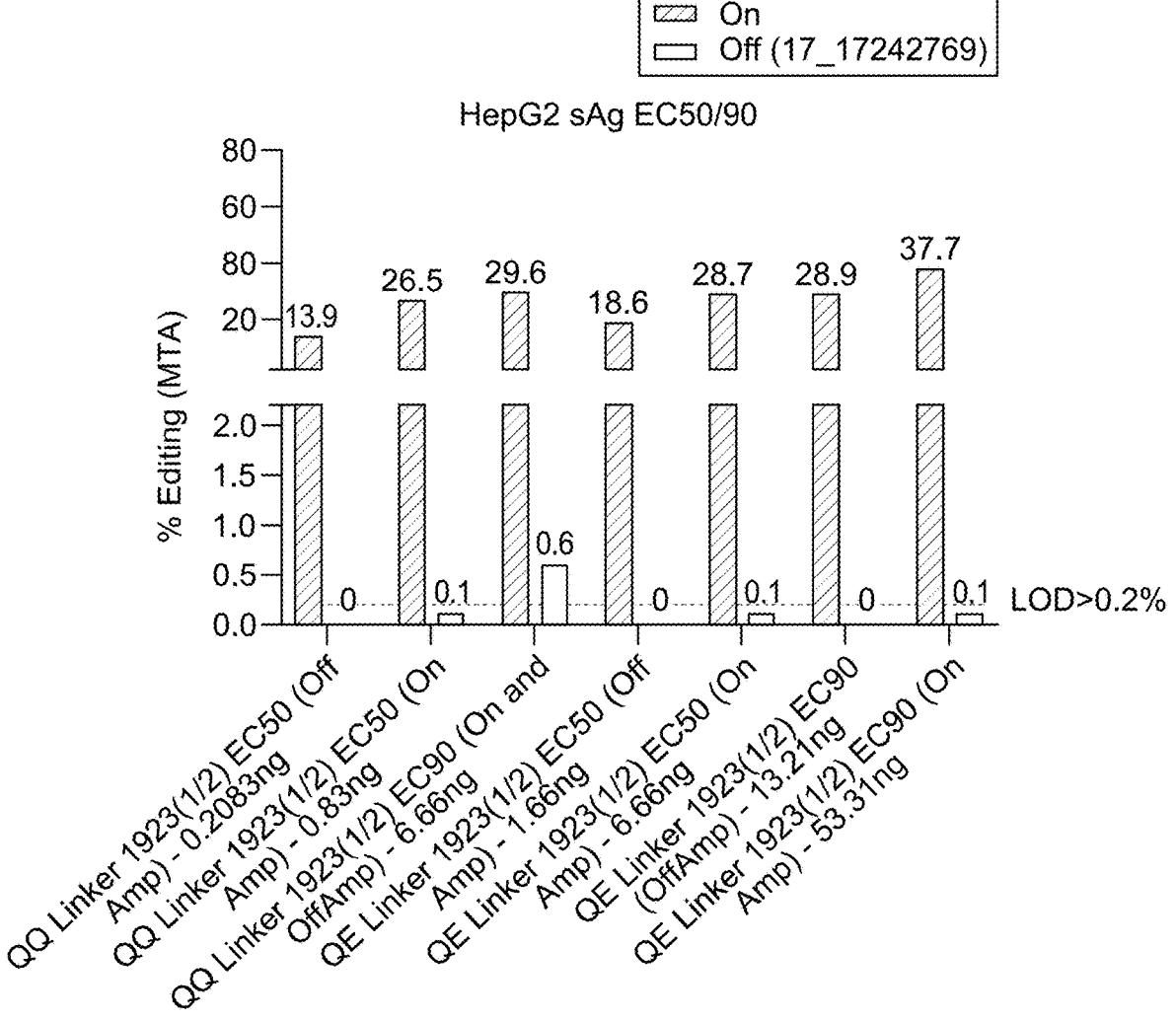
Figure 11C:
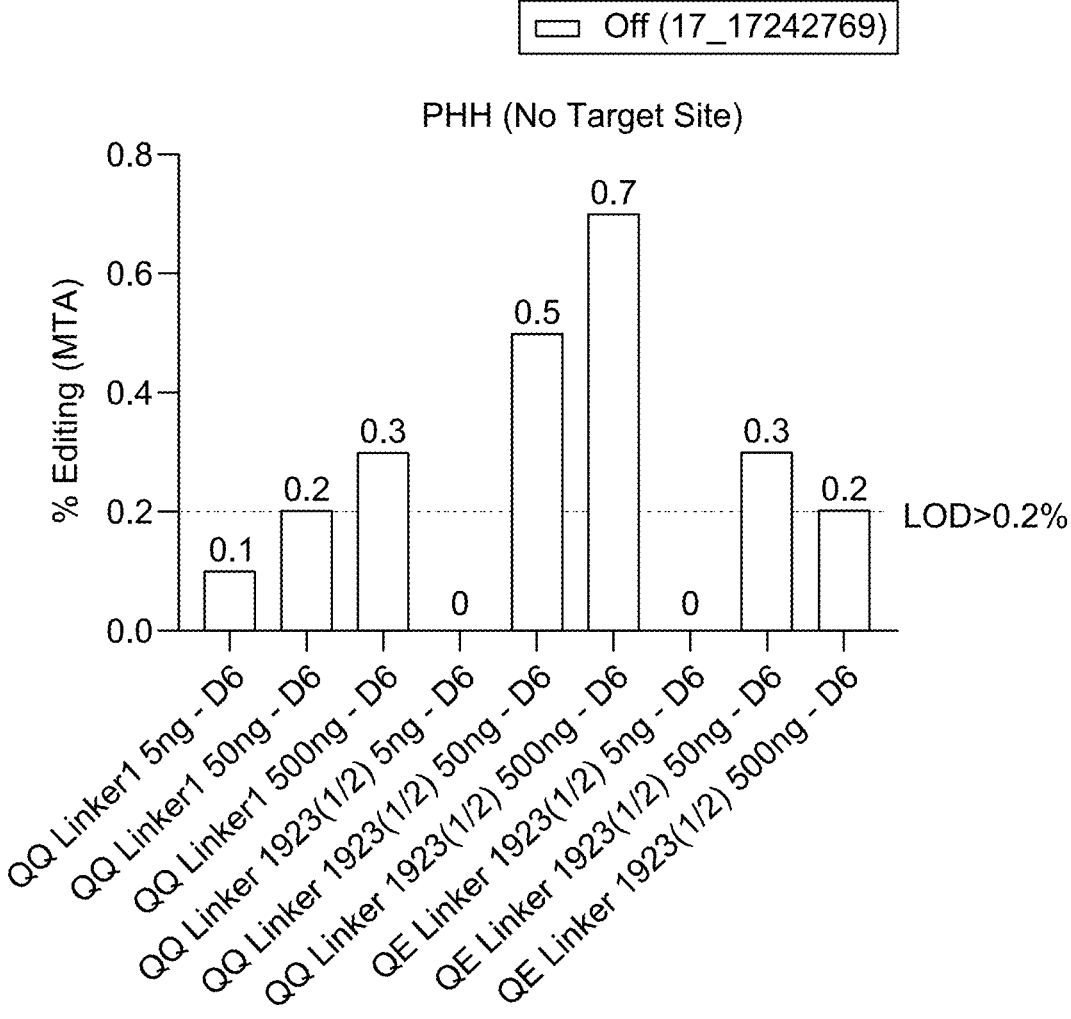

Within the limited dose curve, no editing at the top off-target site (Chr. 17; Pos. 17242769) was seen with the QE variant compared to 2% editing at the 100 ng dose with the QQ Linker1923(1/2) variant (FIG. 11A). No editing above the limit of detection was observed with the QE variant at the $EC_{50}$ and $EC_{90}$ doses compared to 0.6% editing at the $EC_{90}$ with the QQ Linker1923(1/2) variant (FIG. 11B). In naive PHHs at the 500 ng dose, the QQ Linker 1923(1/2) variant showed 0.7% editing at the top off-target site while the QE variant showed 0.2% editing (FIG. 11C). Notably, these naïve PHH cells do not have any HBV integration, and therefore, have no possible on-target site for the nuclease to target.

3. Conclusions

These data demonstrate that the HBV11-12L.1090QE Linker1923(1/2) meganuclease is a more specific meganuclease than either the QQ Linker1 meganuclease or the QQ Linker1923(1/2) meganuclease.

Example 8

Generation of Indels at the HBV 11-12 Recognition Sequence and HBV sAG Inhibition by HBV 11-12 Meganucleases in HepG2 and Huh-1 Cells 1. Methods All previous studies have used the engineered HepG2-sAg cell line that was transduced with a lentivirus containing a partial HBV sequence. In this study, we assessed the editing activity and HBsAg reduction of HBV11-12L.1090QQ Linker1923(1/2) and HBV11-12L.1090QE Linker1923(1/2) meganucleases in Huh-1 cells, which contain multiple natural integrations of HBV. Huh-1 is a human hepatocellular carcinoma (HCC) cell line from liver tissue of an adult infected with HBV. It was determined empirically that this cell line contains 6-7 integrations of HBV and requires the addition of 1 uM of dexamethasone (Abcam) to secrete measurable levels of HBsAg into cell culture media.

HepG2-sAg and Huh-1 cells were electroporated in tandem as described in Example 1 with 100 ng, 10 ng, or 1 ng of mRNA encoding either the QQ Linker1923(1/2) or the QE Linker1923(1/2) meganuclease or 100 ng of mCherry. Cells and supernatant were collected on day 3 and 6 post-electroporation. Transfection efficiency was evaluated at >90% for both cell lines. Genomic DNA was isolated from cells using the MagMax DNA Multi-Sample Ultra 2.0 kit with the KingFisher Apex. To assess reduction of secreted HBsAg in cell supernatants, HBsAg CLIA was performed as described in Example 4. Digital droplet PCR was utilized to calculate percent indel formation.

HBV integrations in the Huh-1 cell line contain mutations in the primer and probe binding sites of the previously described ddPCR assays for indel detection in HepG2-sAg cells. Therefore, new primers and probes were designed and validated to be used for indel detection in this cell line. A new probe design is unnecessary for the target site amplicon due to conserved sequence between cell lines at its location. To assess percent indel formation, digital droplet PCR was performed in a similar approach to Example 2 with variations in the primers, probes and cycling conditions used. Cycling conditions were as follows: 1 cycle of 95° C. (2° C./s ramp) for 10 minutes, 45 cycles of 95° C. (1° C./s ramp) for 10 seconds, 55° C. (1° C./s ramp) for 30 seconds, 72° C. (0.2° C./s ramp) for 2 minutes, 1 cycle of 98° C. for 10 minutes, 4° C. hold. Cycling conditions remain the same between the two cell type assays. The sequences for the primers and probes used for the Huh-1 cell specific assay in this study are provided in the table below.

TABLE 6

| Primer and probe sequences for Example 8 | |
| --- | --- |
| Primer Identifier | SEQ ID NO: |
| P1: [5'-CGATCCATACTGCGGAA-3'] | 32 |
| F1: [5'-AGGTCTCTGCCAAGTGTTTGCTG-3'] | 33 |
| R1: [5'-ACGGGACGTAGACAAAGGACGTC-3'] | 34 |
| P2: [5'-TTCAGTGGTTCGTAGGGCTTTCCC-3'] | 35 |
| F2: [5'-CTCAGTTTACTAGTGCCATTTG-3'] | 36 |
| R2: [5'-TTCAGTGGTTCGTAGGGCTTTCCC-3'] | 37 |

2. Results

Figures 12A, 12B:
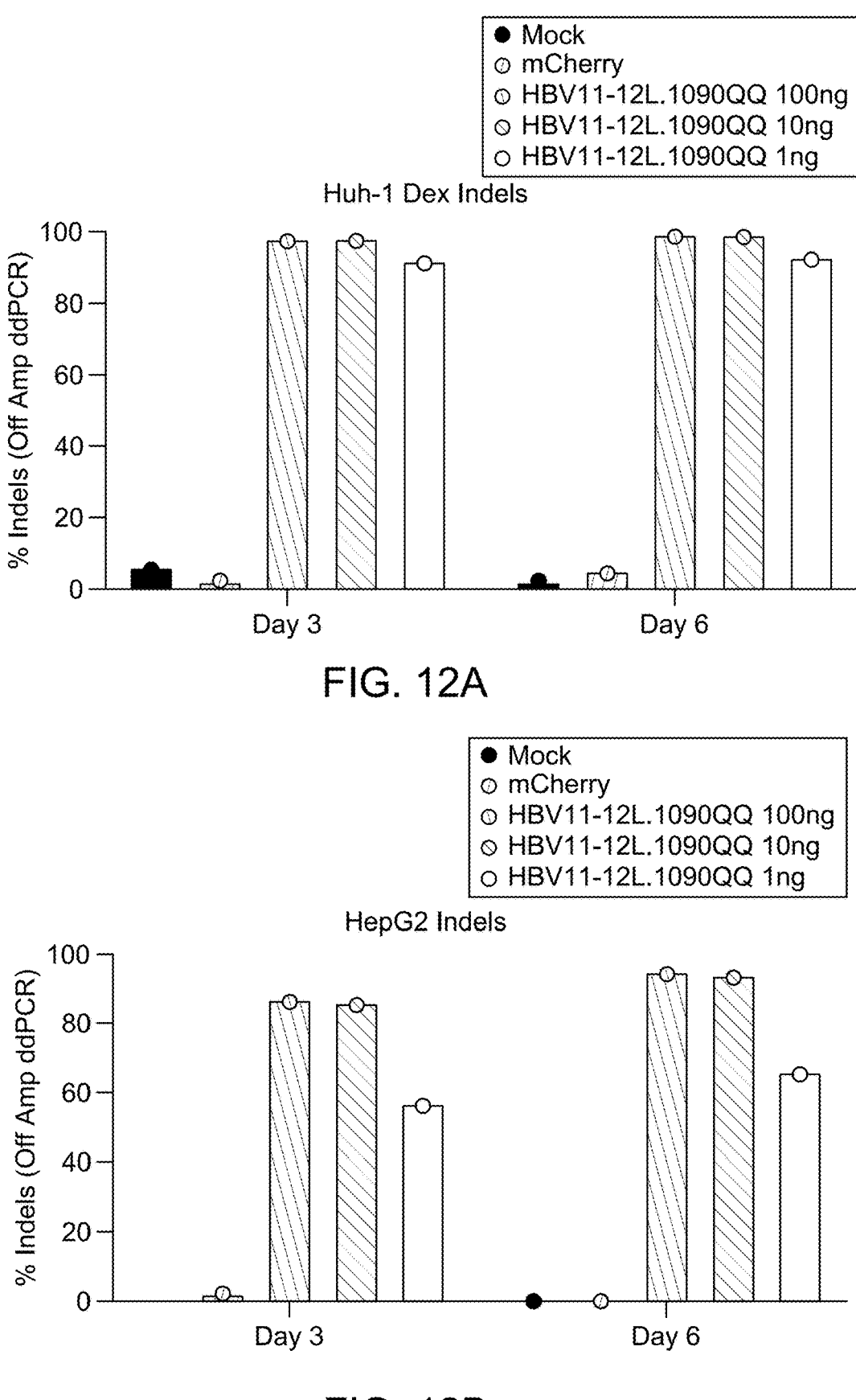
FIG. 12A and FIG. 12B. Provides a bar graph that shows the percentage indels by ddPCR at day 3 and day 6 from Huh-1 Dex cells (FIG. 12A) or HepG2 cells (FIG. 12B) transfected at either a 100 ng, 10 ng, or 1 ng and 10 ng dosage of the HBV11-12L.1090QQ Linker 1923(1/2) meganuclease (labelled as HBV11-12L.1090 QQ). A mock and mCherry control is also shown.

HBV11-12L.1090QQ Linker1923(1/2) and HBV11-12L.1090QE Linker1923(1/2) were evaluated for editing efficiency and HBsAg knockdown in HepG2-sAg and Huh-1 cells. At 6 days post-transfection, the QQ Linker1923(1/2) meganuclease (FIG. 12A) and QE Linker1923(1/2) meganuclease (FIG. 13A) reached greater peak indel formation in Huh-1 cells (99% and 98%, respectively) than the QQ Linker1923(1/2) meganuclease (FIG. 12B) and QE Linker1923(1/2) meganuclease (FIG. 13B) in HepG2-sAg cells (95% and 89%, respectively). Additionally, the QQ Linker1923(1/2) and QE Linker1923(1/2) achieved higher levels of editing with lower doses of mRNA (1 ng) in Huh-1 cells (93% and 84%, respectively) than the HepG2-sAg cells (66% and 33%, respectively). The high levels of editing in Huh-1 cells correlates to a greater amount of HBsAg reduction for both QQ Linker1923(1/2) and QE Linker1923(1/2) meganucleases. At 6 days post-transfection with 1 ng of mRNA, the QQ Linker1923(1/2) meganuclease (FIG. 14A) and QE Linker1923(1/2) meganuclease (FIG. 15A) reached lower HBsAg levels in Huh-1 cells (2 and 1 IU/mL) than did the QQ Linker1923(1/2) meganuclease (FIG. 14B) and QE Linker1923(1/2) meganuclease (FIG. 15B) in HepG2-sAg cells (11 and 18 IU/mL).

3. Conclusions

These data demonstrate that the QQ Linker1923(1/2) and QE Linker1923(1/2) meganucleases successfully generate edits within cells containing multiple natural HBV integrations.

Example 9

Quantification of HBsAg, HBeAg, HBV DNA, HBV RNA, cccDNA, and Cell Viability of HBV Infected PHH Cells Transfected with HBV 11-12 Meganucleases 1. Methods In this study, the antiviral endpoints were determined over a range of doses to characterize efficacy of HBV11-12L.1090QQ Linker1923(1/2) in PHH cells infected with HBV. Cryopreserved PHH cells were infected with HBV serotype B (800 genome equivalents/cell). 6e5 cells were transfected on day 3 and 6 post-HBV infection with 0.1 or 1.0 μg of HBV11-12L.1090QQ Linker1923(1/2) (MAX) using TransIT®-mRNA Transfection Kit according to manufacturer's instructions. An HBV-targeting siRNA was tested at a single dose as the positive control. Supernatant and cells were collected for analysis 6-, 9-, 12- and 15-days post-infection. Extracellular HBV DNA, extracellular HBV pgRNA, HBsAg, and HBeAg levels were analyzed. Detection of cccDNA was measured by Southern blot using DNA isolated via the Hirt method.

The cell viability was assessed by Cell Counting Kit-8 (Biolite) according to manufacturer's instructions after collection of the cell culture supernatants. Absorbance was measured using a Spectra Max-M2 (SoftMax Pro 7.0.3). The cell viability was calculated with the formula below: Viability Percent=(raw data of sample−AVG. of blank)/(AVG. of medium control−AVG. of blank)×100.

Extracellular HBV DNA was determined by qPCR. In brief, the extracellular HBV DNA was isolated from 100 μL of cell culture supernatant using the QIAamp® 96 DNA Blood Kit (Qiagen-51162). The DNA was quantified by qPCR using an HBV specific primer/probe set targeting the HBsAg sequence region. A standard curve of 107-10 copies of pAAV2-HBV1.3 plasmid DNA was used. qPCR was run with a 10 μL reaction containing 1× Probes Master (Roche-04914058001), 200 nM of probe, 400 nM of a forward and reverse primer, 2 μL of AE buffer (10 mM Tris-Cl, 0.5 mM EDTA; pH 9.0) and 2 µL of sample or plasmid standard. Cycling conditions were as follows: 1 cycle of 95° C. for 10 minutes, 45 cycles of 95° C. for 15 seconds and 60° C. for 1 minute. qPCR was conducted using a 7900 Real-time PCR system (software version SDS Automation Controller 2.4) or a QuantStudio 6 Flex system (software version QuantStudio Real-time PCR Software v1.3) The % inhibition of HBV DNA was calculated with the formula below:

$$\% \text{ Inh. HBV DNA} = (1 - \text{value of sample/AVG. value of medium control}) \times 100$$

The sequences for the primers used for HBV DNA qPCR are provided in the table below.

TABLE 7

Primer sequences for Example 9

| Primer Identifier | SEQ ID NO: |
|---|---|
| F1: [5' GTGTCTGCGGCGTTTTATCA 3'] | 38 |
| R1: [5' GACAAACGGGCAACATACCTT 3'] | 39 |

Extracellular HBV RNA was determined by RT-PCR. In brief, the extracellular RNA was isolated from 130 µL of cell supernatant using the PureLink™ Pro 96 Viral RNA/DNA Kit (Cat: 12280096A). Rapid reverse transcription of RNA into cDNA using the FastQuant cDNA RT Kit (Cat: KR116-02) was performed. The HBV cDNA was quantified by qPCR with HBV probe and primers. qPCR of HBV RNA was with a 10 µL reaction containing 1× Universal PCR Master Mix, 200 nM of probe, 400 nM of a forward and reverse primer, and 2 µL of sample or plasmid standard. Percent HBV RNA inhibition was calculated with the same formula as HBV DNA.

HBsAg was quantified as described in Example 4 using a SpectraMax iD3 microplate reader. HBeAg was quantified using an HBeAg specific ELISA from AutoBio according to manufacturer's instructions. Luminescence was measured using a SpectraMax iD3 microplate reader. The percent inhibition of HBeAg or HBsAg was calculated with the formula below: Percent Inh. HBeAg or HBsAg=(1−value of sample/AVG. value of medium control)×100.

Southern blot was used to quantify percent inhibition of cccDNA in cells. To generate Hirt DNA, cells were lysed with lysis buffer and 10% SDS. 5M NaCl solution was added and lysates were subjected to 3 rounds of extraction with Phenol-chloroform-Isoamyl alcohol. Hirt DNA was eluted into AE buffer. The Hirt DNA was resolved on a 1.2% agarose gel and transferred onto positive-charged Nylon membrane. For the detection of HBV cccDNA, the membrane was probed with DIG-labeled HBV DNA probe. Hybridization was carried out in 10 ml of the hybridization buffer with a 1-hour pre-hybridization at 60° C. and overnight hybridization at 60° C., followed by 2×5 min washes with 2×SSC, 0.1% SDS at room temperature and 3×20 min washes with 0.2×SSC, 0.1% SDS at 60° C. The membrane was incubated with blocking buffer for 50 min and followed by 60 min incubation with the antibody solution. After equilibration with the detection buffer for 10 min, the membranes were rinsed with CDP-star. Analysis was conducted with ImageQuant LAS 4010 at room temperature.

2. Results

Figure 16C:
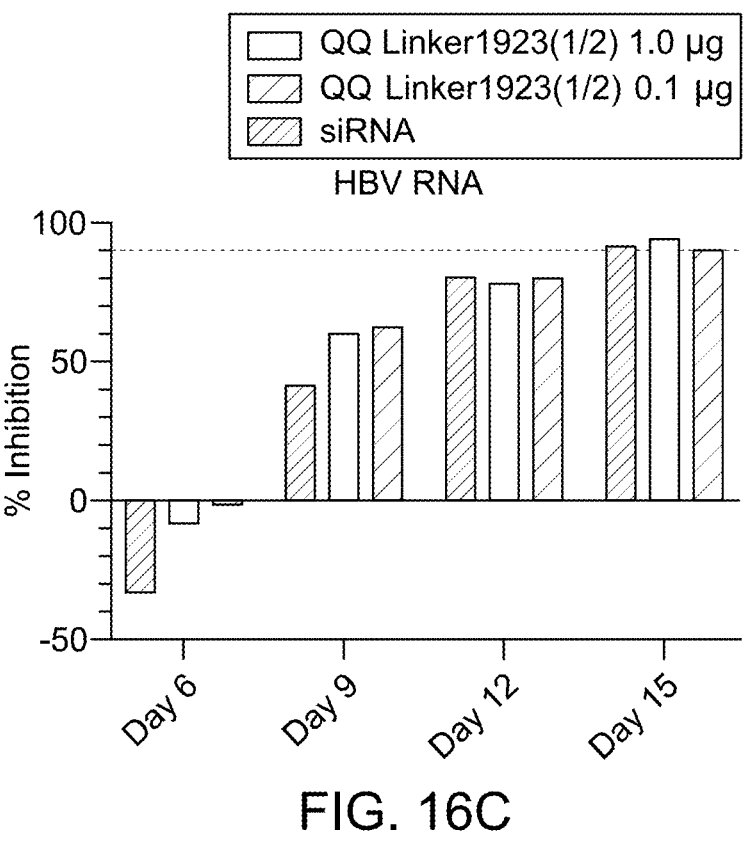
Figure 16D:
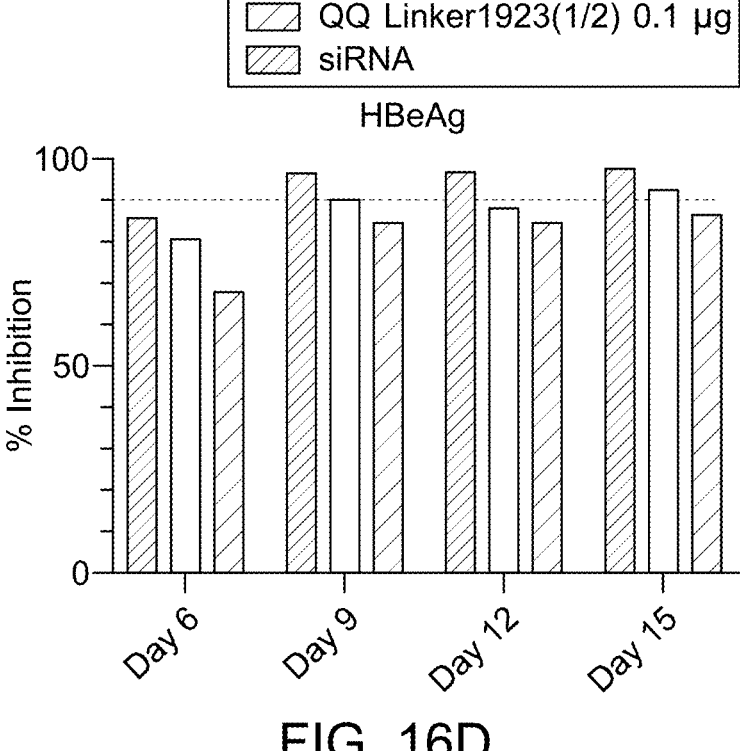
Figure 16E:
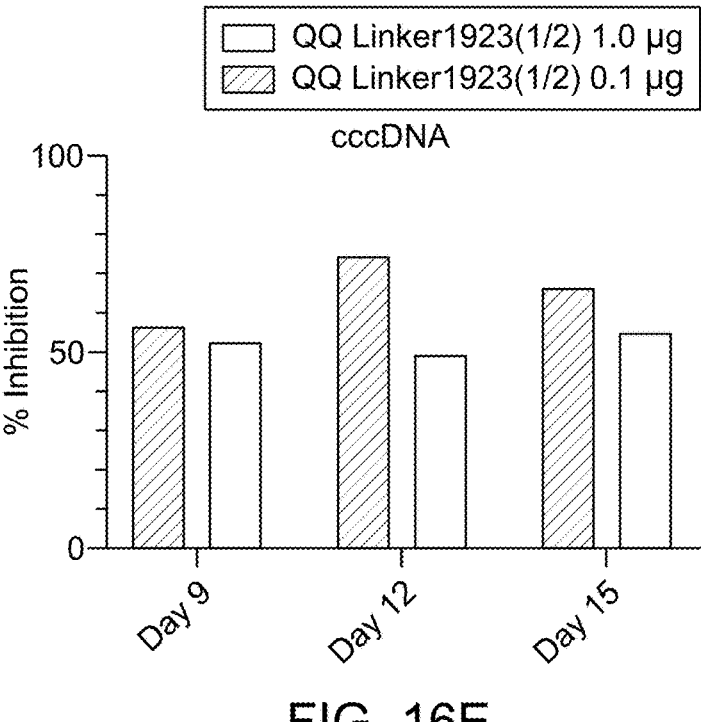
Figure 16F:
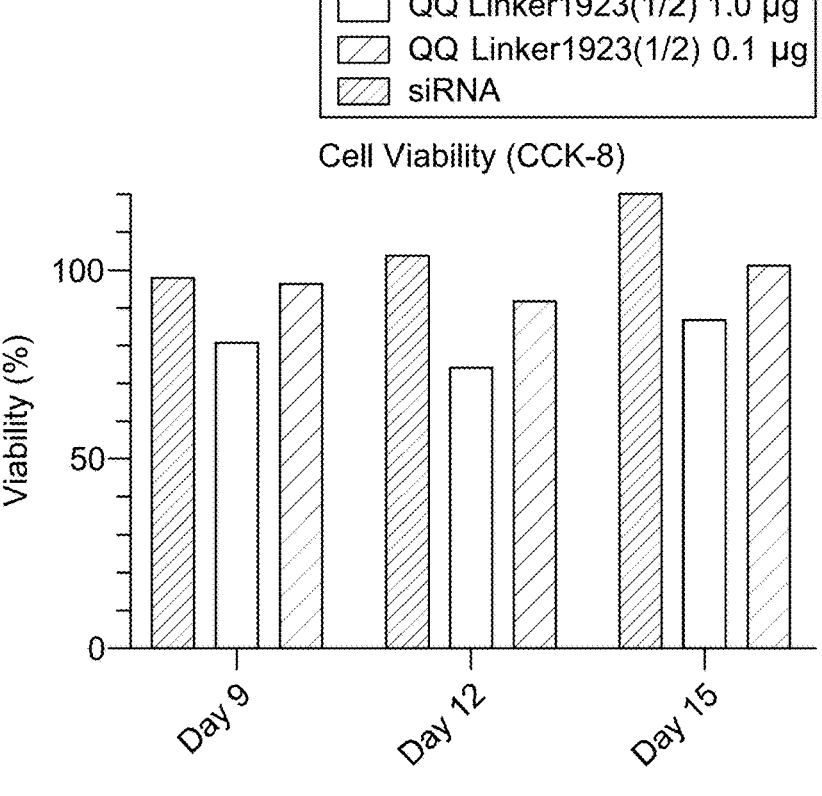

The efficacy of HBV11-12L.1090QQ Linker1923(1/2) in reducing viral readouts of HBV infected PHHs over time at two doses was determined. A 1 log reduction in HBsAg (FIG. 16A), HBV DNA (FIG. 16B), and HBV RNA was observed at both dose levels (FIG. 16C). A 1 log reduction in HBeAg (FIG. 16D) was observed at the high dose. A dose response in HBsAg and HBeAg was observed at all time-points. A dose response for HBV DNA and RNA was observed at 15 days post infection. At least 50% reduction in cccDNA was observed in all conditions (FIG. 16E). Cell viability at the 1 µg dose decreased to 75% by 12 days post-transfection and 88% at 15 days post-transfection, indicating some toxicity to PHHs with mRNA transfection at the high dose (FIG. 16F). However, PHHs transfected at the low dose demonstrated little loss of viability concomitant with equivalent or higher overall activity in reducing each of the viral readouts.

3. Conclusions

These data demonstrate that the HBV11-12L.1090QQ Linker1923(1/2) meganuclease can reduce each of the viral readouts tested. Importantly, cccDNA levels were significantly reduced resulting in high levels of antiviral efficacy in the context of HBV infected PHHs.

Example 10

Quantification of HBsAg, HBeAg, HBV DNA, HBV RNA, cccDNA, and Cell Viability of HBV Infected PHH Cells Transfected with HBV 11-12 Meganucleases 1. Methods In this study, antiviral endpoints were determined over a range of doses to compare efficacy of HBV11-12L.1090QQ Linker1923(1/2) and HBV11-12L.1090QE Linker1923(1/2) in PHH cells infected with HBV. Cryopreserved PHH cells were infected with HBV serotype D (800 genome equivalents/cell). 6e5 cells were transfected on day 3 and 6 post-HBV infection with a wide dose range (1 ug-0.001 ug) of the QQ and QE Linker1923(1/2) meganucleases using TransIT®-mRNA Transfection Kit according to manufacturer's instructions. An HBV-targeting siRNA was tested at a single dose as the positive control. The current treatment for HBV includes the use of nucleoside analogs such as Lamivudine (LAM). LAM was tested at 6 nM (EC$_{50}$) in combination with the above nucleases at 1 µg and 0.1 µg doses to assess safety and potential additive effects. LAM began at day 1 post HBV infection and was stopped at day 6. Supernatant was collected for analysis 3-, 6-, 9-, 12- and 15-days post-infection. Cells were collected 9- and 15-days post-infection. Extracellular HBV DNA, extracellular HBV pgRNA, HBsAg, HBeAg, and cccDNA were analyzed as described in Example 9. Additionally, on-target editing in cccDNA was measured with NGS on exonuclease treated cellular DNA. To quantitate on-target indels in PHH cells, total DNA was extracted and treated with T5 exonuclease (NEB) according to the manufacturer's protocol. PCR was used to amplify across the nuclease target site, and NGS was utilized to quantitate indels. The sequences for the primers used for on-target editing of cccDNA are provided in the table below:

TABLE 8

Primer and probe sequences for Example 10

| Primer Identifier | SEQ ID NO: |
|---|---|
| F1: [5'-GCCAGGTCTGTGCCAAGTGTTTG-3'] | 40 |
| R1: [5'-CAGGATCCAGTTGGCAGCAC-3'] | 41 |

Total inactivation was calculated with the formula: Total inactivation=(% of remaining cccDNA compared to no treatment control quantified by Southern blot x % Indels in cccDNA by NGS)+% Decrease in cccDNA compared to no treatment controls).

2. Results

Figure 17A:
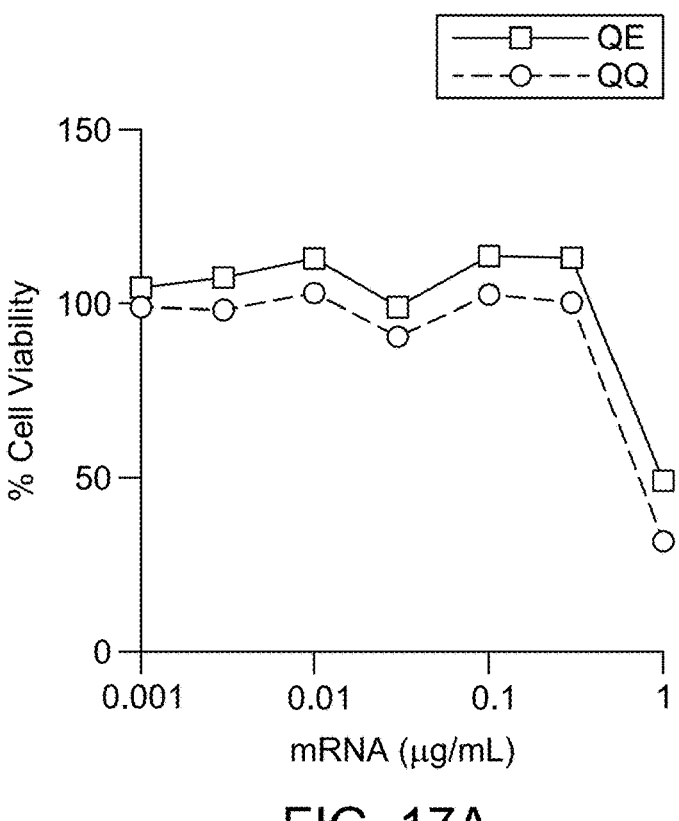
FIG. 17A-FIG. 17F. Provides bar graphs showing the percentage of cell viability (FIG. 17A), HBV DNA inhibition (FIG. 17B), HBV RNA inhibition (FIG. 17C), HBsAg inhibition (FIG. 17D), HBeAg inhibition (FIG. 17E), and cccDNA inhibition (FIG. 17F), in PHH cells infected with 800 GE/cell HBV serotype B and transfected on days 3 and 6 post-infection with a range of 0.001 µg to 1 µg/mL of mRNA encoding the HBV 11-12L.1090QQ Linker1923(1/ 2) (labelled as QQ) or HBV 11-12L.1090QE Linker1923(1/ 2) (labelled as QE) engineered meganuclease.
Figure 17B:
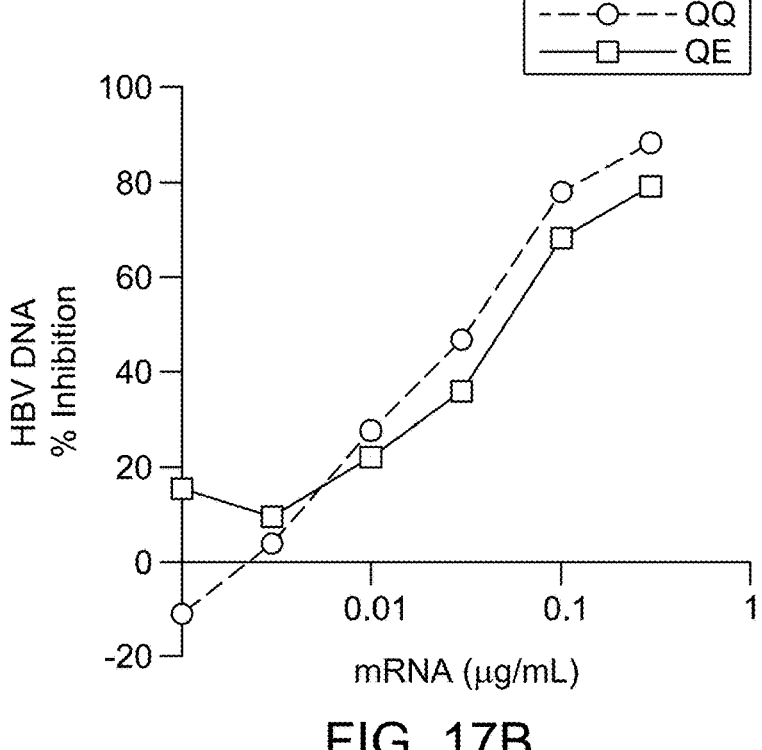
Figure 17C:
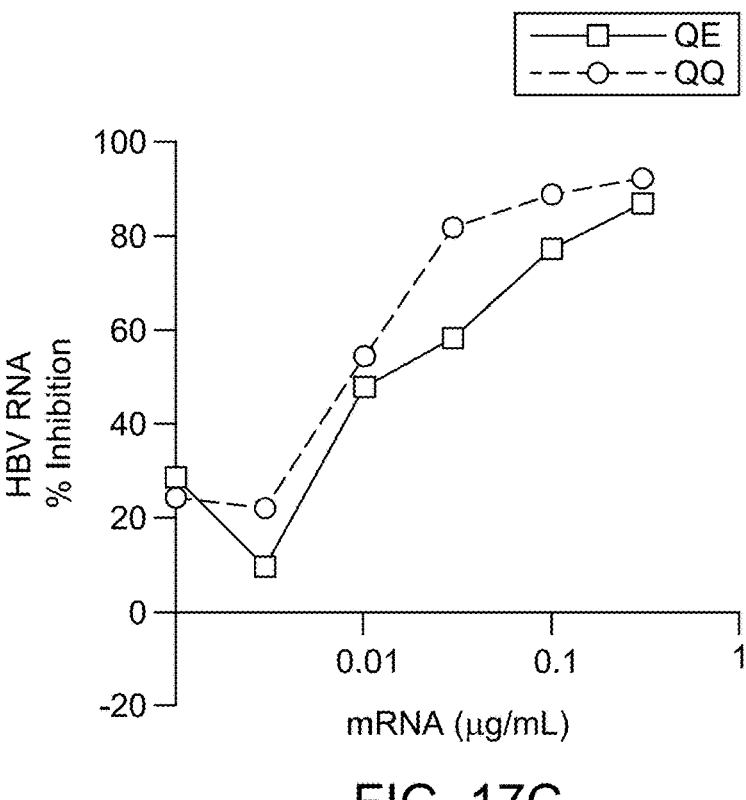
Figure 17D:
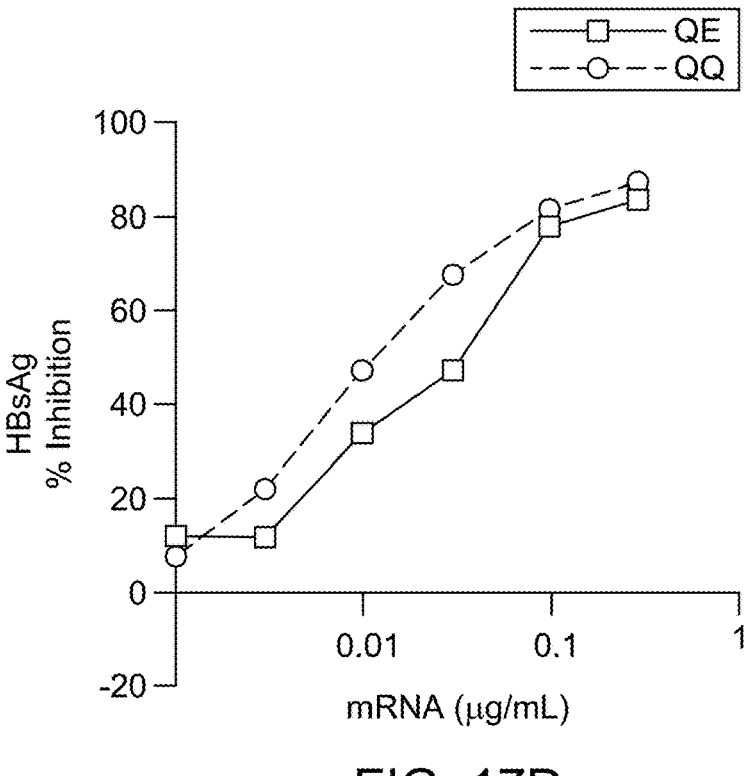
Figure 17E:
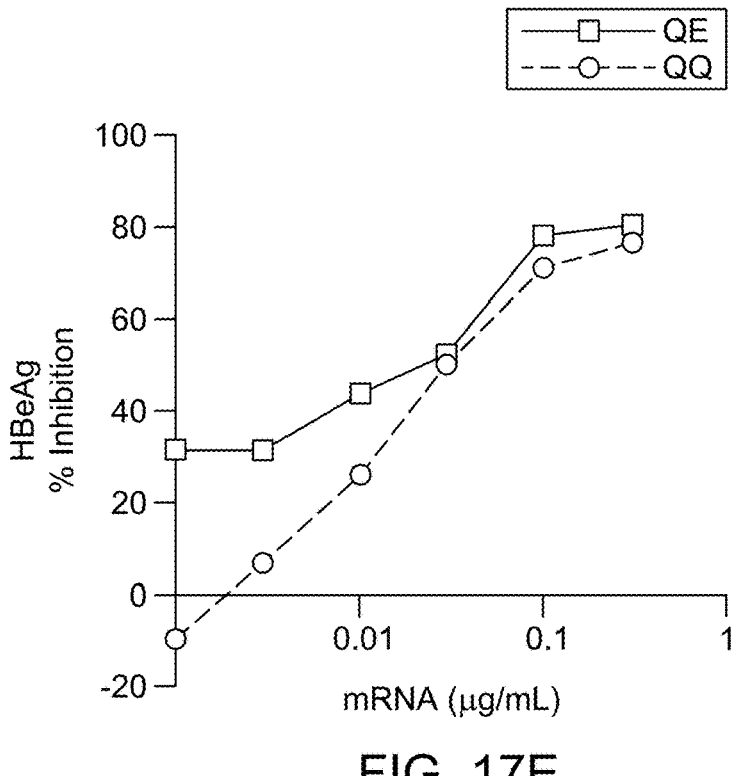
Figure 17F:
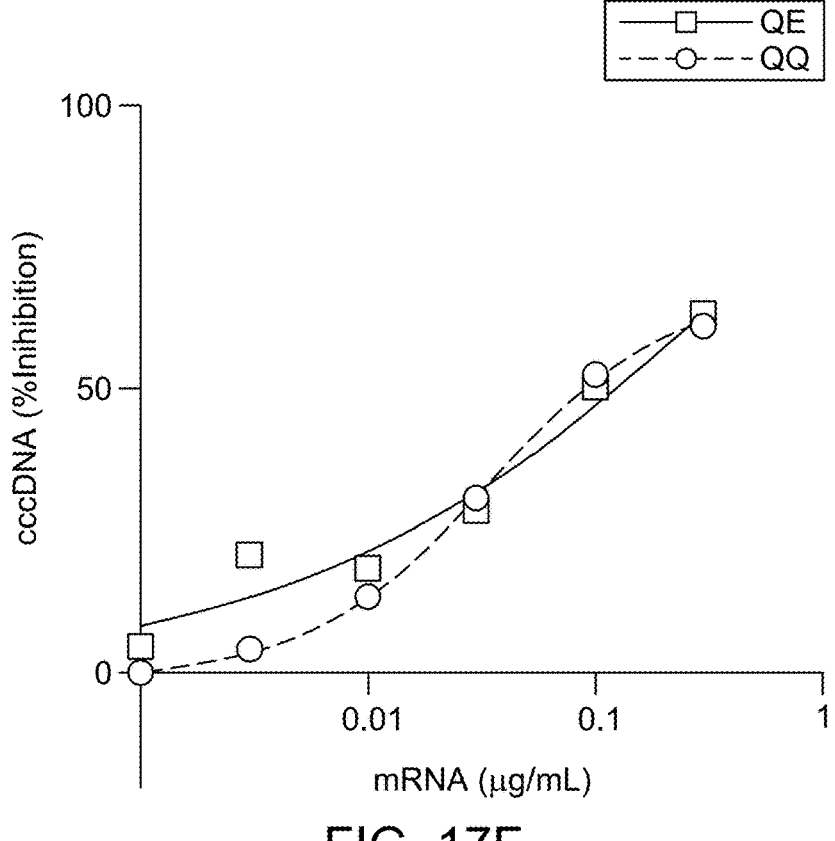
Figure 18A:
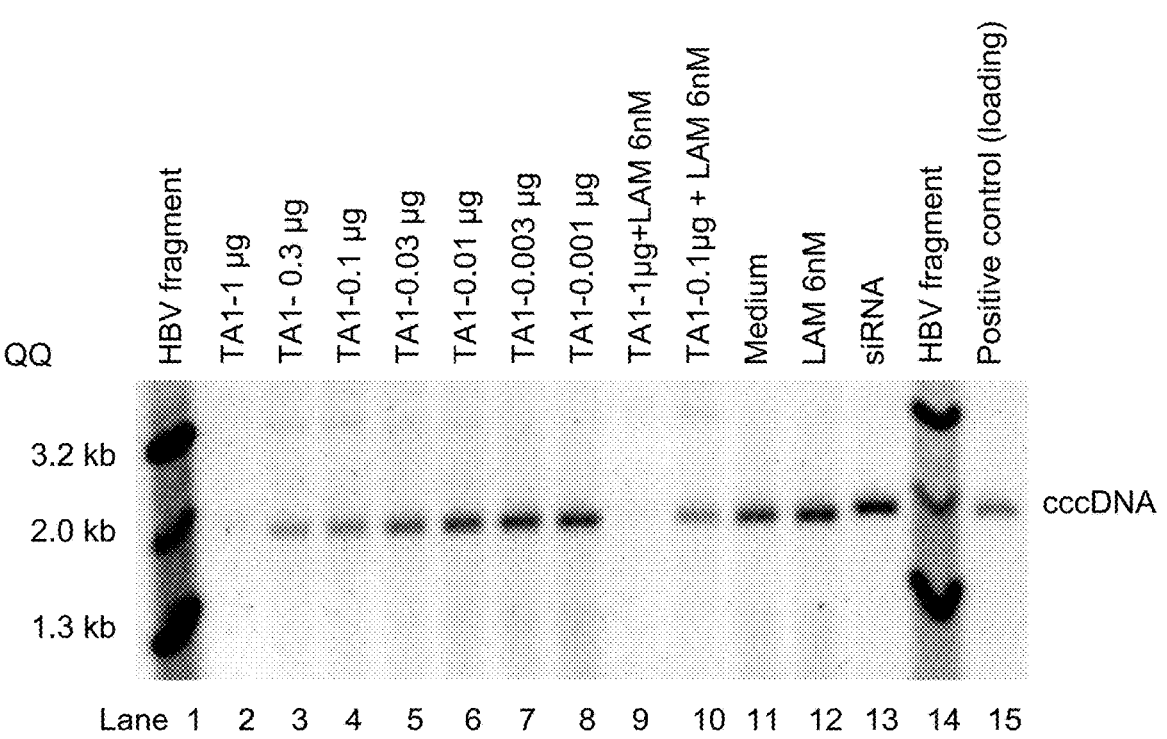
FIG. 18A and FIG. 18B Provide a Southern blot of cccDNA levels in PHH cells infected with 800 GE/cell HBV serotype B and transfected on days 3 and 6 post-infection with a range of 0.001 µg to 1 µg of mRNA encoding the HBV 11-12L.1090QQ Linker1923(1/2) (labelled as QQ.
Figure 18B:
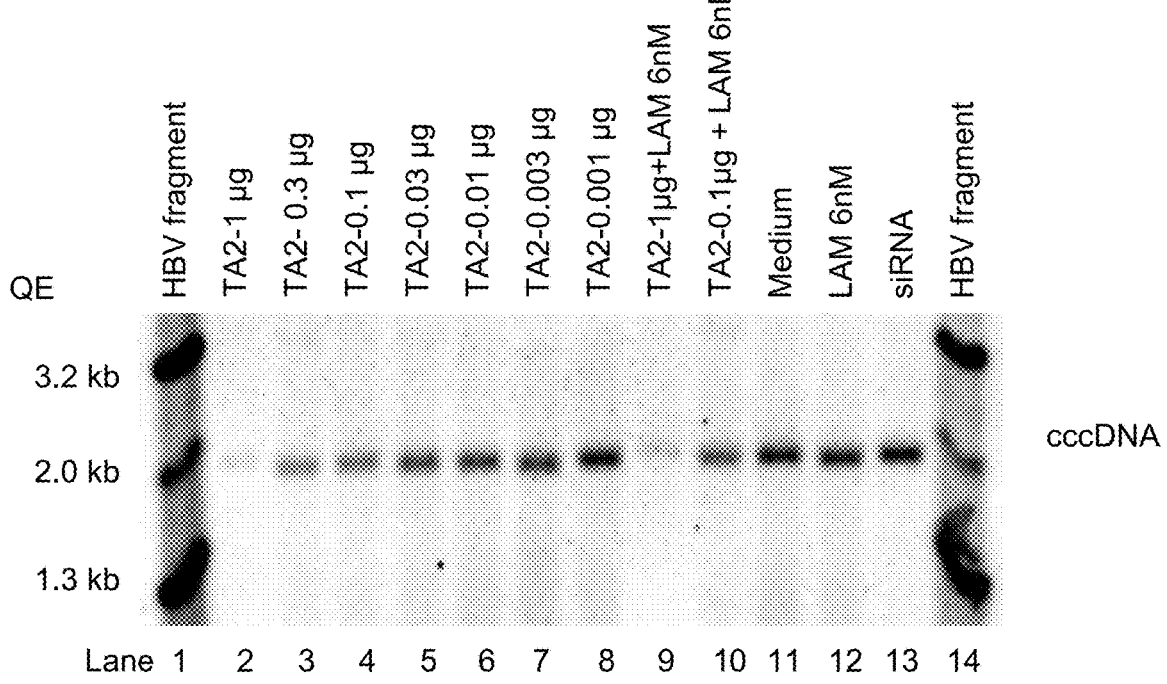
Figure 19:
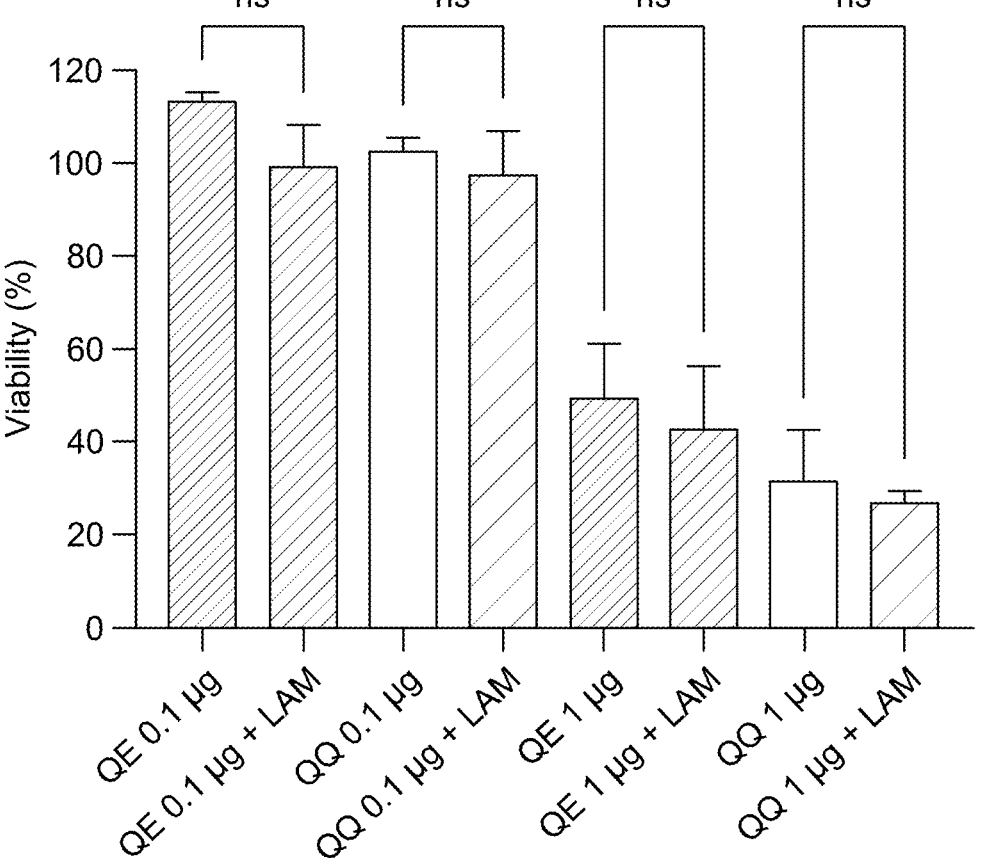
FIG. 19 Provides a bar graph showing the percentage of cell viability of PHH cells infected with 800 GE/cell HBV serotype B and transfected on days 3 and 6 post-infection with either 0.1 μg or 1 μg of mRNA encoding the HBV 11-12L.1090QQ Linker1923(1/2) (labelled as QQ) or HBV 11-12L.1090QE Linker1923(1/2) (labelled as QE) engineered meganuclease alone or in combination with the nucleoside analog, LAM.
Figures 20A, 20B:
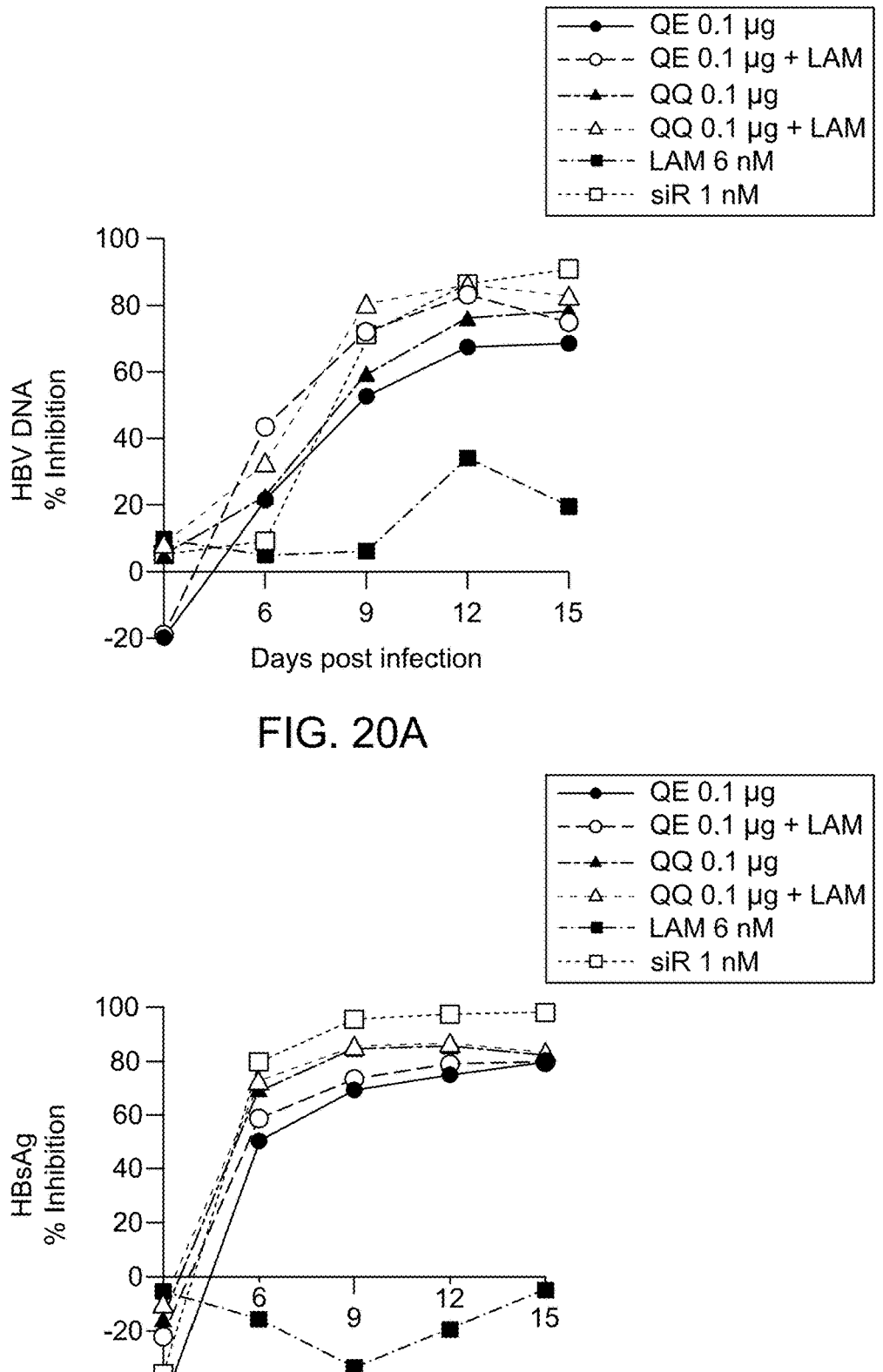
FIG. 20A-FIG. 20D. Provides line graphs showing the percentage of HBV DNA inhibition (FIG. 20A), HBsAg inhibition (FIG. 20B), HBeAg inhibition (FIG. 20C), and HBV RNA inhibition (FIG. 20D), in PHH cells infected with 800 GE/cell HBV serotype B and transfected on days 3 and 6 post-infection with 0.1 μg of mRNA encoding the HBV 11-12L.1090QQ Linker1923(1/2) (labelled as QQ) or HBV 11-12L.1090QE Linker1923(1/2) (labelled as QE) engineered meganuclease. As indicated, some of the cells were also treated with the nucleoside analog, LAM, or an HBV-targeting siRNA.
Figure 20C:
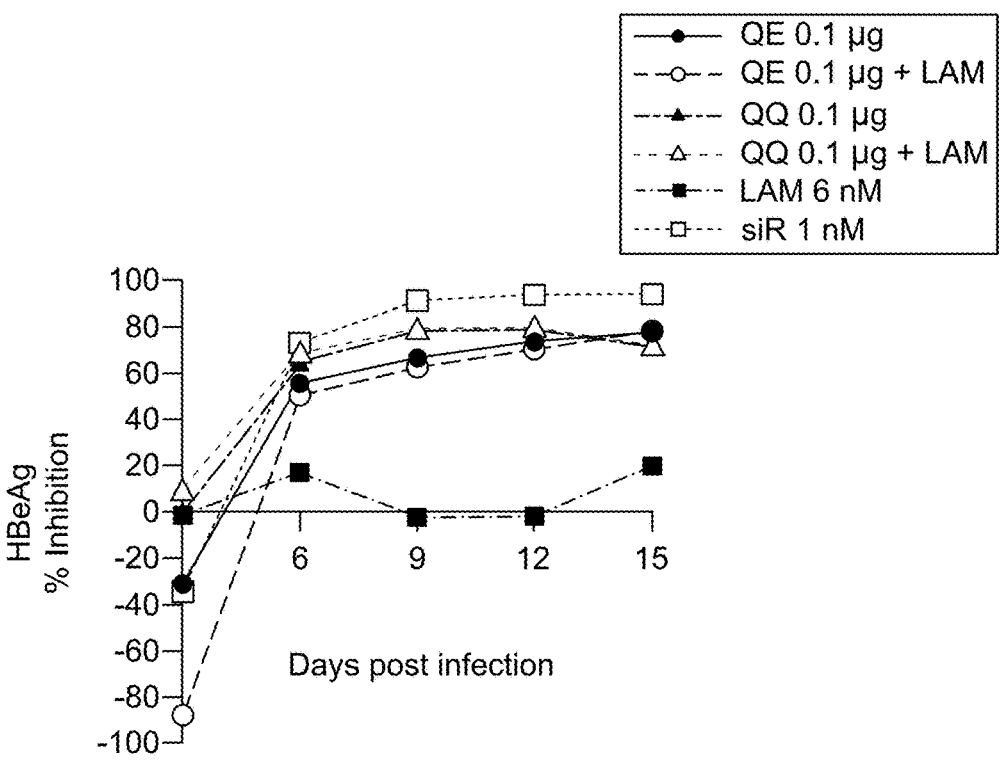
Figure 20D:
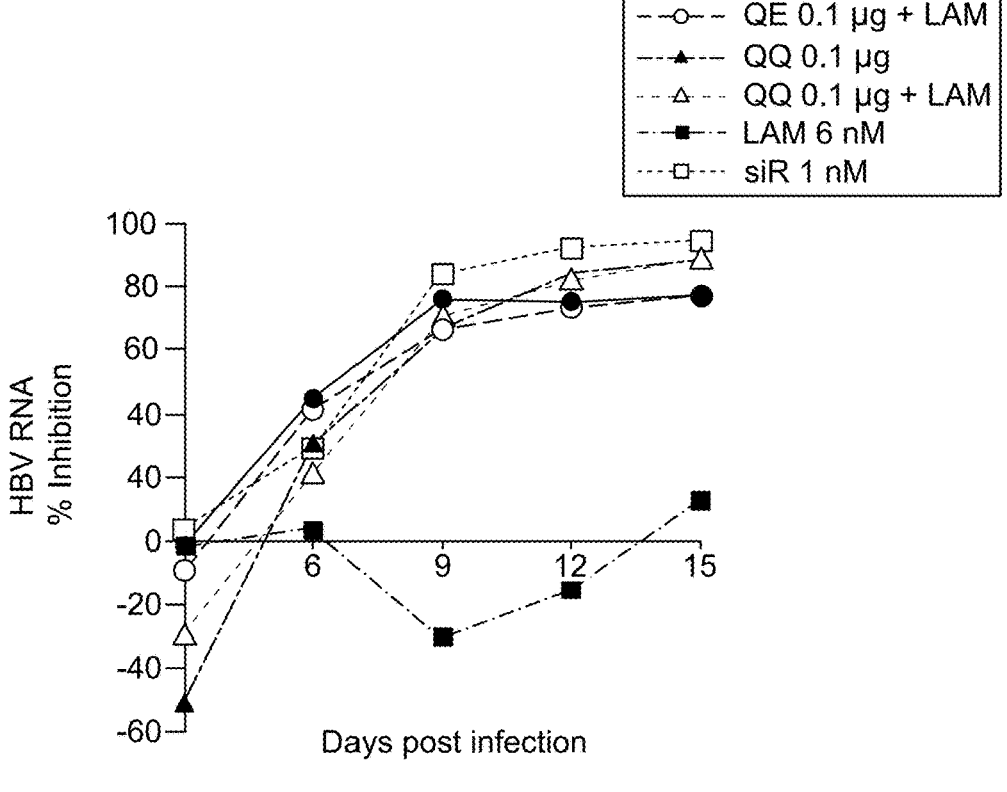

The QQ and QE Linker1923(1/2) meganucleases were assessed in HBV-infected PHHs for efficacy and safety in combination with a nucleoside analog, LAM. High toxicity was observed via the CCK-8 cell viability assay in the 1 µg dose, and therefore, removed from all analyses of subsequent viral end points (FIG. 17A). At 15 days post HBV infection, an approximate 80% reduction in extracellular HBV DNA (FIG. 17B), extracellular HBV RNA (FIG. 17C), HBsAg (FIG. 17D) and HBeAg (FIG. 17E) was observed at 0.3 µg of mRNA for both nucleases tested. Both meganucleases showed dose dependent decreases in cccDNA and achieved an approximate 62% reduction in cccDNA at 15 days post-infection (FIG. 17F). There was also a dose-dependent increase in edited cccDNA reaching ~30% at the high dose for both QQ and QE nucleases (FIG. 18A). Combining cccDNA reduction and editing cccDNA inactivation reached 73% inactivation for both the QQ and QE nucleases (FIG. 18B). The addition of LAM did not affect cell viability (FIG. 19). The QQ and QE Linker1923(1/2) meganucleases achieved sustained reductions in all viral endpoints up to 15 days post HBV infection with or without the addition of LAM (FIG. 20A-FIG. 20D).

3. Conclusions

These data suggest that certain nucleoside analog treatments can be effectively combined with the disclosed HBV11-12 meganucleases without affecting cell viability. Additionally, both the QQ and QE Linker1923(1/2) meganucleases are able to reduce cccDNA levels, edit remaining cccDNA, and generate large reductions in several viral readouts of HBV infection.

---

Sequence Listing

SEQ ID NO: 1
MNTKYNKEFLLYLAGFVDGDGSIIAQIKPNQSYKFKHQLSLAFQVTQKTQRRWFLDKLVDEIGVGY

VRDRGSVSDYILSEIKPLHNFLTQLQPFLKLKQKQANLVLKIIWRLPSAKESPDKFLEVCTWVDQI

AALNDSKTRKTTSETVRAVLDSLSEKKKSSP

SEQ ID NO: 2
LAGLIDADG

SEQ ID NO: 3
TGCCGATCCATACTGCGGAACT

SEQ ID NO: 4
AGTTCCGCAGTATGGATCGGCA

SEQ ID NO: 5
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 6
MNTKYNKEFLLYLAGEVDSDGSINASISPRQSFKFKHGLKLRFEVGQKTQHRWFLDKLVDEIGVGY

VYDNGSVSVYSLSQIKPLHNELTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRWFLDYLVDTIGVGYVIDWRGASTYKLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 7
KEFLLYLAGFVDGDGSIFASIRPRQHAKFKHDLELCENVRQKTQRRWFLDYLVDTIGVGYVIDWRG

ASTYKLSQIKPLHNFLTQLQPFLKLKQKQANLVLKIIEQLPSAKESPDKFLEVCTWVDQIAALNDS

KTRKTTSETVRAVLD

SEQ ID NO: 8
KEFLLYLAGFVDGDGSIFASIRPRQHAKFKHDLELCENVRQKTQRRWFLDYLVDTIGVGYVIDWRG

ASTYKLSEIKPLHNFLTQLQPFLKLKQKQANLVLKIIEQLPSAKESPDKFLEVCTWVDQIAALNDS

KTRKTTSETVRAVLD

103

-continued

Sequence Listing

SEQ ID NO: 9
KEFLLYLAGFVDSDGSINASISPRQSFKFKHGLKLRFEVGQKTQHRWFLDKLVDEIGVGYVYDNGS

VSVYSLSQIKPLHNFLTQLQPFLALKADQANLVLKIIEQLPSAKESPDKFLEVCTWVDQIAALNDS

KTRKTTSETVRAVLD

SEQ ID NO: 10

KEFLLYLAGFVDSDGSINASISPRQSFKFKHGLKLRFEVGQKTQHRWFLDKLVDEIGVGYVYDNGS

VSVYSLSQIKPLHNELTQLQPFLALKADQANLVLKIIEQLPSAKESPDKFLEVCTWVDQIAALNDS

KTRKTTSETVRAVLD

SEQ ID NO: 11
ATGAACACCAAGTACAACAAGGAGTTCCTGCTGTACCTGGCCGGCTTCGTGGACAGCGACGGCAGC

ATCAACGCCAGCATCAGCCCCCGCCAGAGCTTCAAGTTCAAGCACGGCCTGAAGCTGCGCTTCGAG

GTGGGCCAGAAGACCCAGCACCGCTGGTTCCTGGACAAGCTGGTGGACGAGATCGGCGTGGGCTAC

GTGTACGACAACGGCAGCGTGAGCGTGTACAGCCTGAGCCAGATCAAGCCCCTGCACAACTTCCTG

ACCCAGCTGCAGCCCTTCCTGGCCCTGAAGGCCGACCAGGCCAACCTGGTGCTGAAGATCATCGAG

CAGCTGCCCAGCGCCAAGGAGAGCCCCGACAAGTTCCTGGAGGTGTGCACCTGGGTGGACCAGATC

GCCGCCCTGAACGACAGCAAGACCCGCAAGACCACCAGCGAGACCGTGCGCGCCGTGCTGGACAGC

CTGCCCGGCATCCAGCTGAACAAGGAGAGCAACAACAACGCCAGCACCCAGCGCCCCAGCCGCAAC

GTGAACAACTTCCCCTACAGCGGCTACAACAAGGAGTTCCTGCTGTACCTGGCCGGCTTCGTGGAC

GGCGACGGCAGCATCTTCGCCAGCATCCGCCCCCGCCAGCACGCCAAGTTCAAGCACGACCTGGAG

CTGTGCTTCAACGTGCGCCAGAAGACCCAGCGCCGCTGGTTCCTGGACTACCTGGTGGACACCATC

GGCGTGGGCTACGTGATCGACTGGCGCGGCGCCAGCACCTACAAGCTGAGCCAGATCAAGCCCCTG

CACAACTTCCTGACCCAGCTGCAGCCCTTCCTGAAGCTGAAGCAGAAGCAGGCCAACCTGGTGCTG

AAGATCATCGAGCAGCTGCCCAGCGCCAAGGAGAGCCCCGACAAGTTCCTGGAGGTGTGCACCTGG

GTGGACCAGATCGCCGCCCTGAACGACAGCAAGACCCGCAAGACCACCAGCGAGACCGTGCGCGCC

GTTCTAGACAGCCTGAGCGAGAAGAAGAAAAGCAGCCCC

SEQ ID NO: 12
ATGAACACCAAGTACAACAAGGAGTTCCTGCTGTACCTGGCCGGCTTCGTGGACAGCGACGGCAGC

ATCAACGCCAGCATCAGCCCCCGCCAGAGCTTCAAGTTCAAGCACGGCCTGAAGCTGCGCTTCGAG

GTGGGCCAGAAGACCCAGCACCGCTGGTTCCTGGACAAGCTGGTGGACGAGATCGGCGTGGGCTAC

GTGTACGACAACGGCAGCGTGAGCGTGTACAGCCTGAGCCAGATCAAGCCCCTGCACAACTTCCTG

ACCCAGCTGCAGCCCTTCCTGGCCCTGAAGGCCGACCAGGCCAACCTGGTGCTGAAGATCATCGAG

CAGCTGCCCAGCGCCAAGGAGAGCCCCGACAAGTTCCTGGAGGTGTGCACCTGGGTGGACCAGATC

GCCGCCCTGAACGACAGCAAGACCCGCAAGACCACCAGCGAGACCGTGCGCGCCGTGCTGGACAGC

CTGCCCGGCATCCAGCTGAACAAGGAGAGCAACAACAACGCCAGCACCCAGCGCCCCAGCCGCAAC

GTGAACAACTTCCCCTACAGCGGCTACAACAAGGAGTTCCTGCTGTACCTGGCCGGCTTCGTGGAC

GGCGACGGCAGCATCTTCGCCAGCATCCGCCCCCGCCAGCACGCCAAGTTCAAGCACGACCTGGAG

CTGTGCTTCAACGTGCGCCAGAAGACCCAGCGCCGCTGGTTCCTGGACTACCTGGTGGACACCATC

GGCGTGGGCTACGTGATCGACTGGCGCGGCGCCAGCACCTACAAGCTGAGCGAGATCAAGCCCCTG

CACAACTTCCTGACCCAGCTGCAGCCCTTCCTGAAGCTGAAGCAGAAGCAGGCCAACCTGGTGCTG

AAGATCATCGAGCAGCTGCCCAGCGCCAAGGAGAGCCCCGACAAGTTCCTGGAGGTGTGCACCTGG

-continued

---
Sequence Listing
---

GTGGACCAGATCGCCGCCCTGAACGACAGCAAGACCCGCAAGACCACCAGCGAGACCGTGCGCGCC

GTTCTAGACAGCCTGAGCGAGAAGAAGAAAAGCAGCCCC

SEQ ID NO: 13
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFASIRPRQHAKFKHDLELCFNVRQKTQRRWFLDKLVDEIGVGYVIDWRGA

STYKLSQIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 14

MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFASIRPRQHAKFKHDLELCFNVRQKTQRRWFLDKLVDEIGVGYVIDWRGA

STYKLSEIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 15
SLPGIQLNKESNNNASTQRPSRNVNNFPYSG

SEQ ID NO: 16
SLPGSVGGLSPSQASSAASSASSSPGSGISEALRAGAGSGTG

SEQ ID NO: 17
MAPKKKRKVH

SEQ ID NO: 18
AATTATTGGTTAAAGAAGTATATTAGTGCTAATTTCCCTCCGTTTGTCCTAGCTTTTCTCTTCTGT

CAACCCCACACGCCTTTGCCAC

SEQ ID NO: 19
ACTCATCTTGGCCCTCCTCAGCTCCCTGCCTGTTTCCCGTAAGGCTGTACATAGTCCTTTTATCTC

CTTGTGGCCTATGAAACTGGTTTATAATAAACTCTTAAGAGAACATTA

SEQ ID NO: 20
AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAA

SEQ ID NO: 21
GCCACCATGG

SEQ ID NO: 22
TGCCGATCCATACTGCGGAACT

SEQ ID NO: 23
GGTCTGTGCCAAGTGTTTG

SEQ ID NO: 24
GCTGCGAGCAAAACAAG

SEQ ID NO: 25
CCCGCCTGTAACACG

SEQ ID NO: 26
CATCAGGATTCCTAGGACC

SEQ ID NO: 27
AGTCCACCACGAGTCTA

Sequence Listing

SEQ ID NO: 28
GTATATTTCCGCGAGAGGAC

SEQ ID NO: 29
CTTGGCCCCCAATACCACATCATC

SEQ ID NO: 30
GGATGGAAATTGCACCTGTATTC

SEQ ID NO: 31
GGGTTTAAATGTATACCCAGAGAC

SEQ ID NO: 32
CGATCCATACTGCGGAA

SEQ ID NO: 33
AGGTCTCTGCCAAGTGTTTGCTG

SEQ ID NO: 34
ACGGGACGTAGACAAAGGACGTC

SEQ ID NO: 35
TTCAGTGGTTCGTAGGGCTTTCCC

SEQ ID NO: 36
CTCAGTTTACTAGTGCCATTTG

SEQ ID NO: 37
TTCAGTGGTTCGTAGGGCTTTCCC

SEQ ID NO: 38
GTGTCTGCGGCGTTTTATCA

SEQ ID NO: 39
GACAAACGGGCAACATACCTT

SEQ ID NO: 40
GCCAGGTCTGTGCCAAGTGTTTG

SEQ ID NO: 41
CAGGATCCAGTTGGCAGCAC

SEQ ID NO: 42
SLPGIGVQVHRNNNASTQRPSRNVNNFPYKG

SEQ ID NO: 43
SLPGVRLHCPLNNNASTQRPSRNVNNFPQG

SEQ ID NO: 44
SLPGIRLSQGANNNASTQRPSRNVNNFPLG

SEQ ID NO: 45
SLPGARPGGVSNNNASTQRPSRNVNNFPYSG

SEQ ID NO: 46
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 47
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDYLVDTIGVGYVIDWRGASTYKLSQIKPL

-continued

Sequence Listing

HNFLTQLQPFLKLKQKQANLVLKIIEQLPSAKESPDKFLEVCTWVDQIAALNDSKTRKTTSETVRA

VLDSLSEKKKSSP

SEQ ID NO: 48
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 49
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRFFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 50
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 51
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLKLKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRFFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 52
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 53
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFASIRPRQHAKFKHDLELCENVRQKTQRRWFLDKLVDEIGVGYVIDWRGASTYKLSQIKPL

-continued

Sequence Listing

HNFLTQLQPFLKLKQKQANLVLKIIEQLPSAKESPDKFLEVCTWVDQIAALNDSKTRKTTSETVRA

VLDSLSEKKKSSP

SEQ ID NO: 54
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFASIRPRQHAKFKHDLELCFNVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 55
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFASIRPRQHAKFKHDLELCFNVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 56
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCENVRQKTQRRWFLDKLVDEIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 57
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCFNVRQKTQRRWFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 58
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCENVRQKTQRRFFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 59
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

-continued

---

Sequence Listing

---

DGSIFASIRPRQHAKFKHDLELCENVRQKTQRRWFLDKLVDEIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 60
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFASIRPRQHAKFKHDLELCFNVRQKTQRRWFLDYLVDTIGVGYVIDWRGASTYKLSQIKPLH

NFLTQLQPFLKLKQKQANLVLKIIEQLPSAKESPDKFLEVCTWVDQIAALNDSKIRKTTSETVRAV

LDSLSEKKKSSP

SEQ ID NO: 61
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFASIRPRQHAKFKHDLELCENVRQKTQRRFFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 62
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 63
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCENVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 64
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCENVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 65
PKKKRKV

-continued

Sequence Listing

SEQ ID NO: 66
AATTATTGGTTAAAGAAGTATATTAGTGCTAATTTCCCTCCGTTTGTCCTAGCTTTTCTCTTCTGT

CAACCCCACACGCCTTTGCCACCATGGCCCCCAAGAAGAAGCGCAAGGTGCATATGAACACCAAGT

ACAACAAGGAGTTCCTGCTGTACCTGGCCGGCTTCGTGGACAGCGACGGCAGCATCAACGCCAGCA

TCAGCCCCCGCCAGAGCTTCAAGTTCAAGCACGGCCTGAAGCTGCGCTTCGAGGTGGGCCAGAAGA

CCCAGCACCGCTGGTTCCTGGACAAGCTGGTGGACGAGATCGGCGTGGGCTACGTGTACGACAACG

GCAGCGTGAGCGTGTACAGCCTGAGCCAGATCAAGCCCCTGCACAACTTCCTGACCCAGCTGCAGC

CCTTCCTGGCCCTGAAGGCCGACCAGGCCAACCTGGTGCTGAAGATCATCGAGCAGCTGCCCAGCG

CCAAGGAGAGCCCCGACAAGTTCCTGGAGGTGTGCACCTGGGTGGACCAGATCGCCGCCCTGAACG

ACAGCAAGACCCGCAAGACCACCAGCGAGACCGTGCGCGCCGTGCTGGACAGCCTGCCCGGCATCC

AGCTGAACAAGGAGAGCAACAACAACGCCAGCACCCAGCGCCCCAGCCGCAACGTGAACAACTTCC

CCTACAGCGGCTACAACAAGGAGTTCCTGCTGTACCTGGCCGGCTTCGTGGACGGCGACGGCAGCA

TCTTCGCCAGCATCCGCCCCCGCCAGCACGCCAAGTTCAAGCACGACCTGGAGCTGTGCTTCAACG

TGCGCCAGAAGACCCAGCGCCGCTGGTTCCTGGACTACCTGGTGGACACCATCGGCGTGGGCTACG

TGATCGACTGGCGCGGCGCCAGCACCTACAAGCTGAGCCAGATCAAGCCCCTGCACAACTTCCTGA

CCCAGCTGCAGCCCTTCCTGAAGCTGAAGCAGAAGCAGGCCAACCTGGTGCTGAAGATCATCGAGC

AGCTGCCCAGCGCCAAGGAGAGCCCCGACAAGTTCCTGGAGGTGTGCACCTGGGTGGACCAGATCG

CCGCCCTGAACGACAGCAAGACCCGCAAGACCACCAGCGAGACCGTGCGCGCCGTTCTAGACAGCC

TGAGCGAGAAGAAGAAAAGCAGCCCCATGGCCCCCAAGAAGAAGCGCAAGGTGCATTGATGAGGTA

CCAGCGGCCGCACTCATCTTGGCCCTCCTCAGCTCCCTGCCTGTTTCCCGTAAGGCTGTACATAGT

CCTTTTATCTCCTTGTGGCCTATGAAACTGGTTTATAATAAACTCTTAAGAGAACATTAGGCGCGC

CAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAA

AAAAAAAAA

SEQ ID NO: 67
AATTATTGGTTAAAGAAGTATATTAGTGCTAATTTCCCTCCGTTTGTCCTAGCTTTTCTCTTCTGT

CAACCCCACACGCCTTTGCCACCATGGCCCCCAAGAAGAAGCGCAAGGTGCATATGAACACCAAGT

ACAACAAGGAGTTCCTGCTGTACCTGGCCGGCTTCGTGGACAGCGACGGCAGCATCAACGCCAGCA

TCAGCCCCCGCCAGAGCTTCAAGTTCAAGCACGGCCTGAAGCTGCGCTTCGAGGTGGGCCAGAAGA

CCCAGCACCGCTGGTTCCTGGACAAGCTGGTGGACGAGATCGGCGTGGGCTACGTGTACGACAACG

GCAGCGTGAGCGTGTACAGCCTGAGCCAGATCAAGCCCCTGCACAACTTCCTGACCCAGCTGCAGC

CCTTCCTGGCCCTGAAGGCCGACCAGGCCAACCTGGTGCTGAAGATCATCGAGCAGCTGCCCAGCG

CCAAGGAGAGCCCCGACAAGTTCCTGGAGGTGTGCACCTGGGTGGACCAGATCGCCGCCCTGAACG

ACAGCAAGACCCGCAAGACCACCAGCGAGACCGTGCGCGCCGTGCTGGACAGCCTGCCCGGCATCC

AGCTGAACAAGGAGAGCAACAACAACGCCAGCACCCAGCGCCCCAGCCGCAACGTGAACAACTTCC

CCTACAGCGGCTACAACAAGGAGTTCCTGCTGTACCTGGCCGGCTTCGTGGACGGCGACGGCAGCA

TCTTCGCCAGCATCCGCCCCCGCCAGCACGCCAAGTTCAAGCACGACCTGGAGCTGTGCTTCAACG

TGCGCCAGAAGACCCAGCGCCGCTGGTTCCTGGACTACCTGGTGGACACCATCGGCGTGGGCTACG

TGATCGACTGGCGCGGCGCCAGCACCTACAAGCTGAGCCAGATCAAGCCCCTGCACAACTTCCTGA

CCCAGCTGCAGCCCTTCCTGAAGCTGAAGCAGAAGCAGGCCAACCTGGTGCTGAAGATCATCGAGC

-continued

Sequence Listing

AGCTGCCCAGCGCCAAGGAGAGCCCCGACAAGTTCCTGGAGGTGTGCACCTGGGTGGACCAGATCG

CCGCCCTGAACGACAGCAAGACCCGCAAGACCACCAGCGAGACCGTGCGCGCCGTTCTAGACAGCC

TGAGCGAGAAGAAGAAAAGCAGCCCCCCCAAGAAGAAGCGCAAGGTGTGATGAGGTACCAGCGGCC

GCACTCATCTTGGCCCTCCTCAGCTCCCTGCCTGTTTCCCGTAAGGCTGTACATAGTCCTTTTATC

TCCTTGTGGCCTATGAAACTGGTTTATAATAAACTCTTAAGAGAACATTAGGCGCGCCAAAAAAAA

AAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAA

SEQ ID NO: 68
AATTATTGGTTAAAGAAGTATATTAGTGCTAATTTCCCTCCGTTTGTCCTAGCTTTTCTCTTCTGT

CAACCCCACACGCCTTTGCCACCCCCAAGAAGAAGCGCAAGGTGATGAACACCAAGTACAACAAGG

AGTTCCTGCTGTACCTGGCCGGCTTCGTGGACAGCGACGGCAGCATCAACGCCAGCATCAGCCCCC

GCCAGAGCTTCAAGTTCAAGCACGGCCTGAAGCTGCGCTTCGAGGTGGGCCAGAAGACCCAGCACC

GCTGGTTCCTGGACAAGCTGGTGGACGAGATCGGCGTGGGCTACGTGTACGACAACGGCAGCGTGA

GCGTGTACAGCCTGAGCCAGATCAAGCCCCTGCACAACTTCCTGACCCAGCTGCAGCCCTTCCTGG

CCCTGAAGGCCGACCAGGCCAACCTGGTGCTGAAGATCATCGAGCAGCTGCCCAGCGCCAAGGAGA

GCCCCGACAAGTTCCTGGAGGTGTGCACCTGGGTGGACCAGATCGCCGCCCTGAACGACAGCAAGA

CCCGCAAGACCACCAGCGAGACCGTGCGCGCCGTGCTGGACAGCCTGCCCGGCATCCAGCTGAACA

AGGAGAGCAACAACAACGCCAGCACCCAGCGCCCCAGCCGCAACGTGAACAACTTCCCCTACAGCG

GCTACAACAAGGAGTTCCTGCTGTACCTGGCCGGCTTCGTGGACGGCGACGGCAGCATCTTCGCCA

GCATCCGCCCCCGCCAGCACGCCAAGTTCAAGCACGACCTGGAGCTGTGCTTCAACGTGCGCCAGA

AGACCCAGCGCCGCTGGTTCCTGGACTACCTGGTGGACACCATCGGCGTGGGCTACGTGATCGACT

GGCGCGGCGCCAGCACCTACAAGCTGAGCCAGATCAAGCCCCTGCACAACTTCCTGACCCAGCTGC

AGCCCTTCCTGAAGCTGAAGCAGAAGCAGGCCAACCTGGTGCTGAAGATCATCGAGCAGCTGCCCA

GCGCCAAGGAGAGCCCCGACAAGTTCCTGGAGGTGTGCACCTGGGTGGACCAGATCGCCGCCCTGA

ACGACAGCAAGACCCGCAAGACCACCAGCGAGACCGTGCGCGCCGTTCTAGACAGCCTGAGCGAGA

AGAAGAAAAGCAGCCCCATGGCCCCCAAGAAGAAGCGCAAGGTGCATTGATGAGGTACCAGCGGCC

GCACTCATCTTGGCCCTCCTCAGCTCCCTGCCTGTTTCCCGTAAGGCTGTACATAGTCCTTTTATC

TCCTTGTGGCCTATGAAACTGGTTTATAATAAACTCTTAAGAGAACATTAGGCGCGCCAAAAAAAA

AAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAA

SEQ ID NO: 69
AATTATTGGTTAAAGAAGTATATTAGTGCTAATTTCCCTCCGTTTGTCCTAGCTTTTCTCTTCTGT

CAACCCCACACGCCTTTGCCACCCCCAAGAAGAAGCGCAAGGTGATGAACACCAAGTACAACAAGG

AGTTCCTGCTGTACCTGGCCGGCTTCGTGGACAGCGACGGCAGCATCAACGCCAGCATCAGCCCCC

GCCAGAGCTTCAAGTTCAAGCACGGCCTGAAGCTGCGCTTCGAGGTGGGCCAGAAGACCCAGCACC

GCTGGTTCCTGGACAAGCTGGTGGACGAGATCGGCGTGGGCTACGTGTACGACAACGGCAGCGTGA

GCGTGTACAGCCTGAGCCAGATCAAGCCCCTGCACAACTTCCTGACCCAGCTGCAGCCCTTCCTGG

CCCTGAAGGCCGACCAGGCCAACCTGGTGCTGAAGATCATCGAGCAGCTGCCCAGCGCCAAGGAGA

GCCCCGACAAGTTCCTGGAGGTGTGCACCTGGGTGGACCAGATCGCCGCCCTGAACGACAGCAAGA

-continued

Sequence Listing

CCCGCAAGACCACCAGCGAGACCGTGCGCGCCGTGCTGGACAGCCTGCCCGGCATCCAGCTGAACA

AGGAGAGCAACAACAACGCCAGCACCCAGCGCCCCAGCCGCAACGTGAACAACTTCCCCTACAGCG

GCTACAACAAGGAGTTCCTGCTGTACCTGGCCGGCTTCGTGGACGGCGACGGCAGCATCTTCGCCA

GCATCCGCCCCCGCCAGCACGCCAAGTTCAAGCACGACCTGGAGCTGTGCTTCAACGTGCGCCAGA

AGACCCAGCGCCGCTGGTTCCTGGACTACCTGGTGGACACCATCGGCGTGGGCTACGTGATCGACT

GGCGCGGCGCCAGCACCTACAAGCTGAGCCAGATCAAGCCCCTGCACAACTTCCTGACCCAGCTGC

AGCCCTTCCTGAAGCTGAAGCAGAAGCAGGCCAACCTGGTGCTGAAGATCATCGAGCAGCTGCCCA

GCGCCAAGGAGAGCCCCGACAAGTTCCTGGAGGTGTGCACCTGGGTGGACCAGATCGCCGCCCTGA

ACGACAGCAAGACCCGCAAGACCACCAGCGAGACCGTGCGCGCCGTTCTAGACAGCCTGAGCGAGA

AGAAGAAAGCAGCCCCCCCAAGAAGAAGCGCAAGGTGTGATGAGGTACCAGCGGCCGCACTCATC

TTGGCCCTCCTCAGCTCCCTGCCTGTTTCCCGTAAGGCTGTACATAGTCCTTTTATCTCCTTGTGG

CCTATGAAACTGGTTTATAATAAACTCTTAAGAGAACATTAGGCGCGCCAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

SEQ ID NO: 70
AATTATTGGTTAAAGAAGTATATTAGTGCTAATTTCCCTCCGTTTGTCCTAGCTTTTCTCTTCTGT

CAACCCCACACGCCTTTGCCACCATGGCCCCCAAGAAGAAGCGCAAGGTGCATATGAACACCAAGT

ACAACAAGGAGTTCCTGCTGTACCTGGCCGGCTTCGTGGACAGCGACGGCAGCATCAACGCCAGCA

TCAGCCCCCGCCAGAGCTTCAAGTTCAAGCACGGCCTGAAGCTGCGCTTCGAGGTGGGCCAGAAGA

CCCAGCACCGCTGGTTCCTGGACAAGCTGGTGGACGAGATCGGCGTGGGCTACGTGTACGACAACG

GCAGCGTGAGCGTGTACAGCCTGAGCCAGATCAAGCCCCTGCACAACTTCCTGACCCAGCTGCAGC

CCTTCCTGGCCCTGAAGGCCGACCAGGCCAACCTGGTGCTGAAGATCATCGAGCAGCTGCCCAGCG

CCAAGGAGAGCCCCGACAAGTTCCTGGAGGTGTGCACCTGGGTGGACCAGATCGCCGCCCTGAACG

ACAGCAAGACCCGCAAGACCACCAGCGAGACCGTGCGCGCCGTGCTGGACAGCCTGCCCGGCATCC

AGCTGAACAAGGAGAGCAACAACAACGCCAGCACCCAGCGCCCCAGCCGCAACGTGAACAACTTCC

CCTACAGCGGCTACAACAAGGAGTTCCTGCTGTACCTGGCCGGCTTCGTGGACGGCGACGGCAGCA

TCTTCGCCAGCATCCGCCCCCGCCAGCACGCCAAGTTCAAGCACGACCTGGAGCTGTGCTTCAACG

TGCGCCAGAAGACCCAGCGCCGCTGGTTCCTGGACTACCTGGTGGACACCATCGGCGTGGGCTACG

TGATCGACTGGCGCGGCGCCAGCACCTACAAGCTGAGCGAGATCAAGCCCCTGCACAACTTCCTGA

CCCAGCTGCAGCCCTTCCTGAAGCTGAAGCAGAAGCAGGCCAACCTGGTGCTGAAGATCATCGAGC

AGCTGCCCAGCGCCAAGGAGAGCCCCGACAAGTTCCTGGAGGTGTGCACCTGGGTGGACCAGATCG

CCGCCCTGAACGACAGCAAGACCCGCAAGACCACCAGCGAGACCGTGCGCGCCGTTCTAGACAGCC

TGAGCGAGAAGAAGAAAGCAGCCCCATGGCCCCCAAGAAGAAGCGCAAGGTGCATTGATGAGGTA

CCAGCGGCCGCACTCATCTTGGCCCTCCTCAGCTCCCTGCCTGTTTCCCGTAAGGCTGTACATAGT

CCTTTTATCTCCTTGTGGCCTATGAAACTGGTTTATAATAAACTCTTAAGAGAACATTAGGCGCGC

CAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAA

-continued

Sequence Listing

SEQ ID NO: 71
AATTATTGGTTAAAGAAGTATATTAGTGCTAATTTCCCTCCGTTTGTCCTAGCTTTTCTCTTCTGT

CAACCCCACACGCCTTTGCCACCATGGCCCCCAAGAAGAAGCGCAAGGTGCATATGAACACCAAGT

ACAACAAGGAGTTCCTGCTGTACCTGGCCGGCTTCGTGGACAGCGACGGCAGCATCAACGCCAGCA

TCAGCCCCCGCCAGAGCTTCAAGTTCAAGCACGGCCTGAAGCTGCGCTTCGAGGTGGGCCAGAAGA

CCCAGCACCGCTGGTTCCTGGACAAGCTGGTGGACGAGATCGGCGTGGGCTACGTGTACGACAACG

GCAGCGTGAGCGTGTACAGCCTGAGCCAGATCAAGCCCCTGCACAACTTCCTGACCCAGCTGCAGC

CCTTCCTGGCCCTGAAGGCCGACCAGGCCAACCTGGTGCTGAAGATCATCGAGCAGCTGCCCAGCG

CCAAGGAGAGCCCCGACAAGTTCCTGGAGGTGTGCACCTGGGTGGACCAGATCGCCGCCCTGAACG

ACAGCAAGACCCGCAAGACCACCAGCGAGACCGTGCGCGCCGTGCTGGACAGCCTGCCCGGCATCC

AGCTGAACAAGGAGAGCAACAACAACGCCAGCACCCAGCGCCCCAGCCGCAACGTGAACAACTTCC

CCTACAGCGGCTACAACAAGGAGTTCCTGCTGTACCTGGCCGGCTTCGTGGACGGCGACGGCAGCA

TCTTCGCCAGCATCCGCCCCCGCCAGCACGCCAAGTTCAAGCACGACCTGGAGCTGTGCTTCAACG

TGCGCCAGAAGACCCAGCGCCGCTGGTTCCTGGACTACCTGGTGGACACCATCGGCGTGGGCTACG

TGATCGACTGGCGCGGCGCCAGCACCTACAAGCTGAGCGAGATCAAGCCCCTGCACAACTTCCTGA

CCCAGCTGCAGCCCTTCCTGAAGCTGAAGCAGAAGCAGGCCAACCTGGTGCTGAAGATCATCGAGC

AGCTGCCCAGCGCCAAGGAGAGCCCCGACAAGTTCCTGGAGGTGTGCACCTGGGTGGACCAGATCG

CCGCCCTGAACGACAGCAAGACCCGCAAGACCACCAGCGAGACCGTGCGCGCCGTTCTAGACAGCC

TGAGCGAGAAGAAGAAAAGCAGCCCCCCCAAGAAGAAGCGCAAGGTGTGATGAGGTACCAGCGGCC

GCACTCATCTTGGCCCTCCTCAGCTCCCTGCCTGTTTCCCGTAAGGCTGTACATAGTCCTTTTATC

TCCTTGTGGCCTATGAAACTGGTTTATAATAAACTCTTAAGAGAACATTAGGCGCGCCAAAAAAAA

AAAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAA

SEQ ID NO: 72
AATTATTGGTTAAAGAAGTATATTAGTGCTAATTTCCCTCCGTTTGTCCTAGCTTTTCTCTTCTGT

CAACCCCACACGCCTTTGCCACCCCCAAGAAGAAGCGCAAGGTGATGAACACCAAGTACAACAAGG

AGTTCCTGCTGTACCTGGCCGGCTTCGTGGACAGCGACGGCAGCATCAACGCCAGCATCAGCCCCC

GCCAGAGCTTCAAGTTCAAGCACGGCCTGAAGCTGCGCTTCGAGGTGGGCCAGAAGACCCAGCACC

GCTGGTTCCTGGACAAGCTGGTGGACGAGATCGGCGTGGGCTACGTGTACGACAACGGCAGCGTGA

GCGTGTACAGCCTGAGCCAGATCAAGCCCCTGCACAACTTCCTGACCCAGCTGCAGCCCTTCCTGG

CCCTGAAGGCCGACCAGGCCAACCTGGTGCTGAAGATCATCGAGCAGCTGCCCAGCGCCAAGGAGA

GCCCCGACAAGTTCCTGGAGGTGTGCACCTGGGTGGACCAGATCGCCGCCCTGAACGACAGCAAGA

CCCGCAAGACCACCAGCGAGACCGTGCGCGCCGTGCTGGACAGCCTGCCCGGCATCCAGCTGAACA

AGGAGAGCAACAACAACGCCAGCACCCAGCGCCCCAGCCGCAACGTGAACAACTTCCCCTACAGCG

GCTACAACAAGGAGTTCCTGCTGTACCTGGCCGGCTTCGTGGACGGCGACGGCAGCATCTTCGCCA

GCATCCGCCCCCGCCAGCACGCCAAGTTCAAGCACGACCTGGAGCTGTGCTTCAACGTGCGCCAGA

AGACCCAGCGCCGCTGGTTCCTGGACTACCTGGTGGACACCATCGGCGTGGGCTACGTGATCGACT

GGCGCGGCGCCAGCACCTACAAGCTGAGCGAGATCAAGCCCCTGCACAACTTCCTGACCCAGCTGC

AGCCCTTCCTGAAGCTGAAGCAGAAGCAGGCCAACCTGGTGCTGAAGATCATCGAGCAGCTGCCCA

GCGCCAAGGAGAGCCCCGACAAGTTCCTGGAGGTGTGCACCTGGGTGGACCAGATCGCCGCCCTGA

-continued

Sequence Listing

ACGACAGCAAGACCCGCAAGACCACCAGCGAGACCGTGCGCGCCGTTCTAGACAGCCTGAGCGAGA

AGAAGAAAAGCAGCCCCATGGCCCCCAAGAAGAAGCGCAAGGTGCATTGATGAGGTACCAGCGGCC

GCACTCATCTTGGCCCTCCTCAGCTCCCTGCCTGTTTCCCGTAAGGCTGTACATAGTCCTTTTATC

TCCTTGTGGCCTATGAAACTGGTTTATAATAAACTCTTAAGAGAACATTAGGCGCGCCAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

SEQ ID NO: 73
AATTATTGGTTAAAGAAGTATATTAGTGCTAATTTCCCTCCGTTTGTCCTAGCTTTTCTCTTCTGT

CAACCCCACACGCCTTTGCCACCCCCAAGAAGAAGCGCAAGGTGATGAACACCAAGTACAACAAGG

AGTTCCTGCTGTACCTGGCCGGCTTCGTGGACAGCGACGGCAGCATCAACGCCAGCATCAGCCCCC

GCCAGAGCTTCAAGTTCAAGCACGGCCTGAAGCTGCGCTTCGAGGTGGGCCAGAAGACCCAGCACC

GCTGGTTCCTGGACAAGCTGGTGGACGAGATCGGCGTGGGCTACGTGTACGACAACGGCAGCGTGA

GCGTGTACAGCCTGAGCCAGATCAAGCCCCTGCACAACTTCCTGACCCAGCTGCAGCCCTTCCTGG

CCCTGAAGGCCGACCAGGCCAACCTGGTGCTGAAGATCATCGAGCAGCTGCCCAGCGCCAAGGAGA

GCCCCGACAAGTTCCTGGAGGTGTGCACCTGGGTGGACCAGATCGCCGCCCTGAACGACAGCAAGA

CCCGCAAGACCACCAGCGAGACCGTGCGCGCCGTGCTGGACAGCCTGCCCGGCATCCAGCTGAACA

AGGAGAGCAACAACAACGCCAGCACCCAGCGCCCCAGCCGCAACGTGAACAACTTCCCCTACAGCG

GCTACAACAAGGAGTTCCTGCTGTACCTGGCCGGCTTCGTGGACGGCGACGGCAGCATCTTCGCCA

GCATCCGCCCCCGCCAGCACGCCAAGTTCAAGCACGACCTGGAGCTGTGCTTCAACGTGCGCCAGA

AGACCCAGCGCCGCTGGTTCCTGGACTACCTGGTGGACACCATCGGCGTGGGCTACGTGATCGACT

GGCGCGGCGCCAGCACCTACAAGCTGAGCGAGATCAAGCCCCTGCACAACTTCCTGACCCAGCTGC

AGCCCTTCCTGAAGCTGAAGCAGAAGCAGGCCAACCTGGTGCTGAAGATCATCGAGCAGCTGCCCA

GCGCCAAGGAGAGCCCCGACAAGTTCCTGGAGGTGTGCACCTGGGTGGACCAGATCGCCGCCCTGA

ACGACAGCAAGACCCGCAAGACCACCAGCGAGACCGTGCGCGCCGTTCTAGACAGCCTGAGCGAGA

AGAAGAAAGCAGCCCCCCCAAGAAGAAGCGCAAGGTGTGATGAGGTACCAGCGGCCGCACTCATC

TTGGCCCTCCTCAGCTCCCTGCCTGTTTCCCGTAAGGCTGTACATAGTCCTTTTATCTCCTTGTGG

CCTATGAAACTGGTTTATAATAAACTCTTAAGAGAACATTAGGCGCGCCAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

SEQ ID NO: 74
AAUUAUUGGUUAAAGAAGUAUAUUAGUGCUAAUUUCCCUCCGUUUGUCCUAGCUUUUCUCUUCUGU

CAACCCCACACGCCUUUGCCACCAUGGCCCCCAAGAAGAAGCGCAAGGUGCAUAUGAACACCAAGU

ACAACAAGGAGUUCCUGCUGUACCUGGCCGGCUUCGUGGACAGCGACGGCAGCAUCAACGCCAGCA

UCAGCCCCCGCCAGAGCUUCAAGUUCAAGCACGGCCUGAAGCUGCGCUUCGAGGUGGGCCAGAAGA

CCCAGCACCGCUGGUUCCUGGACAAGCUGGUGGACGAGAUCGGCGUGGGCUACGUGUACGACAACG

GCAGCGUGAGCGUGUACAGCCUGAGCCAGAUCAAGCCCCUGCACAACUUCCUGACCCAGCUGCAGC

CCUUCCUGGCCCUGAAGGCCGACCAGGCCAACCUGGUGCUGAAGAUCAUCGAGCAGCUGCCCAGCG

CCAAGGAGAGCCCCGACAAGUUCCUGGAGGUGUGCACCUGGGUGGACCAGAUCGCCGCCCUGAACG

ACAGCAAGACCCGCAAGACCACCAGCGAGACCGUGCGCGCCGUGCUGGACAGCCUGCCCGGCAUCC

-continued

---
Sequence Listing
---

AGCUGAACAAGGAGAGCAACAACAACGCCAGCACCCAGCGCCCCAGCCGCAACGUGAACAACUUCC

CCUACAGCGGCUACAACAAGGAGUUCCUGCUGUACCUGGCCGGCUUCGUGGACGGCGACGGCAGCA

UCUUCGCCAGCAUCCGCCCCCGCCAGCACGCCAAGUUCAAGCACGACCUGGAGCUGUGCUUCAACG

UGCGCCAGAAGACCCAGCGCCGCUGGUUCCUGGACUACCUGGUGGACACCAUCGGCGUGGGCUACG

UGAUCGACUGGCGCGGCGCCAGCACCUACAAGCUGAGCCAGAUCAAGCCCCUGCACAACUUCCUGA

CCCAGCUGCAGCCCUUCCUGAAGCUGAAGCAGAAGCAGGCCAACCUGGUGCUGAAGAUCAUCGAGC

AGCUGCCCAGCGCCAAGGAGAGCCCCGACAAGUUCCUGGAGGUGUGCACCUGGGUGGACCAGAUCG

CCGCCCUGAACGACAGCAAGACCCGCAAGACCACCAGCGAGACCGUGCGCGCCGUUCUAGACAGCC

UGAGCGAGAAGAAGAAAAGCAGCCCCAUGGCCCCCAAGAAGAAGCGCAAGGUGCAUUGAUGAGGUA

CCAGCGGCCGCACUCAUCUUGGCCCUCCUCAGCUCCCUGCCUGUUUCCCGUAAGGCUGUACAUAGU

CCUUUUAUCUCCUUGUGGCCUAUGAAACUGGUUUAUAAUAAACUCUUAAGAGAACAUUAGGCGCGC

CAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAA

SEQ ID NO: 75
AAUUAUUGGUUAAAGAAGUAUAUUAGUGCUAAUUUCCCUCCGUUUGUCCUAGCUUUUCUCUUCUGU

CAACCCCACACGCCUUUGCCACCAUGGCCCCCAAGAAGAAGCGCAAGGUGCAUAUGAACACCAAGU

ACAACAAGGAGUUCCUGCUGUACCUGGCCGGCUUCGUGGACAGCGACGGCAGCAUCAACGCCAGCA

UCAGCCCCCGCCAGAGCUUCAAGUUCAAGCACGGCCUGAAGCUGCGCUUCGAGGUGGGCCAGAAGA

CCCAGCACCGCUGGUUCCUGGACAAGCUGGUGGACGAGAUCGGCGUGGGCUACGUGUACGACAACG

GCAGCGUGAGCGUGUACAGCCUGAGCCAGAUCAAGCCCCUGCACAACUUCCUGACCCAGCUGCAGC

CCUUCCUGGCCCUGAAGGCCGACCAGGCCAACCUGGUGCUGAAGAUCAUCGAGCAGCUGCCCAGCG

CCAAGGAGAGCCCCGACAAGUUCCUGGAGGUGUGCACCUGGGUGGACCAGAUCGCCGCCCUGAACG

ACAGCAAGACCCGCAAGACCACCAGCGAGACCGUGCGCGCCGUGCUGGACAGCCUGCCCGGCAUCC

AGCUGAACAAGGAGAGCAACAACAACGCCAGCACCCAGCGCCCCAGCCGCAACGUGAACAACUUCC

CCUACAGCGGCUACAACAAGGAGUUCCUGCUGUACCUGGCCGGCUUCGUGGACGGCGACGGCAGCA

UCUUCGCCAGCAUCCGCCCCCGCCAGCACGCCAAGUUCAAGCACGACCUGGAGCUGUGCUUCAACG

UGCGCCAGAAGACCCAGCGCCGCUGGUUCCUGGACUACCUGGUGGACACCAUCGGCGUGGGCUACG

UGAUCGACUGGCGCGGCGCCAGCACCUACAAGCUGAGCCAGAUCAAGCCCCUGCACAACUUCCUGA

CCCAGCUGCAGCCCUUCCUGAAGCUGAAGCAGAAGCAGGCCAACCUGGUGCUGAAGAUCAUCGAGC

AGCUGCCCAGCGCCAAGGAGAGCCCCGACAAGUUCCUGGAGGUGUGCACCUGGGUGGACCAGAUCG

CCGCCCUGAACGACAGCAAGACCCGCAAGACCACCAGCGAGACCGUGCGCGCCGUUCUAGACAGCC

UGAGCGAGAAGAAGAAAAGCAGCCCCCCCAAGAAGAAGCGCAAGGUGUGAUGAGGUACCAGCGGCC

GCACUCAUCUUGGCCCUCCUCAGCUCCCUGCCUGUUUCCCGUAAGGCUGUACAUAGUCCUUUUAUC

UCCUUGUGGCCUAUGAAACUGGUUUAUAAUAAACUCUUAAGAGAACAUUAGGCGCGCCAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

SEQ ID NO: 76
AAUUAUUGGUUAAAGAAGUAUAUUAGUGCUAAUUUCCCUCCGUUUGUCCUAGCUUUUCUCUUCUGU

CAACCCCACACGCCUUUGCCACCCCCAAGAAGAAGCGCAAGGUGAUGAACACCAAGUACAACAAGG

-continued

Sequence Listing

AGUUCCUGCUGUACCUGGCCGGCUUCGUGGACAGCGACGGCAGCAUCAACGCCAGCAUCAGCCCCC

GCCAGAGCUUCAAGUUCAAGCACGGCCUGAAGCUGCGCUUCGAGGUGGGCCAGAAGACCCAGCACC

GCUGGUUCCUGGACAAGCUGGUGGACGAGAUCGGCGUGGGCUACGUGUACGACAACGGCAGCGUGA

GCGUGUACAGCCUGAGCCAGAUCAAGCCCCUGCACAACUUCCUGACCCAGCUGCAGCCCUUCCUGG

CCCUGAAGGCCGACCAGGCCAACCUGGUGCUGAAGAUCAUCGAGCAGCUGCCCAGCGCCAAGGAGA

GCCCCGACAAGUUCCUGGAGGUGUGCACCUGGGUGGACCAGAUCGCCGCCCUGAACGACAGCAAGA

CCCGCAAGACCACCAGCGAGACCGUGCGCGCCGUGCUGGACAGCCUGCCCGGCAUCCAGCUGAACA

AGGAGAGCAACAACAACGCCAGCACCCAGCGCCCCAGCCGCAACGUGAACAACUUCCCCUACAGCG

GCUACAACAAGGAGUUCCUGCUGUACCUGGCCGGCUUCGUGGACGGCGACGGCAGCAUCUUCGCCA

GCAUCCGCCCCCGCCAGCACGCCAAGUUCAAGCACGACCUGGAGCUGUGCUUCAACGUGCGCCAGA

AGACCCAGCGCCGCUGGUUCCUGGACUACCUGGUGGACACCAUCGGCGUGGGCUACGUGAUCGACU

GGCGCGGCGCCAGCACCUACAAGCUGAGCCAGAUCAAGCCCCUGCACAACUUCCUGACCCAGCUGC

AGCCCUUCCUGAAGCUGAAGCAGAAGCAGGCCAACCUGGUGCUGAAGAUCAUCGAGCAGCUGCCCA

GCGCCAAGGAGAGCCCCGACAAGUUCCUGGAGGUGUGCACCUGGGUGGACCAGAUCGCCGCCCUGA

ACGACAGCAAGACCCGCAAGACCACCAGCGAGACCGUGCGCGCCGUUCUAGACAGCCUGAGCGAGA

AGAAGAAAGCAGCCCCAUGGCCCCCAAGAAGAAGCGCAAGGUGCAUUGAUGAGGUACCAGCGGCC

GCACUCAUCUUGGCCCUCCUCAGCUCCCUGCCUGUUUCCCGUAAGGCUGUACAUAGUCCUUUUAUC

UCCUUGUGGCCUAUGAAACUGGUUUAUAAUAAACUCUUAAGAGAACAUUAGGCGCGCCAAAAAAAA

AAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAA

SEQ ID NO: 77
AAUUAUUGGUUAAAGAAGUAUAUUAGUGCUAAUUUCCCUCCGUUUGUCCUAGCUUUUCUCUUCUGU

CAACCCCACACGCCUUUGCCACCCCCAAGAAGAAGCGCAAGGUGAUGAACACCAAGUACAACAAGG

AGUUCCUGCUGUACCUGGCCGGCUUCGUGGACAGCGACGGCAGCAUCAACGCCAGCAUCAGCCCCC

GCCAGAGCUUCAAGUUCAAGCACGGCCUGAAGCUGCGCUUCGAGGUGGGCCAGAAGACCCAGCACC

GCUGGUUCCUGGACAAGCUGGUGGACGAGAUCGGCGUGGGCUACGUGUACGACAACGGCAGCGUGA

GCGUGUACAGCCUGAGCCAGAUCAAGCCCCUGCACAACUUCCUGACCCAGCUGCAGCCCUUCCUGG

CCCUGAAGGCCGACCAGGCCAACCUGGUGCUGAAGAUCAUCGAGCAGCUGCCCAGCGCCAAGGAGA

GCCCCGACAAGUUCCUGGAGGUGUGCACCUGGGUGGACCAGAUCGCCGCCCUGAACGACAGCAAGA

CCCGCAAGACCACCAGCGAGACCGUGCGCGCCGUGCUGGACAGCCUGCCCGGCAUCCAGCUGAACA

AGGAGAGCAACAACAACGCCAGCACCCAGCGCCCCAGCCGCAACGUGAACAACUUCCCCUACAGCG

GCUACAACAAGGAGUUCCUGCUGUACCUGGCCGGCUUCGUGGACGGCGACGGCAGCAUCUUCGCCA

GCAUCCGCCCCCGCCAGCACGCCAAGUUCAAGCACGACCUGGAGCUGUGCUUCAACGUGCGCCAGA

AGACCCAGCGCCGCUGGUUCCUGGACUACCUGGUGGACACCAUCGGCGUGGGCUACGUGAUCGACU

GGCGCGGCGCCAGCACCUACAAGCUGAGCCAGAUCAAGCCCCUGCACAACUUCCUGACCCAGCUGC

AGCCCUUCCUGAAGCUGAAGCAGAAGCAGGCCAACCUGGUGCUGAAGAUCAUCGAGCAGCUGCCCA

GCGCCAAGGAGAGCCCCGACAAGUUCCUGGAGGUGUGCACCUGGGUGGACCAGAUCGCCGCCCUGA

ACGACAGCAAGACCCGCAAGACCACCAGCGAGACCGUGCGCGCCGUUCUAGACAGCCUGAGCGAGA

AGAAGAAAGCAGCCCCCCCAAGAAGAAGCGCAAGGUGUGAUGAGGUACCAGCGGCCGCACUCAUC

-continued

---

Sequence Listing

---

UUGGCCCUCCUCAGCUCCCUGCCUGUUUCCCGUAAGGCUGUACAUAGUCCUUUUAUCUCCUUGUGG

CCUAUGAAACUGGUUUAUAAUAAACUCUUAAGAGAACAUUAGGCGCGCCAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

SEQ ID NO: 78
AAUUAUUGGUUAAAGAAGUAUAUUAGUGCUAAUUUCCCUCCGUUUGUCCUAGCUUUUCUCUUCUGU

CAACCCCACACGCCUUUGCCACCAUGGCCCCCAAGAAGAAGCGCAAGGUGCAUAUGAACACCAAGU

ACAACAAGGAGUUCCUGCUGUACCUGGCCGGCUUCGUGGACAGCGACGGCAGCAUCAACGCCAGCA

UCAGCCCCCGCCAGAGCUUCAAGUUCAAGCACGGCCUGAAGCUGCGCUUCGAGGUGGGCCAGAAGA

CCCAGCACCGCUGGUUCCUGGACAAGCUGGUGGACGAGAUCGGCGUGGGCUACGUGUACGACAACG

GCAGCGUGAGCGUGUACAGCCUGAGCCAGAUCAAGCCCCUGCACAACUUCCUGACCCAGCUGCAGC

CCUUCCUGGCCCUGAAGGCCGACCAGGCCAACCUGGUGCUGAAGAUCAUCGAGCAGCUGCCCAGCG

CCAAGGAGAGCCCCGACAAGUUCCUGGAGGUGUGCACCUGGGUGGACCAGAUCGCCGCCCUGAACG

ACAGCAAGACCCGCAAGACCACCAGCGAGACCGUGCGCGCCGUGCUGGACAGCCUGCCCGGCAUCC

AGCUGAACAAGGAGAGCAACAACAACGCCAGCACCCAGCGCCCCAGCCGCAACGUGAACAACUUCC

CCUACAGCGGCUACAACAAGGAGUUCCUGCUGUACCUGGCCGGCUUCGUGGACGGCGACGGCAGCA

UCUUCGCCAGCAUCCGCCCCCGCCAGCACGCCAAGUUCAAGCACGACCUGGAGCUGUGCUUCAACG

UGCGCCAGAAGACCCAGCGCCGCUGGUUCCUGGACUACCUGGUGGACACCAUCGGCGUGGGCUACG

UGAUCGACUGGCGCGGCGCCAGCACCUACAAGCUGAGCGAGAUCAAGCCCCUGCACAACUUCCUGA

CCCAGCUGCAGCCCUUCCUGAAGCUGAAGCAGAAGCAGGCCAACCUGGUGCUGAAGAUCAUCGAGC

AGCUGCCCAGCGCCAAGGAGAGCCCCGACAAGUUCCUGGAGGUGUGCACCUGGGUGGACCAGAUCG

CCGCCCUGAACGACAGCAAGACCCGCAAGACCACCAGCGAGACCGUGCGCGCCGUUCUAGACAGCC

UGAGCGAGAAGAAGAAAAGCAGCCCCAUGGCCCCCAAGAAGAAGCGCAAGGUGCAUUGAUGAGGUA

CCAGCGGCCGCACUCAUCUUGGCCCUCCUCAGCUCCCUGCCUGUUUCCCGUAAGGCUGUACAUAGU

CCUUUUAUCUCCUUGUGGCCUAUGAAACUGGUUUAUAAUAAACUCUUAAGAGAACAUUAGGCGCGC

CAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAA

SEQ ID NO: 79
AAUUAUUGGUUAAAGAAGUAUAUUAGUGCUAAUUUCCCUCCGUUUGUCCUAGCUUUUCUCUUCUGU

CAACCCCACACGCCUUUGCCACCAUGGCCCCCAAGAAGAAGCGCAAGGUGCAUAUGAACACCAAGU

ACAACAAGGAGUUCCUGCUGUACCUGGCCGGCUUCGUGGACAGCGACGGCAGCAUCAACGCCAGCA

UCAGCCCCCGCCAGAGCUUCAAGUUCAAGCACGGCCUGAAGCUGCGCUUCGAGGUGGGCCAGAAGA

CCCAGCACCGCUGGUUCCUGGACAAGCUGGUGGACGAGAUCGGCGUGGGCUACGUGUACGACAACG

GCAGCGUGAGCGUGUACAGCCUGAGCCAGAUCAAGCCCCUGCACAACUUCCUGACCCAGCUGCAGC

CCUUCCUGGCCCUGAAGGCCGACCAGGCCAACCUGGUGCUGAAGAUCAUCGAGCAGCUGCCCAGCG

CCAAGGAGAGCCCCGACAAGUUCCUGGAGGUGUGCACCUGGGUGGACCAGAUCGCCGCCCUGAACG

ACAGCAAGACCCGCAAGACCACCAGCGAGACCGUGCGCGCCGUGCUGGACAGCCUGCCCGGCAUCC

AGCUGAACAAGGAGAGCAACAACAACGCCAGCACCCAGCGCCCCAGCCGCAACGUGAACAACUUCC

-continued

---

Sequence Listing

---

CCUACAGCGGCUACAACAAGGAGUUCCUGCUGUACCUGGCCGGCUUCGUGGACGGCGACGGCAGCA

UCUUCGCCAGCAUCCGCCCCCGCCAGCACGCCAAGUUCAAGCACGACCUGGAGCUGUGCUUCAACG

UGCGCCAGAAGACCCAGCGCCGCUGGUUCCUGGACUACCUGGUGGACACCAUCGGCGUGGGCUACG

UGAUCGACUGGCGCGGCGCCAGCACCUACAAGCUGAGCGAGAUCAAGCCCCUGCACAACUUCCUGA

CCCAGCUGCAGCCCUUCCUGAAGCUGAAGCAGAAGCAGGCCAACCUGGUGCUGAAGAUCAUCGAGC

AGCUGCCCAGCGCCAAGGAGAGCCCCGACAAGUUCCUGGAGGUGUGCACCUGGGUGGACCAGAUCG

CCGCCCUGAACGACAGCAAGACCCGCAAGACCACCAGCGAGACCGUGCGCGCCGUUCUAGACAGCC

UGAGCGAGAAGAAGAAAAGCAGCCCCCCCAAGAAGAAGCGCAAGGUGUGAUGAGGUACCAGCGGCC

GCACUCAUCUUGGCCCUCCUCAGCUCCCUGCCUGUUUCCCGUAAGGCUGUACAUAGUCCUUUUAUC

UCCUUGUGGCCUAUGAAACUGGUUUAUAAUAAACUCUUAAGAGAACAUUAGGCGCGCCAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

SEQ ID NO: 80
AAUUAUUGGUUAAAGAAGUAUAUUAGUGCUAAUUUCCCUCCGUUUGUCCUAGCUUUUCUCUUCUGU

CAACCCCACACGCCUUUGCCACCCCCAAGAAGAAGCGCAAGGUGAUGAACACCAAGUACAACAAGG

AGUUCCUGCUGUACCUGGCCGGCUUCGUGGACAGCGACGGCAGCAUCAACGCCAGCAUCAGCCCCC

GCCAGAGCUUCAAGUUCAAGCACGGCCUGAAGCUGCGCUUCGAGGUGGGCCAGAAGACCCAGCACC

GCUGGUUCCUGGACAAGCUGGUGGACGAGAUCGGCGUGGGCUACGUGUACGACAACGGCAGCGUGA

GCGUGUACAGCCUGAGCCAGAUCAAGCCCCUGCACAACUUCCUGACCCAGCUGCAGCCCUUCCUGG

CCCUGAAGGCCGACCAGGCCAACCUGGUGCUGAAGAUCAUCGAGCAGCUGCCCAGCGCCAAGGAGA

GCCCCGACAAGUUCCUGGAGGUGUGCACCUGGGUGGACCAGAUCGCCGCCCUGAACGACAGCAAGA

CCCGCAAGACCACCAGCGAGACCGUGCGCGCCGUGCUGGACAGCCUGCCCGGCAUCCAGCUGAACA

AGGAGAGCAACAACAACGCCAGCACCCAGCGCCCCAGCCGCAACGUGAACAACUUCCCCUACAGCG

GCUACAACAAGGAGUUCCUGCUGUACCUGGCCGGCUUCGUGGACGGCGACGGCAGCAUCUUCGCCA

GCAUCCGCCCCCGCCAGCACGCCAAGUUCAAGCACGACCUGGAGCUGUGCUUCAACGUGCGCCAGA

AGACCCAGCGCCGCUGGUUCCUGGACUACCUGGUGGACACCAUCGGCGUGGGCUACGUGAUCGACU

GGCGCGGCGCCAGCACCUACAAGCUGAGCGAGAUCAAGCCCCUGCACAACUUCCUGACCCAGCUGC

AGCCCUUCCUGAAGCUGAAGCAGAAGCAGGCCAACCUGGUGCUGAAGAUCAUCGAGCAGCUGCCCA

GCGCCAAGGAGAGCCCCGACAAGUUCCUGGAGGUGUGCACCUGGGUGGACCAGAUCGCCGCCCUGA

ACGACAGCAAGACCCGCAAGACCACCAGCGAGACCGUGCGCGCCGUUCUAGACAGCCUGAGCGAGA

AGAAGAAAAGCAGCCCCAUGGCCCCCAAGAAGAAGCGCAAGGUGCAUUGAUGAGGUACCAGCGGCC

GCACUCAUCUUGGCCCUCCUCAGCUCCCUGCCUGUUUCCCGUAAGGCUGUACAUAGUCCUUUUAUC

UCCUUGUGGCCUAUGAAACUGGUUUAUAAUAAACUCUUAAGAGAACAUUAGGCGCGCCAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAAAAA

SEQ ID NO: 81
AAUUAUUGGUUAAAGAAGUAUAUUAGUGCUAAUUUCCCUCCGUUUGUCCUAGCUUUUCUCUUCUGU

CAACCCCACACGCCUUUGCCACCCCCAAGAAGAAGCGCAAGGUGAUGAACACCAAGUACAACAAGG

AGUUCCUGCUGUACCUGGCCGGCUUCGUGGACAGCGACGGCAGCAUCAACGCCAGCAUCAGCCCCC

GCCAGAGCUUCAAGUUCAAGCACGGCCUGAAGCUGCGCUUCGAGGUGGGCCAGAAGACCCAGCACC

Sequence Listing

GCUGGUUCCUGGACAAGCUGGUGGACGAGAUCGGCGUGGGCUACGUGUACGACAACGGCAGCGUGA

GCGUGUACAGCCUGAGCCAGAUCAAGCCCCUGCACAACUUCCUGACCCAGCUGCAGCCCUUCCUGG

CCCUGAAGGCCGACCAGGCCAACCUGGUGCUGAAGAUCAUCGAGCAGCUGCCCAGCGCCAAGGAGA

GCCCCGACAAGUUCCUGGAGGUGUGCACCUGGGUGGACCAGAUCGCCGCCCUGAACGACAGCAAGA

CCCGCAAGACCACCAGCGAGACCGUGCGCGCCGUGCUGGACAGCCUGCCCGGCAUCCAGCUGAACA

AGGAGAGCAACAACAACGCCAGCACCCAGCGCCCCAGCCGCAACGUGAACAACUUCCCCUACAGCG

GCUACAACAAGGAGUUCCUGCUGUACCUGGCCGGCUUCGUGGACGGCGACGGCAGCAUCUUCGCCA

GCAUCCGCCCCCGCCAGCACGCCAAGUUCAAGCACGACCUGGAGCUGUGCUUCAACGUGCGCCAGA

AGACCCAGCGCCGCUGGUUCCUGGACUACCUGGUGGACACCAUCGGCGUGGGCUACGUGAUCGACU

GGCGCGGCGCCAGCACCUACAAGCUGAGCGAGAUCAAGCCCCUGCACAACUUCCUGACCCAGCUGC

AGCCCUUCCUGAAGCUGAAGCAGAAGCAGGCCAACCUGGUGCUGAAGAUCAUCGAGCAGCUGCCCA

GCGCCAAGGAGAGCCCCGACAAGUUCCUGGAGGUGUGCACCUGGGUGGACCAGAUCGCCGCCCUGA

ACGACAGCAAGACCCGCAAGACCACCAGCGAGACCGUGCGCGCCGUUCUAGACAGCCUGAGCGAGA

AGAAGAAAGCAGCCCCCCCAAGAAGAAGCGCAAGGUGUGAUGAGGUACCAGCGGCCGCACUCAUC

UUGGCCCUCCUCAGCUCCCUGCCUGUUUCCCGUAAGGCUGUACAUAGUCCUUUUAUCUCCUUGUGG

CCUAUGAAACUGGUUUAUAAUAAACUCUUAAGAGAACAUUAGGCGCGCCAAAAAAAAAAAAAAAAA

AAAAAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

SEQ ID NO: 82
AAUUAUUGGUUAAAGAAGUAUAUUAGUGCUAAUUUCCCUCCGUUUGUCCUAGCUUUUCUCUUCUGU

CAACCCCACACGCCUUUGCCAC

SEQ ID NO: 83
ACUCAUCUUGGCCCUCCUCAGCUCCCUGCCUGUUUCCCGUAAGGCUGUACAUAGUCCUUUUAUCUC

CUUGUGGCCUAUGAAACUGGUUUAUAAUAAACUCUUAAGAGAACAUUA

SEQ ID NO: 84
GCCACCAUGG

---

The invention claimed is:

1. An engineered meganuclease that binds and cleaves a recognition sequence consisting of SEQ ID NO: 3 within a Hepatitis B virus (HBV) genome, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region, and wherein said engineered meganuclease comprises the amino acid sequence of SEQ ID NO: 5 or SEQ ID NO: 6.

2. The engineered meganuclease of claim 1, wherein said engineered meganuclease is encoded by the nucleic acid sequence of SEQ ID NO: 11 or SEQ ID NO: 12.

3. A polynucleotide comprising a nucleic acid sequence encoding said engineered meganuclease of claim 1.

4. The polynucleotide of claim 3, wherein said polynucleotide is an mRNA.

5. A recombinant DNA construct comprising said polynucleotide of claim 3.

6. The recombinant DNA construct of claim 5, wherein said recombinant DNA construct is a plasmid DNA.

7. A composition comprising lipid nanoparticles comprising the mRNA of claim 4.

8. A composition comprising a pharmaceutically acceptable carrier and said mRNA of claim 4.

9. A composition comprising a pharmaceutically acceptable carrier and said lipid nanoparticle composition of claim 7.

* * * * *

SEQUENCE LISTING

Sequence total quantity: 84
SEQ ID NO: 1              moltype = AA   length = 163
FEATURE                   Location/Qualifiers
source                    1..163
                          mol_type = protein
                          organism = Chlamydomonas reinhardtii
SEQUENCE: 1
MNTKYNKEFL LYLAGFVDGD GSIIAQIKPN QSYKFKHQLS LAFQVTQKTQ RRWFLDKLVD  60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                    163

SEQ ID NO: 2              moltype = AA   length = 9
FEATURE                   Location/Qualifiers
source                    1..9
                          mol_type = protein
                          organism = Chlamydomonas reinhardtii
SEQUENCE: 2
LAGLIDADG                                                           9

SEQ ID NO: 3              moltype = DNA   length = 22
FEATURE                   Location/Qualifiers -continued

```
source                    1..22
                          mol_type = genomic DNA
                          organism = Homo sapiens
SEQUENCE: 3
tgccgatcca tactgcggaa ct                                      22

SEQ ID NO: 4              moltype = DNA   length = 22
FEATURE                   Location/Qualifiers
source                    1..22
                          mol_type = genomic DNA
                          organism = Homo sapiens
SEQUENCE: 4
agttccgcag tatggatcgg ca                                      22

SEQ ID NO: 5              moltype = AA   length = 343
FEATURE                   Location/Qualifiers
source                    1..343
                          mol_type = protein
                          organism = synthetic construct
SEQUENCE: 5
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                    343

SEQ ID NO: 6              moltype = AA   length = 343
FEATURE                   Location/Qualifiers
source                    1..343
                          mol_type = protein
                          organism = synthetic construct
SEQUENCE: 6
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDYLVD  240
TIGVGYVIDW RGASTYKLSE IKPLHNFLTQ LQPFLKLKQK QANLVLKIIE QLPSAKESPD  300
KFLEVCTWVD QIAALNDSKT RKTTSETVRA VLDSLSEKKK SSP                    343

SEQ ID NO: 7              moltype = AA   length = 147
FEATURE                   Location/Qualifiers
source                    1..147
                          mol_type = protein
                          organism = synthetic construct
SEQUENCE: 7
KEFLLYLAGF VDGDGSIFAS IRPRQHAKFK HDLELCFNVR QKTQRRWFLD YLVDTIGVGY   60
VIDWRGASTY KLSQIKPLHN FLTQLQPFLK LKQKQANLVL KIIEQLPSAK ESPDKFLEVC  120
TWVDQIAALN DSKTRKTTSE TVRAVLD                                      147

SEQ ID NO: 8              moltype = AA   length = 147
FEATURE                   Location/Qualifiers
source                    1..147
                          mol_type = protein
                          organism = synthetic construct
SEQUENCE: 8
KEFLLYLAGF VDGDGSIFAS IRPRQHAKFK HDLELCFNVR QKTQRRWFLD YLVDTIGVGY   60
VIDWRGASTY KLSEIKPLHN FLTQLQPFLK LKQKQANLVL KIIEQLPSAK ESPDKFLEVC  120
TWVDQIAALN DSKTRKTTSE TVRAVLD                                      147

SEQ ID NO: 9              moltype = AA   length = 147
FEATURE                   Location/Qualifiers
source                    1..147
                          mol_type = protein
                          organism = synthetic construct
SEQUENCE: 9
KEFLLYLAGF VDSDGSINAS ISPRQSFKFK HGLKLRFEVG QKTQHRWFLD KLVDEIGVGY   60
VYDNGSVSVY SLSQIKPLHN FLTQLQPFLA LKADQANLVL KIIEQLPSAK ESPDKFLEVC  120
TWVDQIAALN DSKTRKTTSE TVRAVLD                                      147

SEQ ID NO: 10             moltype = AA   length = 147
FEATURE                   Location/Qualifiers
source                    1..147
                          mol_type = protein
                          organism = synthetic construct
SEQUENCE: 10
KEFLLYLAGF VDSDGSINAS ISPRQSFKFK HGLKLRFEVG QKTQHRWFLD KLVDEIGVGY   60
VYDNGSVSVY SLSQIKPLHN FLTQLQPFLA LKADQANLVL KIIEQLPSAK ESPDKFLEVC  120
TWVDQIAALN DSKTRKTTSE TVRAVLD                                      147
```

-continued

```
SEQ ID NO: 11              moltype = DNA  length = 1029
FEATURE                    Location/Qualifiers
source                     1..1029
                           mol_type = other DNA
                           organism = synthetic construct
SEQUENCE: 11
atgaacacca agtacaacaa ggagttcctg ctgtacctgg ccggcttcgt ggacagcgac    60
ggcagcatca acgccagcat cagcccccgc cagagcttca agttcaagca cggcctgaag   120
ctgcgcttcg aggtggggcca gaagacccag caccgctggt tcctggacaa gctggtggac   180
gagatcggcg tgggctacgt gtacgacaac ggcagcgtga gcgtgtacag cctgagccag   240
atcaagcccc tgcacaactt cctgacccag ctgcagccct tcctggccct gaaggccgac   300
caggccaacc tggtgctgaa gatcatcgag cagctgccca gcgccaagga gagccccgac   360
aagttcctgg aggtgtgcac ctgggtggac cagatcgccg ccctgaacga cagcaagacc   420
cgcaagacca ccagcgagac cgtgcgcgcc gtgctggaca gcctgcccgg catccagctg   480
aacaaggaga gcaacaacaa cgccagcacc cagcgcccca gccgcaacgt gaacaacttc   540
ccctacagcg gctacaacaa ggagttcctg ctgtacctgg ccggcttcgt ggacggcgac   600
ggcagcatct tcgccagcat ccgcccccgc cagcacgcca agttcaagca cgacctggac   660
ctgtgcttca acgtgcgcca gaagacccag cgccgctggt tcctggacta cctggtggac   720
accatcggcg tgggctacgt gatcgactgg cgcggcgcca gcacctacaa gctgagccag   780
atcaagcccc tgcacaactt cctgacccag ctgcagccct tcctgaagct gaagcagaag   840
caggccaacc tggtgctgaa gatcatcgag cagctgccca gcgccaagga gagccccgac   900
aagttcctgg aggtgtgcac ctgggtggac cagatcgccg ccctgaacga cagcaagacc   960
cgcaagacca ccagcgagac cgtgcgcgcc gttctagaca gcctgagcga gaagaagaaa  1020
agcagcccc                                                           1029

SEQ ID NO: 12              moltype = DNA  length = 1029
FEATURE                    Location/Qualifiers
source                     1..1029
                           mol_type = other DNA
                           organism = synthetic construct
SEQUENCE: 12
atgaacacca agtacaacaa ggagttcctg ctgtacctgg ccggcttcgt ggacagcgac    60
ggcagcatca acgccagcat cagcccccgc cagagcttca agttcaagca cggcctgaag   120
ctgcgcttcg aggtgggcca gaagacccag caccgctggt tcctggacaa gctggtggac   180
gagatcggcg tgggctacgt gtacgacaac ggcagcgtga gcgtgtacag cctgagccag   240
atcaagcccc tgcacaactt cctgacccag ctgcagccct tcctggccct gaaggccgac   300
caggccaacc tggtgctgaa gatcatcgag cagctgccca gcgccaagga gagccccgac   360
aagttcctgg aggtgtgcac ctgggtggac cagatcgccg ccctgaacga cagcaagacc   420
cgcaagacca ccagcgagac cgtgcgcgcc gtgctggaca gcctgcccgg catccagctg   480
aacaaggaga gcaacaacaa cgccagcacc cagcgcccca gccgcaacgt gaacaacttc   540
ccctacagcg gctacaacaa ggagttcctg ctgtacctgg ccggcttcgt ggacggcgac   600
ggcagcatct tcgccagcat ccgcccccgc cagcacgcca agttcaagca cgacctggac   660
ctgtgcttca acgtgcgcca gaagacccag cgccgctggt tcctggacta cctggtggac   720
accatcggcg tgggctacgt gatcgactgg cgcggcgcca gcacctacaa gctgagcgag   780
atcaagcccc tgcacaactt cctgacccag ctgcagccct tcctgaagct gaagcagaag   840
caggccaacc tggtgctgaa gatcatcgag cagctgccca gcgccaagga gagccccgac   900
aagttcctgg aggtgtgcac ctgggtggac cagatcgccg ccctgaacga cagcaagacc   960
cgcaagacca ccagcgagac cgtgcgcgcc gttctagaca gcctgagcga gaagaagaaa  1020
agcagcccc                                                           1029

SEQ ID NO: 13              moltype = AA  length = 354
FEATURE                    Location/Qualifiers
source                     1..354
                           mol_type = protein
                           organism = synthetic construct
SEQUENCE: 13
MNTKYNKEFL LYLAGFVDSD GSINASISPR QSFKFKHGLK LRFEVGQKTQ HRWFLDKLVD    60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIRP RQHAKFKHDL ELCFNVRQKT   240
QRRWFLDKLV DEIGVGYVID WRGASTYKLS QIKPLHNFLT QLQPFLKLKQ KQANLVLKII   300
EQLPSAKESP DKFLEVCTWV DQIAALNDSK TRKTTSETVR AVLDSLSEKK KSSP          354

SEQ ID NO: 14              moltype = AA  length = 354
FEATURE                    Location/Qualifiers
source                     1..354
                           mol_type = protein
                           organism = synthetic construct
SEQUENCE: 14
MNTKYNKEFL LYLAGFVDSD GSINASISPR QSFKFKHGLK LRFEVGQKTQ HRWFLDKLVD    60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIRP RQHAKFKHDL ELCFNVRQKT   240
QRRWFLDKLV DEIGVGYVID WRGASTYKLS EIKPLHNFLT QLQPFLKLKQ KQANLVLKII   300
EQLPSAKESP DKFLEVCTWV DQIAALNDSK TRKTTSETVR AVLDSLSEKK KSSP          354

SEQ ID NO: 15              moltype = AA  length = 31
FEATURE                    Location/Qualifiers
```

-continued

```
source                   1..31
                         mol_type = protein
                         organism = synthetic construct
SEQUENCE: 15
SLPGIQLNKE SNNNASTQRP SRNVNNFPYS G                              31

SEQ ID NO: 16            moltype = AA   length = 42
FEATURE                  Location/Qualifiers
source                   1..42
                         mol_type = protein
                         organism = synthetic construct
SEQUENCE: 16
SLPGSVGGLS PSQASSAASS ASSSPGSGIS EALRAGAGSG TG                  42

SEQ ID NO: 17            moltype = AA   length = 10
FEATURE                  Location/Qualifiers
source                   1..10
                         mol_type = protein
                         organism = synthetic construct
SEQUENCE: 17
MAPKKKRKVH                                                      10

SEQ ID NO: 18            moltype = DNA   length = 88
FEATURE                  Location/Qualifiers
source                   1..88
                         mol_type = other DNA
                         organism = synthetic construct
SEQUENCE: 18
aattattggt taaagaagta tattagtgct aatttccctc cgtttgtcct agcttttctc  60
ttctgtcaac cccacacgcc tttgccac                                  88

SEQ ID NO: 19            moltype = DNA   length = 114
FEATURE                  Location/Qualifiers
source                   1..114
                         mol_type = other DNA
                         organism = synthetic construct
SEQUENCE: 19
actcatcttg gccctcctca gctccctgcc tgtttcccgt aaggctgtac atagtccttt  60
tatctccttg tggcctatga aactggttta taataaactc ttaagagaac atta       114

SEQ ID NO: 20            moltype = DNA   length = 140
FEATURE                  Location/Qualifiers
source                   1..140
                         mol_type = other DNA
                         organism = synthetic construct
SEQUENCE: 20
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa                                           140

SEQ ID NO: 21            moltype = DNA   length = 10
FEATURE                  Location/Qualifiers
source                   1..10
                         mol_type = other DNA
                         organism = synthetic construct
SEQUENCE: 21
gccaccatgg                                                      10

SEQ ID NO: 22            moltype = DNA   length = 22
FEATURE                  Location/Qualifiers
source                   1..22
                         mol_type = other DNA
                         organism = synthetic construct
SEQUENCE: 22
tgccgatcca tactgcggaa ct                                        22

SEQ ID NO: 23            moltype = DNA   length = 19
FEATURE                  Location/Qualifiers
source                   1..19
                         mol_type = other DNA
                         organism = synthetic construct
SEQUENCE: 23
ggtctgtgcc aagtgtttg                                            19

SEQ ID NO: 24            moltype = DNA   length = 17
FEATURE                  Location/Qualifiers
source                   1..17
                         mol_type = other DNA
                         organism = synthetic construct
```

```
SEQUENCE: 24
gctgcgagca aaacaag                                                      17

SEQ ID NO: 25          moltype = DNA  length = 15
FEATURE                Location/Qualifiers
source                 1..15
                       mol_type = other DNA
                       organism = synthetic construct
SEQUENCE: 25
cccgcctgta acacg                                                        15

SEQ ID NO: 26          moltype = DNA  length = 19
FEATURE                Location/Qualifiers
source                 1..19
                       mol_type = other DNA
                       organism = synthetic construct
SEQUENCE: 26
catcaggatt cctaggacc                                                    19

SEQ ID NO: 27          moltype = DNA  length = 17
FEATURE                Location/Qualifiers
source                 1..17
                       mol_type = other DNA
                       organism = synthetic construct
SEQUENCE: 27
agtccaccac gagtcta                                                      17

SEQ ID NO: 28          moltype = DNA  length = 20
FEATURE                Location/Qualifiers
source                 1..20
                       mol_type = other DNA
                       organism = synthetic construct
SEQUENCE: 28
gtatatttcc gcgagaggac                                                   20

SEQ ID NO: 29          moltype = DNA  length = 24
FEATURE                Location/Qualifiers
source                 1..24
                       mol_type = other DNA
                       organism = synthetic construct
SEQUENCE: 29
cttggccccc aataccacat catc                                              24

SEQ ID NO: 30          moltype = DNA  length = 23
FEATURE                Location/Qualifiers
source                 1..23
                       mol_type = other DNA
                       organism = synthetic construct
SEQUENCE: 30
ggatggaaat tgcacctgta ttc                                               23

SEQ ID NO: 31          moltype = DNA  length = 24
FEATURE                Location/Qualifiers
source                 1..24
                       mol_type = other DNA
                       organism = synthetic construct
SEQUENCE: 31
gggtttaaat gtatacccag agac                                              24

SEQ ID NO: 32          moltype = DNA  length = 17
FEATURE                Location/Qualifiers
source                 1..17
                       mol_type = other DNA
                       organism = synthetic construct
SEQUENCE: 32
cgatccatac tgcggaa                                                      17

SEQ ID NO: 33          moltype = DNA  length = 23
FEATURE                Location/Qualifiers
source                 1..23
                       mol_type = other DNA
                       organism = synthetic construct
SEQUENCE: 33
aggtctctgc caagtgtttg ctg                                               23

SEQ ID NO: 34          moltype = DNA  length = 23
FEATURE                Location/Qualifiers
source                 1..23
                       mol_type = other DNA
```

```
                              organism = synthetic construct
SEQUENCE: 34
acgggacgta gacaaaggac gtc                                              23

SEQ ID NO: 35              moltype = DNA   length = 24
FEATURE                    Location/Qualifiers
source                     1..24
                           mol_type = other DNA
                           organism = synthetic construct
SEQUENCE: 35
ttcagtggtt cgtagggctt tccc                                            24

SEQ ID NO: 36              moltype = DNA   length = 22
FEATURE                    Location/Qualifiers
source                     1..22
                           mol_type = other DNA
                           organism = synthetic construct
SEQUENCE: 36
ctcagtttac tagtgccatt tg                                              22

SEQ ID NO: 37              moltype = DNA   length = 24
FEATURE                    Location/Qualifiers
source                     1..24
                           mol_type = other DNA
                           organism = synthetic construct
SEQUENCE: 37
ttcagtggtt cgtagggctt tccc                                            24

SEQ ID NO: 38              moltype = DNA   length = 20
FEATURE                    Location/Qualifiers
source                     1..20
                           mol_type = other DNA
                           organism = synthetic construct
SEQUENCE: 38
gtgtctgcgg cgttttatca                                                 20

SEQ ID NO: 39              moltype = DNA   length = 21
FEATURE                    Location/Qualifiers
source                     1..21
                           mol_type = other DNA
                           organism = synthetic construct
SEQUENCE: 39
gacaaacggg caacatacct t                                               21

SEQ ID NO: 40              moltype = DNA   length = 23
FEATURE                    Location/Qualifiers
source                     1..23
                           mol_type = other DNA
                           organism = synthetic construct
SEQUENCE: 40
gccaggtctg tgccaagtgt ttg                                             23

SEQ ID NO: 41              moltype = DNA   length = 20
FEATURE                    Location/Qualifiers
source                     1..20
                           mol_type = other DNA
                           organism = synthetic construct
SEQUENCE: 41
caggatccag ttggcagcac                                                 20

SEQ ID NO: 42              moltype = AA   length = 31
FEATURE                    Location/Qualifiers
source                     1..31
                           mol_type = protein
                           organism = synthetic construct
SEQUENCE: 42
SLPGIGVQVH RNNNASTQRP SRNVNNFPYK G                                     31

SEQ ID NO: 43              moltype = AA   length = 30
FEATURE                    Location/Qualifiers
source                     1..30
                           mol_type = protein
                           organism = synthetic construct
SEQUENCE: 43
SLPGVRLHCP LNNNASTQRP SRNVNNFPQG                                       30

SEQ ID NO: 44              moltype = AA   length = 30
FEATURE                    Location/Qualifiers
source                     1..30
```

```
                             mol_type = protein
                             organism = synthetic construct
SEQUENCE: 44
SLPGIRLSQG ANNNASTQRP SRNVNNFPLG                                          30

SEQ ID NO: 45            moltype = AA   length = 31
FEATURE                  Location/Qualifiers
source                   1..31
                         mol_type = protein
                         organism = synthetic construct
SEQUENCE: 45
SLPGARPGGV SNNNASTQRP SRNVNNFPYS G                                        31

SEQ ID NO: 46            moltype = AA   length = 343
FEATURE                  Location/Qualifiers
source                   1..343
                         mol_type = protein
                         organism = synthetic construct
SEQUENCE: 46
MNTKYNKEFL LYLAGFVDSD GSINASISPR QSFKFKHGLK LRFEVGQKTQ HRWFLDKLVD        60
EIGVGYVYDN GSVSVYSLSQ IKPLHNFLTQ LQPFLKLKQK QANLVLKIIE QLPSAKESPD        120
KFLEVCTWVD QIAALNDSKT RKTTSETVRA VLDSLPGIQL NKESNNNAST QRPSRNVNNF        180
PYSGYNKEFL LYLAGFVDGD GSIFASIRPR QHAKFKHDLE LCFNVRQKTQ RRWFLDKLVD        240
EIGVGYVIDW RGASTYKLSQ IKPLHNFLTQ LQPFLKLKQK QANLVLKIIE QLPSAKESPD        300
KFLEVCTWVD QIAALNDSKT RKTTSETVRA VLDSLSEKKK SSP                          343

SEQ ID NO: 47            moltype = AA   length = 343
FEATURE                  Location/Qualifiers
source                   1..343
                         mol_type = protein
                         organism = synthetic construct
SEQUENCE: 47
MNTKYNKEFL LYLAGFVDSD GSINASISPR QSFKFKHGLK LRFEVGQKTQ HRWFLDKLVD        60
EIGVGYVYDN GSVSVYSLSQ IKPLHNFLTQ LQPFLALKQK QANLVLKIIE QLPSAKESPD        120
KFLEVCTWVD QIAALNDSKT RKTTSETVRA VLDSLPGIQL NKESNNNAST QRPSRNVNNF        180
PYSGYNKEFL LYLAGFVDGD GSIFASIRPR QHAKFKHDLE LCFNVRQKTQ RRWFLDYLVD        240
TIGVGYVIDW RGASTYKLSQ IKPLHNFLTQ LQPFLKLKQK QANLVLKIIE QLPSAKESPD        300
KFLEVCTWVD QIAALNDSKT RKTTSETVRA VLDSLSEKKK SSP                          343

SEQ ID NO: 48            moltype = AA   length = 343
FEATURE                  Location/Qualifiers
source                   1..343
                         mol_type = protein
                         organism = synthetic construct
SEQUENCE: 48
MNTKYNKEFL LYLAGFVDSD GSINASISPR QSFKFKHGLK LRFEVGQKTQ HRWFLDKLVD        60
EIGVGYVYDN GSVSVYSLSQ IKPLHNFLTQ LQPFLKLKAD QANLVLKIIE QLPSAKESPD        120
KFLEVCTWVD QIAALNDSKT RKTTSETVRA VLDSLPGIQL NKESNNNAST QRPSRNVNNF        180
PYSGYNKEFL LYLAGFVDGD GSIFASIRPR QHAKFKHDLE LCFNVRQKTQ RRWFLDKLVD        240
EIGVGYVIDW RGASTYKLSQ IKPLHNFLTQ LQPFLKLKQK QANLVLKIIE QLPSAKESPD        300
KFLEVCTWVD QIAALNDSKT RKTTSETVRA VLDSLSEKKK SSP                          343

SEQ ID NO: 49            moltype = AA   length = 343
FEATURE                  Location/Qualifiers
source                   1..343
                         mol_type = protein
                         organism = synthetic construct
SEQUENCE: 49
MNTKYNKEFL LYLAGFVDSD GSINASISPR QSFKFKYGLK LRFEVGQKTQ HRWFLDKLVD        60
EIGVGYVYDN GSVSVYSLSQ IKPLHNFLTQ LQPFLKLKQK QANLVLKIIE QLPSAKESPD        120
KFLEVCTWVD QIAALNDSKT RKTTSETVRA VLDSLPGIQL NKESNNNAST QRPSRNVNNF        180
PYSGYNKEFL LYLAGFVDGD GSIFASIRPR QHAKFKHDLE LCFNVRQKTQ RRFFLDKLVD        240
EIGVGYVIDW RGASTYKLSQ IKPLHNFLTQ LQPFLKLKQK QANLVLKIIE QLPSAKESPD        300
KFLEVCTWVD QIAALNDSKT RKTTSETVRA VLDSLSEKKK SSP                          343

SEQ ID NO: 50            moltype = AA   length = 343
FEATURE                  Location/Qualifiers
source                   1..343
                         mol_type = protein
                         organism = synthetic construct
SEQUENCE: 50
MNTKYNKEFL LYLAGFVDSD GSINASISPR QSFKFKYGLK LRFEVGQKTQ HRWFLDKLVD        60
EIGVGYVYDN GSVSVYSLSQ IKPLHNFLTQ LQPFLALKQK QANLVLKIIE QLPSAKESPD        120
KFLEVCTWVD QIAALNDSKT RKTTSETVRA VLDSLPGIQL NKESNNNAST QRPSRNVNNF        180
PYSGYNKEFL LYLAGFVDGD GSIFASIRPR QHAKFKHDLE LCFNVRQKTQ RRFFLDYLVD        240
TIGVGYVIDW RGASTYKLSQ IKPLHNFLTQ LQPFLKLKQK QANLVLKIIE QLPSAKESPD        300
KFLEVCTWVD QIAALNDSKT RKTTSETVRA VLDSLSEKKK SSP                          343

SEQ ID NO: 51            moltype = AA   length = 343
```

```
FEATURE                    Location/Qualifiers
source                     1..343
                           mol_type = protein
                           organism = synthetic construct
SEQUENCE: 51
MNTKYNKEFL LYLAGFVDSD GSINASISPR QSFKFKYGLK LRFEVGQKTQ HRWFLDKLVD    60
EIGVGYVYDN GSVSVYSLSQ IKPLHNFLTQ LQPFLKLKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFASIRPR QHAKFKHDLE LCFNVRQKTQ RRFFLDKLVD   240
EIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 52             moltype = AA  length = 343
FEATURE                    Location/Qualifiers
source                     1..343
                           mol_type = protein
                           organism = synthetic construct
SEQUENCE: 52
MNTKYNKEFL LYLAGFVDSD GSINASISPR QSFKFKYGLK LRFEVGQKTQ HRWFLDKLVD    60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFASIRPR QHAKFKHDLE LCFNVRQKTQ RRFFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 53             moltype = AA  length = 343
FEATURE                    Location/Qualifiers
source                     1..343
                           mol_type = protein
                           organism = synthetic construct
SEQUENCE: 53
MNTKYNKEFL LYLAGFVDSD GSINASISPR QSFKFKHGLK LRFEVGQKTQ HRWFLDKLVD    60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGIQL QVHRNNNAST QRPSRNVNNF   180
PYKGYNKEFL LYLAGFVDGD GSIFASIRPR QHAKFKHDLE LCFNVRQKTQ RRWFLDKLVD   240
EIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 54             moltype = AA  length = 343
FEATURE                    Location/Qualifiers
source                     1..343
                           mol_type = protein
                           organism = synthetic construct
SEQUENCE: 54
MNTKYNKEFL LYLAGFVDSD GSINASISPR QSFKFKHGLK LRFEVGQKTQ HRWFLDKLVD    60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGIGV QVHRNNNAST QRPSRNVNNF   180
PYKGYNKEFL LYLAGFVDGD GSIFASIRPR QHAKFKHDLE LCFNVRQKTQ RRWFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 55             moltype = AA  length = 343
FEATURE                    Location/Qualifiers
source                     1..343
                           mol_type = protein
                           organism = synthetic construct
SEQUENCE: 55
MNTKYNKEFL LYLAGFVDSD GSINASISPR QSFKFKYGLK LRFEVGQKTQ HRWFLDKLVD    60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGIGV QVHRNNNAST QRPSRNVNNF   180
PYKGYNKEFL LYLAGFVDGD GSIFASIRPR QHAKFKHDLE LCFNVRQKTQ RRFFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 56             moltype = AA  length = 342
FEATURE                    Location/Qualifiers
source                     1..342
                           mol_type = protein
                           organism = synthetic construct
SEQUENCE: 56
MNTKYNKEFL LYLAGFVDSD GSINASISPR QSFKFKHGLK LRFEVGQKTQ HRWFLDKLVD    60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGVRL HCPLNNNAST QRPSRNVNNF   180
PQGYNKEFLL YLAGFVDGDG SIFASIRPRQ HAKFKHDLEL CFNVRQKTQR RWFLDKLVDE   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                      342

SEQ ID NO: 57             moltype = AA  length = 342
FEATURE                    Location/Qualifiers
```

```
source                     1..342
                           mol_type = protein
                           organism = synthetic construct
SEQUENCE: 57
MNTKYNKEFL LYLAGFVDSD GSINASISPR QSFKFKHGLK LRFEVGQKTQ HRWFLDKLVD     60
EIGVGYVYDN GSVSVYSLSQ IKPLHNFLTQ LQPFLALKAD QANLVLKIIE QLPSAKESPD    120
KFLEVCTWVD QIAALNDSKT RKTTSETVRA VLDSLPGVRL HCPLNNNAST QRPSRNVNNF    180
PQGYNKEFLL YLAGFVDGDG SIFASIRPRQ HAKFKHDLEL CFNVRQKTQR RWFLDYLVDT    240
IGVGYVIDWR GASTYKLSQI KPLHNFLTQL QPFLKLKQKQ ANLVLKIIEQ LPSAKESPDK    300
FLEVCTWVDQ IAALNDSKTR KTTSETVRAV LDSLSEKKKS SP                       342

SEQ ID NO: 58             moltype = AA   length = 342
FEATURE                   Location/Qualifiers
source                    1..342
                          mol_type = protein
                          organism = synthetic construct
SEQUENCE: 58
MNTKYNKEFL LYLAGFVDSD GSINASISPR QSFKFKYGLK LRFEVGQKTQ HRWFLDKLVD     60
EIGVGYVYDN GSVSVYSLSQ IKPLHNFLTQ LQPFLALKAD QANLVLKIIE QLPSAKESPD    120
KFLEVCTWVD QIAALNDSKT RKTTSETVRA VLDSLPGVRL HCPLNNNAST QRPSRNVNNF    180
PQGYNKEFLL YLAGFVDGDG SIFASIRPRQ HAKFKHDLEL CFNVRQKTQR RFFLDYLVDT    240
IGVGYVIDWR GASTYKLSQI KPLHNFLTQL QPFLKLKQKQ ANLVLKIIEQ LPSAKESPDK    300
FLEVCTWVDQ IAALNDSKTR KTTSETVRAV LDSLSEKKKS SP                       342

SEQ ID NO: 59             moltype = AA   length = 342
FEATURE                   Location/Qualifiers
source                    1..342
                          mol_type = protein
                          organism = synthetic construct
SEQUENCE: 59
MNTKYNKEFL LYLAGFVDSD GSINASISPR QSFKFKHGLK LRFEVGQKTQ HRWFLDKLVD     60
EIGVGYVYDN GSVSVYSLSQ IKPLHNFLTQ LQPFLKLKQK QANLVLKIIE QLPSAKESPD    120
KFLEVCTWVD QIAALNDSKT RKTTSETVRA VLDSLPGIRL SQGANNNAST QRPSRNVNNF    180
PLGYNKEFLL YLAGFVDGDG SIFASIRPRQ HAKFKHDLEL CFNVRQKTQR RWFLDKLVDE    240
IGVGYVIDWR GASTYKLSQI KPLHNFLTQL QPFLKLKQKQ ANLVLKIIEQ LPSAKESPDK    300
FLEVCTWVDQ IAALNDSKTR KTTSETVRAV LDSLSEKKKS SP                       342

SEQ ID NO: 60             moltype = AA   length = 342
FEATURE                   Location/Qualifiers
source                    1..342
                          mol_type = protein
                          organism = synthetic construct
SEQUENCE: 60
MNTKYNKEFL LYLAGFVDSD GSINASISPR QSFKFKHGLK LRFEVGQKTQ HRWFLDKLVD     60
EIGVGYVYDN GSVSVYSLSQ IKPLHNFLTQ LQPFLALKAD QANLVLKIIE QLPSAKESPD    120
KFLEVCTWVD QIAALNDSKT RKTTSETVRA VLDSLPGIRL SQGANNNAST QRPSRNVNNF    180
PLGYNKEFLL YLAGFVDGDG SIFASIRPRQ HAKFKHDLEL CFNVRQKTQR RWFLDKLVDT    240
IGVGYVIDWR GASTYKLSQI KPLHNFLTQL QPFLKLKQKQ ANLVLKIIEQ LPSAKESPDK    300
FLEVCTWVDQ IAALNDSKTR KTTSETVRAV LDSLSEKKKS SP                       342

SEQ ID NO: 61             moltype = AA   length = 342
FEATURE                   Location/Qualifiers
source                    1..342
                          mol_type = protein
                          organism = synthetic construct
SEQUENCE: 61
MNTKYNKEFL LYLAGFVDSD GSINASISPR QSFKFKYGLK LRFEVGQKTQ HRWFLDKLVD     60
EIGVGYVYDN GSVSVYSLSQ IKPLHNFLTQ LQPFLALKAD QANLVLKIIE QLPSAKESPD    120
KFLEVCTWVD QIAALNDSKT RKTTSETVRA VLDSLPGIRL SQGANNNAST QRPSRNVNNF    180
PLGYNKEFLL YLAGFVDGDG SIFASIRPRQ HAKFKHDLEL CFNVRQKTQR RFFLDYLVDT    240
IGVGYVIDWR GASTYKLSQI KPLHNFLTQL QPFLKLKQKQ ANLVLKIIEQ LPSAKESPDK    300
FLEVCTWVDQ IAALNDSKTR KTTSETVRAV LDSLSEKKKS SP                       342

SEQ ID NO: 62             moltype = AA   length = 343
FEATURE                   Location/Qualifiers
source                    1..343
                          mol_type = protein
                          organism = synthetic construct
SEQUENCE: 62
MNTKYNKEFL LYLAGFVDSD GSINASISPR QSFKFKHGLK LRFEVGQKTQ HRWFLDKLVD     60
EIGVGYVYDN GSVSVYSLSQ IKPLHNFLTQ LQPFLKLKQK QANLVLKIIE QLPSAKESPD    120
KFLEVCTWVD QIAALNDSKT RKTTSETVRA VLDSLPGARP GGVSNNNAST QRPSRNVNNF    180
PYSGYNKEFL LYLAGFVDGD GSIFASIRPR QHAKFKHDLE LCFNVRQKTQ RRWFLDKLVD    240
EIGVGYVIDW RGASTYKLSQ IKPLHNFLTQ LQPFLKLKQK QANLVLKIIE QLPSAKESPD    300
KFLEVCTWVD QIAALNDSKT RKTTSETVRA VLDSLSEKKK SSP                      343

SEQ ID NO: 63             moltype = AA   length = 343
FEATURE                   Location/Qualifiers
source                    1..343
```

```
                        mol_type = protein
                        organism = synthetic construct
SEQUENCE: 63
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGARP GGVSNNNAST QRPSRNVNNF  180
PYSGYNKEFL LYLAGFVDGD GSIFASIRPR QHAKFKHDLE LCFNVRQKTQ RRWFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                    343

SEQ ID NO: 64          moltype = AA   length = 343
FEATURE                Location/Qualifiers
source                 1..343
                        mol_type = protein
                        organism = synthetic construct
SEQUENCE: 64
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGARP GGVSNNNAST QRPSRNVNNF  180
PYSGYNKEFL LYLAGFVDGD GSIFASIRPR QHAKFKHDLE LCFNVRQKTQ RRFFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                    343

SEQ ID NO: 65          moltype = AA   length = 7
FEATURE                Location/Qualifiers
source                 1..7
                        mol_type = protein
                        organism = synthetic construct
SEQUENCE: 65
PKKKRKV                                                               7

SEQ ID NO: 66          moltype = DNA   length = 1461
FEATURE                Location/Qualifiers
source                 1..1461
                        mol_type = other DNA
                        organism = synthetic construct
SEQUENCE: 66
aattattggt taaagaagta tattagtgct aatttccctc cgtttgtcct agcttttctc   60
ttctgtcaac cccacacgcc tttgccacca tggccccaa gaagaagcgc aaggtgcata  120
tgaacaccaa gtacaacaag gagttcctgc tgtacctggc cggcttcgtg gacagcgacg  180
gcagcatcaa cgccagcatc agcccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgga ggtgtgcacc tgggtggacc agatcgccgc cctgaacgac agcaagaccc  540
gcaagaccac cagcgagacc gtgcgcgccg tgctggacag cctgcccggc atccagctga  600
acaaggagag caacaacaac gccagcaccc agcgccccag ccgcaacgtg aacaacttcc  660
cctacagcgg ctacaacaag gagttcctgc tgtacctggc cggcttcgtg gacggcgacg  720
gcagcatctt cgccagcatc cgcccccgcc agcacgccaa gttcaagcac gacctggagc  780
tgtgcttcaa cgtgcgccag aagacccagc gccgctggtt cctggactac ctggtggaca  840
ccatcggcgt gggctacgtg atcgactggc gcggcgccag cacctacaag ctgagccaga  900
tcaagcccct gcacaacttc ctgacccagc tgcagccctt cctgaagctg aagcagaagc  960
aggccaacct ggtgctgaag atcatcgagc agctgcccag cgccaaggag agccccgaca 1020
agttcctgga ggtgtgcacc tgggtggacc agatcgccgc cctgaacgac agcaagaccc 1080
gcaagaccac cagcgagacc gtgcgcgccg ttctagacag cctgagcgag aagaagaaaa 1140
gcagccccat ggcccccaag aagaagcgca aggtgcattg atgaggtacc agcggccgca 1200
ctcatcttgg ccctcctcag ctccctgcct gtttcccgta aggctgtaca tagtcctttt 1260
atctccttgt ggcctatgaa actggtttat aataaactct taagacgcgc ttaggcgcgc 1320
caaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa a                                           1461

SEQ ID NO: 67          moltype = DNA   length = 1452
FEATURE                Location/Qualifiers
source                 1..1452
                        mol_type = other DNA
                        organism = synthetic construct
SEQUENCE: 67
aattattggt taaagaagta tattagtgct aatttccctc cgtttgtcct agcttttctc   60
ttctgtcaac cccacacgcc tttgccacca tggccccaa gaagaagcgc aaggtgcata  120
tgaacaccaa gtacaacaag gagttcctgc tgtacctggc cggcttcgtg gacagcgacg  180
gcagcatcaa cgccagcatc agcccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgga ggtgtgcacc tgggtggacc agatcgccgc cctgaacgac agcaagaccc  540
gcaagaccac cagcgagacc gtgcgcgccg tgctggacag cctgcccggc atccagctga  600
```

-continued

```
acaaggagag caacaacaac gccagcaccc agcgccccag ccgcaacgtg aacaacttcc    660
cctacagcgg ctacaacaag gagttcctgc tgtacctggc cggcttcgtg gacggcgacg    720
gcagcatctt cgccagcatc cgccccgcc agcacgccaa gttcaagcac gacctggagc     780
tgtgcttcaa cgtgcgccag aagacccagc gccgctggtt cctggactac ctggtggaca    840
ccatcggcgt gggctacgtg atcgactggc gcggcgcgca cacctacaag ctgagccaga    900
tcaagcccct gcacaacttc ctgacccagc tgcagcccet cctgaagctg aagcagaagc    960
aggccaacct ggtgctgaag atcatcgagc agctgcccag cgccaaggag agccccgaca   1020
agttcctgga ggtgtgcacc tgggtggacc agatcgccgc cctgaacgac agcaagaccc   1080
gcaagaccac cagcgagacc gtgcgcgccg ttctagacag cctgagcgag aagaagaaaa   1140
gcagcccccc caagaagaag cgcaaggtgt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                        1452

SEQ ID NO: 68          moltype = DNA   length = 1452
FEATURE                Location/Qualifiers
source                 1..1452
                       mol_type = other DNA
                       organism = synthetic construct
SEQUENCE: 68
aattattggt taaagaagta tattagtgct aatttccctc cgtttgtcct agcttttctc    60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagccag atcaagcccc   900
tgcacaactt cctgacccag ctgcagccct tcctgaagct gaagcagaag caggccaacc   960
tggtgctgaa gatcatcgag cagctgccca gcgccaagga gagccccgac aagttcctgg  1020
aggtgtgcac ctgggtggac cagatcgccg ccctgaacga cagcaagacc cgcaagacca  1080
ccagcgagac cgtgcgcgcc gttctagaca gcctgagcga gaagaagaaa gcagccccca  1140
tggccccaa gaagaagcgc aaggtgcatt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                       1452

SEQ ID NO: 69          moltype = DNA   length = 1443
FEATURE                Location/Qualifiers
source                 1..1443
                       mol_type = other DNA
                       organism = synthetic construct
SEQUENCE: 69
aattattggt taaagaagta tattagtgct aatttccctc cgtttgtcct agcttttctc    60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagccag atcaagcccc   900
tgcacaactt cctgacccag ctgcagccct tcctgaagct gaagcagaag caggccaacc   960
tggtgctgaa gatcatcgag cagctgccca gcgccaagga gagccccgac aagttcctgg  1020
aggtgtgcac ctgggtggac cagatcgccg ccctgaacga cagcaagacc cgcaagacca  1080
ccagcgagac cgtgcgcgcc gttctagaca gcctgagcga gaagaagaaa gcagccccc   1140
ccaagaagaa gcgcaaggtg tgatgaggta ccagcggccg cactcatctt ggccctcctc  1200
agctccctgc ctgtttcccg taaggctgta catagtcctt ttatctcctt gtggcctatg  1260
aaactggttt ataataaact cttaagagaa cattaggcgc gccaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaa                                                                 1443
```

-continued

```
SEQ ID NO: 70          moltype = DNA  length = 1461
FEATURE                Location/Qualifiers
source                 1..1461
                       mol_type = other DNA
                       organism = synthetic construct
SEQUENCE: 70
aattattggt taaagaagta tattagtgct aatttccctc cgtttgtcct agcttttctc   60
ttctgtcaac cccacacgcc tttgccacca tggcccccaa gaagaagcgc aaggtgcata  120
tgaacaccaa gtacaacaag gagttcctgc tgtacctggc cggcttcgtg gacagcgacg  180
gcagcatcaa cgccagcatc agcccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgga ggtgtgcacc tgggtggacc agatcgccgc cctgaacgac agcaagaccc  540
gcaagaccac cagcgagacc gtgcgcgccg tgctggacag cctgcccggc atccagctga  600
acaaggagag caacaacaac gccagcaccc agcgccccag ccgcaacgtg aacaacttcc  660
cctacagcgg ctacaacaag gagttcctgc tgtacctggc cggcttcgtg gacggcgacg  720
gcagcatctt cgccagcatc cgcccccgcc agcacgccaa gttcaagcac gacctggagc  780
tgtgcttcaa cgtgcgccag aagacccagc gccgctggtt cctggactac ctggtggaca  840
ccatcggcgt gggctacgtg atcgactggc gcggcgccag cacctacaag ctgagcgaga  900
tcaagcccct gcacaacttc ctgacccagc tgcagccctt cctgaagctg aagcagaagc  960
aggccaacct ggtgctgaag atcatcgagc agctgcccag cgccaaggag agccccgaca 1020
agttcctgga ggtgtgcacc tgggtggacc agatcgccgc cctgaacgac agcaagaccc 1080
gcaagaccac cagcgagacc gtgcgcgccg ttctagacag cctgagcgag aagaagaaaa 1140
gcagccccat ggcccccaag aagaagcgca aggtgcattg atgaggtacc agcggccgca 1200
ctcatcttgg ccctcctcag ctccctgcct gtttcccgta aggctgtaca tagtcctttt 1260
atctccttgt ggcctatgaa actggtttat aataaactct taagagaaca ttaggcgcgc 1320
caaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa a                                           1461

SEQ ID NO: 71          moltype = DNA  length = 1452
FEATURE                Location/Qualifiers
source                 1..1452
                       mol_type = other DNA
                       organism = synthetic construct
SEQUENCE: 71
aattattggt taaagaagta tattagtgct aatttccctc cgtttgtcct agcttttctc   60
ttctgtcaac cccacacgcc tttgccacca tggcccccaa gaagaagcgc aaggtgcata  120
tgaacaccaa gtacaacaag gagttcctgc tgtacctggc cggcttcgtg gacagcgacg  180
gcagcatcaa cgccagcatc agcccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgga ggtgtgcacc tgggtggacc agatcgccgc cctgaacgac agcaagaccc  540
gcaagaccac cagcgagacc gtgcgcgccg tgctggacag cctgcccggc atccagctga  600
acaaggagag caacaacaac gccagcaccc agcgccccag ccgcaacgtg aacaacttcc  660
cctacagcgg ctacaacaag gagttcctgc tgtacctggc cggcttcgtg gacggcgacg  720
gcagcatctt cgccagcatc cgcccccgcc agcacgccaa gttcaagcac gacctggagc  780
tgtgcttcaa cgtgcgccag aagacccagc gccgctggtt cctggactac ctggtggaca  840
ccatcggcgt gggctacgtg atcgactggc gcggcgccag cacctacaag ctgagcgaga  900
tcaagcccct gcacaacttc ctgacccagc tgcagccctt cctgaagctg aagcagaagc  960
aggccaacct ggtgctgaag atcatcgagc agctgcccag cgccaaggag agccccgaca 1020
agttcctgga ggtgtgcacc tgggtggacc agatcgccgc cctgaacgac agcaagaccc 1080
gcaagaccac cagcgagacc gtgcgcgccg ttctagacag cctgagcgag aagaagaaaa 1140
gcagcccccc caagaagaag cgcaaggtgt gatgaggtac cagcggccgc actcatcttg 1200
gccctcctca gctccctgcc tgtttcccgt aaggctgtac atagtccttt tatctccttg 1260
tggcctatga aactggttta taataaactc ttaagagaac attaggcgcg ccaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aa                                                     1452

SEQ ID NO: 72          moltype = DNA  length = 1452
FEATURE                Location/Qualifiers
source                 1..1452
                       mol_type = other DNA
                       organism = synthetic construct
SEQUENCE: 72
aattattggt taaagaagta tattagtgct aatttccctc cgtttgtcct agcttttctc   60
ttctgtcaac cccacacgcc tttgccaccc caagaagaag cgcaaggtg atgaacacca  120
agtacaacaa ggagttcctg ctgtacctgg ccggcttcgt ggacagcatca  180
acgccagcat cagcccccgc cagagcttca agttcaagca cggcctgaag ctgcgcttcg  240
aggtgggcca gaagacccag caccgctggt tcctggacaa gctggtggac gagatcggcg  300
tgggctacgt gtacgacaac ggcagcgtga gcgtgtacag cctgagccag atcaagcccc  360
tgcacaactt cctgacccag ctgcagccct tcctggccct gaaggccgac caggccaacc  420
tggtgctgaa gatcatcgag cagctgccca cgccaagga gagccccgac aagttcctgg  480
```

-continued

```
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagcgag atcaagcccc   900
tgcacaactt cctgacccag ctgcagccct tcctgaagct gaagcagaag caggccaacc   960
tggtgctgaa gatcatcgag cagctgccca gcgccaagga gagcccccgac aagttcctgg   1020
aggtgtgcac ctgggtggac cagatcgccg ccctgaacga cagcaagacc cgcaagacca   1080
ccagcgagac cgtgcgcgcc gttctagaca gcctgagcga gaagaagaaa agcagcccca   1140
tggcccccaa gaagaagcgc aaggtgcatt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                       1452

SEQ ID NO: 73          moltype = DNA   length = 1443
FEATURE                Location/Qualifiers
source                 1..1443
                       mol_type = other DNA
                       organism = synthetic construct
SEQUENCE: 73
aattattggt taaagaagta tattagtgct aatttccctc cgtttgtcct agcttttctc   60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag ctgagccaga atcaagcccc   360
tgcacaactt cctgacccag ctgcagccct tcctggccct gaaggccgac caggccaacc   420
tggtgctgaa gatcatcgag cagctgccca gcgccaagga gagcccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagcgag atcaagcccc   900
tgcacaactt cctgacccag ctgcagccct tcctgaagct gaagcagaag caggccaacc   960
tggtgctgaa gatcatcgag cagctgccca gcgccaagga gagcccccgac aagttcctgg   1020
aggtgtgcac ctgggtggac cagatcgccg ccctgaacga cagcaagacc cgcaagacca   1080
ccagcgagac cgtgcgcgcc gttctagaca gcctgagcga gaagaagaaa agcagcccca   1140
ccaagaagaa gcgcaaggtg tgatgaggta ccagcggccg cactcatctt ggccctcctc   1200
agctccctgc ctgtttcccg taaggctgta catagtcctt ttatctcctt gtggcctatg   1260
aaactggttt ataataaact cttaagagaa cattaggcgc gccaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaa                                                                 1443

SEQ ID NO: 74          moltype = RNA   length = 1461
FEATURE                Location/Qualifiers
source                 1..1461
                       mol_type = other RNA
                       organism = synthetic construct
SEQUENCE: 74
aattattggt taaagaagta tattagtgct aatttccctc cgtttgtcct agcttttctc   60
ttctgtcaac cccacacgcc tttgccacca tggcccccaa gaagaagcgc aaggtgcata   120
tgaacaccaa gtacaacaag gagttcctgc tgtacctggc cggcttcgtg gacagcgacg   180
gcagcatcaa cgccagcatc agcccccgcc agagcttcaa gttcaagcac ggcctgaagc   240
tgcgcttcga ggtgggccag aagacccagc accgctggtt cctggacaag ctggtggacg   300
agatcggcgt gggctacgtg tacgacaacg gcagcgtgag cgtgtacagc ctgagccaga   360
tcaagcccct gcacaacttc ctgacccagc tgcagccctt cctggccctg aaggccgacc   420
aggccaacct ggtgctgaag atcatcgagc agctgcccag cgccaaggag agcccccgaca   480
agttcctgga ggtgtgcacc tgggtggacc agatcgccgc cctgaacgac agcaagaccc   540
gcaagaccac cagcgagacc gtgcgcgccg tgctggacag cctgcccggc atccagctga   600
acaaggagag caacaacaac gccagcaccc agcgccccag ccgcaacgtg aacaacttcc   660
cctacagcgg ctacaacaag gagttcctgc tgtacctggc cggcttcgtg gacggcgacg   720
gcagcatctt cgccagcatc cgcccccgcc agcacgccaa gttcaagcac gacctggagc   780
tgtgcttcaa cgtgcgccag aagacccagc gccgctggtt cctggactac ctggtggaca   840
ccatcggcgt gggctacgtg atcgactggc gcggcgccag cacctacaag ctgagccaga   900
tcaagcccct gcacaacttc ctgacccagc tgcagccctt cctgaagctg aagcagaagc   960
aggccaacct ggtgctgaag atcatcgagc agctgcccag cgccaaggag agcccccgaca   1020
agttcctgga ggtgtgcacc tgggtggacc agatcgccgc cctgaacgac agcaagaccc   1080
gcaagaccac cagcgagacc gtgcgcgccg ttctagacag cctgagcgag aagaagaaaa   1140
gcagccccat ggcccccaag aagaagcgca aggtgcattg atgaggtacc agcggccgca   1200
ctcatcttgg ccctcctcag ctccctgcct gtttcccgta aggctgtaca tagtcctttt   1260
atctccttgg ggcctatgaa actggtttat aataaactct aagagaaca ttaggcgcgc   1320
caaaaaaaaa aaaaaaaaaa aaaaaaaaaa aaaaaaaaaa aaaaaaaaaa aaaaaaaaaa   1380
```

```
aaaaaaaaaa aaaaaaaaaa aaaaaaaaaa aaaaaaaaaa aaaaaaaaaa aaaaaaaaaa   1440
aaaaaaaaaa aaaaaaaaaa a                                            1461

SEQ ID NO: 75          moltype = RNA  length = 1452
FEATURE                Location/Qualifiers
source                 1..1452
                       mol_type = other RNA
                       organism = synthetic construct
SEQUENCE: 75
aattattggt taaagaagta tattagtgct aatttccctc cgtttgtcct agcttttctc   60
ttctgtcaac cccacacgcc tttgccacca tggcccccaa gaagaagcgc aaggtgcata   120
tgaacaccaa gtacaacaag gagttcctgc tgtacctggc cggcttcgtg dacagcgacg   180
gcagcatcaa cgccagcatc agcccccgcc agagcttcaa gttcaagcac ggcctgaagc   240
tgcgcttcga ggtgggccag aagacccagc accgctggtt cctggacaag ctggtggacg   300
agatcggcgt gggctacgtg tacgacaacg gcagcgtgag cgtgtacagc ctgagccaga   360
tcaagcccct gcacaacttc ctgacccagc tgcagccctt cctggccctg aaggccgacc   420
aggccaacct ggtgctgaag atcatcgagc agctgcccag cgccaaggag agccccgaca   480
agttcctgga ggtgtgcacc tgggtggacc agatcgccgc cctgaacgac agcaagaccc   540
gcaagaccac cagcgagacc gtgcgcgccg tgctggacac cctgcccggc atccagctga   600
acaaggagag caacaacaac gccagcaccc agcgccccag ccgcaacgtg aacaacttcc   660
cctacagcgg ctacaacaag gagttcctgc tgtacctggc cggcttcgtg dacggcgacg   720
gcagcatctt cgccagcatc cgcccccgcc agcacgcca gttcaagcac gacctggagc   780
tgtgcttcaa cgtgcgccag aagacccagc gccgctggtt cctggactac ctggtggaca   840
ccatcggcgt gggctacgtg atcgactggc gcggcgccag cacctacaag ctgagccaga   900
tcaagcccct gcacaacttc ctgacccagc tgcagcccct cctgaagctg aagcagaagc   960
aggccaacct ggtgctgaag atcatcgagc agctgcccag cgccaaggag agccccgaca   1020
agttcctgga ggtgtgcacc tgggtggacc agatcgccgc cctgaacgac agcaagaccc   1080
gcaagaccac cagcgagacc gtgcgcgccg ttctagacag cctgagcgag aagaagaaaa   1140
gcagcccccc caagaagaag cgcaaggtgt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                      1452

SEQ ID NO: 76          moltype = RNA  length = 1452
FEATURE                Location/Qualifiers
source                 1..1452
                       mol_type = other RNA
                       organism = synthetic construct
SEQUENCE: 76
aattattggt taaagaagta tattagtgct aatttccctc cgtttgtcct agcttttctc   60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca cctgccccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca gttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagccag atcaagcccc   900
tgcacaactt cctgacccag ctgcagcccc tcctgaagct gaagcagaag caggccaacc   960
tggtgctgaa gatcatcgag cagctgccca gcgccaagga gagccccgac aagttcctgg   1020
aggtgtgcac ctgggtggac cagatcgccg ccctgaacga cagcaagacc cgcaagacca   1080
ccagcgagac cgtgcgcgcc gttctagaca gcctgagcga gaagaagaaa agcagccca   1140
tggcccccaa gaagaagcgc aaggtgcatt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                      1452

SEQ ID NO: 77          moltype = RNA  length = 1443
FEATURE                Location/Qualifiers
source                 1..1443
                       mol_type = other RNA
                       organism = synthetic construct
SEQUENCE: 77
aattattggt taaagaagta tattagtgct aatttccctc cgtttgtcct agcttttctc   60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
```

```
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagccag atcaagcccc   900
tgcacaactt cctgacccag ctgcagccct tcctgaagct gaagcagaag caggccaacc   960
tggtgctgaa gatcatcgag cagctgccca gcgccaagga gagccccgac aagttcctgg  1020
aggtgtgcac ctgggtggac cagatcgccg ccctgaacga cagcaagacc cgcaagacca  1080
ccagcgagac cgtgcgcgcc gttctagaca gcctgagcga gaagaagaaa agcagccccc  1140
ccaagaagaa gcgcaaggtg tgatgaggta ccagcggccg cactcatctt ggccctcctc  1200
agctccctgc ctgtttcccg taaggctgta catagtcctt ttatctcctt gtggcctatg  1260
aaaactggtt ataataaaact cttaagagaa cattaggcgc gccaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaa                                                                1443

SEQ ID NO: 78            moltype = RNA  length = 1461
FEATURE                  Location/Qualifiers
source                   1..1461
                         mol_type = other RNA
                         organism = synthetic construct
SEQUENCE: 78
aattattggt taaagaagta tattagtgct aatttccctc cgtttgtcct agctttttctc   60
ttctgtcaac cccacacgcc tttgccacca tggcccccaa gaagaagcgc aaggtgcata  120
tgaacaccaa gtacaacaag gagttcctgc tgtacctggc cggcttcgtg gacagcgacg  180
gcagcatcaa cgccagcatc agccccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgag ggtgtgcacc tgggtggacc agatcgccgc cctgaacgac agcaagaccc  540
gcaagaccac cagcgagacc gtgcgcgccg tgctggacag cctgcccggc atccagctga  600
acaaggagag caacaacaac gccagcaccc agcgccccag ccgcaacgtg aacaacttcc  660
cctacagcgg ctacaacaag gagttcctgc tgtacctggc cggcttcgtg gacggcgacg  720
gcagcatctt cgccagcatc cgcccccgcc agcacgccaa gttcaagcac gacctggagc  780
tgtgcttcaa cgtgcgccag aagacccagc gccgctggtt cctggactac ctggtggaca  840
ccatcggcgt gggctacgtg atcgactggc gcggcgccag cacctacaag ctgagcgaga  900
tcaagcccct gcacaacttc ctgacccagc tgcagccctt cctgaagctg aagcagaagc  960
aggccaacct ggtgctgaag atcatcgagc agctgcccag cgccaaggag agccccgaca 1020
agttcctgga ggtgtgcacc tgggtggacc agatcgccgc cctgaacgac agcaagaccc 1080
gcaagaccac cagcgagacc gtgcgcgccg ttctagacag cctgagcgag aagaagaaaa 1140
gcagcccccat ggcccccaag aagaagcgca aggtgcattg atgaggtacc agcggccgca 1200
ctcatcttgg ccctcctcag ctccctgcct gtttcccgta aggctgtaca tagtcctttt 1260
atctccttgt ggcctatgaa actggtttat aataaactct taagagaaca ttaggcgcgc 1320
caaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa a                                           1461

SEQ ID NO: 79            moltype = RNA  length = 1452
FEATURE                  Location/Qualifiers
source                   1..1452
                         mol_type = other RNA
                         organism = synthetic construct
SEQUENCE: 79
aattattggt taaagaagta tattagtgct aatttccctc cgtttgtcct agctttttctc   60
ttctgtcaac cccacacgcc tttgccacca tggcccccaa gaagaagcgc aaggtgcata  120
tgaacaccaa gtacaacaag gagttcctgc tgtacctggc cggcttcgtg gacagcgacg  180
gcagcatcaa cgccagcatc agccccccgcc agagcttcaa gttcaagcac ggcctgaagc  240
tgcgcttcga ggtgggccag aagacccagc accgctggtt cctggacaag ctggtggacg  300
agatcggcgt gggctacgtg tacgacaacg gcagcgtgag cgtgtacagc ctgagccaga  360
tcaagcccct gcacaacttc ctgacccagc tgcagccctt cctggccctg aaggccgacc  420
aggccaacct ggtgctgaag atcatcgagc agctgcccag cgccaaggag agccccgaca  480
agttcctgga ggtgtgcacc tgggtggacc agatcgccgc cctgaacgac agcaagaccc  540
gcaagaccac cagcgagacc gtgcgcgccg tgctggacag cctgcccggc atccagctga  600
acaaggagag caacaacaac gccagcaccc agcgccccag ccgcaacgtg aacaacttcc  660
cctacagcgg ctacaacaag gagttcctgc tgtacctggc cggcttcgtg gacggcgacg  720
gcagcatctt cgccagcatc cgcccccgcc agcacgccaa gttcaagcac gacctggagc  780
tgtgcttcaa cgtgcgccag aagacccagc gccgctggtt cctggactac ctggtggaca  840
ccatcggcgt gggctacgtg atcgactggc gcggcgccag cacctacaag ctgagcgaga  900
tcaagcccct gcacaacttc ctgacccagc tgcagccctt cctgaagctg aagcagaagc  960
aggccaacct ggtgctgaag atcatcgagc agctgcccag cgccaaggag agccccgaca 1020
agttcctgga ggtgtgcacc tgggtggacc agatcgccgc cctgaacgac agcaagaccc 1080
gcaagaccac cagcgagacc gtgcgcgccg ttctagacag cctgagcgag aagaagaaaa 1140
gcagcccccc caagaagaag cgcaaggtgt gatgaggtac cagcggccgc actcatcttg 1200
gccctcctca gctccctgcc tgtttcccgt aaggctgtac atagtccttt tatctccttg 1260
```

```
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                       1452

SEQ ID NO: 80          moltype = RNA   length = 1452
FEATURE                Location/Qualifiers
source                 1..1452
                       mol_type = other RNA
                       organism = synthetic construct
SEQUENCE: 80
aattattggt taaagaagta tattagtgct aatttccctc cgtttgtcct agcttttctc   60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagcgag atcaagcccc   900
tgcacaactt cctgacccag ctgcagccct tcctgaagct gaagcagaag caggccaacc   960
tggtgctgaa gatcatcgag cagctgccca gcgccaagga gagccccgac aagttcctgg   1020
aggtgtgcac ctgggtggac cagatcgccg ccctgaacga cagcaagacc cgcaagacca   1080
ccagcgagac cgtgcgcgcc gttctagaca gcctgagcga gaagaagaaa agcagcccca   1140
tggcccccaa gaagaagcgc aaggtgcatt gatgaggtac cagcggccgc actcatcttg   1200
gccctcctca gctccctgcc tgtttcccgt aaggctgtac atagtccttt tatctccttg   1260
tggcctatga aactggttta taataaactc ttaagagaac attaggcgcg ccaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aa                                                       1452

SEQ ID NO: 81          moltype = RNA   length = 1443
FEATURE                Location/Qualifiers
source                 1..1443
                       mol_type = other RNA
                       organism = synthetic construct
SEQUENCE: 81
aattattggt taaagaagta tattagtgct aatttccctc cgtttgtcct agcttttctc   60
ttctgtcaac cccacacgcc tttgccaccc ccaagaagaa gcgcaaggtg atgaacacca   120
agtacaacaa ggagttcctg ctgtacctgg ccggcttcgt ggacagcgac ggcagcatca   180
acgccagcat cagcccccgc cagagcttca agttcaagca cggcctgaag ctgcgcttcg   240
aggtgggcca gaagacccag caccgctggt tcctggacaa gctggtggac gagatcggcg   300
tgggctacgt gtacgacaac ggcagcgtga gcgtgtacag cctgagccag atcaagcccc   360
tgcacaactt cctgacccag ctgcagccct tcctggccct gaaggccgac caggccaacc   420
tggtgctgaa gatcatcgag cagctgccca gcgccaagga gagccccgac aagttcctgg   480
aggtgtgcac ctgggtggac cagatcgccg ccctgaacga cagcaagacc cgcaagacca   540
ccagcgagac cgtgcgcgcc gtgctggaca gcctgcccgg catccagctg aacaaggaga   600
gcaacaacaa cgccagcacc cagcgcccca gccgcaacgt gaacaacttc ccctacagcg   660
gctacaacaa ggagttcctg ctgtacctgg ccggcttcgt ggacggcgac ggcagcatct   720
tcgccagcat ccgcccccgc cagcacgcca agttcaagca cgacctggag ctgtgcttca   780
acgtgcgcca gaagacccag cgccgctggt tcctggacta cctggtggac accatcggcg   840
tgggctacgt gatcgactgg cgcggcgcca gcacctacaa gctgagcgag atcaagcccc   900
tgcacaactt cctgacccag ctgcagccct tcctgaagct gaagcagaag caggccaacc   960
tggtgctgaa gatcatcgag cagctgccca gcgccaagga gagccccgac aagttcctgg   1020
aggtgtgcac ctgggtggac cagatcgccg ccctgaacga cagcaagacc cgcaagacca   1080
ccagcgagac cgtgcgcgcc gttctagaca gcctgagcga gaagaagaaa agcagcccc   1140
ccaagaagaa gcgcaaggtg tgatgaggta ccagcggccg cactcatctt ggccctcctg   1200
agctccctgc ctgtttcccg taaggctgta catagtcctt ttatctcctt gtggcctatg   1260
aaactggttt ataataaact cttaagagaa cattaggcgc gccaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaa                                                                 1443

SEQ ID NO: 82          moltype = RNA   length = 88
FEATURE                Location/Qualifiers
source                 1..88
                       mol_type = other RNA
                       organism = synthetic construct
SEQUENCE: 82
aattattggt taaagaagta tattagtgct aatttccctc cgtttgtcct agcttttctc   60
ttctgtcaac cccacacgcc tttgccac                                      88

SEQ ID NO: 83          moltype = RNA   length = 114
```

-continued

```
FEATURE              Location/Qualifiers
source               1..114
                     mol_type = other RNA
                     organism = synthetic construct
SEQUENCE: 83
actcatcttg gccctcctca gctccctgcc tgtttcccgt aaggctgtac atagtccttt  60
tatctccttg tggcctatga aactggttta taataaactc ttaagagaac atta         114

SEQ ID NO: 84        moltype = RNA   length = 10
FEATURE              Location/Qualifiers
source               1..10
                     mol_type = other RNA
                     organism = synthetic construct
SEQUENCE: 84
gccaccatgg                                                           10
```